US011208377B2

(12) United States Patent
Hein et al.

(10) Patent No.: US 11,208,377 B2
(45) Date of Patent: Dec. 28, 2021

(54) 3,4-DISUBSTITUTED 3-CYCLOBUTENE-1,2-DIONES AND USE THEREOF

(71) Applicant: ALLERGAN, INC., Irvine, CA (US)

(72) Inventors: Christopher D. Hein, Costa Mesa, CA (US); Tien T. Duong, Rancho Santa Margarita, CA (US); Santosh Sinha, Ladera Ranch, CA (US); Ling Li, Irvine, CA (US); Jeremiah H. Nguyen, La Puente, CA (US); David W. Old, Irvine, CA (US); Robert Burk, Laguna Beach, CA (US); Veena Viswanath, Irvine, CA (US); Sandhya Rao, Irvine, CA (US); John E. Donello, Dana Point, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 16/103,607

(22) Filed: Aug. 14, 2018

(65) Prior Publication Data

US 2019/0047947 A1 Feb. 14, 2019

Related U.S. Application Data

(60) Provisional application No. 62/545,331, filed on Aug. 14, 2017.

(51) Int. Cl.
| | |
|---|---|
| C07C 311/39 | (2006.01) |
| A61P 17/06 | (2006.01) |
| C07C 237/44 | (2006.01) |
| A61P 27/02 | (2006.01) |
| C07C 211/52 | (2006.01) |
| C07D 307/36 | (2006.01) |
| C07D 307/79 | (2006.01) |
| C07D 215/42 | (2006.01) |
| C07B 59/00 | (2006.01) |
| C07D 333/54 | (2006.01) |
| C07C 311/43 | (2006.01) |
| A61P 29/00 | (2006.01) |

(52) U.S. Cl.
CPC ............ *C07C 311/39* (2013.01); *A61P 17/06* (2018.01); *A61P 27/02* (2018.01); *A61P 29/00* (2018.01); *C07B 59/00* (2013.01); *C07C 211/52* (2013.01); *C07C 237/44* (2013.01); *C07C 311/43* (2013.01); *C07D 215/42* (2013.01); *C07D 307/36* (2013.01); *C07D 307/79* (2013.01); *C07D 333/54* (2013.01); *C07B 2200/05* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2602/10* (2017.05); *C07C 2602/12* (2017.05); *C07C 2603/70* (2017.05); *C07C 2603/97* (2017.05)

(58) Field of Classification Search
CPC ..................................................... C07C 311/39
See application file for complete search history.

(56) References Cited

U.S. PATENT DOCUMENTS

| | | | |
|---|---|---|---|
| 5,354,763 | A | 10/1994 | Butera et al. |
| 5,397,790 | A | 3/1995 | Butera et al. |
| 5,401,753 | A | 3/1995 | Butera et al. |
| 5,403,853 | A | 4/1995 | Butera et al. |
| 5,403,854 | A | 4/1995 | Butera et al. |
| 5,506,252 | A | 4/1996 | Butera et al. |
| 7,008,962 | B2 | 3/2006 | Palovich et al. |
| 7,132,445 | B2 | 11/2006 | Taveras et al. |
| 7,947,720 | B2 | 5/2011 | Taveras et al. |
| 7,960,433 | B2 | 6/2011 | Taveras et al. |
| 7,964,646 | B2 | 6/2011 | Taveras et al. |
| 7,989,497 | B2 | 8/2011 | Baettig et al. |
| 8,183,281 | B2 | 5/2012 | Press et al. |
| 8,288,588 | B2 | 10/2012 | Baettig et al. |
| 8,329,754 | B2 | 12/2012 | Baettig et al. |
| 8,722,925 | B2 | 5/2014 | Baettig et al. |
| 9,090,596 | B2 | 7/2015 | Musicki et al. |
| 9,115,087 | B2 | 8/2015 | Baettig et al. |
| 9,340,509 | B2 | 5/2016 | Dairaghi et al. |
| 9,388,149 | B2 | 7/2016 | Musicki et al. |
| 9,526,732 | B2 | 12/2016 | Musicki et al. |

(Continued)

FOREIGN PATENT DOCUMENTS

| | | |
|---|---|---|
| WO | 02057230 | 7/2002 |
| WO | 02076926 A1 | 10/2002 |

(Continued)

OTHER PUBLICATIONS

STN Abstract of U.S. Pat. No. 7,132,445 B2 (2006) (Year: 2006).*

(Continued)

*Primary Examiner* — Brenda L Coleman

(74) *Attorney, Agent, or Firm* — Jonathan Bass

(57) ABSTRACT

Described herein are compounds, or pharmaceutically acceptable salts thereof, of the following formula:

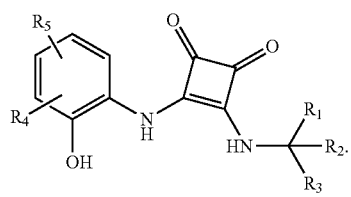

The compounds are useful for treating inflammatory and autoimmune diseases.

6 Claims, No Drawings

(56) References Cited

U.S. PATENT DOCUMENTS

| | | | |
|---|---|---|---|
| 9,580,412 | B2 | 2/2017 | Musicki et al. |
| 2004/0097547 | A1 | 5/2004 | Taveras et al. |
| 2004/0106794 | A1 | 6/2004 | Taveras et al. |
| 2008/0262096 | A1 | 10/2008 | Mederski et al. |
| 2009/0053169 | A1 | 2/2009 | Castillo et al. |
| 2014/0296254 | A1 | 10/2014 | Musicki et al. |
| 2014/0309208 | A1 | 10/2014 | Musicki et al. |
| 2015/0175547 | A1 | 6/2015 | Dairaghi et al. |
| 2015/0212088 | A1 | 7/2015 | Zou et al. |
| 2015/0374708 | A1 | 12/2015 | Musicki et al. |
| 2017/0144996 | A1 | 5/2017 | Chen et al. |
| 2017/0144997 | A1 | 5/2017 | Chen et al. |

FOREIGN PATENT DOCUMENTS

| | | | | |
|---|---|---|---|---|
| WO | 02083624 | A1 | 10/2002 | |
| WO | 02079122 | | 11/2002 | |
| WO | WO0210137 | | 2/2003 | |
| WO | 2004011418 | | 2/2004 | |
| WO | 2009064431 | | 5/2009 | |
| WO | 2009065077 | | 5/2009 | |
| WO | 2009090414 | | 7/2009 | |
| WO | 2009093026 | | 7/2009 | |
| WO | 2009093029 | | 7/2009 | |
| WO | 2009106073 | | 9/2009 | |
| WO | 2010063802 | | 6/2010 | |
| WO | WO2012001076 | | 1/2012 | |
| WO | 2012047630 | | 4/2012 | |
| WO | WO-2012080457 | A1 * | 6/2012 | ........... C07D 413/12 |
| WO | 2013061004 | | 5/2013 | |
| WO | 2013061005 | | 5/2013 | |
| WO | 2015084842 | | 6/2015 | |

OTHER PUBLICATIONS

Phosphonate. (n.d.). In Wikipedia. Retrieved Jun. 9, 2020, from https://en.wikipedia.org/wiki/Phosphonate.*

Ai, L. et al., Molecular Characterization of CCR6: Involvement of Multiple Domains in Ligand Binding and Receptor Signaling, J. Biomed. Sci., 2004, 818-828, 11.

Berge, Stephen M., Pharmaceutical Salts, Journal of Pharmaceutical Sciences, Jan. 1977, 1-19, 66 (1), US.

Bettelli, E., Building Different Mouse Models for Human MS, Ann. N.Y. Acad. Sci., 2007, 11-18, 1103.

Butera, J.A., et al., Design and SAR of Novel Potassium Channel Openers Targeted for Urge Urinary Incontinence. 1. N-Cyanoguanidine Bioisosteres Possessing in Vivo Bladder Selectivity, J. Med. Chem., 2000, 1187-1208, 43.

Carramolino, L. et al., Down-regulation of the β-chemokine receptor CCR6 in dendritic cells mediated by TNF-α and IL-4, Journal of Leukocyte Biology, 1999, 837-844, 66(5).

Chu, X. et al., A genome-wide association study identifies two new risk loci for Graves' disease, Nature Genetics, 2011, 897-903, 43(9).

Comerford, I. et al., An immune paradox: How can the same chemokine axis regulate both immune tolerance and activation?, Bioessays, 2010, 1067-1076, 32.

Cravens, P. et al., Dendritic cells, chemokine receptors and autoimmune inflammatory, Immunology and Cell Biology 2002, 497-505, 80.

Dieu-Nosjean, M.C. et al., Regulation of dendritic cell trafficking: a process that involves, J. Leukoc. Biol., 1999, 252-262, 66.

Dohlman, T. et al., The CCR6/CCL20 Axis Mediates Th17 Cell Migration to the Ocular Surface in Dry Eye Disease, IOVS, 2013, 4081-4091, 54(6).

Gerard, C. et al., Chemokines and disease, Chemokine Reviews, 2001, 108-117, 2 (2).

Guo, H. et al., The role of lymphocytes in the development and treatment of alopecia areata, Expert Rev. Clin. Immunol., 2015, 1335-1351, 11 (12).

Ha, H., et al., Discovery of Novel CXCR2 Inhibitors Using Ligand-Based Pharmacophore Models, J. Chem. Inf. Model., 2015, 1720-1738, 55.

Hedrick, M.N. et al., CCR6 as a possible therapeutic target in psoriasis, Expert Opinion on Therapeutic Targets, 2010, 911-922, 14 (9).

Hieshima, K. et al., Molecular cloning of a novel human CC chemokine liver and activation-regulated chemokine (LARC) expressed in liver, The Journal of Biological Chemistry, 1997, 5846-5853, 272 (9) (LARC).

Homey, B. et al., Up-Regulation of Macrophage Inflammatory Protein-3α/CCL20 and CC Chemokine Receptor 6 in Psoriasis, The Journal of Immunology, 2000, 6622-6632, 164.

Hromas, R. et al., Cloning and Characterization of Exodus, a Novel b-Chemokine, Blood, 1997, 3315-3322, 89 (9).

Ito, T. et al., CCR6 as a mediator of immunity in the lung and gut, Experimental Cell Reseach, 2011, 613-619, 317 (5).

Jin, J. et al., Systemic Sclerosis is a Complex Disease Associted Mainly with Immune Regulatory and Inflammatory Genes, The Open Rheumatology Journal, 2014, 29-42, 8.

Kacther, K. et al., MIP-3α neutralizing monoclonal antibody protects against TNBS-induced colonic injury and inflammation in mice, Am. J. Physiol. Gastrointest. Liver Physiol., 2007, G1263-G1271, 292.

Kagami, S. et al., Circulating Th17, Th22, and Th1 Cells Are Increased in Psoriasis, Journal of Investigative Dermatology, 2010, 1373-1383, 130.

Katsifis, G.E. et al., Systemic and Local Interleukin-17 and Linked Cytokines Associated with Sjoegren's Syndrome Immunopathogenesis, The American Journal of Pathology, 2009, 1167-1177, 175 (3).

Le Baorgne, M. et al., Dendritic Cells Rapidly Recruited into Epithelial Tissues via CCR6/CCL20 Are Responsible for CD8+ T Cell Crosspriming In Vivo, Imuunity, 2006, 191-201, 24.

Liston, A. et al., Inhibition of CCR6 Function Reduces the Severity of Experimental Autoimmune Encephalomyelitis via Effects on the Priming Phase of the Immune Response, The Journal of Immunology, 2009, 3121-3130, 182.

Mabuchi, T. et al., CCR6 Is Required for Epidermal Trafficking of cd-T Cells in an IL-23-Induced Model of Psoriasiform Dermatitis, J. Investigative Dermatology, 2013, 164-171, 133.

McCleland, B.W., et al., Comparison of N,N0-diarylsquaramides and N,N0-diarylureas as antagonists of the CXCR2 chemokine receptor, Bioorganic & Medicinal Chemistry Letters, 2007, 1713-1717, 17.

Paradis, T.J. et al., Essential Role of CCR6 in Directing Activated T Cells to the Skin during Contact Hypersensitivity, Journal of Investigative Dermatology, 2007, 628-633, 128.

Paulissen, S. et al., The role and modulation of CCR6+ Th17 cell populations in rheumatoid arthritis, Cytokine, 2015, 43-53, 74.

Quan, C. et al., Genome-wide association study for vitiligo identifies susceptibilty loci at 6q27 and the MHC, Nature Genetics, 2010, 614-620, 42(7).

Reboldi, A. et al., C-C chemokine receptor 6-regulated entry of TH-17 cells into the CNS through the choroid plexus is required for the initiation of EAE, Nature Immunology, 2009, 514-523, 10 95).

Schutyser, E., et al., The CC chemokine CCL20 and its receptor CCR6, Cytokine & Growth Factor Review, 2003, 409-426, 14.

Stahl, E. et al., Genome-wide association study meta-analysis identifies seven new rheumatoid arthritis risk loci, Nature Genetics, 2010, 508-517, 42 (6).

Stahl, Heinrich et al, Handbook of Pharmaceutical Salts, Verlag Helvetica Chimica Acta—Zurich, 2002, 329-345.

Varona, R. et al., CCR6 has a non-redundant role in the development of inflammatory bowel disease, Eur. J. Immunol., 2003, 2937-2946, 33.

Varona, R. et al., CCR6 regulates CD4 T-cell-mediated acute graft-versus-host disease responses, Blood, 2005, 18-27, 106 (1).

Wallace, Graham et al, The Role of Chemokines and Their Receptors in Ocular Disease, Progress in Retinal and Eye Research, 2004, 435-448, 23, Elsevier Ltd.

Weisberg, Stuart et al, CCR2 Modulates Inflammatory and Metabolic Effects of High-Fat Feeding, The Journal of Clinical Investigation, Jan. 2006, 115-124, 116.

(56) References Cited

OTHER PUBLICATIONS

White, G. et al., CC Chemokine Receptors and Chronic, Pharmacol. Rev., 2013, 47-89, 65.

Yamazaki, T. et al., CCR6 Regulates the Migration of Inflammatory and Regulatory T Cells, The Journal of Immunology, 2008, 8391-8401, 181.

Gunda, S.K., Et Al., Structural investigations of CXCR2 receptor antagonists by CoMFA,CoMISA and flexible docking studies, Acta Pharm., 2012, 287-304, 62.

PCT International Search Report & Written Opinion dated Oct. 31, 2018 for PCT Application No. PCT/US2018/046532, filed Aug. 13, 2018, in the name of Allegan, Inc.

* cited by examiner

3,4-DISUBSTITUTED 3-CYCLOBUTENE-1,2-DIONES AND USE THEREOF

CROSS-REFERENCE TO RELATED APPLICATIONS

This application claims the benefit of U.S. Provisional Application 62/545,331, filed on Aug. 14, 2017, which is herein incorporated by reference in its entirety and serves as the basis for a priority and/or benefit claim for the present application.

TECHNICAL FIELD

The subject matter described herein relates to CCR6 antagonist compounds, and in particular 3,4-disubstituted 3-cyclobutene-1,2-diones, which in some embodiments are useful for treating a variety of diseases responsive to inhibition of CCR6 receptor, including inflammatory skin diseases, autoimmune diseases and ocular inflammatory diseases, such as psoriasis, rheumatoid arthritis, multiple sclerosis, Sjogren's disease, GvHD, alopecia areata, uveitis, dry eye, diabetic retinopathy and allergic diseases.

BACKGROUND

Chemokines are a group of 7- to 14-kDa peptides that play an important role in orchestrating leukocyte recruitment and migration in physiological as well as pathological conditions including inflammation, autoimmunity, tumor growth and metastasis (See Schuyster et. al, The CC chemokine CCL20 and its receptor CCR6, *Cytokine & Growth Factor,* 14, pp. 409-426, 2003). Chemokines represent an important target for anti-inflammatory therapies by binding to seven-transmembrane, G protein-coupled receptors, the chemokine receptors (See White et al., CC chemokine receptors and chronic inflammation-Therapeutic opportunities and pharmacological challenges, *Pharmacol Rev,* 65, pp. 108-115, 2013). The chemokine system is complex, with about 50 chemokines and 20 chemokine receptors identified in humans, often acting with redundancy (See Gerard et al, Chemokines and disease, *Nature Immunology,* 2, pp. 108-115, 2001). In contrast, the only known ligand for chemokine receptor CCR6 is the chemokine CCL20 (MIP3a/Exodus-1/LARC) and is referred to as the CCL20-CCR6 axis (See Hieshima et. al, Molecular cloning of a novel human CC chemokine liver and activation-regulated chemokine (LARC) expressed in liver, *The journal of Biological Chemistry,* 272, pp. 5846-5853, 1997; Hromas et. al, Cloning and characterization of exodus, a novel β-chemokine, *Blood,* 89, pp 3315-3322, 1997; Ai et. al., Molecular characterization of CCR6: Involvement of multiple domains in ligand binding and receptor signaling, *J Biomed Sci.* 11:818-828, 2004).

Chemokine receptor CCR6 is expressed by pro-inflammatory Th17 CD4+ T cells, γδT cells, Regulatory T-cells, B-cells, Natural Killer T cells, and dendritic cells (See Dieu-Nosjean et. al., Regulation of dendritic cell trafficking: a process that involves the participation of selective chemokines, *J. of Leukocyte Biol.* 66:252-262, 1999; Cravens et al., Dendritic cells, chemokine receptors and autoimmune inflammatory diseases, *Immunology and Cell Biology,* 80:497-505, 2002; Yamazaki et. al., CCR6 regulates the migration of inflammatory and regulatory T cells; *J. Immunology,* 181, pp. 8391-8401, 2008; Comerford et. al., An immune paradox: how can the same chemokine axis regulate both immune tolerance and activation? CCR6/CCL20: a chemokine axis balancing immunological tolerance and inflammation in autoimmune diseases; *Bioassays,* 32(12): 1067-1072, 2010). Genetic knockout strategies have confirmed the importance of chemokines, including CCL20, as regulators of immune function. Selectivity is crucial for use of chemokine receptor antagonists in systemic diseases where a single chemokine-receptor system is implicated. For example, in atherosclerosis, the macrophage/monocyte system is the major player to allow a subtle and specific control over immune function (See Weisberg et al., CCR2 modulates inflammatory and metabolic effects in high-fat feeding; *J. Clinical Investigation,* 116 (1): 115-124, 2006).

IL-17 producing Th17 CD4+T cells and γδT cells are implicated in the development of various inflammatory diseases including allergic pulmonary inflammation, psoriasis, contact hypersensitivity, inflammatory bowel disease, Sjogren's syndrome, GvHD, juvenile idiopathic arthritis, rheumatoid arthritis, and multiple sclerosis (See Varona et. al., CCR6 regulates CD4+ T-cell mediated acute graft-versus-host disease responses, *Blood,* 106: 18-26, 2005; Bettelli, Building different mouse models for human MS, *Ann NY Acad Sci.,* 1103:11-82007; Paradis et. al., Essential role of CCR6 in directing activated T cells to the skin during contact hypersensitivity; *J of Invest Dermat.,* 128: 628-633, 2007; Reboldi et. al., C—C chemokine receptor 6-regulated entry of Th17 cells into the CNS through the choroid plexus is required for the initiation of EAE, *Nature Immunology,* 10: 514-523, 2008; Katsifis et. al., Systemic and local IL-17 and linked cytokines associated with Sjogren's syndrome immunopathogenesis, *The American J of Pathology,* 175: 1167-117 2009; Hedrick et. al., CCR6 as a possible therapeutic target in psoriasis, *Expert Opin. Ther. Targets,* 14(9): 911-9222010; Ito et. al., CCR6 as a mediator of immunity in the lung and gut, *Exp. Cell Res.,* 317 (5): 613-6192011; Paulissen et. al., The role and modulation of CCR6+Th17 cell populations in rheumatoid arthritis; *Cytokine,* 74: 43-53, 2015). In alopecia areata lesions, Th17 CD4+ cells have been found around the hair follicles in the dermis (See Guo et. al., The role of lymphocytes in the development and treatment of alopecia areata, *Expert Rev. Clin. Immunol.,* 11(12): 1335-1351, 2015). CCR6 is involved in regulating Th17 CD4+ cell entry to the central nervous system in experimental autoimmune encephalomyelitis, in mouse model of multiple sclerosis (See Liston et. al., Inhibition of CCR6 function reduces the severity of experimental autoimmune encephalomyelitis via effects on the priming phase of the immune response; *J. Immunol.,* 182: 3121-3130, 2009).

Psoriasis is a chronic autoimmune skin disorder with dysregulation of innate and adaptive immune systems and increased expression of CCL20-CCR6 in psoriatic lesions compared to normal/non-lesional donor skin (See Homey et. al., Up-regulation of macrophage inflammatory protein-3a/CCL20 and CC chemokine receptor 6 in psoriasis; *J. Immunol.,* 164:6621-6632, 2000; Kagami et. al., Circulating Th17, Th22, and Th1 cells are increased in psoriasis; *J. Invest. Dermatol,* 130 (5): 1373-1383, 2010; Mabuchi et. al., CCR6 is required for epidermal trafficking of gd T cells in an IL-23 induced model of psoriasiform dermatitis, *J. Invest. Dermatol,* 133(1): 164-171, 2013). Mice lacking CCR6 fail to develop psoriasis-like phenotype and histopathology after injecting ears with IL-23 (See Hedrick et. al., CCR6 as a possible therapeutic target in psoriasis; *Expert Opin. Ther. Targets,* 14(9): 911-922, 2010). Similarly, mice lacking CCR6 or with use of CCL20 neutralizing antibodies show less severe intestinal pathology in the colitis models (See Varona et. al., CCR6 has a non-redundant role in the development of irritable bowel disease, *Eur J. Immunol.*, 33: 2937-29462003; Katchar et. al., MIP3a neutralizing monoclonal antibody protects against TNBS-induced colonic injury and inflammation in mice, *Am. J. Physiol. Gastrointest Liver Physiol.*, 292: G1263-G1271, 2007).

Many ocular conditions are characterized by inappropriate migration and infiltration of cells such as leukocytes and endothelial cells into the eye with deleterious effects to ocular structures (See Wallace et al., The role of chemokines and their receptors in ocular disease, *Progress in retinal and Eye Res.*, 23: 435-448, 2004). Chemokines have been identified in such diseases and misregulation of the chemokine system is apparent in corneal graft rejection, diabetic retinopathy, chronic inflammatory diseases such as uveitis, keratitis, dry eye, etc. For example, CCL20 neutralizing antibodies block the migration of CCR6 expressing Th17 cells in dry eye disease mouse model (See Dohlman et. al, The CCR6/CCL20 axis mediates Th17 cell migration to the ocular surface in dry eye disease, *Immunol and Microbiol.*, *IOVS*, 54: 4081-4091, 2013) and increased expression of CCR6 receptors in experimental autoimmune uveitis (See Wallace et. al., The role of chemokines and their receptors in ocular disease; *Progress in Retinal and Eye Res.*, 23: 435-448, 2004).

CCR6 is also expressed on immature dendritic cells and are recruited to inflamed mucosal tissue by CCL20. Dendritic cells undergo maturation and traffic to lymph nodes for T cell activation (See Carramolino et. al., Down-regulation of the b-chemokine receptor CCR6 in dendritic cells mediated by TNFa and IL-4, *J. of Leukocyte Binding*, 66:837-844, 1999; Le Borgne et. al., Dendritic cells rapidly recruited into epithelial tissues via CCR6/CCL20 are responsible for CD8+ T cell crosspriming in vivo, *Immunity*, 24: 191-201, 2006).

Genome wide association studies have identified genetic polymorphisms in CCR6 correlating to increased risk for rheumatoid arthritis, systemic sclerosis, Graves' disease and generalized vitiligo (See Stahl et. al, Genome-wide association study meta-analysis identifies seven new rheumatoid arthritis risk loci, *Nat. Genet*, 42(6): 508-514, 2010; Quan et. al.; Genome wide association study for vitiligo identifies susceptibility loci 6q27 and the MHC, *Nat. Genet*, 42(7): 614-619, 2010; Chu et. al., A genome-wide association study identifies two new risk loci for Graves' disease, *Nat. Genet*, 3: 897-902, 2011; Jin et. al., Systemic sclerosis is a complex disease associated mainly with immune regulatory and inflammatory genes, *The Open Rheumatology J.*, 8:29-42, 2014). Individuals with CCR6 polymorphisms have higher circulating IL-17 antibodies in rheumatoid arthritis patients and increased levels of auto antibodies in systemic sclerosis.

Given the evidence for CCR6 expression in multiple immune cells and the role of CCL20-CCR6 axis in several inflammatory diseases and with these results, small and large molecule CCR6 inhibitors should be useful in the local and systemic treatments of inflammatory skin diseases, autoimmune diseases and ocular inflammatory diseases including, but not limited to, psoriasis, rheumatoid arthritis, multiple sclerosis, Sjogren's disease, GvHD, alopecia areata, uveitis, dry eye, diabetic retinopathy and allergic diseases. CCR6 inhibition by small molecule pharmacophores therefore represents a novel therapeutic approach in treating multiple inflammatory diseases.

BRIEF SUMMARY

In one aspect, the present specification relates to a compound of Formula I or a pharmaceutically acceptable salt thereof, including an enantiomer, a diastereoisomer, a tautomer thereof:

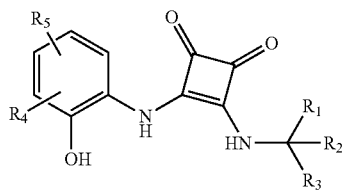

Formula I wherein
R$_1$ is selected from
  i) 6 to 12 membered aryl optionally substituted with at least one group selected from C$_{1-6}$ alkyl, C$_{2-6}$ alkoxyalkyl, C$_{2-6}$ alkenyl, —NR$_6$R$_7$, C$_{1-6}$ alkyl-C(O)O—, —C(O)O—C$_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) 3 to 11 membered cycloalkyl optionally substituted with at least one group selected from C$_{1-6}$ alkyl, C$_{2-6}$ alkoxyalkyl, C$_{2-6}$ alkenyl, —NR$_6$R$_7$, C$_{1-6}$ alkyl-C(O)O—, —C(O)O—C$_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) 4 to 12 membered heterocyclyl optionally substituted with at least one group selected from C$_{1-6}$ alkyl, C$_{2-6}$ alkoxyalkyl, C$_{2-6}$ alkenyl, —NR$_6$R$_7$, C$_{1-6}$ alkyl-C(O)O—, —C(O)O—C$_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iv) 5 to 12 membered heteroaryl optionally with at least one group selected from C$_{1-6}$ alkyl, C$_{2-6}$ alkoxyalkyl, C$_{2-6}$ alkenyl, —NR$_6$R$_7$, C$_{1-6}$ alkyl-C(O)O—, —C(O)O—C$_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  v) tri-C$_{1-5}$ alkylsilyl, and vi) $C_{1-10}$ alkyl optionally substituted with at least one group selected from $OR_6$, 6 to 12 membered aryl, 3 to 11 membered cycloalkyl, $-CO_2R_6$, $-C(O)NR_6R_7$, halo, 5 to 12 membered heteroaryl, 4 to 12 membered heterocyclyl, $C_{2-5}$ alkenyl, and $C_{2-5}$ alkynyl;

$R_2$ is selected from hydrogen, $C_{1-5}$ alkyl, $C_{2-5}$ alkenyl, and $C_{2-5}$ alkynyl;

or $R_1$ and $R_2$ together with the carbon to which they are attached form
  i) a 6 to 12 membered aryl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) a 3 to 11 membered cycloalkyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) a 5 to 12 membered heteroaryl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, $CD_3$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or
  iv) a 4 to 12 membered heterocyclyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
provided that $R_3$ is absent when the carbon to which $R_1$ and $R_2$ are attached is part of an aromatic or double bond;

$R_3$ is selected from
  i) hydrogen, deuterium, $-CO_2R_6$, $-NR_6R_7$, $-C(O)NR_6R_7$, $-OR_6$, $CD_2CD_3$, halo, $C_{2-5}$ alkenyl, $C_{2-5}$ alkynyl, sulfonate, phosphonate,
  ii) 6 to 12 membered aryl optionally substituted with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) 3 to 11 membered cycloalkyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iv) 4 to 12 membered heterocyclyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  v) 5 to 12 membered heteroaryl optionally substituted with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and
  vi) $C_{1-5}$ alkyl optionally substituted with at least one group selected from $OR_6$, 6 to 12 membered aryl, 3 to 11 membered cycloalkyl, $-CO_2R_6$, $-C(O)NR_6R_7$, halo, 5 to 12 membered heteroaryl, 4 to 12 membered heterocyclyl, $-Si(C_{1-6}$ alkyl), $C_{2-5}$ alkenyl, and $C_{2-5}$ alkynyl;

$R_4$ is selected from $-CO_2R_6$, $-C(O)NR_6R_7$, $-NR_6C(O)R_7$, $-NR_6CO_2RT$, $-NR_6C(O)NR_6R_7$, $-NR_7SO_2R_6$, $-NR_7SO_2NR_6R_7$, $C_{1-6}$ hydroxyalkyl, $C_{1-6}$ haloalkyl, halo, CN, $-SO_2NR_6R_7$, and $-SO_2R_6$;

$R_5$ is selected from hydrogen, $C_{1-6}$ alkyl, $-OR_6$, halo, $-NR_6R_7$, CN, $C_{1-6}$ haloalkyl, and $-NO_2$;

$R_6$ and $R_7$ are independently selected from
i) hydrogen,
ii) $C_{1-6}$ alkyl, $C_{1-6}$ haloalkyl, $C_{1-6}$ hydroxyalkyl, $C_{2-6}$ alkoxyalkyl, aralkyl, $CD_3$,
iii) $C_{2-5}$ alkenyl, $C_{2-5}$ alkynyl,
iv) 6 to 12 membered aryl optionally substituted with at least one group selected from W,
v) 3 to 11 membered cycloalkyl optionally substituted with at least one group selected from W,
vi) 5 to 12 membered heteroaryl optionally substituted with at least one group selected from W, and
vii) 4 to 12 membered heterocyclyl optionally substituted with at least one group selected from W,
or $R_6$ and $R_7$ together with the nitrogen to which they are attached form a 4 to 12 membered heterocyclyl optionally substituted with at least one group selected from W;
W is selected from $C_{1-6}$ alkyl, $C_{2-5}$ alkenyl, $C_{2-5}$ alkynyl, halo, $C_{1-6}$ alkoxy, and hydroxyl.

In another aspect, the present specification relates to a compound of Formula I or a pharmaceutically acceptable salt thereof, including an enantiomer, a diastereoisomer, a tautomer thereof:

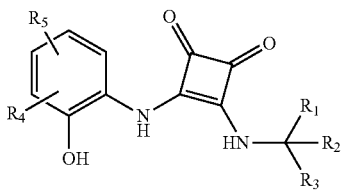

Formula I wherein
$R_1$ is selected from
i) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
ii) 3 to 11 membered cycloalkyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iii) 4 to 12 membered heterocyclyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iv) 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
v) tri-$C_{1-5}$ alkylsilyl, and
vi) $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl;
$R_2$ is selected from hydrogen, $C_{1-5}$ alkyl, $C_{2-5}$ alkenyl, and $C_{2-5}$ alkynyl;
or $R_1$ and $R_2$ together with the carbon to which they are attached form
i) a 6 to 12 membered aryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
ii) a 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iii) a 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, $CD_3$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or iv) a 4 to 12 membered heterocyclyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, provided that $R_3$ is absent when the carbon to which $R_1$ and $R_2$ are attached is part of an aromatic or double bond;

$R_3$ is selected from i) hydrogen, deuterium, $-CO_2R_6$, $-NR_6R_7$, $-C(O)NR_6R_7$, $-OR_6$, $CD_2CD_3$, halo, $C_{2-5}$ alkenyl, $C_{2-5}$ alkynyl, sulfonate, phosphonate, ii) 6 to 12 membered aryl optionally substituted with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, iii) 3 to 11 membered cycloalkyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, iv) 4 to 12 membered heterocyclyl optionally with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, v) 5 to 12 membered heteroaryl optionally substituted with at least one group selected from $C_{1-6}$ alkyl, $C_{2-6}$ alkoxyalkyl, $C_{2-6}$ alkenyl, $-NR_6R_7$, $C_{1-6}$ alkyl-C(O)O—, $-C(O)O-C_{1-6}$ alkyl, $C(O)NR_6R_7$, $-NR_6C(O)R_7$, halo, $OR_6$, $R_6S(O)_2O-$ (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and vi) $C_{1-5}$ alkyl optionally substituted with at least one group selected from $OR_6$, 6 to 12 membered aryl, 3 to 11 membered cycloalkyl, $-CO_2R_6$, $-C(O)NR_6R_7$, halo, 5 to 12 membered heteroaryl, 4 to 12 membered heterocyclyl, $-Si(C_{1-6}$ alkyl), $C_{2-5}$ alkenyl, and $C_{2-5}$ alkynyl;

$R_4$ is selected from $-CO_2R_6$, $-C(O)NR_6R_7$, $-NR_6C(O)R_7$, $-NR_6CO_2RT$, $-NR_6C(O)NR_6R_7$, $-NR_7SO_2R_6$, $-NR_7SO_2NR_6R_7$, $C_{1-6}$ hydroxyalkyl, $C_{1-6}$ haloalkyl, halo, CN, $-SO_2NR_6R_7$, and $-SO_2R_6$;

$R_5$ is selected from hydrogen, $C_{1-6}$ alkyl, $-OR_6$, halo, $-NR_6R_7$, CN, $C_{1-6}$ haloalkyl, and $-NO_2$;

$R_6$ and $R_7$ are independently selected from i) hydrogen, ii) $C_{1-6}$ alkyl, $C_{1-6}$ haloalkyl, $C_{1-6}$ hydroxyalkyl, $C_{2-6}$ alkoxyalkyl, aralkyl, $CD_3$, iii) $C_{2-5}$ alkenyl, $C_{2-5}$ alkynyl, iv) 6 to 12 membered aryl optionally substituted with at least one group selected from W, v) 3 to 11 membered cycloalkyl optionally substituted with at least one group selected from W, vi) 5 to 12 membered heteroaryl optionally substituted with at least one group selected from W, and vii) 4 to 12 membered heterocyclyl optionally substituted with at least one group selected from W, or $R_6$ and $R_7$ together with the nitrogen to which they are attached form a 4 to 12 membered heterocyclyl optionally substituted with at least one group selected from W;

W is selected from $C_{1-6}$ alkyl, $C_{2-5}$ alkenyl, $C_{2-5}$ alkynyl, halo, $C_{1-6}$ alkoxy, and hydroxyl; with the provisos:

a) that when $R_1$ is 6 to 12 membered aryl optionally substituted as described above or 5 to 12 membered heteroaryl optionally substituted as described above, $R_3$ is not a 4 or 5 membered heterocyclyl optionally substituted as described above, and that when $R_3$ is 6 to 12 membered aryl optionally substituted as described above or 5 to 12 membered heteroaryl optionally substituted as described above, $R_1$ is not a 4 or 5 membered heterocyclyl optionally substituted as described above;

b) that when any of $R_1$, $R_2$, or $R_3$ are $C_{1-5}$ alkyl or $C_{1-10}$ alkyl, and $R_4$ is $-SO_2NR_6R_7$, $R_5$ is not hydrogen;

c) that when either $R_1$ or $R_3$ is 4 or 5 membered heterocyclyl optionally substituted as described above, $R_2$ is not $C_{1-10}$ alkyl;

d) that when either $R_1$ or $R_3$ is 5 to 12 membered heteroaryl optionally substituted as described above, and $R_4$ is $-SO_2NR_6R_7$, then neither $R_6$ or $R_7$ in the $-SO_2NR_6R_7$ is hydrogen or 5 to 12 membered heteroaryl optionally substituted as described above;

e) that when $R_1$ and $R_2$ together with the carbon to which they are attached form a 6 to 12 membered aryl optionally substituted as described above, and $R_4$ is $-SO_2NR_6R_7$, $R_5$ is not $C_{1-6}$ alkyl or CN and both $R_6$ and $R_7$ in the $-SO_2NR_6R_7$ are $C_{1-6}$ alkyl; and f) that when $R_1$ and $R_2$ together with the carbon to which they are attached form a 4 to 12 membered heterocyclyl optionally substituted as described above, $R_3$ is not hydrogen.

In another aspect, the present specification relates to a composition comprising a compound of Formula I or a salt thereof. In some embodiments of this aspect, the composition is a pharmaceutical composition comprising a compound of Formula I or a pharmaceutically acceptable salt thereof, and a pharmaceutically acceptable carrier. In some embodiments of this aspect, the composition is a pharmaceutical composition comprising a therapeutically effective amount of a compound of Formula I or a pharmaceutically acceptable salt thereof, and a pharmaceutically acceptable carrier.

In another aspect, the present specification relates to a method of treating an individual suffering from a disease treatable by inhibition of CCR6 receptor function, comprising administering to the individual a pharmaceutical composition comprising a therapeutically effective amount of a compound of Formula I or a pharmaceutically acceptable salt thereof, wherein such administration reduces or eliminates a symptom associated with the disease.

Some non-limiting example embodiments are listed below.

Example Embodiment 1

A compound of Formula I or a pharmaceutically acceptable salt thereof, including an enantiomer, a diastereoisomer, a tautomer thereof:

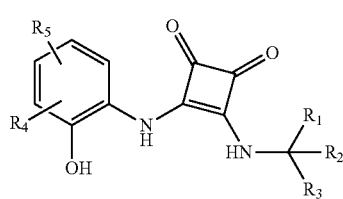

Formula I wherein
$R_1$ is selected from
  i) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) 3 to 11 membered cycloalkyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) 4 to 12 membered heterocyclyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iv) 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  v) tri-$C_{1-5}$ alkylsilyl, and
  vi) $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl;

$R_2$ is selected from hydrogen, $C_{1-5}$ alkyl, $C_{2-5}$ alkenyl, and $C_{2-5}$ alkynyl;
or $R_1$ and $R_2$ together with the carbon to which they are attached form
  i) a 6 to 12 membered aryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) a 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, iii) a 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, $CD_3$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or iv) a 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, provided that $R_3$ is absent when the carbon to which $R_1$ and $R_2$ are attached is part of an aromatic or double bond;

$R_3$ is selected from
  i) hydrogen, deuterium, —$CO_2R_6$, —$NR_6R_7$, —C(O)$NR_6R_7$, —$OR_6$, $CD_2CD_3$, halo, $C_{2-5}$ alkenyl, $C_{2-5}$ alkynyl, sulfonate, phosphonate,
  ii) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iv) 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  v) 5 to 12 membered heteroaryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and
  vi) $C_{1-5}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, —Si($C_{1-6}$ alkyl), $C_{2-5}$ alkenyl, and $C_{2-5}$ alkynyl;

$R_4$ is selected from —$CO_2R_6$, —C(O)$NR_6R_7$, —$NR_6$C(O)$R_7$, —$NR_6CO_2RT$, —$NR_6$C(O)$NR_6R_7$, —$NR_7SO_2R_6$, —$NR_7SO_2NR_6R_7$, $C_{1-6}$ hydroxyalkyl, $C_{1-6}$ haloalkyl, halo, CN, —$SO_2NR_6R_7$, and —$SO_2R_6$;

$R_5$ is selected from hydrogen, $C_{1-6}$ alkyl, —$OR_6$, halo, —$NR_6R_7$, CN, $C_{1-6}$ haloalkyl, and —$NO_2$;

$R_6$ and $R_7$ are independently selected from
  i) hydrogen,
  ii) $C_{1-6}$ alkyl, $C_{1-6}$ haloalkyl, $C_{1-6}$ hydroxyalkyl, $C_{2-6}$ alkoxyalkyl, aralkyl, $CD_3$,
  iii) $C_{2-5}$ alkenyl, $C_{2-5}$ alkynyl,
  iv) 6 to 12 membered aryl optionally substituted with at least one group selected from W,
  v) 3 to 11 membered cycloalkyl optionally substituted with at least one group selected from W,
  vi) 5 to 12 membered heteroaryl optionally substituted with at least one group selected from W, and
  vii) 4 to 12 membered heterocyclyl optionally substituted with at least one group selected from W, or $R_6$ and $R_7$ together with the nitrogen to which they are attached form a 4 to 12 membered heterocyclyl optionally substituted with at least one group selected from W;

W is selected from $C_{1-6}$ alkyl, $C_{2-5}$ alkenyl, $C_{2-5}$ alkynyl, halo, $C_{1-6}$ alkoxy, and hydroxyl; with the provisos:

a) that when $R_1$ is 6 to 12 membered aryl optionally substituted as described above or 5 to 12 membered heteroaryl optionally substituted as described above, $R_3$ is not a 4 or 5 membered heterocyclyl optionally substituted as described above, and that when $R_3$ is 6 to 12 membered aryl optionally substituted as described above or 5 to 12 membered heteroaryl optionally substituted as described above, $R_1$ is not a 4 or 5 membered heterocyclyl optionally substituted as described above;

b) that when any of $R_1$, $R_2$, or $R_3$ are $C_{1-5}$ alkyl or $C_{1-10}$ alkyl, and $R_4$ is —$SO_2NR_6R_7$, $R_5$ is not hydrogen;

c) that when either $R_1$ or $R_3$ is 4 or 5 membered heterocyclyl optionally substituted as described above, $R_2$ is not $C_{1-10}$ alkyl;

d) that when either $R_1$ or $R_3$ is 5 to 12 membered heteroaryl optionally substituted as described above, and $R_4$ is —$SO_2NR_6R_7$, then neither $R_6$ or $R_7$ in the —$SO_2NR_6R_7$ is hydrogen or 5 to 12 membered heteroaryl optionally substituted as described above;

e) that when $R_1$ and $R_2$ together with the carbon to which they are attached form a 6 to 12 membered aryl optionally substituted as described above, and $R_4$ is —$SO_2NR_6R_7$, $R_5$ is not $C_{1-6}$ alkyl or CN and both $R_6$ and $R_7$ in the —$SO_2NR_6R_7$ are $C_{1-6}$ alkyl; and f) that when $R_1$ and $R_2$ together with the carbon to which they are attached form a 4 to 12 membered heterocyclyl optionally substituted as described above, $R_3$ is not hydrogen.

Example Embodiment 2

The compound or a pharmaceutically acceptable salt thereof of example embodiment 1, wherein
$R_1$ is selected from
  i) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) 3 to 11 membered cycloalkyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) 4 to 12 membered heterocyclyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iv) 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  v) tri-$C_{1-5}$ alkylsilyl, and
  vi) $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl;

$R_2$ is selected from hydrogen, $C_{1-5}$ alkyl, $C_{2-5}$ alkenyl, and $C_{2-5}$ alkynyl;

$R_3$, $R_4$, $R_5$, $R_6$, $R_7$, and W are as defined in example embodiment 1;

with the provisos:
  a) that when $R_1$ is 6 to 12 membered aryl optionally substituted as described above or 5 to 12 membered heteroaryl optionally substituted as described above, $R_3$ is not a 4 or 5 membered heterocyclyl optionally substituted as described above, and that when $R_3$ is 6 to 12 membered aryl optionally substituted as described above or 5 to 12 membered heteroaryl optionally substituted as described above, $R_1$ is not a 4 or 5 membered heterocyclyl optionally substituted as described above;
  b) that when any of $R_1$, $R_2$, or $R_3$ are $C_{1-5}$ alkyl or $C_{1-10}$ alkyl, and $R_4$ is —$SO_2NR_6R_7$, $R_5$ is not hydrogen;
  c) that when either $R_1$ or $R_3$ is 4 or 5 membered heterocyclyl optionally substituted as described above, $R_2$ is not $C_{1-10}$ alkyl;
  d) that when either $R_1$ or $R_3$ is 5 to 12 membered heteroaryl optionally substituted as described above, and $R_4$ is —$SO_2NR_6R_7$, then neither $R_6$ or $R_7$ in the —$SO_2NR_6R_7$ is hydrogen or 5 to 12 membered heteroaryl optionally substituted as described above.

Example Embodiment 3

The compound or a pharmaceutically acceptable salt thereof of example embodiment 2, wherein $R_1$ is $C_{1-10}$ alkyl substituted with at least one group selected from $OR_6$ halo, —$CO_2R_6$, and 3 to 11 membered cycloalkyl, and wherein $R_2$, $R_3$, $R_4$, $R_5$, $R_6$, $R_7$, and W are as defined in example embodiment 2.

Example Embodiment 4

The compound or a pharmaceutically acceptable salt thereof of any one of example embodiments 2 or 3, wherein $R_2$ is hydrogen, and wherein $R_3$, $R_4$, $R_5$, $R_6$, and $R_7$, and W are as defined in example embodiment 2.

Example Embodiment 5

The compound or a pharmaceutically acceptable salt thereof of any one of example embodiments 2 to 4, wherein $R_3$ is 6 to 12 membered aryl or $C_{1-5}$ alkyl, and wherein $R_4$, $R_5$, $R_6$, and $R_7$, and W are as defined in example embodiment 2.

Example Embodiment 6

The compound or a pharmaceutically acceptable salt thereof of any one of example embodiments 2 to 5, wherein $R_6$ is hydrogen or $C_{1-6}$ alkyl.

Example Embodiment 7

The compound or a pharmaceutically acceptable salt thereof of example embodiment 6, wherein $R_6$ is hydrogen.

Example Embodiment 8

The compound or a pharmaceutically acceptable salt thereof of example embodiment 2, wherein $R_1$ is $C_{1-10}$ alkyl, and wherein $R_2$, $R_3$, $R_4$, $R_5$, $R_6$, $R_7$, and W are as defined in example embodiment 2.

Example Embodiment 9

The compound or a pharmaceutically acceptable salt thereof of example embodiment 8, wherein $R_2$ is hydrogen, and wherein $R_3$, $R_4$, $R_5$, $R_6$, $R_7$, and W are as defined in example embodiment 2.

Example Embodiment 10

The compound or a pharmaceutically acceptable salt thereof of any one of example embodiments 8 or 9, wherein $R_3$ is 6 to 12 membered aryl.

Example Embodiment 11

The compound or a pharmaceutically acceptable salt thereof of any one of example embodiments 8 or 9, wherein $R_3$ is 5 to 12 membered heteroaryl optionally substituted with at least one $C_{1-6}$ alkyl group.

Example Embodiment 12

The compound or a pharmaceutically acceptable salt thereof of any one of example embodiments 8 or 9, wherein $R_3$ is —C(O)NR$_6$R$_7$, and wherein $R_6$ and $R_7$ are independently selected from hydrogen, $C_{1-6}$ alkyl, and 3 to 11 membered cycloalkyl.

Example Embodiment 13

The compound or a pharmaceutically acceptable salt thereof of example embodiment 8, wherein $R_2$ is $C_{1-5}$ alkyl, and wherein $R_3$, $R_4$, $R_5$, $R_6$, $R_7$, and W are as defined in example embodiment 2.

Example Embodiment 14

The compound or a pharmaceutically acceptable salt thereof of any one of example embodiments 8 or 13, wherein $R_3$ is hydrogen, and wherein $R_4$, $R_5$, $R_6$, $R_7$, and W are as defined in example embodiment 2.

Example Embodiment 15

The compound or a pharmaceutically acceptable salt thereof of example embodiments 8 or 13, wherein $R_3$ is $C_{1-5}$ alkyl, and wherein $R_4$, $R_5$, $R_6$, $R_7$, and W are as defined in example embodiment 2.

Example Embodiment 16

The compound or a pharmaceutically acceptable salt thereof of example embodiments 8 or 13, wherein $R_3$ is 6 to 12 membered aryl, and wherein $R_4$, $R_5$, $R_6$, $R_7$, and W are as defined in example embodiment 2.

Example Embodiment 17

The compound or a pharmaceutically acceptable salt thereof of example embodiment 1, wherein
$R_1$ and $R_2$ together with the carbon to which they are attached form
  i) a 6 to 12 membered aryl optionally with at least one group selected from $C_{1-6}$ alkyl, $C_{2-6}$ alkoxyalkyl, $C_{2-6}$ alkenyl, —NR$_6$R$_7$, $C_{1-6}$ alkyl-C(O)O—, —C(O)O—$C_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) a 3 to 11 membered cycloalkyl optionally with at least one group selected from $C_{1-6}$ alkyl, $C_{2-6}$ alkoxyalkyl, $C_{2-6}$ alkenyl, —NR$_6$R$_7$, $C_{1-6}$ alkyl-C(O)O—, —C(O)O—$C_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) a 5 to 12 membered heteroaryl optionally with at least one group selected from $C_{1-6}$ alkyl, $C_{2-6}$ alkoxyalkyl, $C_{2-6}$ alkenyl, —NR$_6$R$_7$, $C_{1-6}$ alkyl-C(O)O—, —C(O)O—$C_{1-6}$ alkyl, C(O)NR$_6$R$_7$, —NR$_6$C(O)R$_7$, CD$_3$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or
  iv) a 4 to 12 membered heterocyclyl optionally with at least one group selected from $C_{1-6}$ alkyl, $C_{2-6}$ alkoxyalkyl, $C_{2-6}$ alkenyl, —NR$_6$R$_7$, $C_{1-6}$ alkyl-C(O)O—, —C(O)O—$C_{1-6}$ alkyl, C(O)NR$_6$R$_7$, —NR$_6$C(O)R$_7$, halo, OR$_6$, R$_6$S(O)$_2$O— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
provided that $R_3$ is absent when the carbon to which $R_1$ and $R_2$ are attached is part of an aromatic or double bond; and
$R_3$, $R_4$, $R_5$, $R_6$, $R_7$, and W are as defined in example embodiment 1; and
with the provisos:
  a) that when $R_1$ and $R_2$ together with the carbon to which they are attached form a 6 to 12 membered aryl optionally substituted as described above, and $R_4$ is —SO$_2$NR$_6$R$_7$, R$_5$ is not C$_{1-6}$ alkyl or CN and both R$_6$ and R$_7$ in the —SO$_2$NR$_6$R$_7$ are C$_{1-6}$ alkyl; and b) that when R$_1$ and R$_2$ together with the carbon to which they are attached form a 4 to 12 membered heterocyclyl optionally substituted as described above, R$_3$ is not hydrogen.

Example Embodiment 18

The compound or a pharmaceutically acceptable salt thereof of example embodiment 17, wherein R$_1$ and R$_2$ together with the carbon to which they are attached form a 6 to 12 membered aryl optionally substituted with at least one C$_{1-6}$ alkyl group, and wherein R$_2$, R$_3$, R$_4$, R$_5$, R$_6$, R$_7$, and W are as defined in example embodiment 17.

Example Embodiment 19

The compound or a pharmaceutically acceptable salt thereof of example embodiment 17, wherein R$_1$ and R$_2$ together with the carbon to which they are attached form a 5 to 12 membered heteroaryl optionally substituted with at least one C$_{1-6}$ alkyl group, and wherein R$_2$, R$_3$, R$_4$, R$_5$, R$_6$, R$_7$, and W are as defined in example embodiment 17.

Example Embodiment 20

The compound or a pharmaceutically acceptable salt thereof of example embodiment 17, wherein R$_1$ and R$_2$ together with the carbon to which they are attached form a 3 to 11 membered cycloalkyl optionally with at least one group selected from C$_{1-6}$ alkyl, and wherein R$_2$, R$_3$, R$_4$, R$_5$, R$_6$, R$_7$, and W are as defined in example embodiment 17.

Example Embodiment 21

The compound or a pharmaceutically acceptable salt thereof of any one of example embodiments 17 to 20, wherein R$_3$ is hydrogen, and wherein R$_4$, R$_5$, R$_6$, R$_7$, and W are as defined in example embodiment 17.

Example Embodiment 22

The compound or a pharmaceutically acceptable salt thereof of any one of example embodiments 17 to 20, wherein R$_3$ is selected from
i) C$_{1-5}$ alkyl, optionally substituted with at least one group selected from OR$_6$, C$_{2-5}$ alkenyl, and 6 to 12 membered aryl;
ii) 5 to 12 membered heteroaryl;
iii) 6 to 12 membered aryl optionally substituted with at least one group selected from C$_1$-6 alkyl, and halo;
iv) 3 to 11 membered cycloalkyl;
v) C$_{2-5}$ alkynyl;
and wherein R$_4$, R$_5$, R$_6$, R$_7$, and W are as defined in example embodiment 17.

Example Embodiment 23

The compound or a pharmaceutically acceptable salt thereof of example embodiment 1, wherein R$_1$ is selected from methyl, ethyl, isopropyl, tert-butyl, methoxymethyl, trifluoromethyl, cyclopropyl, cyclobutyl, cyclopentyl, cyclohexyl,

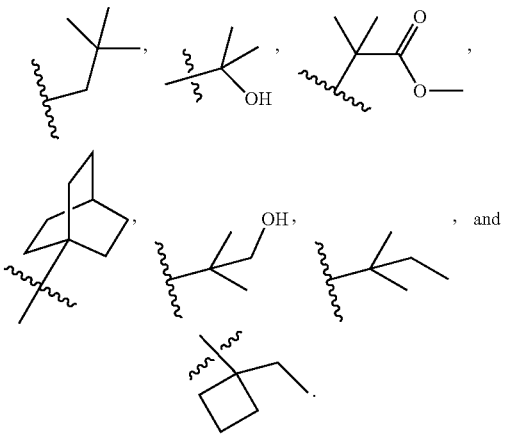

Example Embodiment 24

The compound or a pharmaceutically acceptable salt thereof of example embodiment 1 or example embodiment 17, wherein R$_1$ and R$_2$ together with the carbon to which they are attached form a ring selected from

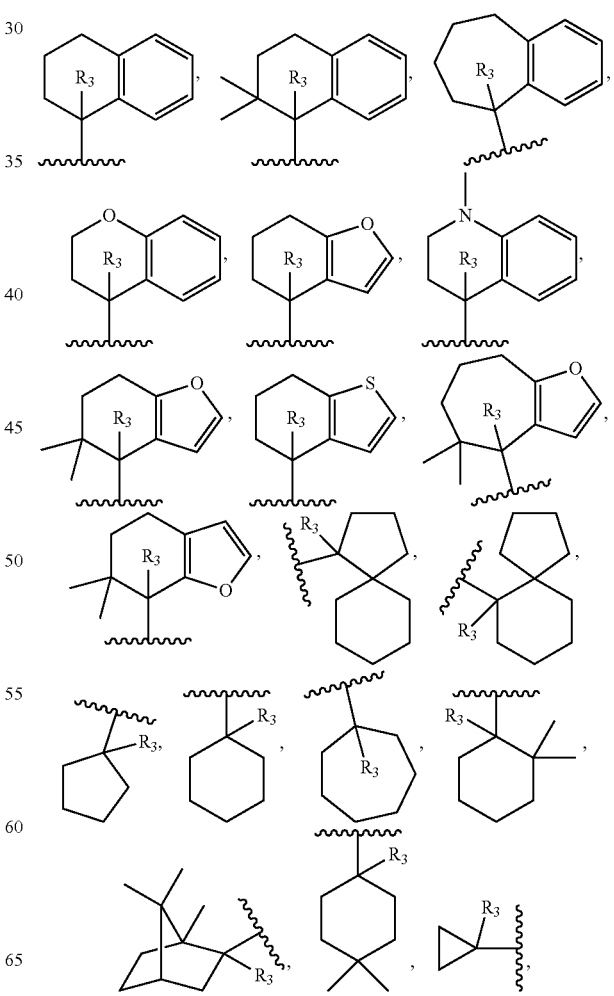

Example Embodiment 25

The compound or a pharmaceutically acceptable salt thereof of example embodiment 1, wherein $R_3$ is selected from hydrogen, methyl, ethyl, propyl, tert-butyl, cyclopropyl, cyclobutyl, cyclopentyl, cyclohexyl, ethynyl, phenyl,

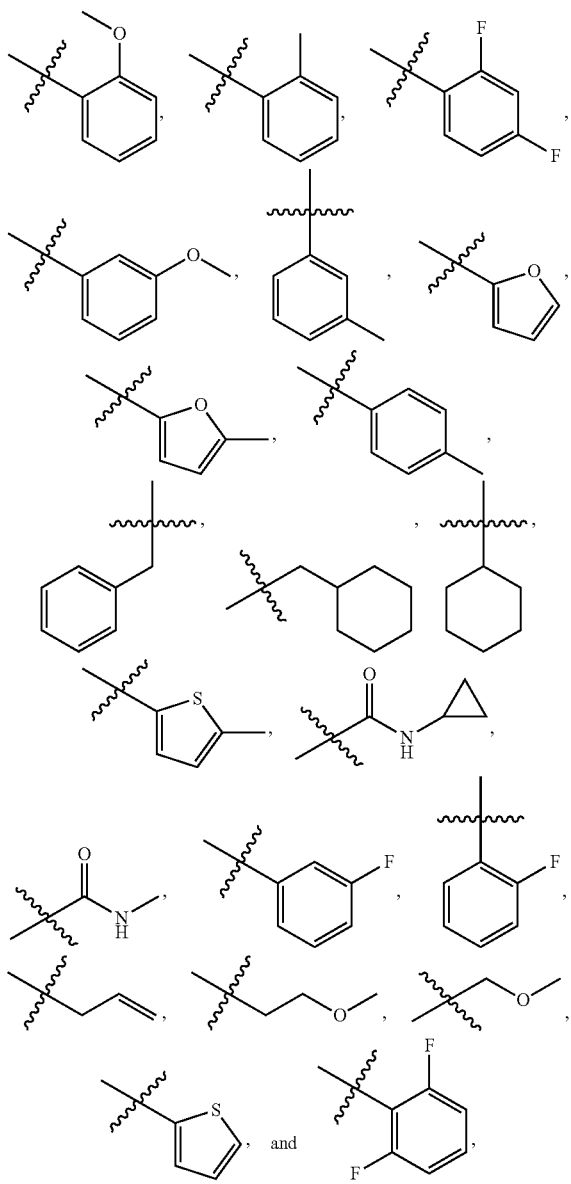

wherein ~ indicates the point of attachment to NH, and wherein $R_3$, $R_4$, $R_5$, $R_6$, $R_7$, and W are as defined in example embodiment 1.

Example Embodiment 26

The compound or a pharmaceutically acceptable salt thereof of any one of example embodiments 1 to 25, wherein $R_4$ is —C(O)NR$_6$R$_7$ or —SO$_2$NR$_6$R$_7$.

Example Embodiment 27

The compound or a pharmaceutically acceptable salt thereof of example embodiment 26, wherein $R_6$ and $R_7$ are independently selected from $C_{1-6}$ alkyl, $C_{1-6}$ hydroxyalkyl, aralkyl, or $R_6$ and $R_7$ together with the nitrogen to which they are attached form a 4 to 12 membered heterocyclyl optionally substituted with at least one group selected from W.

Example Embodiment 28

The compound or a pharmaceutically acceptable salt thereof of example embodiment 27, wherein $R_6$ and $R_7$ are independently selected from $C_{1-6}$ alkyl, $C_{1-6}$ hydroxyalkyl, or aralkyl.

Example Embodiment 29

The compound or a pharmaceutically acceptable salt thereof of any one of example embodiments 27 or 28, wherein both $R_6$ and $R_7$ are $C_{1-6}$ alkyl.

Example Embodiment 30

The compound or a pharmaceutically acceptable salt thereof of any one of example embodiments 27 or 28, wherein $R_6$ is $C_{1-6}$ alkyl and $R_7$ is $C_{1-6}$ hydroxyalkyl.

Example Embodiment 31

The compound or a pharmaceutically acceptable salt thereof of any one of example embodiments 27 or 28, wherein $R_6$ is $C_{1-6}$ alkyl and $R_7$ is aralkyl.

Example Embodiment 32

The compound or a pharmaceutically acceptable salt thereof of example embodiment 27, wherein $R_6$ and $R_7$ together with the nitrogen to which they are attached form a 4 to 12 membered heterocyclyl optionally substituted with at least one group selected from W.

Example Embodiment 33

The compound or a pharmaceutically acceptable salt thereof of any one of example embodiments 26 to 32, wherein $R_4$ is —C(O)NR$_6$R$_7$.

Example Embodiment 34

The compound or a pharmaceutically acceptable salt thereof of any one of example embodiments 26 to 32, wherein $R_4$ is —SO$_2$NR$_6$R$_7$.

Example Embodiment 35

The compound or a pharmaceutically acceptable salt thereof of any one of example embodiments 26 to 32, wherein $R_4$ is halo.

Example Embodiment 36

The compound or a pharmaceutically acceptable salt thereof of any one of example embodiments 1 to 35, wherein the moiety:

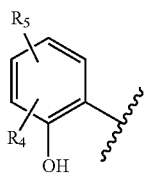

is of the form:

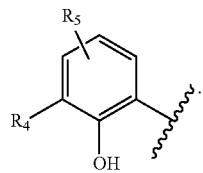

Example Embodiment 37

The compound or a pharmaceutically acceptable salt thereof of any one of example embodiments 1 to 35, wherein the moiety:

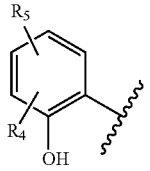

is of the form:

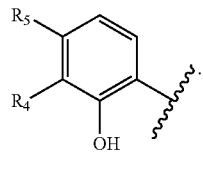

Example Embodiment 38

The compound or a pharmaceutically acceptable salt thereof of example embodiment 1, which is selected from

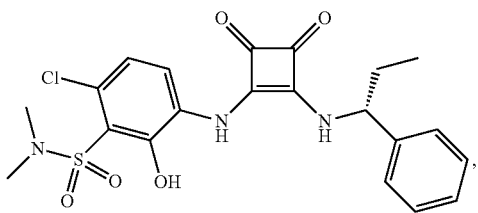

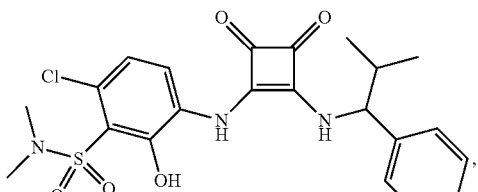

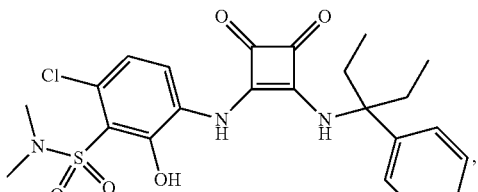

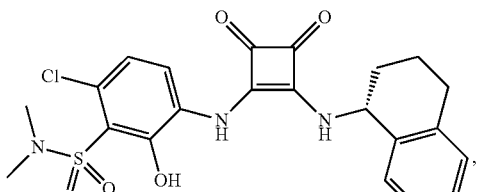

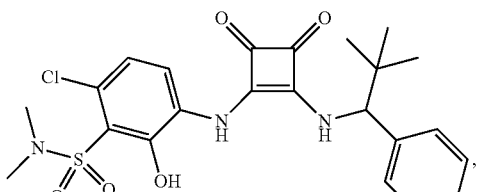

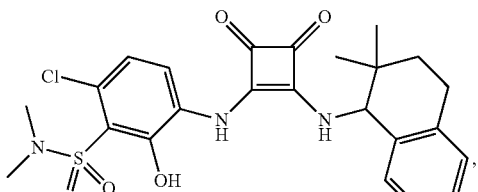

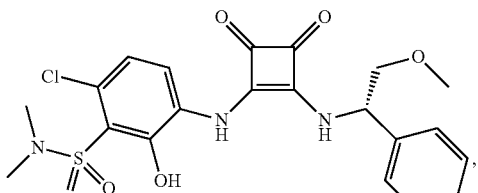

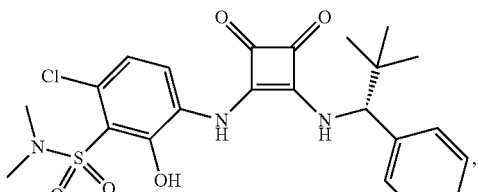

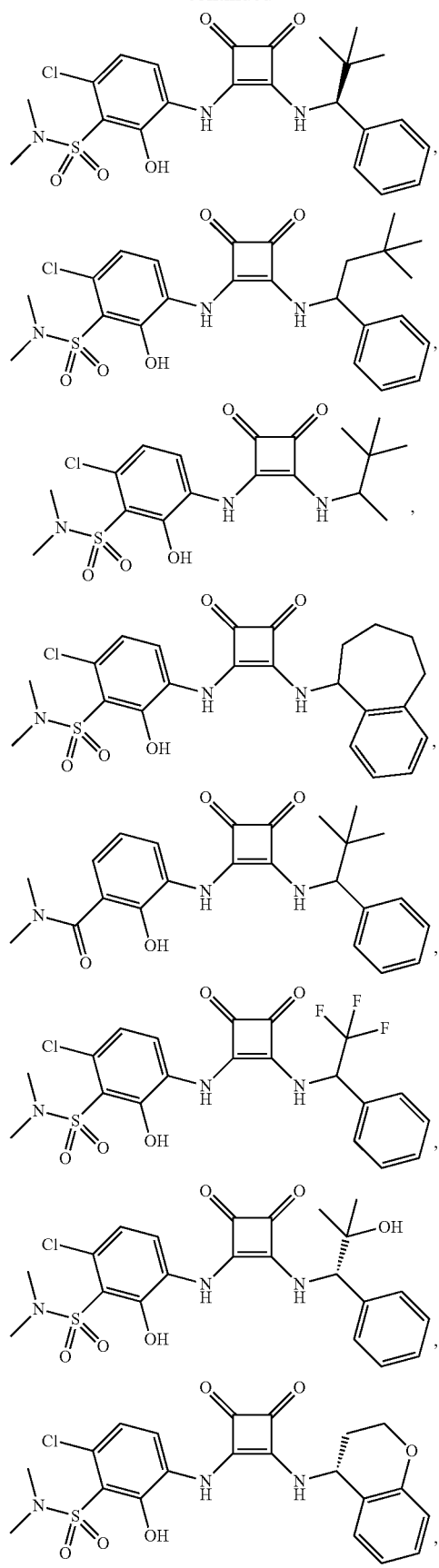
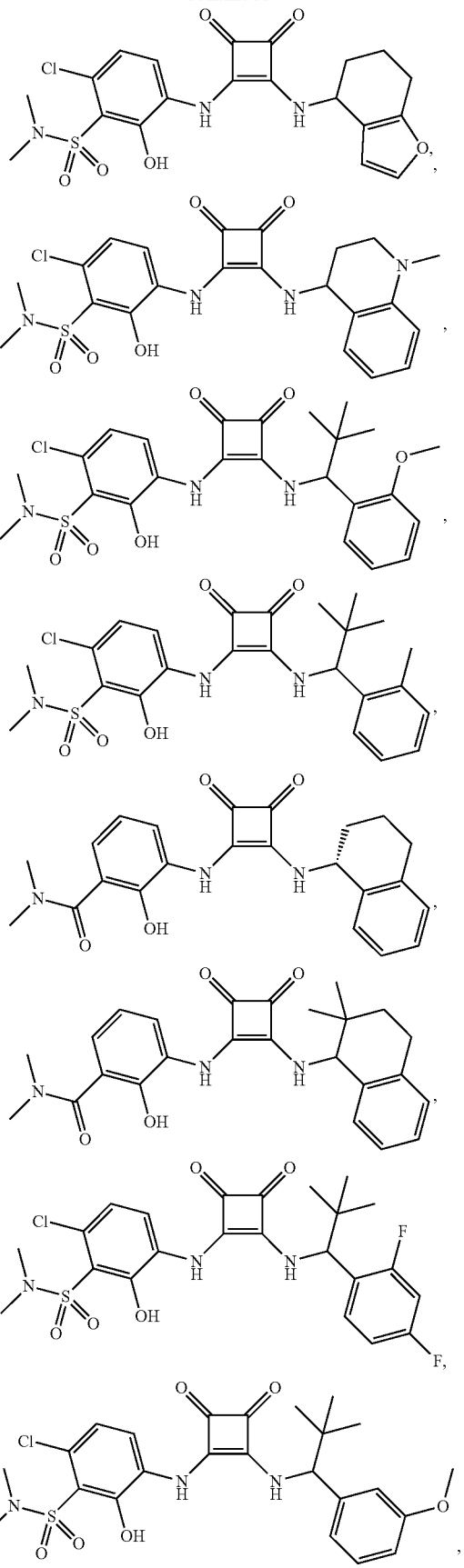

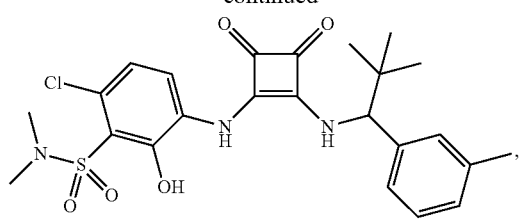,
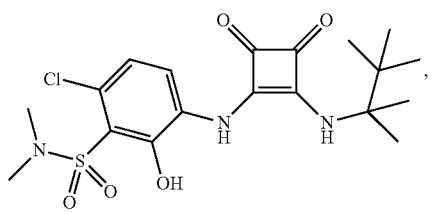,
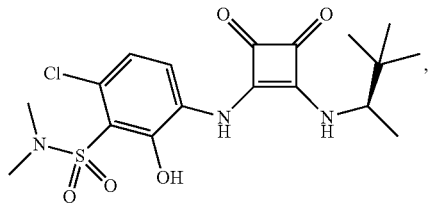,
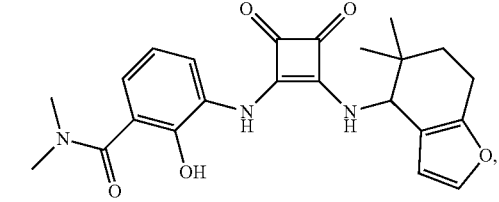,
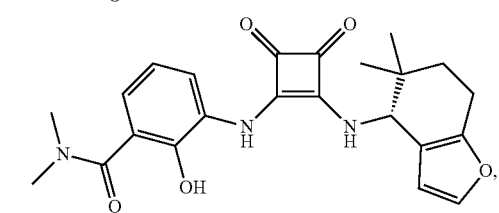,
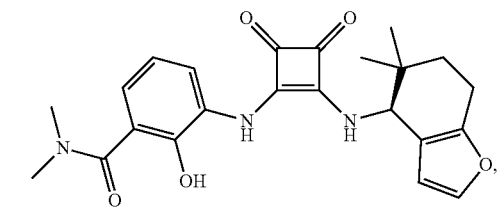,
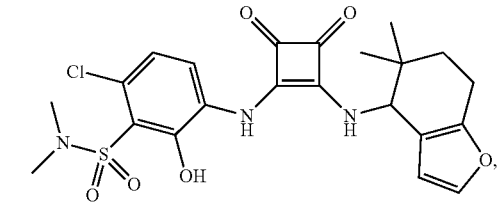,
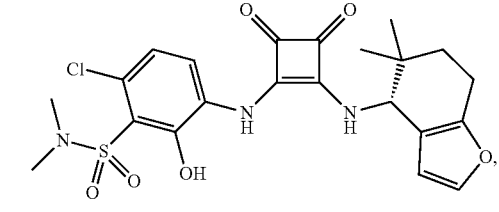,
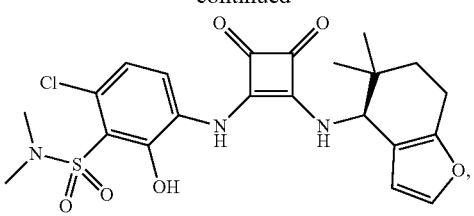,
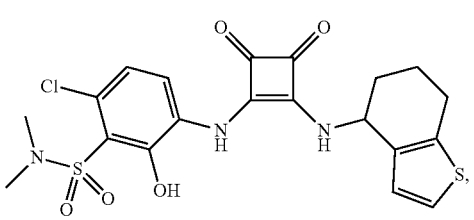,
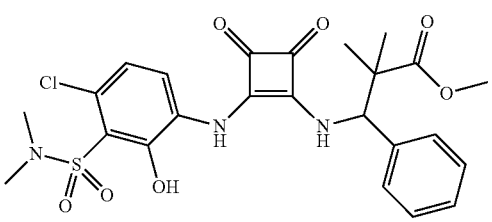,
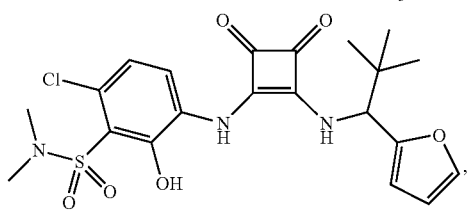,
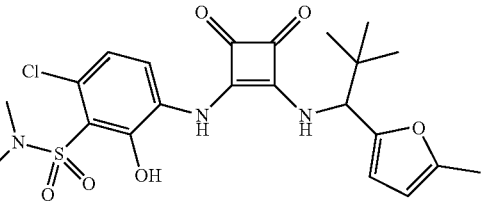,
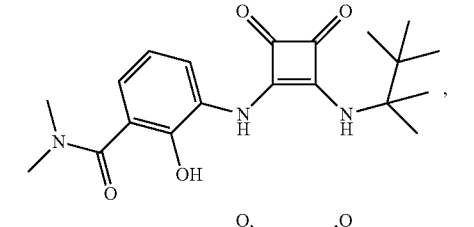,
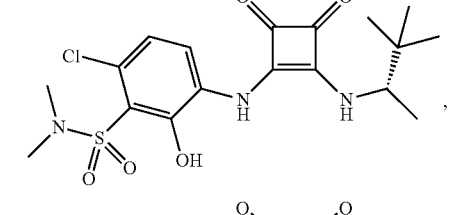,
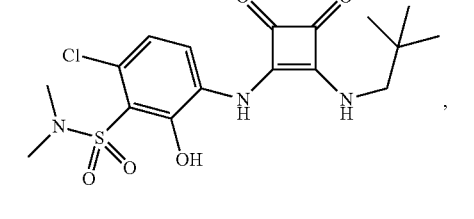,

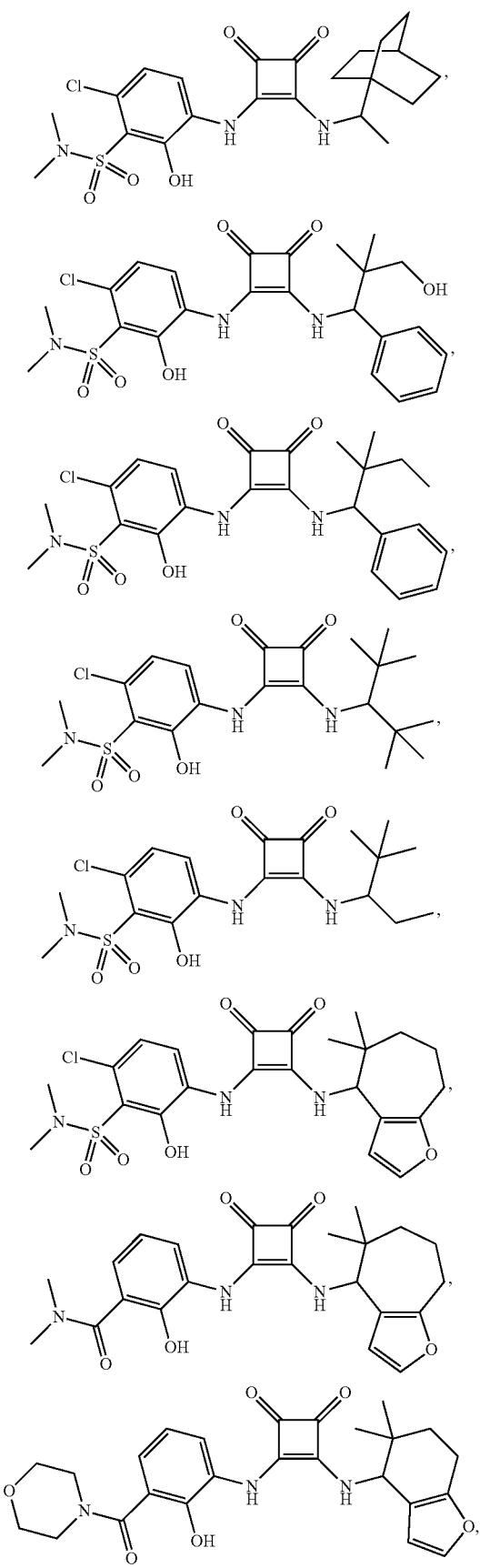
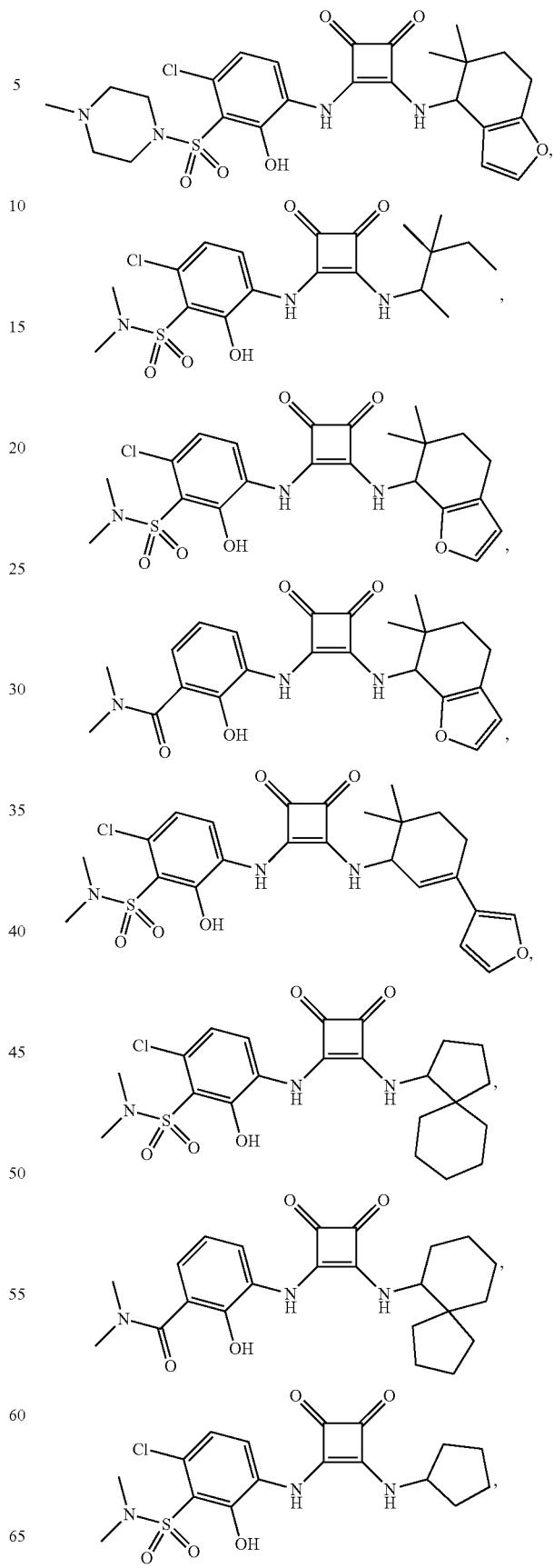

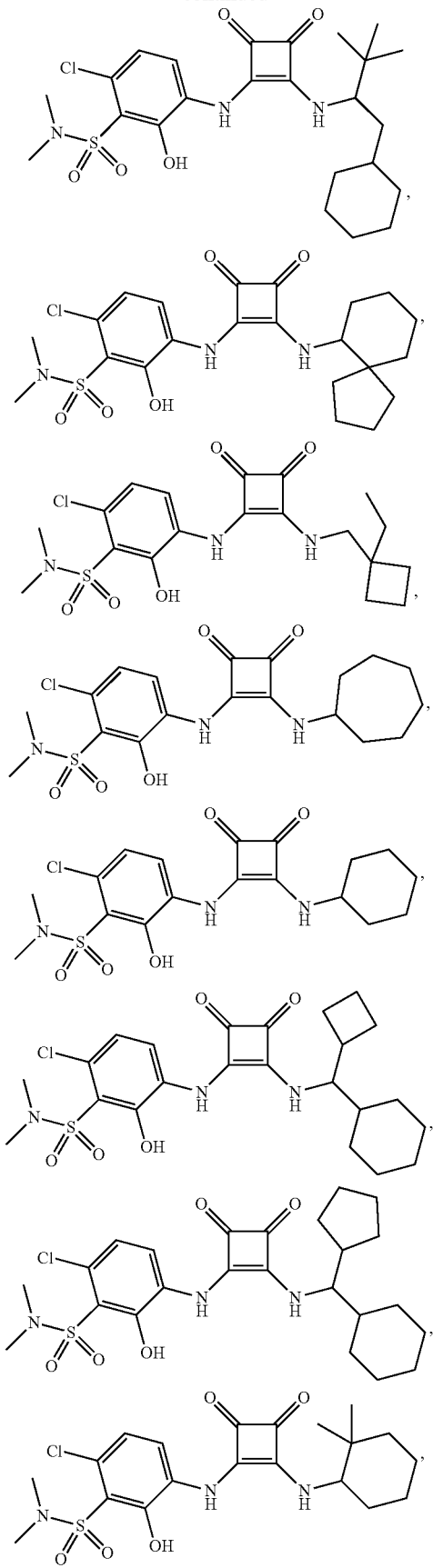
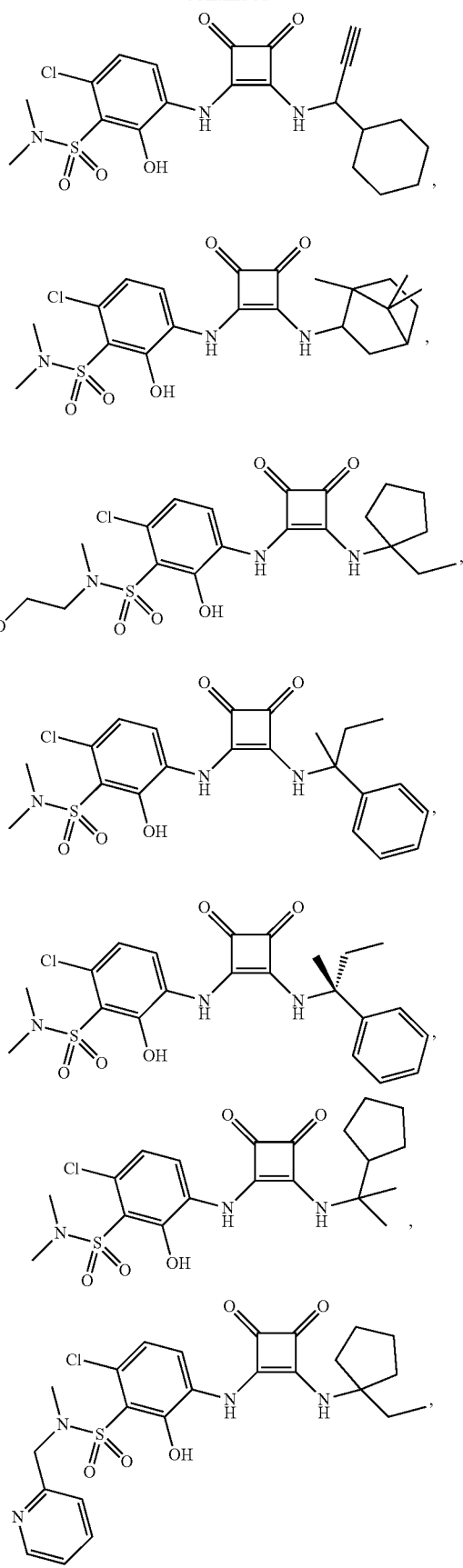

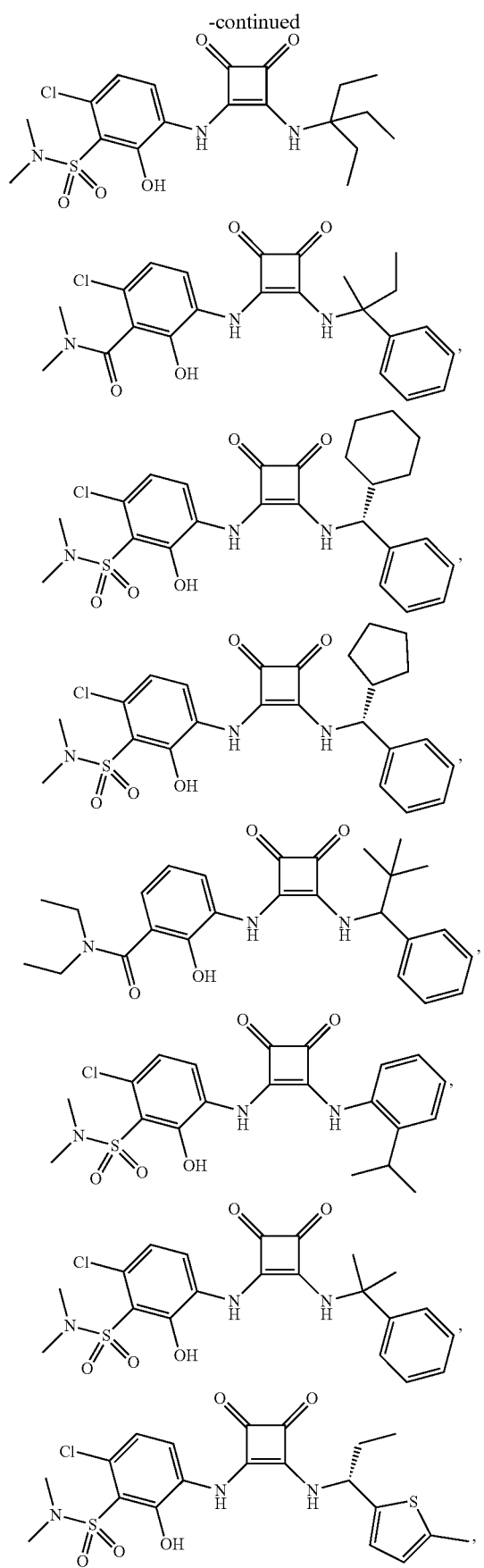

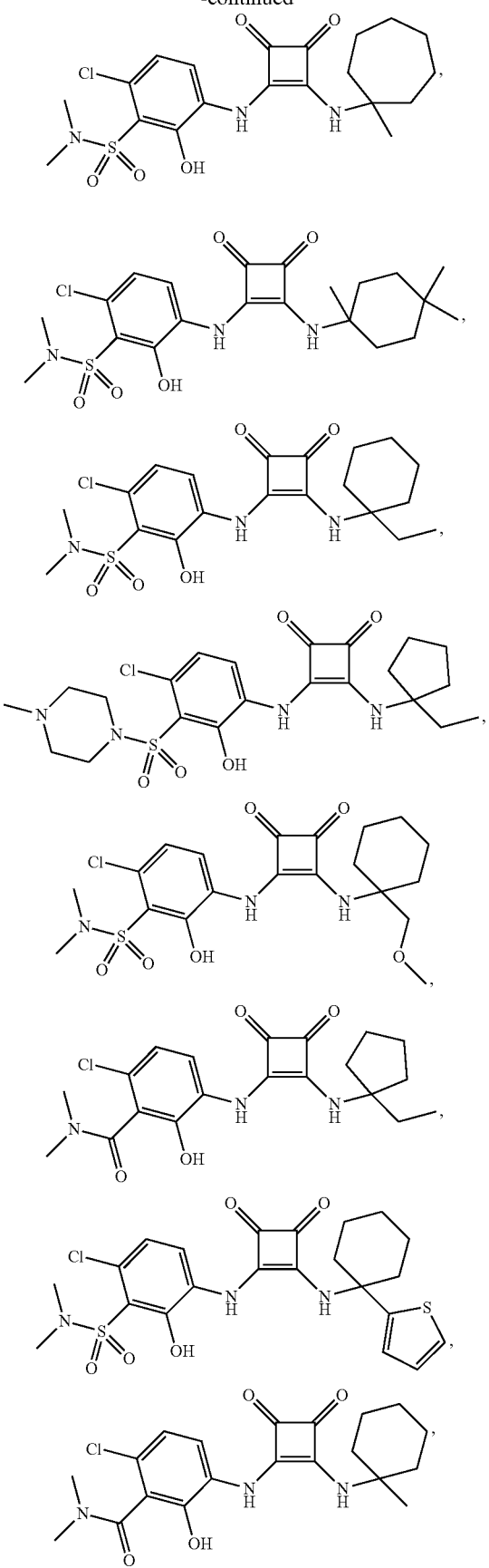
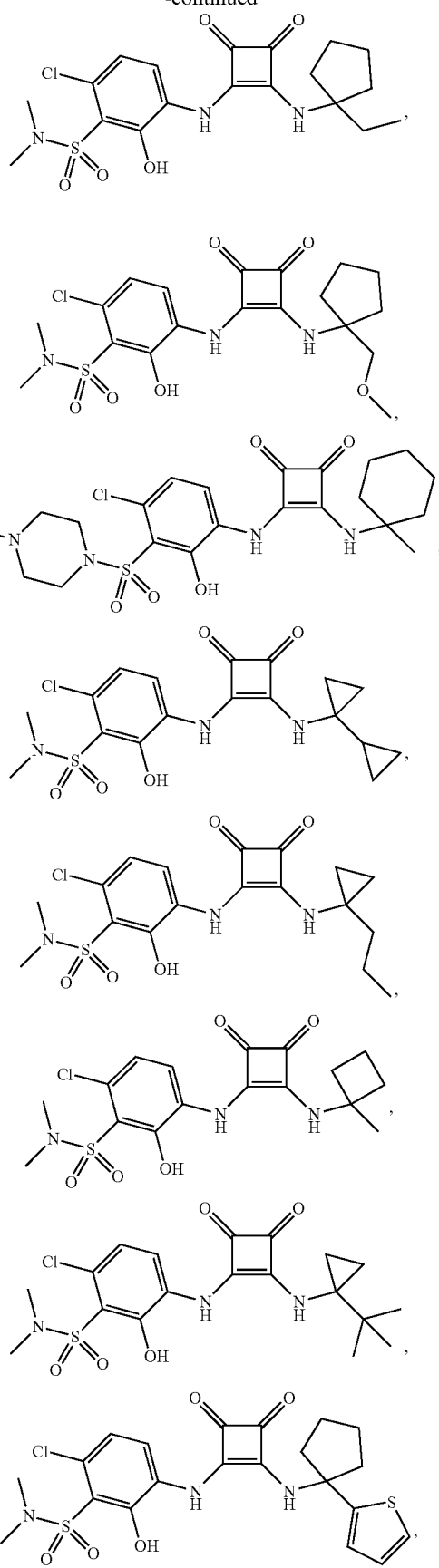

37
-continued
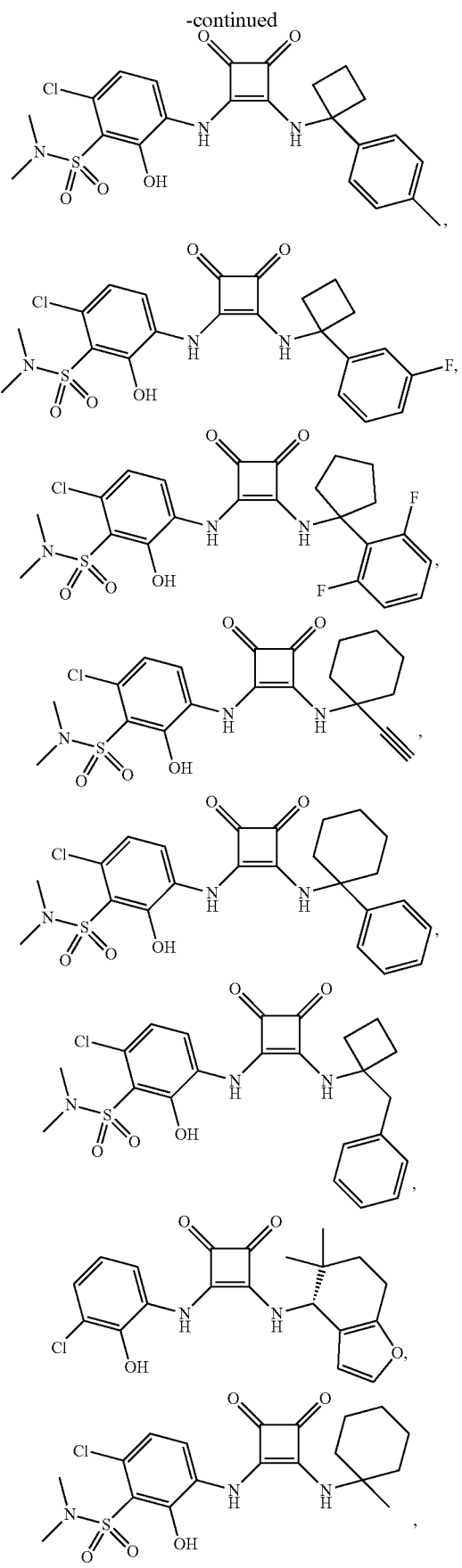
38
-continued
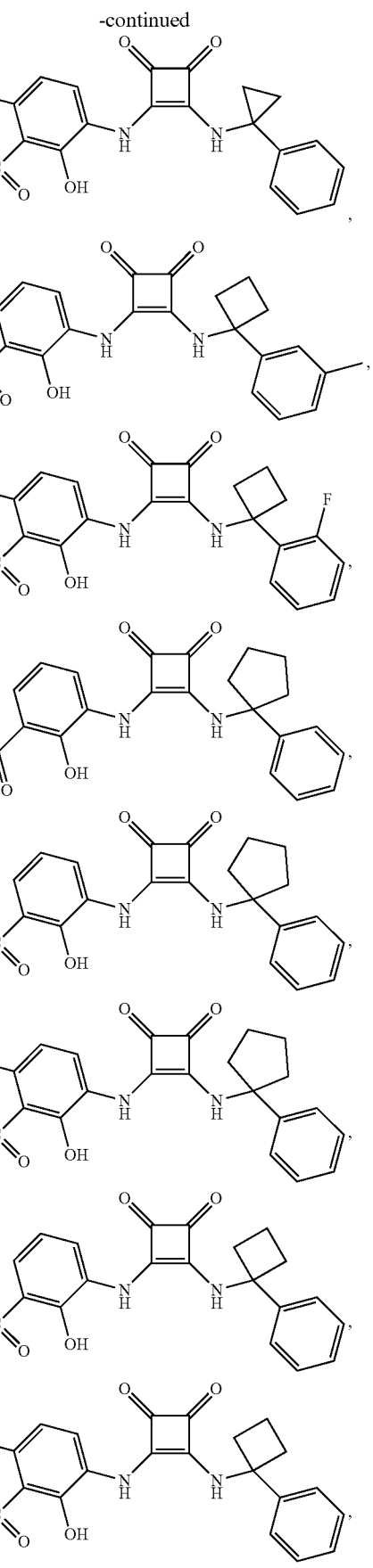

39

-continued

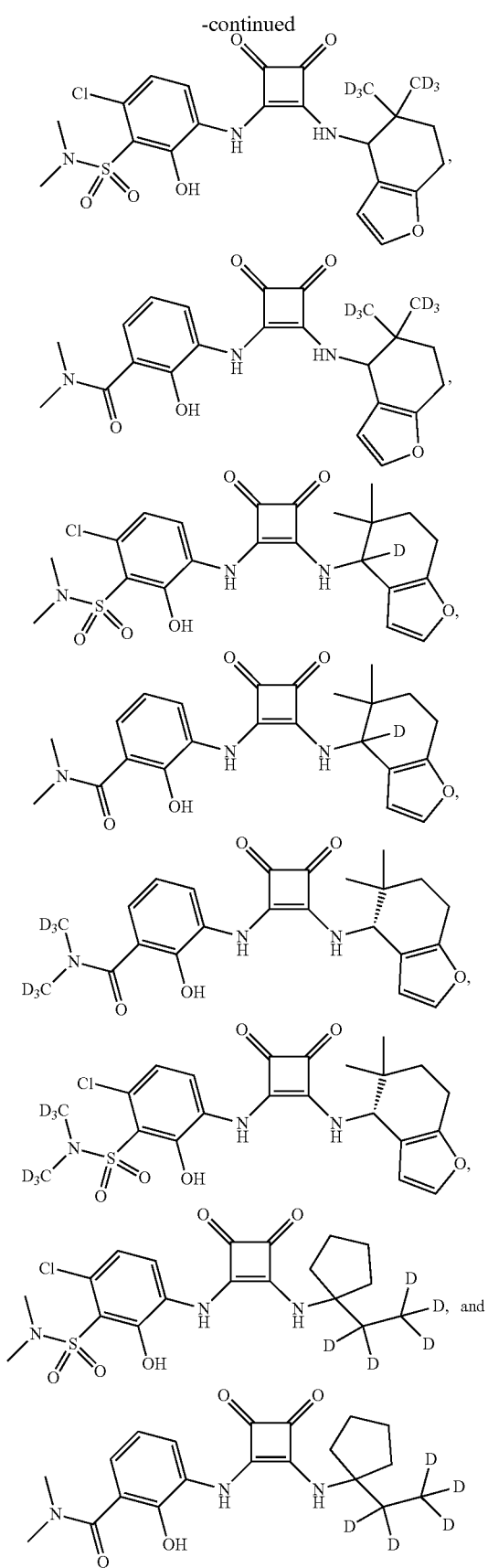

or a pharmaceutically acceptable salt thereof.

40

Example Embodiment 39

A pharmaceutical composition comprising a compound of any one of example embodiments 1 to 38, or a pharmaceutically acceptable salt thereof, and a pharmaceutically acceptable carrier.

Example Embodiment 40

A method of treating an inflammatory or autoimmune disease in a mammal in need thereof which method comprises administering to the mammal in need thereof, a pharmaceutical composition comprising a therapeutically effective amount of a compound or a pharmaceutically acceptable salt thereof of any one of example embodiments 1 to 38, and a pharmaceutically acceptable carrier.

Example Embodiment 41

The method of example embodiment 40, wherein the inflammatory or autoimmune disease is selected from the group consisting of psoriasis, rheumatoid arthritis, multiple sclerosis, Sjogren's disease, GvHD, alopecia areata, uveitis, dry eye, diabetic retinopathy and allergic diseases.

Example Embodiment 42

The method of example embodiment 41, wherein the inflammatory or autoimmune disease is selected from the group consisting of psoriasis and dry eye.

Example Embodiment 43

The method of example embodiment 42, wherein the inflammatory or autoimmune disease is psoriasis.

Example Embodiment 44

The method of example embodiment 42, wherein the inflammatory or autoimmune disease is dry eye.

DETAILED DESCRIPTION

I. Definitions

In all of the above formulae, as well as in those provided hereinafter, the straight lines represent bonds. Where there is no symbol for the atoms between the bonds, the appropriate carbon-containing radical is to be inferred.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H"

are understood to have identical meaning. Standard techniques may be used for chemical syntheses, chemical analyses, and formulation.

The wavy line " ⌇ " indicates the point of attachment of the moiety to the remaining molecule.

When a moiety is a cyclic ring, the term "n membered" is used to describe the number of ring atoms a cyclic ring has. For example, a 4 membered cycloalkyl refers to a cycloalkyl having 4 ring atoms, such as cyclobutane.

When ranges of values are disclosed, and the notation "from n1 . . . to n2" or "n1 . . . to n2" is used, where n1 and n2 are the numbers, then unless otherwise specified, this notation is intended to include the numbers themselves and the range between them. This range may be integral or continuous between and including the end values. By way of example, the range "3 to 11 membered cycloalkyl" is intended to include cycloalkyl having three, four, five, six, seven, eight, nine, ten, or eleven ring atoms. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.). When n is set at 0 in the context of "0 carbon atoms", it is intended to indicate a bond or null.

As used herein, "at least one" means one, two, three, or four.

As used herein, either alone or in combination, the term "alkyl" refers to a functional group comprising a straight-chain or branched-chain hydrocarbon containing from 1 to 20 carbon atoms linked exclusively by single bonds and not having any cyclic structure. An alkyl group may be optionally substituted as defined herein. Examples of alkyl groups includes, without limitation methyl, ethyl, n-propyl, isopropyl, n-butyl, isobutyl, sec-butyl, tert-butyl, pentyl, isoamyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and the like.

As used herein, either alone or in combination, the term "alkenyl" refers to a functional group comprising a straight-chain or branched-chain hydrocarbon containing from 2 to 20 carbon atoms and having one or more carbon-carbon double bonds and not having any cyclic structure. An alkenyl group may be optionally substituted as defined herein. Examples of alkenyl groups include, without limitation, ethenyl, propenyl, 2-methylpropenyl, butenyl, 1,4-butadienyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, and the like. The point of attachment can be on the double bond carbon or on any single bond carbon.

As used herein, either alone or in combination, the term "alkynyl" refers to a functional group comprising a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like. The point of attachment can be on the triple bond carbon or on any single bond carbon.

As used herein, either alone or in combination, the term "alkoxy" refers to —O-alkyl, —O— alkenyl, or —O-alknyl, wherein alkyl, alkenyl, and alkynyl are as defined above.

As used herein, either alone or in combination, the term "alkoxyalkyl" means an alkyl as defined above substituted with an alkoxy group as defined above (in one embodiment one or two alkoxy groups). $C_{2-6}$ alkoxyalkyl means the total number of carbon atoms. Examples include but not limited to 2-methoxyethyl, 1-, 2-, or 3-methoxypropyl, 2-ethoxyethyl, and the like.

As used herein, either alone or in combination, the term "aryl" refers to monocyclic, bicyclic (fused), and tricyclic (fused or spiro) hydrocarbon ring system having a total of five to fourteen ring atoms. When aryl is monocyclic, the monocyclic is aromatic and contains no heteroatom. When aryl is bicyclic or tricyclic, at least one of the ring in the bicyclic or tricyclic is aromatic and contains no heteroatom, and when the other ring(s) is aromatic, the other ring(s) does not contain a heteroatom, but when the other ring(s) is not aromatic, the other ring(s) may or may not contain a heteroatom. The point of attachment can be on any ring atom. Examples of aryl include, without limitation, benzene, naphthalene, indane, 1,2,3,4-tetrahydronaphthalene, chromane, isochromane, 1,2,3,4-tetrahydroquinoline, thiochromane 1,1-dioxide, 6,7,8,9-tetrahydro-5H-benzo[7]annulene, and 2,3-dihydrobenzofuran.

As used herein, either alone or in combination, the term "aralkyl" refers to a 5 to 12 membered heteroaryl or 6 to 12 membered aryl, as defined herein, substituted for a hydrogen of an $C_{1-6}$ alkyl. Examples include but not limited to benzyl and

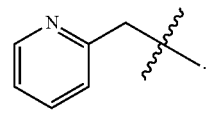 [SMILES: *Cc1ccccn1]

As used herein, either alone or in combination, the term "cycloalkyl" refers to a monocyclic, bicyclic (fused, bridged, or spiro), or tricyclic (fused or spiro) hydrocarbon ring system having a total of three to fourteen ring atoms, which is completely saturated or contains one or more units of unsaturation, but none of the individual ring in the monocyclic, bicyclic, or tricyclic hydrocarbon is aromatic, and none of the ring atoms is a heteroatom. The point of attachment can be on the saturated or unsaturated carbon. A bridged bicyclic cycloalkyl refers to two hydrocarbon rings share three or more carbon atoms, separating the two bridgehead carbon atoms by a bridge containing at least one atom. Examples of cycloalkyl include, but not limited to, cyclopropane, cyclobutane, cyclopentane, cyclohexane, bicyclo[2.2.2]octane, bicyclo[2.2.1]heptane, spiro[2.5]octane, spiro[3.5]nonane, spiro[4.5]decane, and spiro[5.5]undecane.

As used herein, either alone or in combination, the term "heteroaryl" refers to monocyclic, bicyclic (fused), and tricyclic (fused or spiro) ring systems having a total of five to fourteen ring atoms wherein the monocyclic or at least one of the ring in the bicyclic and tricyclic is aromatic and contains at least one heteroatom. The point of attachment can be on any ring atom. Examples of heteroaryl include, without limitation, furan, thiophene, indole, benzofuran, 4,5,6,7-tetrahydrobenzofuran, 4,5,6,7-tetrahydrobenzo[b] thiophene, and 4,5,6,7-tetrahydro-1H-indole.

As used herein, either alone or in combination, the term "heterocyclyl" refers to monocyclic, bicyclic (fused, bridged, or spiro), or tricyclic (fused or spiro) hydrocarbon ring systems having four to fifteen ring atoms, which is completely saturated or contains one or more units of unsaturation, but none of the individual ring in the monocyclic, bicyclic, or tricyclic hydrocarbon is aromatic, and further at least one of the ring atoms is a heteroatom. A bridged bicyclic heterocyclyl is a bridged bicyclic cycloalkyl wherein at least one carbon is replaced with a heteroatom. Examples of heterocyclyl include, but not limited to, azetidine, oxetane, pyrrolidine, piperidine, piperazine, morpholine, and tetrahydrofuran. The point of attachment can be on the saturated or unsaturated carbon or heteroatom.

As used herein, either alone or in combination, the term "heteroatom" refers to oxygen, nitrogen, sulfur, silicon, or phosphorous, including any oxidized form of nitrogen, sulfur, silicon, or phosphorous.

As used herein, either alone or in combination, the term "haloalkyl" refers to alkyl as defined above, wherein one or one to five hydrogens are replaced with halogen atom(s), including those substituted with different halogen atoms. Examples of haloalkyl includes, but not limited to, —$CF_3$, —$CH_2Cl$, —$CHF_2$, and —$CF_2CF_3$.

As used herein, either alone or in combination, the term "haloalkoxy" refers to alkoxy as defined above, wherein one or one to five hydrogens are replaced with halogen atom(s), including those substituted with different halogen atoms. Examples of haloalkoxy includes, but not limited to, —$OCF_3$ and —$OCHF_2$.

As used herein, alone or in combination, the term "halo" or "halogen" means fluoro, chloro, bromo, or iodo; in one embodiment fluoro or chloro.

As used herein, either alone or in combination, the term "alkylsilyl" refers to a silicon atom to which is attached one, two, or three alkyl groups and in which the silicon atom serves as the point of attachment. In particular, the term "tri-$C_{1-5}$ alkylsilyl" refers to a silicon atom to which is attached three independently selected $C_1$ to $C_5$ alkyl groups. Examples of tri-$C_{1-5}$ alkylsilyl groups include, without limitation, trimethylsilyl, triethylsilyl, triisopropylsilyl, dimethylisopropylsilyl, diethylisopropylsilyl, tert-butyldimethylsilyl, di-tert-butylmethyl, and the like.

As used herein, the term "optionally substituted" refers to a group or molecule that may be either substituted or unsubstituted.

As used herein, either alone or in combination, the term "spiro" refers to a moiety comprising two rings sharing one common atom.

The compounds disclosed in the present specification may be present in the form of an isomer. As used herein, the term "isomer" refers to compounds disclosed in the present specification that has the same composition and molecular weight but differs in one or more physical and/or chemical properties. Such isomers have the same number and kind of atoms but differ in structure. The structural difference may be in constitution (geometric isomers), in an ability to rotate the plane of polarized light (stereoisomers), or in the position of a hydrogen atom or proton (tautomeric isomers). Unless otherwise indicated, the compounds disclosed in the present specification include the individual isomers of compounds that form more than one type of isomerism, or mixtures of one or more of the isomers. In particular, reference to a compound or compounds described herein is intended to encompass that compound in each of its possible stereoisomeric forms and mixtures thereof unless the particular isomeric form is referred to specifically. Also included are acid addition salts wherein the counterion is optically active, for example, D-lactate or L-lysine, or racemic, for example, DL-tartrate or DL-arginine.

As used herein, the term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) or "chair" configuration, the substituents are on opposite sides in relationship to the carbon-carbon double bond. In the "Z" (same sided) or "boat" configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring. In the "trans" configuration, the substituents are on opposite sides in relationship to the plane of the ring. Compounds having a mixture of "cis" and "trans" species are designated "cis/trans." Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

As used herein, the term "stereoisomer" refers to isomers of identical constitution that differs in the arrangement of their atoms in space. Enantiomers and diastereomers are stereoisomers wherein an asymmetrically substituted carbon atom acts as a chiral center. As used herein, the term "chiral" refers to a molecule that is not superimposable on its mirror image, implying the absence of an axis and a plane or center of symmetry. As used herein, the term "enantiomer" refers to one of a pair of molecular species that are mirror images of each other and are not superimposable. As used herein, the term "diastereomer" refers to stereoisomers that are not related as mirror images.

In the specification, the term "ambient temperature" and "room temperature" are used interchangeably. They in general refer to a temperature in a range of from 15° C. to 25° C.

In the specification, the term "individual" and "mammal" are used interchangeably. Both of them refer to a human or an animal.

The compounds disclosed in the present specification may be present in the form of a pharmaceutically acceptable salt. As used herein, the term "a pharmaceutically acceptable salt" refers to non-toxic acidic/anionic or basic/cationic salt forms of the compounds disclosed in the present specification. Suitable pharmaceutically acceptable salts include acid addition salts which may, e.g., be formed by mixing a solution of the compound disclosed in the present specification with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, when the compounds disclosed in the present specification carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, without limitation, acetate, aspirate, benzenesulfonate, benzoate, besylate, bicarbonate, bisulfate, bitartrate, borate, bromide, calcium, camsylate (or camphorsulphonate), carbonate, chloride, citrate, clavulanate, dihydrochloride, edetate, edisylate, esylate, formate, fumarate, gluceptate, gluconate, glucuronate, glutamate, hexafluorophosphate, hibenzate, hydrabamine, hydrobromide, hydrobromine, hydrochloride, hydroiodide, iodide, isethionate, isothionate, lactate, malate, maleate, malonate, mandelate, mesylate, methylsulfate, nitrate, naphthylate, 2-napsylate, nicotinate, nitrate, oleate, orotate, oxalate, pamoate, palmitate, phosphate/diphosphate/hydrogen phosphate, saccharate, salicylate, stearate, sulfate, succinate, tartrate, tosylate and trifluoroacetate. (see, e.g., *Handbook of Pharmaceutical Salts*, P. Heinrich Stahl & Camille G. Wermuth (Eds), Verlag; *Helvetica Chimica Acta*-Zürich, 2002, 329-345; and Berge et al., *Journal of Pharmaceutical Science*, 1977, 66:1-19).

The compounds disclosed in the present specification may be present in the form of an unsolvated or solvated form. As used herein, the term 'solvate' describes a molecular complex comprising a compound disclosed in the present specification and one or more pharmaceutically acceptable solvent molecules, for example, water, ethanol, DMSO, or other organic solvents. When a compound disclosed in the present specification forms a solvate with water, the term "hydrate" may be used instead of "solvate." Pharmaceutically acceptable solvates include hydrates and solvates wherein the solvent may be isotopically substituted, e.g., $D_2O$, d6-acetone, d6-DMSO.

II. Compounds

In one aspect, the present specification relates to a compound of Formula I or a pharmaceutically acceptable salt thereof, including an enantiomer, a diastereoisomer, a tautomer thereof:

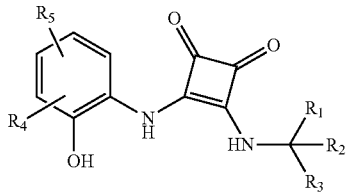

Formula I wherein
  $R_1$ is selected from
    i) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
    ii) 3 to 11 membered cycloalkyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
    iii) 4 to 12 membered heterocyclyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
    iv) 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
    v) tri-$C_{1-5}$ alkylsilyl, and
    vi) $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl;
  $R_2$ is selected from hydrogen, $C_{1-5}$ alkyl, $C_{2-5}$ alkenyl, and $C_{2-5}$ alkynyl;
  or $R_1$ and $R_2$ together with the carbon to which they are attached form
    i) a 6 to 12 membered aryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
    ii) a 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, iii) a 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, $CD_3$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or iv) a 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, provided that $R_3$ is absent when the carbon to which $R_1$ and $R_2$ are attached is part of an aromatic or double bond;

$R_3$ is selected from
i) hydrogen, deuterium, —$CO_2R_6$, —$NR_6R_7$, —C(O)$NR_6R_7$, —$OR_6$, $CD_2CD_3$, halo, $C_{2-5}$ alkenyl, $C_{2-5}$ alkynyl, sulfonate, phosphonate, ii) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, iii) 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, iv) 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, v) 5 to 12 membered heteroaryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and vi) $C_{1-5}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, —Si($C_{1-6}$ alkyl), $C_{2-5}$ alkenyl, and $C_{2-5}$ alkynyl;

$R_4$ is selected from —$CO_2R_6$, —C(O)$NR_6R_7$, —$NR_6C(O)R_7$, —$NR_6CO_2R_7$, —$NR_6C(O)NR_6R_7$, —$NR_7SO_2R_6$, —$NR_7SO_2NR_6R_7$, $C_{1-6}$ hydroxyalkyl, $C_{1-6}$ haloalkyl, halo, CN, —$SO_2NR_6R_7$, and —$SO_2R_6$;

$R_5$ is selected from hydrogen, $C_{1-6}$ alkyl, —$OR_6$, halo, —$NR_6R_7$, CN, $C_{1-6}$ haloalkyl, and —$NO_2$;

$R_6$ and $R_7$ are independently selected from
i) hydrogen,
ii) $C_{1-6}$ alkyl, $C_{1-6}$ haloalkyl, $C_{1-6}$ hydroxyalkyl, $C_{2-6}$ alkoxyalkyl, aralkyl, $CD_3$,
iii) $C_{2-5}$ alkenyl, $C_{2-5}$ alkynyl,
iv) 6 to 12 membered aryl optionally substituted with at least one group selected from W,
v) 3 to 11 membered cycloalkyl optionally substituted with at least one group selected from W,
vi) 5 to 12 membered heteroaryl optionally substituted with at least one group selected from W, and
vii) 4 to 12 membered heterocyclyl optionally substituted with at least one group selected from W, or $R_6$ and $R_7$ together with the nitrogen to which they are attached form a 4 to 12 membered heterocyclyl optionally substituted with at least one group selected from W;

W is selected from $C_{1-6}$ alkyl, $C_{2-5}$ alkenyl, $C_{2-5}$ alkynyl, halo, $C_{1-6}$ alkoxy, and hydroxyl.

In some embodiments, the compounds of Formula I described above can be compounds of Formula I with one or more of the following provisos:

a) that when $R_1$ is 6 to 12 membered aryl optionally substituted as described above or 5 to 12 membered heteroaryl optionally substituted as described above, $R_3$ is not a 4 or 5 membered heterocyclyl optionally substituted as described above, and that when $R_3$ is 6 to 12 membered aryl optionally substituted as described above or 5 to 12 membered heteroaryl optionally substituted as described above, $R_1$ is not a 4 or 5 membered heterocyclyl optionally substituted as described above;

b) that when any of $R_1$, $R_2$, or $R_3$ are $C_{1-5}$ alkyl or $C_{1-10}$ alkyl, and $R_4$ is —$SO_2NR_6R_7$, $R_5$ is not hydrogen;

c) that when either $R_1$ or $R_3$ is 4 or 5 membered heterocyclyl optionally substituted as described above, $R_2$ is not $C_{1-10}$ alkyl;
d) that when either $R_1$ or $R_3$ is 5 to 12 membered heteroaryl optionally substituted as described above, and $R_4$ is —$SO_2NR_6R_7$, then neither $R_6$ or $R_7$ in the —$SO_2NR_6R_7$ is hydrogen or 5 to 12 membered heteroaryl optionally substituted as described above;
e) that when $R_1$ and $R_2$ together with the carbon to which they are attached form a 6 to 12 membered aryl optionally substituted as described above, and $R_4$ is —$SO_2NR_6R_7$, $R_5$ is not $C_{1-6}$ alkyl or CN and both $R_6$ and $R_7$ in the —$SO_2NR_6R_7$ are $C_{1-6}$ alkyl; and
f) that when $R_1$ and $R_2$ together with the carbon to which they are attached form a 4 to 12 membered heterocyclyl optionally substituted as described above, $R_3$ is not hydrogen.

Accordingly, in another aspect, the present specification relates to a compound of Formula I or a pharmaceutically acceptable salt thereof, including an enantiomer, a diastereoisomer, a tautomer thereof:

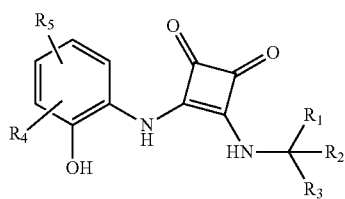

Formula I wherein
$R_1$ is selected from
  i) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) 3 to 11 membered cycloalkyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) 4 to 12 membered heterocyclyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iv) 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  v) tri-$C_{1-5}$ alkylsilyl, and
  vi) $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl;
$R_2$ is selected from hydrogen, $C_{1-5}$ alkyl, $C_{2-5}$ alkenyl, and $C_{2-5}$ alkynyl;
or $R_1$ and $R_2$ together with the carbon to which they are attached form
  i) a 6 to 12 membered aryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  ii) a 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
  iii) a 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, $CD_3$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or
iv) a 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, provided that $R_3$ is absent when the carbon to which $R_1$ and $R_2$ are attached is part of an aromatic or double bond;

$R_3$ is selected from
i) hydrogen, deuterium, —$CO_2R_6$, —$NR_6R_7$, —C(O)$NR_6R_7$, —$OR_6$, $CD_2CD_3$, halo, $C_{2-5}$ alkenyl, $C_{2-5}$ alkynyl, sulfonate, phosphonate,
ii) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iii) 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iv) 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
v) 5 to 12 membered heteroaryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and
vi) $C_{1-5}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, —Si($C_{1-6}$ alkyl), $C_{2-5}$ alkenyl, and $C_{2-5}$ alkynyl;

$R_4$ is selected from —$CO_2R_6$, —C(O)$NR_6R_7$, —$NR_6C(O)R_7$, —$NR_6CO_2RT$, —$NR_6C(O)NR_6R_7$, —$NR_7SO_2R_6$, —$NR_7SO_2NR_6R_7$, $C_{1-6}$ hydroxyalkyl, $C_{1-6}$ haloalkyl, halo, CN, —$SO_2NR_6R_7$, and —$SO_2R_6$;

$R_5$ is selected from hydrogen, $C_{1-6}$ alkyl, —$OR_6$, halo, —$NR_6R_7$, CN, $C_{1-6}$ haloalkyl, and —$NO_2$;

$R_6$ and $R_7$ are independently selected from
i) hydrogen,
ii) $C_{1-6}$ alkyl, $C_{1-6}$ haloalkyl, $C_{1-6}$ hydroxyalkyl, $C_{2-6}$ alkoxyalkyl, aralkyl, $CD_3$,
iii) $C_{2-5}$ alkenyl, $C_{2-5}$ alkynyl,
iv) 6 to 12 membered aryl optionally substituted with at least one group selected from W,
v) 3 to 11 membered cycloalkyl optionally substituted with at least one group selected from W,
vi) 5 to 12 membered heteroaryl optionally substituted with at least one group selected from W, and
vii) 4 to 12 membered heterocyclyl optionally substituted with at least one group selected from W, or $R_6$ and $R_7$ together with the nitrogen to which they are attached form a 4 to 12 membered heterocyclyl optionally substituted with at least one group selected from W;

W is selected from $C_{1-6}$ alkyl, $C_{2-5}$ alkenyl, $C_{2-5}$ alkynyl, halo, $C_{1-6}$ alkoxy, and hydroxyl; with the provisos:
a) that when $R_1$ is 6 to 12 membered aryl optionally substituted as described above or 5 to 12 membered heteroaryl optionally substituted as described above, $R_3$ is not a 4 or 5 membered heterocyclyl optionally substituted as described above, and that when $R_3$ is 6 to 12 membered aryl optionally substituted as described above or 5 to 12 membered heteroaryl optionally substituted as described above, $R_1$ is not a 4 or 5 membered heterocyclyl optionally substituted as described above;
b) that when any of $R_1$, $R_2$, or $R_3$ are $C_{1-5}$ alkyl or $C_{1-10}$ alkyl, and $R_4$ is —$SO_2NR_6R_7$, $R_5$ is not hydrogen;
c) that when either $R_1$ or $R_3$ is 4 or 5 membered heterocyclyl optionally substituted as described above, $R_2$ is not $C_{1-10}$ alkyl;
d) that when either $R_1$ or $R_3$ is 5 to 12 membered heteroaryl optionally substituted as described above, and $R_4$ is —$SO_2NR_6R_7$, then neither $R_6$ or $R_7$ in the —$SO_2NR_6R_7$ is hydrogen or 5 to 12 membered heteroaryl optionally substituted as described above;
e) that when $R_1$ and $R_2$ together with the carbon to which they are attached form a 6 to 12 membered aryl optionally substituted as described above, and $R_4$ is —$SO_2NR_6R_7$, $R_5$ is not $C_{1-6}$ alkyl or CN and both $R_6$ and $R_7$ in the —$SO_2NR_6R_7$ are $C_{1-6}$ alkyl; and f) that when $R_1$ and $R_2$ together with the carbon to which they are attached form a 4 to 12 membered heterocyclyl optionally substituted as described above, $R_3$ is not hydrogen.

In some embodiments $R_1$ is selected from
i) 6 to 12 membered aryl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
ii) 3 to 11 membered cycloalkyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iii) 4 to 12 membered heterocyclyl optionally substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iv) 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
v) tri-$C_{1-5}$ alkylsilyl, and
vi) $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl; and
$R_2$ is selected from hydrogen, $C_{1-5}$ alkyl, $C_{2-5}$ alkenyl, and $C_{2-5}$ alkynyl; and
$R_3$, $R_4$, $R_5$, $R_6$, $R_7$, and W are as defined in Formula I.

In some embodiments, $R_1$ is $C_{1-10}$ alkyl optionally substituted as described in Formula I.

In some embodiments, $R_1$ is $C_{1-10}$ alkyl substituted with at least one group selected from $OR_6$ and 3 to 11 membered cycloalkyl.

In some embodiments, $R_1$ is unsubstituted $C_{1-10}$ alkyl.

In some embodiments, $R_2$ is hydrogen.

In some embodiments, $R_3$ is 6 to 12 membered aryl optionally substituted as in Formula I.

In some embodiments, $R_3$ is unsubstituted 6 to 12 membered aryl.

In some embodiments, $R_6$ is hydrogen or $C_{1-6}$ alkyl optionally substituted as described in Formula I.

In some embodiments, $R_6$ is hydrogen or unsubstituted $C_{1-6}$ alkyl.

In some embodiments, $R_6$ is hydrogen.

In some embodiments, $R_2$ is hydrogen.

In some embodiments, $R_3$ is 5 to 12 membered heteroaryl optionally substituted as described in Formula I.

In some embodiments, $R_3$ is 5 to 12 membered heteroaryl optionally substituted with at least one $C_{1-6}$ alkyl group.

In some embodiments, $R_3$ is unsubstituted 5 to 12 membered heteroaryl.

In some embodiments $R_3$ is —C(O)$NR_6R_7$, wherein $R_6$ and $R_7$ are as defined in Formula I.

In some embodiments, $R_2$ is $C_{1-5}$ alkyl optionally substituted as described in Formula I.

In some embodiments, $R_3$ is hydrogen.

In some embodiments, $R_3$ is $C_{1-5}$ alkyl optionally substituted as described in Formula I.

In some embodiments, $R_3$ is unsubstituted $C_{1-5}$ alkyl.

In some embodiments, $R_3$ is 6 to 12 membered aryl optionally substituted as described in Formula I.

In some embodiments, $R_3$ is unsubstituted 6 to 12 membered aryl.

In some embodiments $R_1$ and $R_2$ together with the carbon to which they are attached form
i) a 6 to 12 membered aryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
ii) a 3 to 11 membered cycloalkyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W,
iii) a 5 to 12 membered heteroaryl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6$C(O)$R_7$, $CD_3$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, or iv) a 4 to 12 membered heterocyclyl optionally with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, provided that $R_3$ is absent when the carbon to which $R_1$ and $R_2$ are attached is part of an aromatic or double bond; and $R_3$, $R_4$, $R_5$, $R_6$, $R_7$, and W are as defined in Formula 1.

In some embodiments, $R_1$ and $R_2$ together with the carbon to which they are attached form a 6 to 12 membered aryl optionally substituted as described in Formula I.

In some embodiments, $R_1$ and $R_2$ together with the carbon to which they are attached form a 6 to 12 membered aryl optionally substituted with at least one $C_{1-6}$ alkyl group.

In some embodiments, $R_1$ and $R_2$ together with the carbon to which they are attached form a 5 to 12 membered heteroaryl optionally substituted as described in Formula I.

In some embodiments, $R_1$ and $R_2$ together with the carbon to which they are attached form a 5 to 12 membered heteroaryl optionally substituted with at least one $C_{1-6}$ alkyl group.

In some embodiments $R_1$ and $R_2$ together with the carbon to which they are attached form a 4 to 12 membered heterocyclyl optionally substituted as described in Formula I.

In some embodiments $R_1$ and $R_2$ together with the carbon to which they are attached form a 4 to 12 membered heterocyclyl optionally substituted with at least one group selected from $C_{1-6}$ alkyl, $C_{2-6}$ alkoxyalkyl, $C_{2-6}$ alkenyl, and 5 to 12 membered heteroaryl optionally substituted with at least one group selected from W.

In some embodiments, $R_1$ is selected from 3 to 11 membered cycloalkyl, tri-$C_{1-5}$ alkylsilyl, and $C_{1-10}$ alkyl optionally substituted with at least one group selected from $OR_6$, 6 to 12 membered aryl, 3 to 11 membered cycloalkyl, —$CO_2R_6$, —C(O)$NR_6R_7$, halo, 5 to 12 membered heteroaryl, 4 to 12 membered heterocyclyl, $C_{2-5}$ alkenyl, and $C_{2-5}$ alkynyl, wherein each of the 6 to 12 membered aryl, 3 to 11 membered cycloalkyl, 5 to 12 membered heteroaryl, and 4 to 12 membered heterocyclyl is optionally further substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and wherein $R_6$, $R_7$, and W are the same as defined for Formula I.

In some embodiments, $R_1$ is selected from 3 to 8 membered cycloalkyl, tri-$C_{1-5}$ alkylsilyl, and $C_{1-6}$ alkyl optionally substituted with at least one group selected from $OR_6$, —$CO_2R_6$, —C(O)$NR_6R_7$, and halo, wherein the 3 to 8 membered cycloalkyl is optionally substituted with at least one group selected from $C_{1-6}$ alkyl, alkoxylalkyl, $C_{2-6}$ alkenyl, halo, and $OR_6$, $R_6$ and $R_7$ are independently selected from hydrogen, $C_{1-6}$ alkyl, 3 to 7 membered cycloalkyl, $C_{1-6}$ haloalkyl, $C_{2-5}$ alkenyl, and $C_{2-5}$ alkynyl.

In some embodiments, $R_1$ is selected from methyl, ethyl, isopropyl, tert-butyl, methoxymethyl, trifluoromethyl, cyclopropyl, cyclobutyl, cyclopentyl, cyclohexyl,

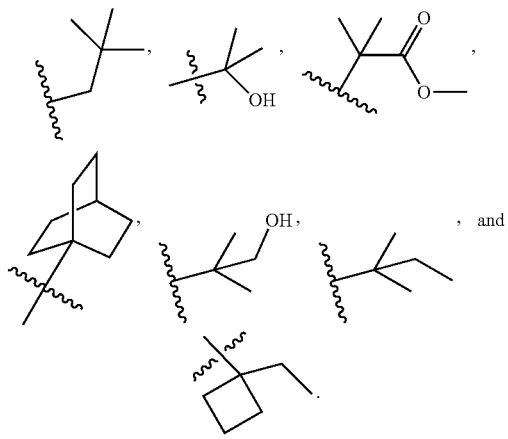

In some embodiments, $R_2$ is selected from hydrogen, $C_{1-5}$ alkyl, $C_{2-5}$ alkenyl, and $C_{2-5}$ alkynyl. In some embodiments, $R_2$ is hydrogen or $C_{1-5}$ alkyl.

In some embodiments, $R_2$ is selected from hydrogen, methyl, and ethyl.

In some embodiments, $R_1$ and $R_2$ together with the carbon to which they are attached from a 6 to 12 membered aryl, 3 to 11 membered cycloalkyl, 5 to 12 membered heteroaryl, or 4 to 12 membered heterocyclyl, and provided that $R_3$ is absent when the carbon to which $R_1$ and $R_2$ are attached is part of an aromatic or double bond, wherein each of the 6 to 12 membered aryl, 3 to 11 membered cycloalkyl, 5 to 12 membered heteroaryl, and 4 to 12 membered heterocyclyl is optionally further substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and wherein $R_6$, $R_7$, and W are the same as defined for Formula I.

In some embodiments, $R_1$ and $R_2$ together with the carbon to which they are attached from a 6 to 12 membered aryl, 3 to 11 membered cycloalkyl, or 5 to 12 membered heteroaryl, provided that $R_3$ is absent when the carbon to which $R_1$ and $R_3$ are attached is part of an aromatic or double bond, wherein each of the 6 to 12 membered aryl, 3 to 11 membered cycloalkyl, and 5 to 12 membered heteroaryl is optionally further substituted with at least one group selected from $C_{1-6}$ alkyl, $C_{2-6}$ alkoxyalkyl, $C_{2-6}$ alkenyl, —$NR_6R_7$, $C_{1-6}$ alkyl-C(O)O—, —C(O)O—$C_{1-6}$ alkyl, C(O)$NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and wherein $R_6$, $R_7$, and W are the same as defined for Formula I.

In some embodiments, $R_1$ and $R_2$ together with the carbon to which they are attached form 6 to 12 membered aryl, 3 to 11 membered cycloalkyl, or 5 to 12 membered heteroaryl, provided that $R_3$ is absent when the carbon to which $R_1$ and $R_3$ are attached is part of an aromatic or double bond, wherein each of the 6 to 12 membered aryl, 3 to 11 membered cycloalkyl, and 5 to 12 membered heteroaryl is optionally substituted with at least one group selected from $C_{1-6}$ alkyl, $OR_6$, and halo, and wherein $R_6$ is selected from hydrogen, $C_{1-6}$ alkyl, 3 to 7 membered cycloalkyl, $C_{1-6}$ haloalkyl, $C_{2-5}$ alkenyl, and $C_{2-5}$ alkynyl.

In some embodiments, $R_1$ and $R_2$ together with the carbon to which they are attached form phenyl, indane, 1,2,3,4-tetrahydronaphthalene, chromane, isochromane, 1,2,3,4-tetrahydroquinoline, thiochromane 1,1-dioxide, 6,7,8,9-tetrahydro-5H-benzo[7]annulene, 2,3-dihydrobenzofuran, cyclopropyl, cyclobutyl, cyclopentane, cyclohexane, cyclohexene, cycloheptane, (1s,4s)-bicyclo[2.2.1]heptane, spiro[2.5]octane, spiro[3.5]nonane, spiro[4.5]decane, [5.5]undecane, 5,6,7,8-tetrahydro-4H-cyclohepta[b]furan, 4,5,6,7-tetrahydrobenzofuran, 4,5,6,7-tetrahydrobenzo[b]thiophene, or 4,5,6,7-tetrahydro-1H-indole, each of which is optionally substituted with least one group selected from $C_{1-6}$ alkyl, $C_{1-6}$ alkoxy, 5 to 8 membered heteroaryl, and halo.

In some embodiments, $R_1$ and $R_2$ together with the carbon to which they are attached form a ring selected from

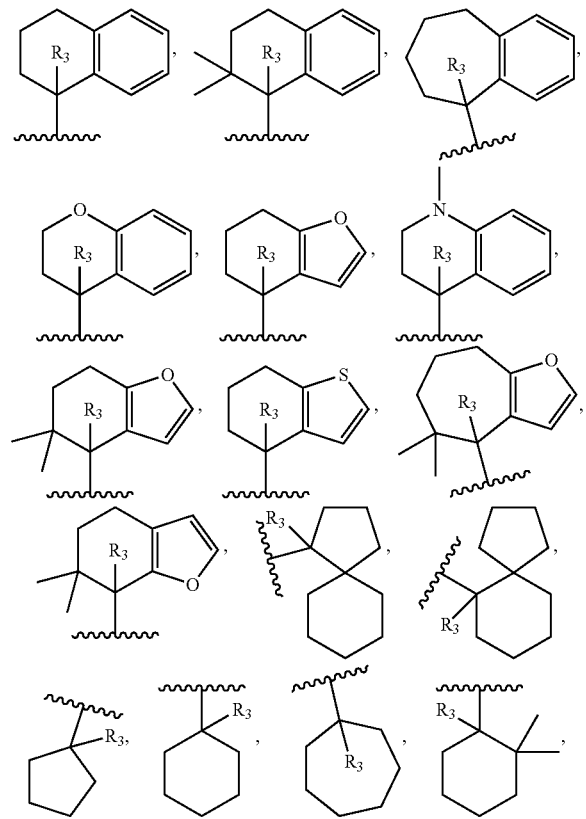

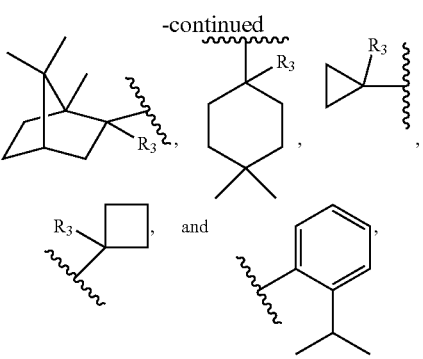

wherein ⌇ indicates the point of attachment to NH.

In some embodiments, $R_3$ is selected from hydrogen, —$CO_2R_6$, —$C(O)NR_6R_7$, $C_{2-5}$ alkenyl, $C_{2-5}$ alkynyl, 6 to 12 membered aryl, 3 to 11 membered cycloalkyl, 5 to 12 membered heteroaryl, and $C_{1-10}$ alkyl optionally substituted with at least one group selected from $OR_6$, 6 to 12 membered aryl, 3 to 11 membered cycloalkyl, —$CO_2R_6$, —$C(O)NR_6R_7$, halo, 5 to 12 membered heteroaryl, 4 to 12 membered heterocyclyl, $C_{2-5}$ alkenyl, and $C_{2-5}$ alkynyl, wherein each of the 6 to 12 membered aryl, 3 to 11 membered cycloalkyl, 5 to 12 membered heteroaryl, and 4 to 12 membered heterocyclyl is optionally further substituted with at least one group selected from $C_{1-6}$ alkyl, $C_{2-6}$ alkoxyalkyl, $C_{2-6}$ alkenyl, —$NR_6R_7$, $C_{1-6}$ alkyl-$C(O)O$—, —$C(O)O$—$C_{1-6}$ alkyl, $C(O)NR_6R_7$, —$NR_6C(O)R_7$, halo, $OR_6$, $R_6S(O)_2O$— (sulfonate), phosphonate, 6 to 12 membered aryl optionally substituted with at least one group selected from W, 3 to 11 membered cycloalkyl optionally substituted with at least one group selected from W, 5 to 12 membered heteroaryl optionally substituted with at least one group selected from W, and 4 to 12 membered heterocyclyl optionally substituted with at least one group selected from W, and wherein $R_6$, $R_7$, and W are the same as defined for Formula I.

In some embodiments, $R_3$ is selected from hydrogen, —$C(O)NR_6R_7$, $C_{2-5}$ alkenyl, $C_{2-5}$ alkynyl, phenyl, 3 to 8 membered cycloalkyl, 5 to 8 membered heteroaryl, and $C_{1-6}$ alkyl optionally substituted with at least one group selected from $OR_6$, 3 to 8 membered cycloalkyl, and phenyl, wherein each of the phenyl, 3 to 8 membered cycloalkyl, and 5 to 8 membered heteroaryl is optionally further substituted with at least one group selected from $C_{1-6}$ alkyl, alkoxylalkyl, $C_{2-6}$ alkenyl, halo, and $OR_6$, and wherein $R_6$ and $R_7$ are independently selected from hydrogen, $C_{1-6}$ alkyl, 3 to 6 membered cycloalkyl, $C_{1-6}$ haloalkyl, $C_{2-5}$ alkenyl, and $C_{2-5}$ alkynyl.

In some embodiments, $R_3$ is selected from hydrogen, —$C(O)NR_6R_7$, $C_{2-5}$ alkenyl, $C_{2-5}$ alkynyl, phenyl, 3 to 8 membered cycloalkyl, 5 to 8 membered heteroaryl, and $C_{1-6}$ alkyl optionally substituted with at least one group selected from methoxy, ethoxy, cyclobutyl, cyclopentyl, cyclohexyl, and phenyl, wherein each of the phenyl, 3 to 8 membered cycloalkyl, and 5 to 8 membered heteroaryl is optionally substituted with at least one group selected from $C_{1-6}$ alkyl, $OR_6$, and halo, and wherein $R_6$ and $R_7$ are independently selected from hydrogen, $C_{1-6}$ alkyl, and 3 to 6 membered cycloalkyl.

In some embodiments, $R_3$ is selected from hydrogen, methyl, ethyl, propyl, tert-butyl, cyclopropyl, cyclobutyl, cyclopentyl, cyclohexyl, ethynyl, phenyl,

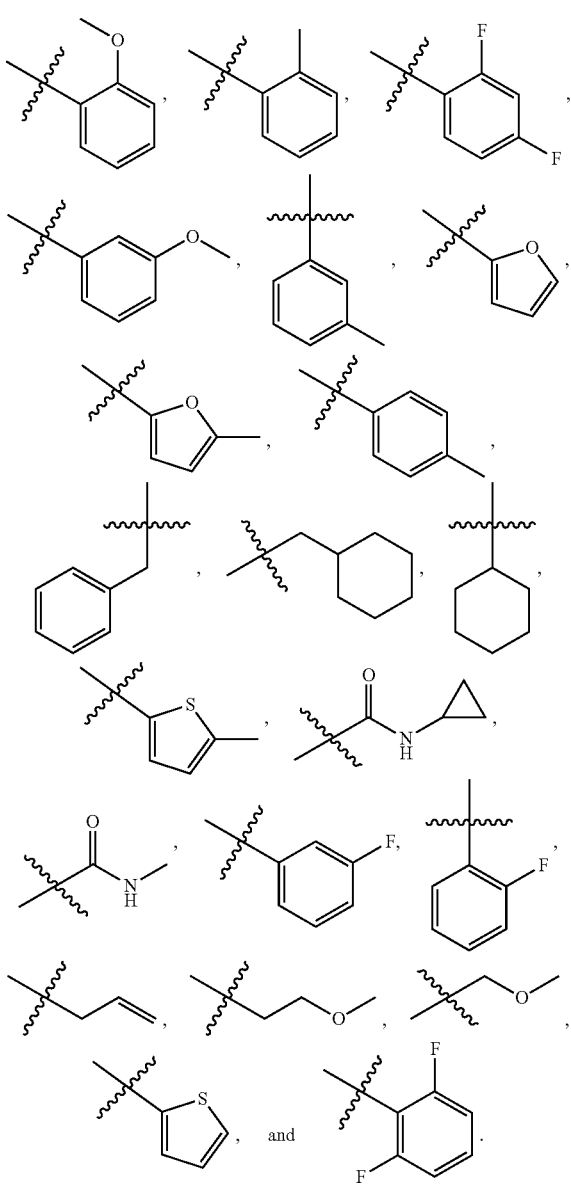

In some embodiments, $R_4$ is selected from —C(O)NR$_6$R$_7$ and —SO$_2$NR$_6$R$_7$, $R_6$ and $R_7$ are independently selected from i) hydrogen, ii) $C_{1-6}$ alkyl, $C_{1-6}$ haloalkyl, $C_{1-6}$ hydroxyalkyl, $C_{2-6}$ alkoxyalkyl, aralkyl, iii) $C_{2-5}$ alkenyl, $C_{2-5}$ alkynyl, iv) 6 to 12 membered aryl optionally substituted with at least one group selected from W, v) 3 to 11 membered cycloalkyl optionally substituted with at least one group selected from W, vi) 5 to 12 membered heteroaryl optionally substituted with at least one group selected from W, and vii) 4 to 12 membered heterocyclyl optionally substituted with at least one group selected from W, or $R_6$ and $R_7$ together with the nitrogen to which they are attached form a 4 to 12 membered heterocyclyl optionally substituted with at least one group selected from W, W consists of $C_{1-6}$ alkyl, $C_{2-5}$ alkenyl, $C_{2-5}$ alkynyl, halo, $C_{1-6}$ alkoxy, and hydroxyl.

In some embodiments, $R_4$ is selected from —C(O)NR$_6$R$_7$ and —SO$_2$NR$_6$R$_7$, $R_6$ and $R_7$ are independently selected from hydrogen, $C_{1-6}$ alkyl, $C_{1-6}$ haloalkyl, $C_{1-6}$ hydroxyalkyl, $C_{2-6}$ alkoxyalkyl, and aralkyl, or $R_6$ and $R_7$ together with the nitrogen to which they are attached form a 4 to 12 membered heterocyclyl optionally substituted with at least one group selected from $C_{1-6}$ alkyl, halo, $C_{1-6}$ alkoxy, and hydroxyl. In some embodiments, $R_6$ and $R_7$ together with the nitrogen to which they are attached form a pyrrolidine, piperidine, piperazine, or morpholine, wherein each of the pyrrolidine, piperidine, piperazine, and morpholine is optionally substituted with at least one group selected from $C_{1-6}$ alkyl.

In some embodiments, $R_4$ is —C(O)NR$_6$R$_7$, $R_6$ and $R_7$ are independently selected from hydrogen, $C_{1-6}$ alkyl, $C_{1-6}$ haloalkyl, $C_{1-6}$ hydroxyalkyl, and aralkyl, or $R_6$ and $R_7$ together with the nitrogen to which they are attached form a 4 to 12 membered heterocyclyl optionally substituted with at least one group selected from $C_{1-6}$ alkyl, halo, $C_{1-6}$ alkoxy, and hydroxyl. In some embodiments, $R_6$ and $R_7$ are independently selected from $C_{1-6}$ alkyl, $C_{1-6}$ hydroxyalkyl, and aralkyl. In some embodiments, $R_6$ and $R_7$ together with the nitrogen to which they are attached form a 4 to 12 membered heterocyclyl optionally substituted with at least one group selected from $C_{1-6}$ alkyl. In some embodiments, $R_6$ and $R_7$ together with the nitrogen to which they are attached form a pyrrolidine, piperidine, piperazine, or morpholine, wherein each of the pyrrolidine, piperidine, piperazine, and morpholine is optionally substituted with at least one group selected from $C_{1-6}$ alkyl.

In some embodiments, $R_4$ is —SO$_2$NR$_6$R$_7$, $R_6$ and $R_7$ are independently selected from hydrogen, $C_{1-6}$ alkyl, $C_{1-6}$ haloalkyl, $C_{1-6}$ hydroxyalkyl, and aralkyl, or $R_6$ and $R_7$ together with the nitrogen to which they are attached form a 4 to 12 membered heterocyclyl optionally substituted with at least one group selected from $C_{1-6}$ alkyl, halo, $C_{1-6}$ alkoxy, and hydroxyl. In some embodiments, $R_6$ and $R_7$ are independently selected from $C_{1-6}$ alkyl, $C_{1-6}$ hydroxyalkyl, and aralkyl. In some embodiments, $R_6$ and $R_7$ together with the nitrogen to which they are attached form a 4 to 12 membered heterocyclyl optionally substituted with at least one group selected from $C_{1-6}$ alkyl. In some embodiments, $R_6$ and $R_7$ together with the nitrogen to which they are attached form a pyrrolidine, piperidine, piperazine, or morpholine, wherein each of the pyrrolidine, piperidine, piperazine, and morpholine is optionally substituted with at least one group selected from $C_{1-6}$ alkyl.

In some embodiments, $R_4$ is selected from

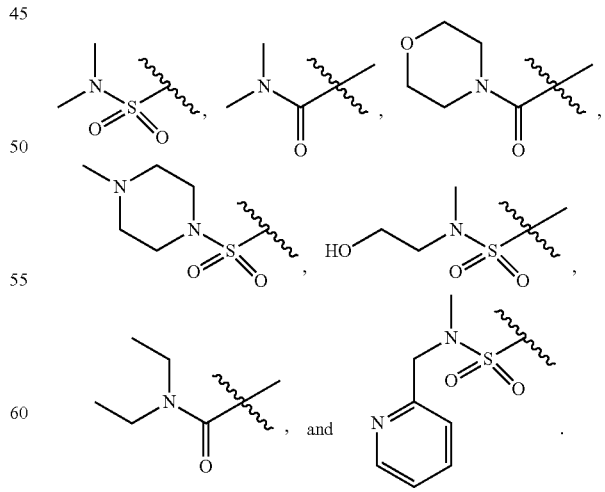

In some embodiments, $R_4$ is halo.
In some embodiments, $R_5$ is selected from hydrogen, $C_{1-6}$ alkyl, and halo.

In some embodiments, $R_5$ is hydrogen or halo. In some embodiments, $R_5$ is hydrogen. In some embodiments, $R_5$ is halo. In some embodiments, $R_5$ is chlorine.

In some embodiments, $R_6$ and $R_7$ are independently selected from hydrogen, $C_{1-6}$ alkyl, $C_{1-6}$ haloalkyl, $C_{1-6}$ hydroxyalkyl, and aralkyl, or $R_6$ and $R_7$ together with the nitrogen to which they are attached form a 4 to 12 membered heterocyclyl optionally substituted with at least one group selected from $C_{1-6}$ alkyl, halo, $C_{1-6}$ alkoxy, and hydroxyl.

In some embodiments, the moiety:

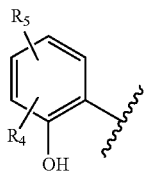

in Formula I is of the form:

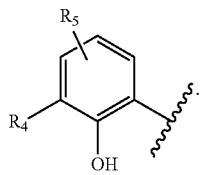

In some embodiments, the moiety:

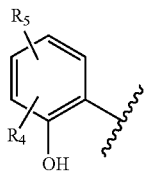

in Formula I is of the form:

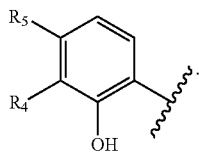

Each embodiment for each of $R_1$-$R_7$, as disclosed herein, can be in any combination with one another, unless otherwise provided for.

In some embodiments, the compound of Formula I or a pharmaceutically acceptable salt thereof is selected from

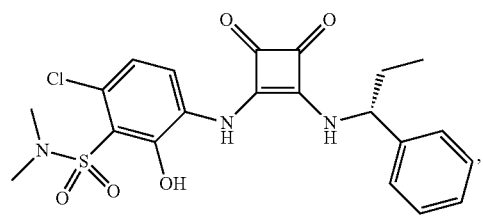

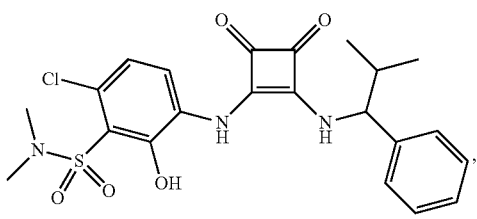

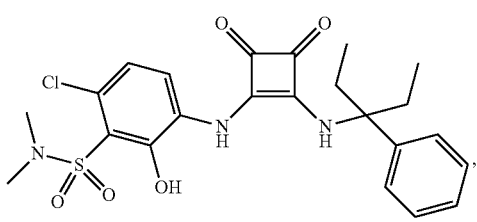

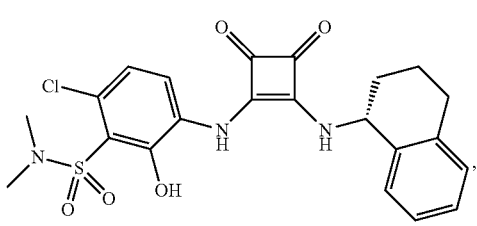

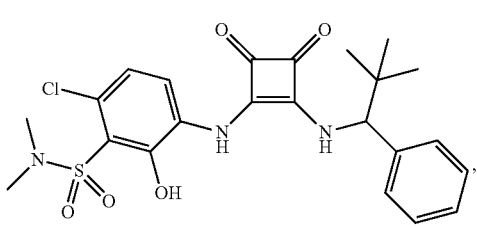

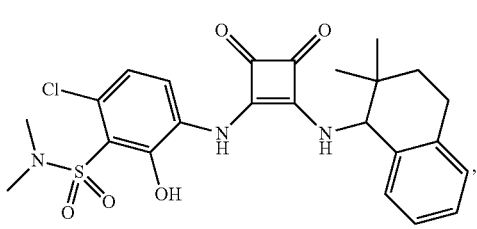

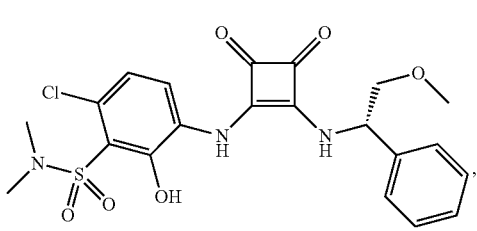

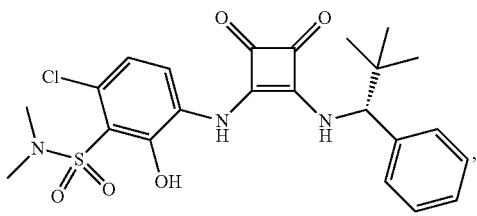

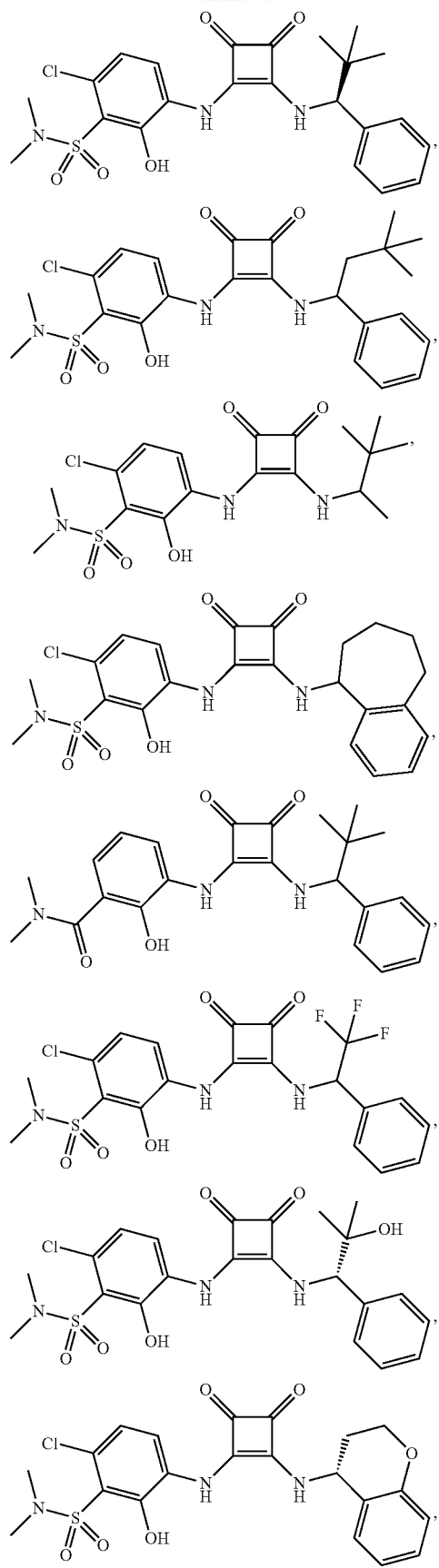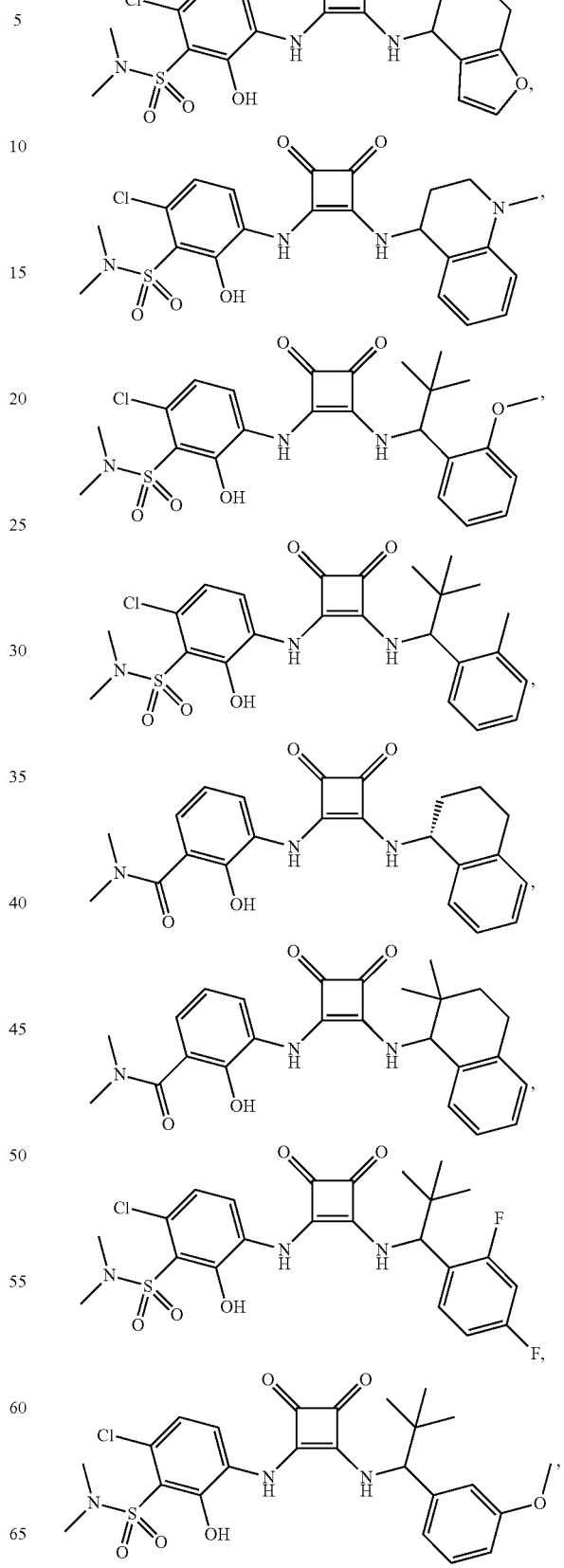

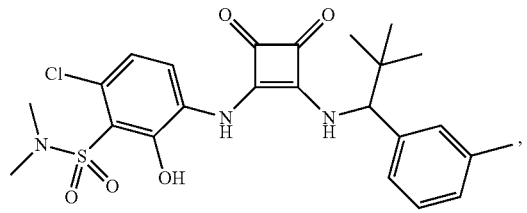
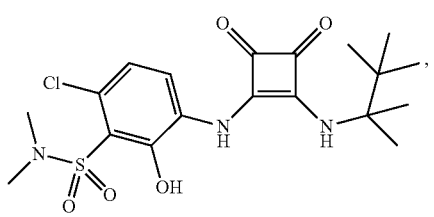
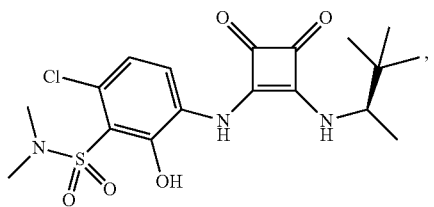
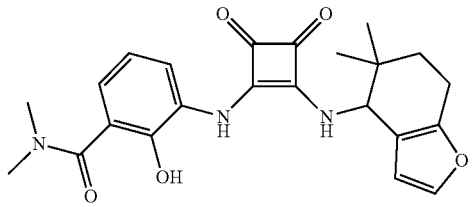
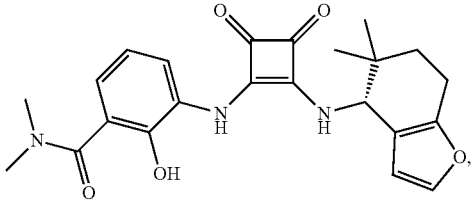
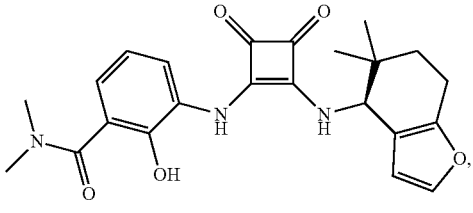
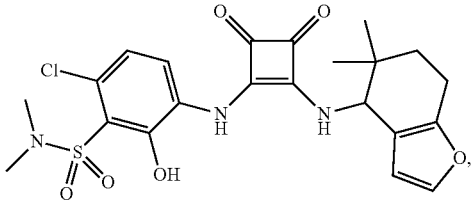
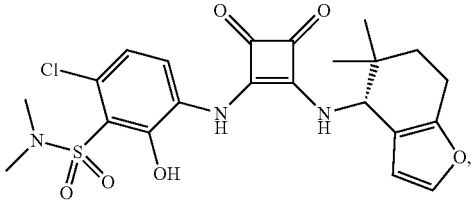
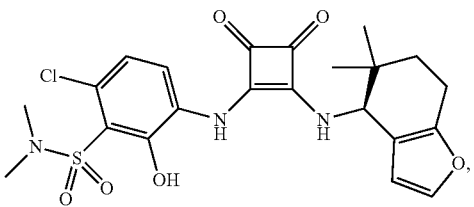
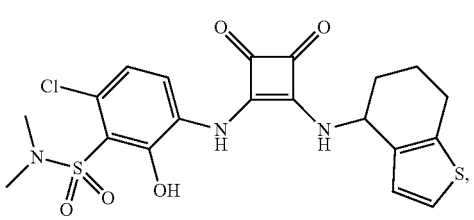
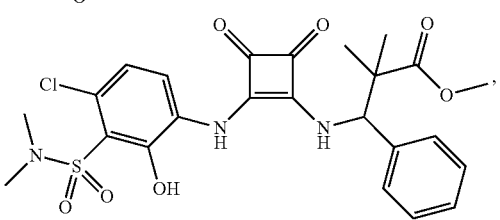
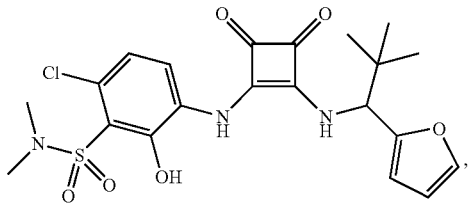
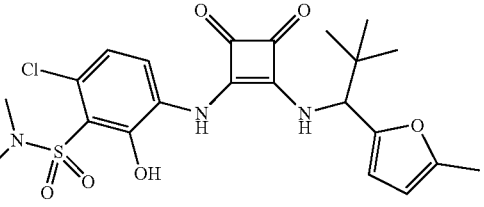
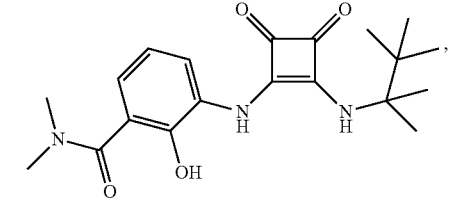
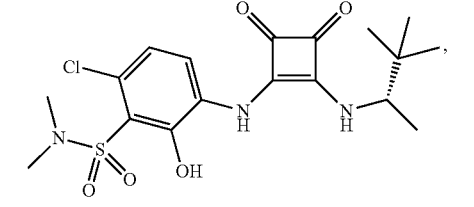
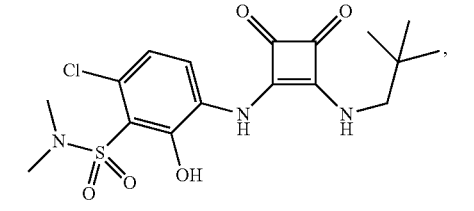

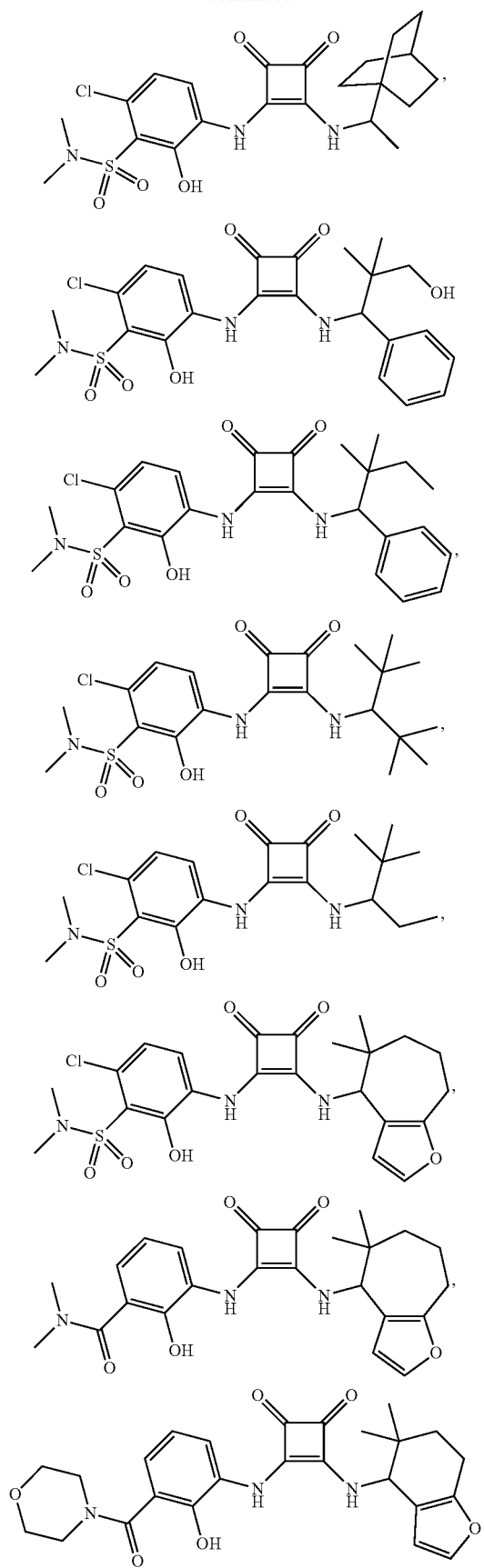
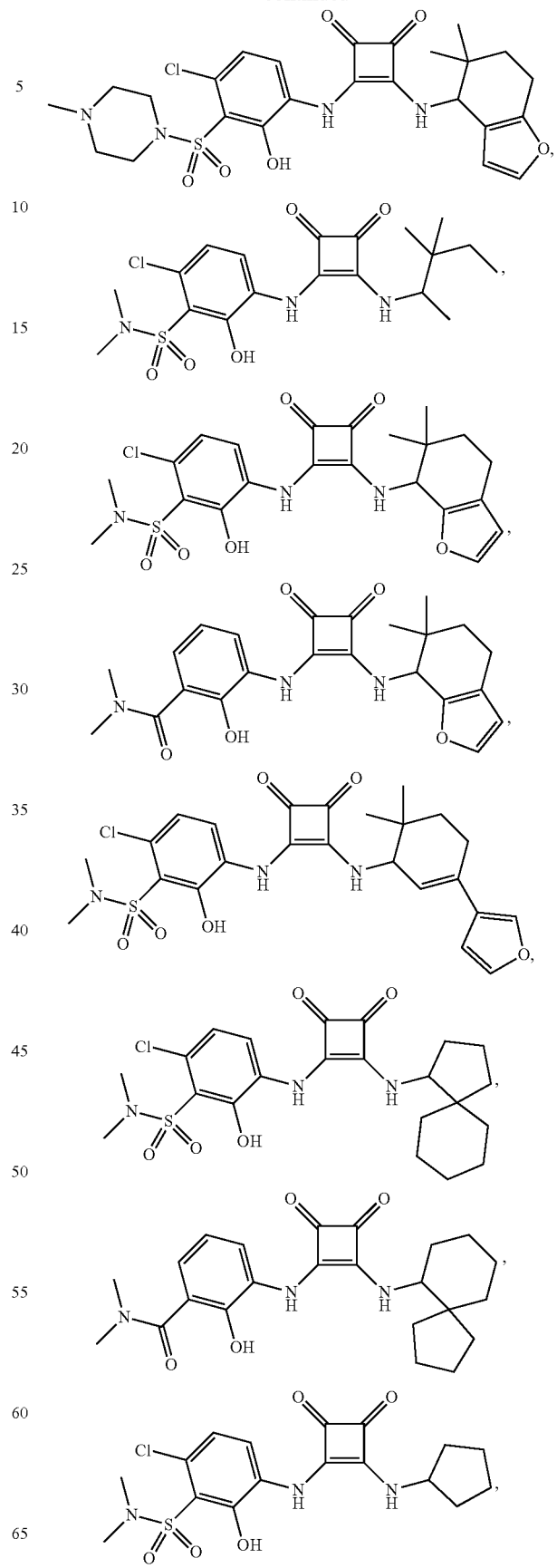

69
-continued
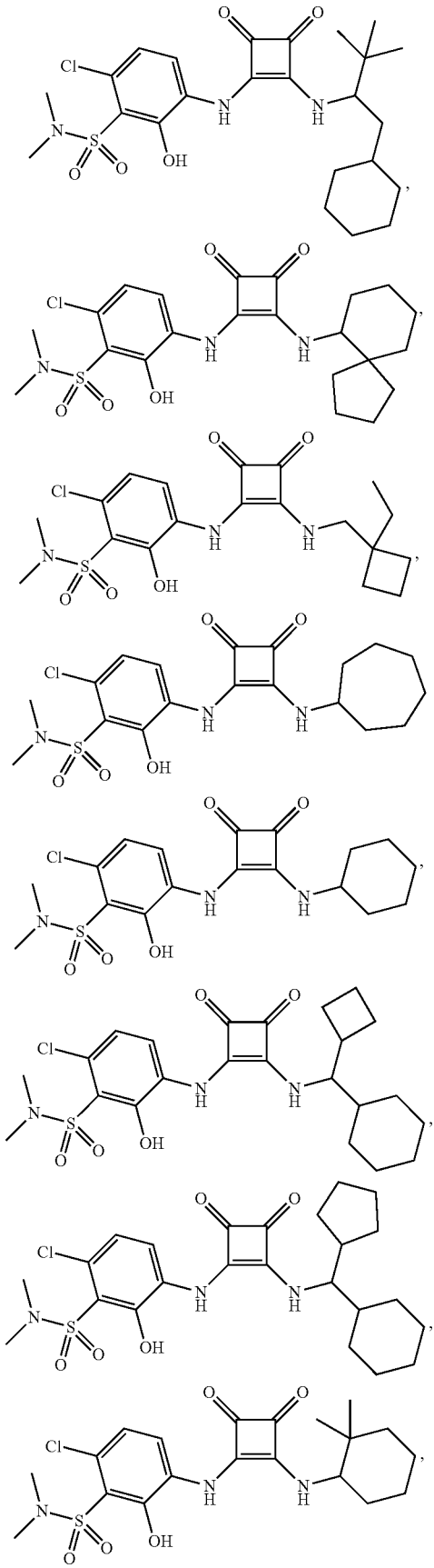
70
-continued
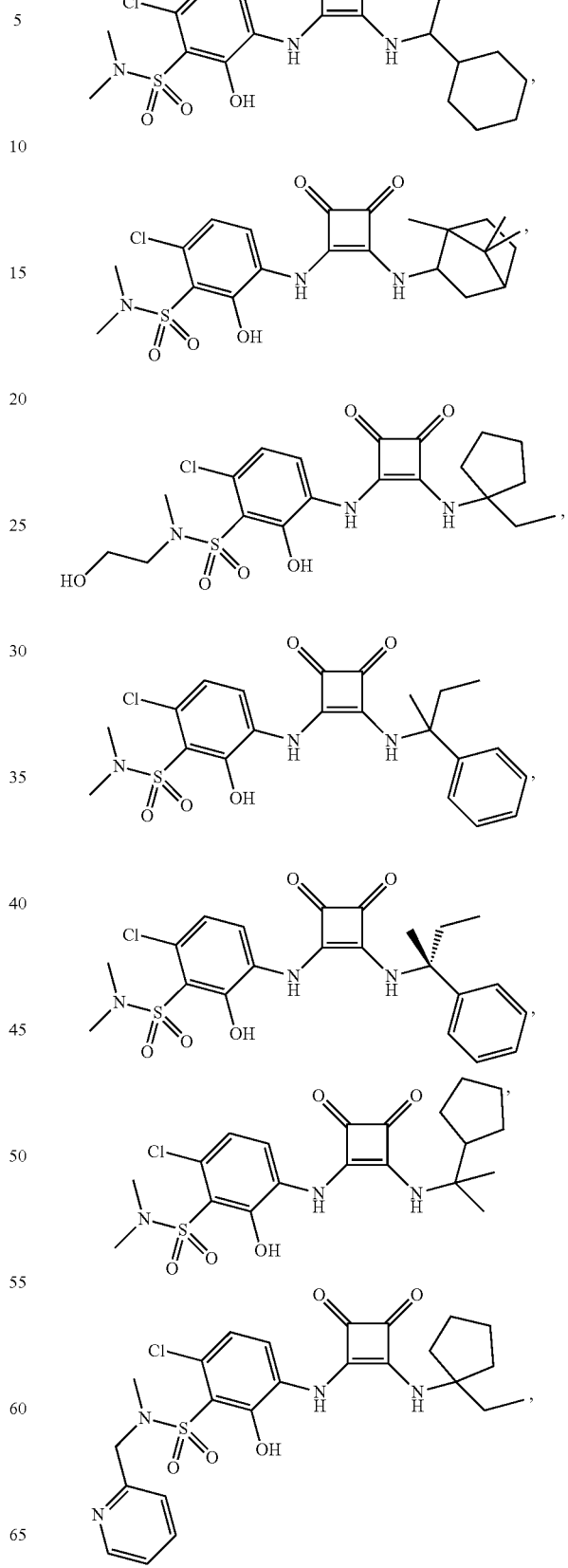

-continued
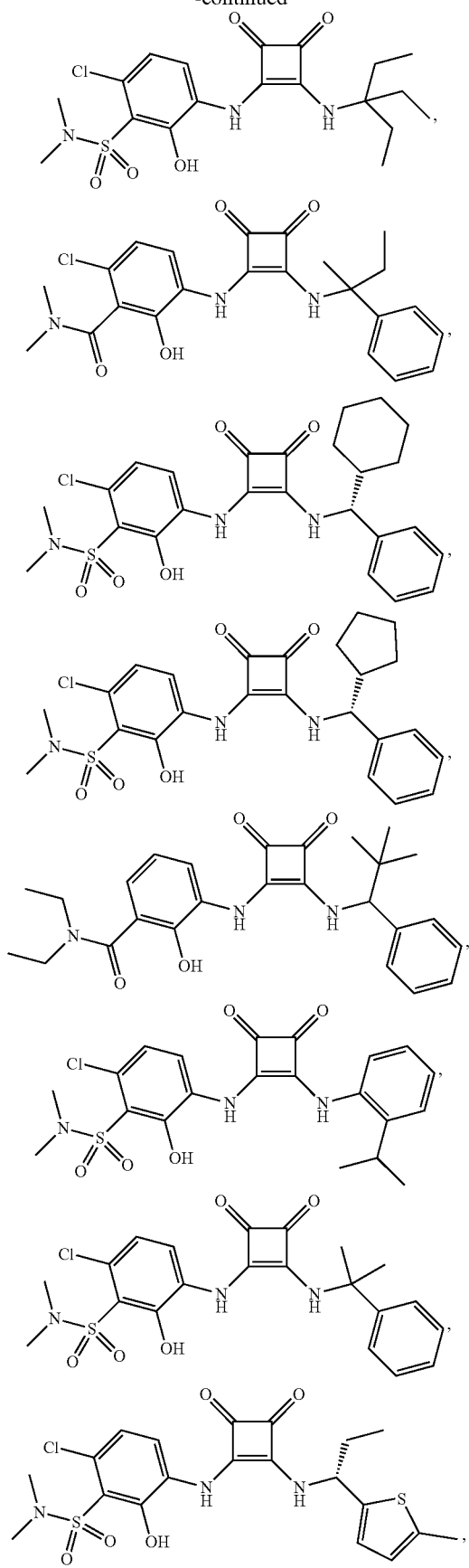
-continued
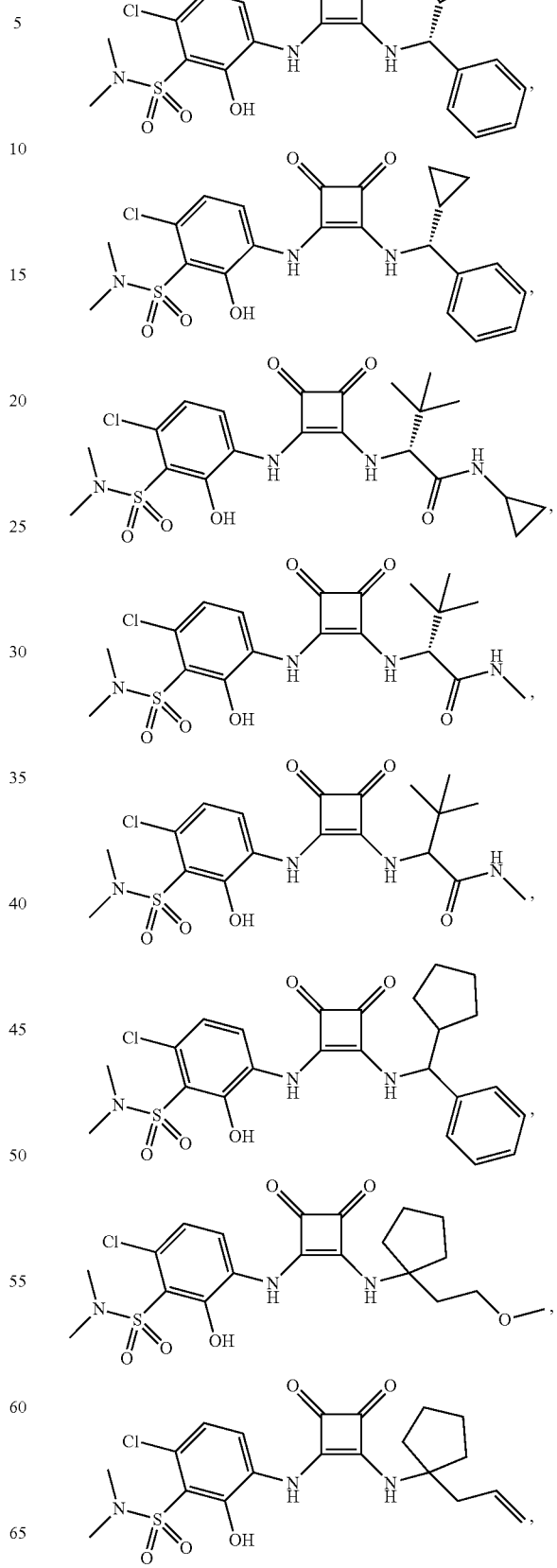

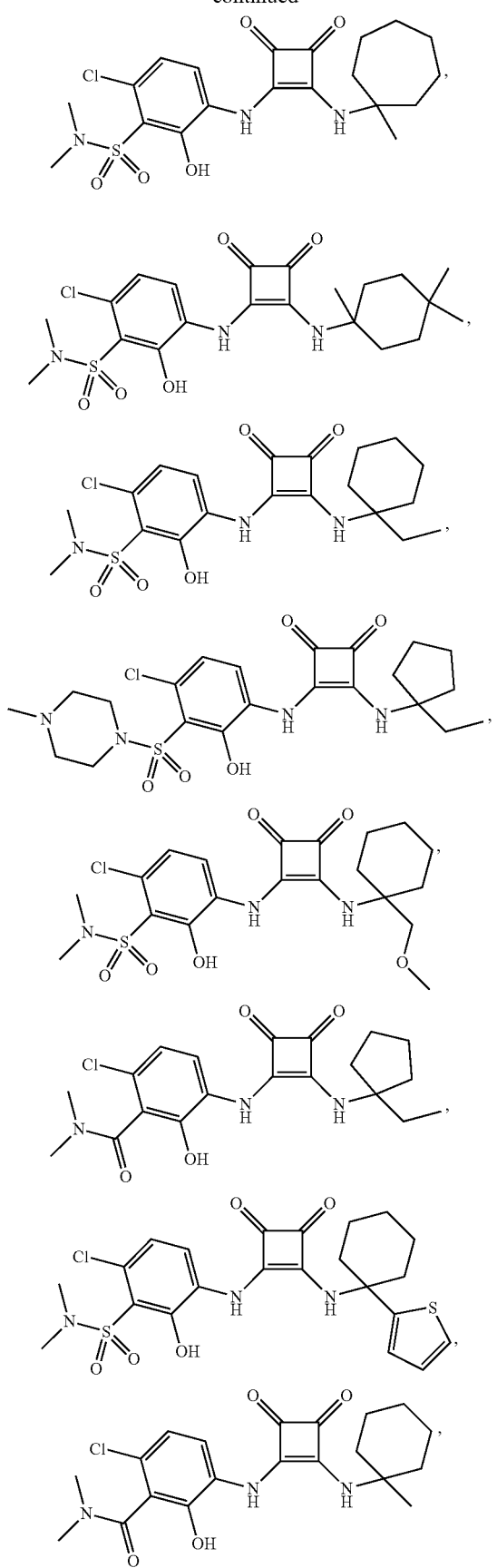
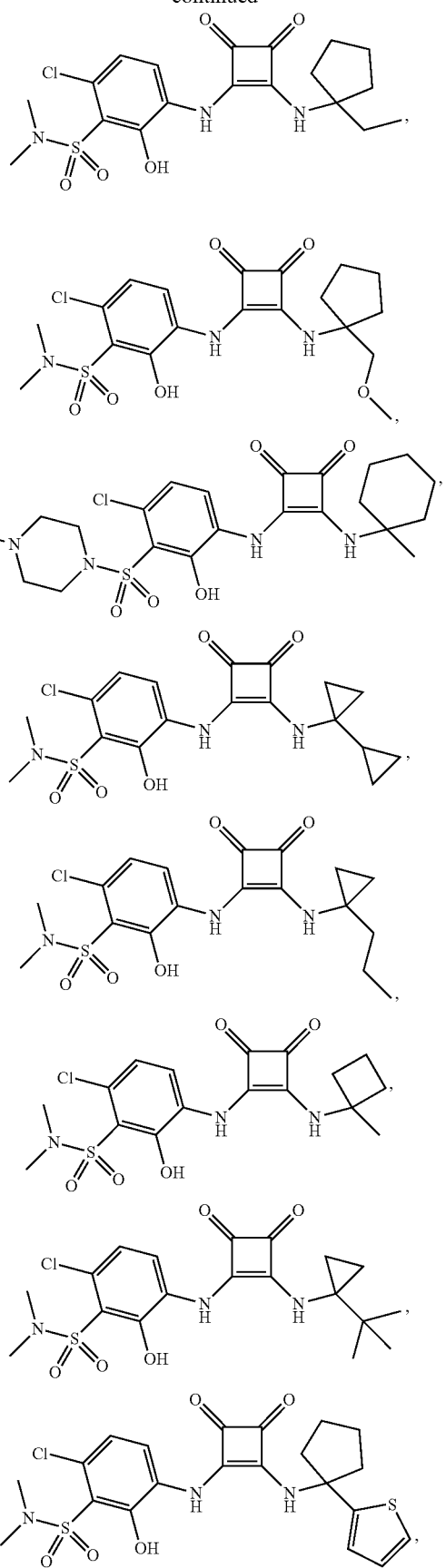

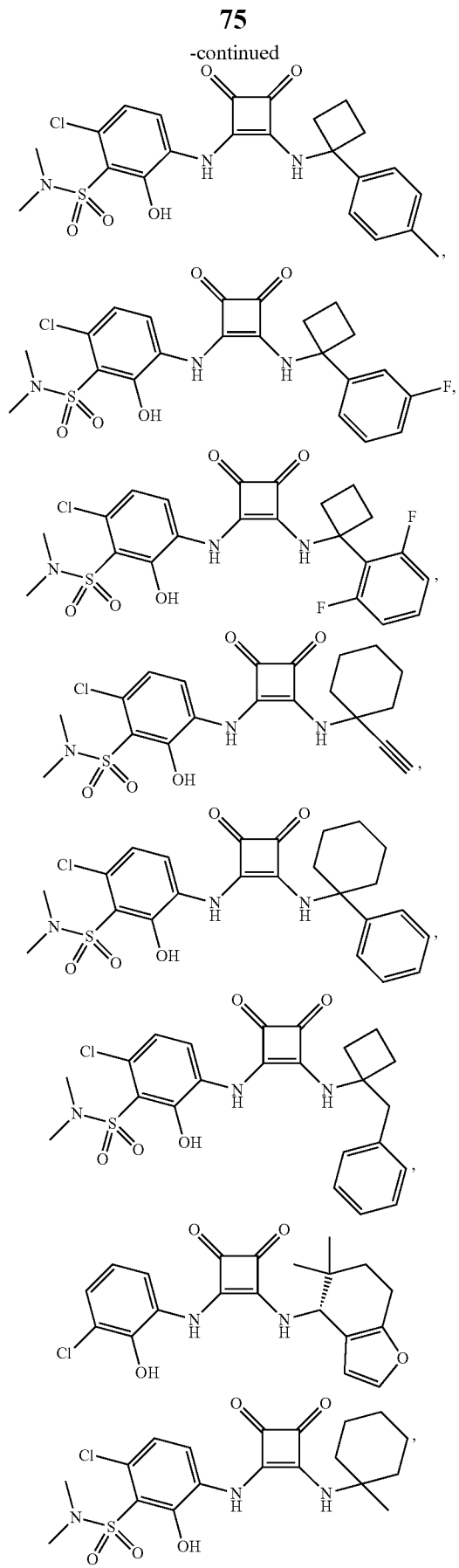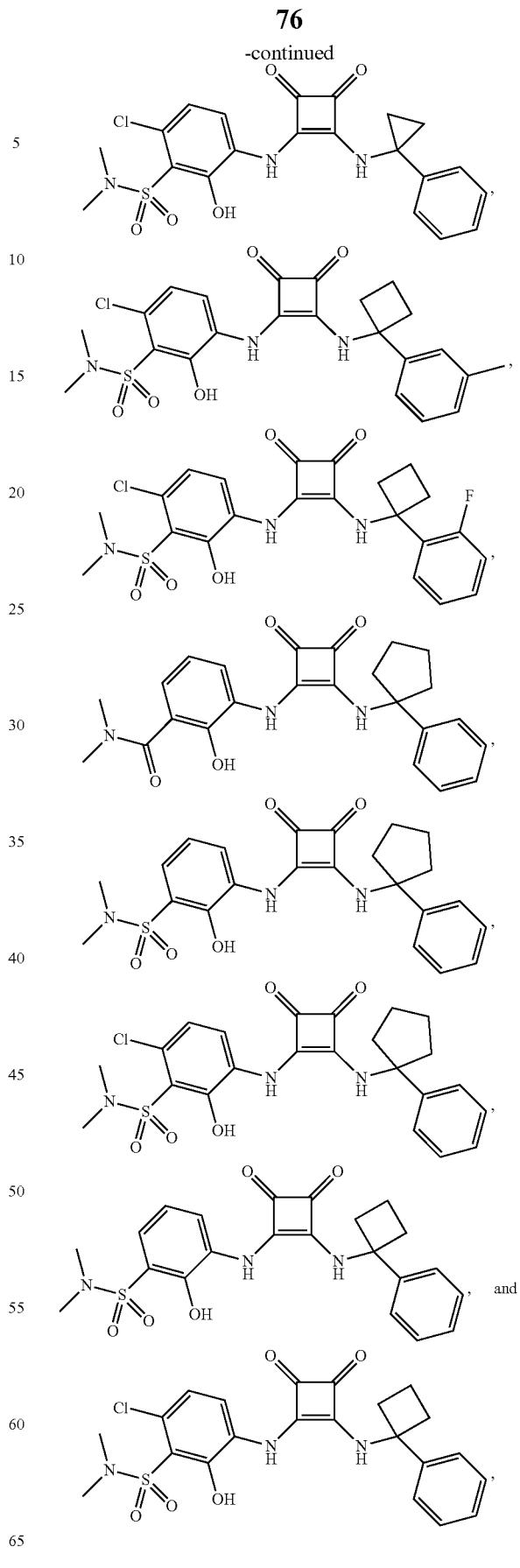
or a pharmaceutically acceptable salt thereof.

In some embodiments, the compounds described herein (e.g. compounds of Formula I) can be deuterated, wherein one or more of the hydrogens atoms ($^1H$ atoms) are replaced with deuterium ($^2H$ or D). Non-limiting example deuterated compounds and syntheses are shown in schemes 1-8 below.
Scheme 1:
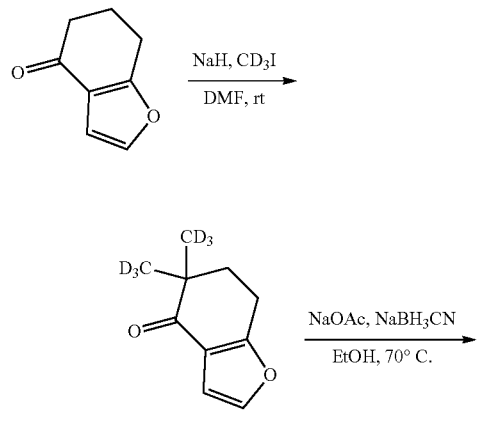
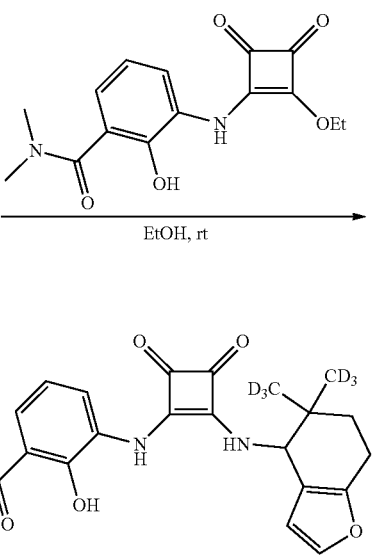
Scheme 3:
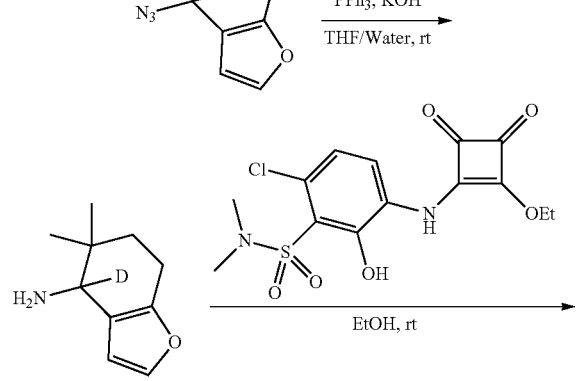
Scheme 2:
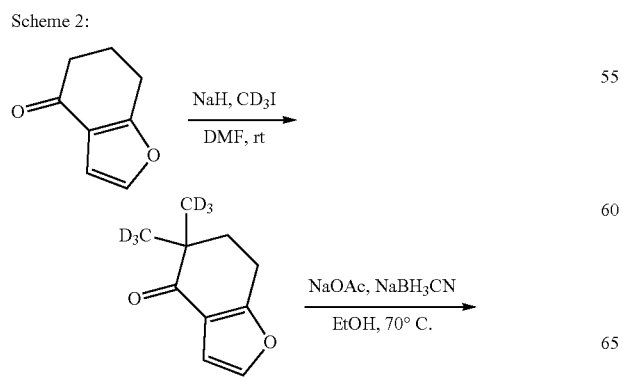
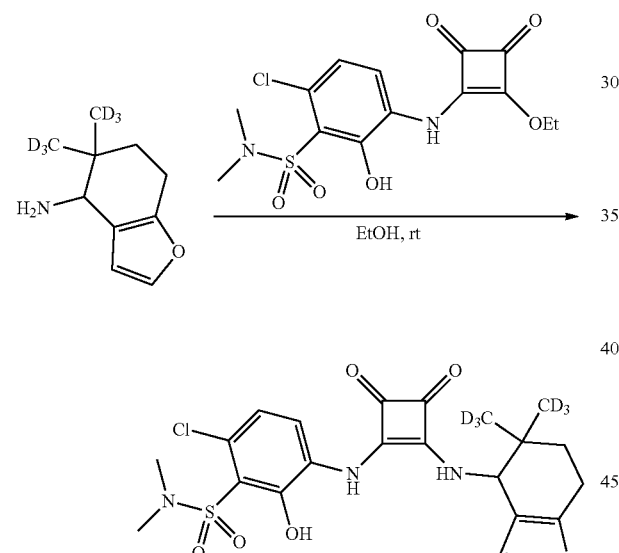

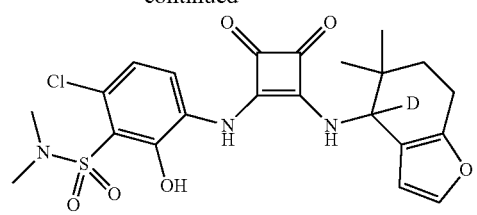
Scheme 4:
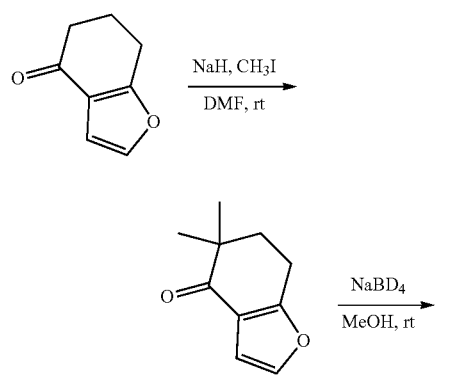
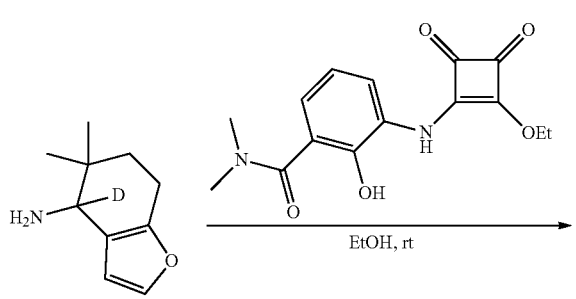
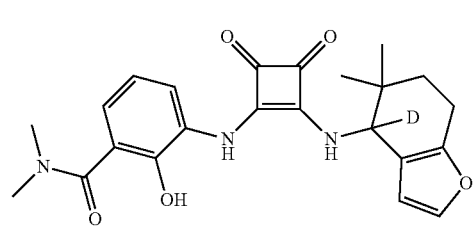
Scheme 5:
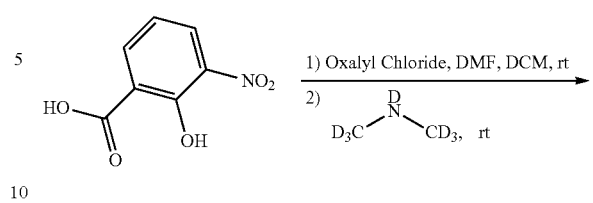
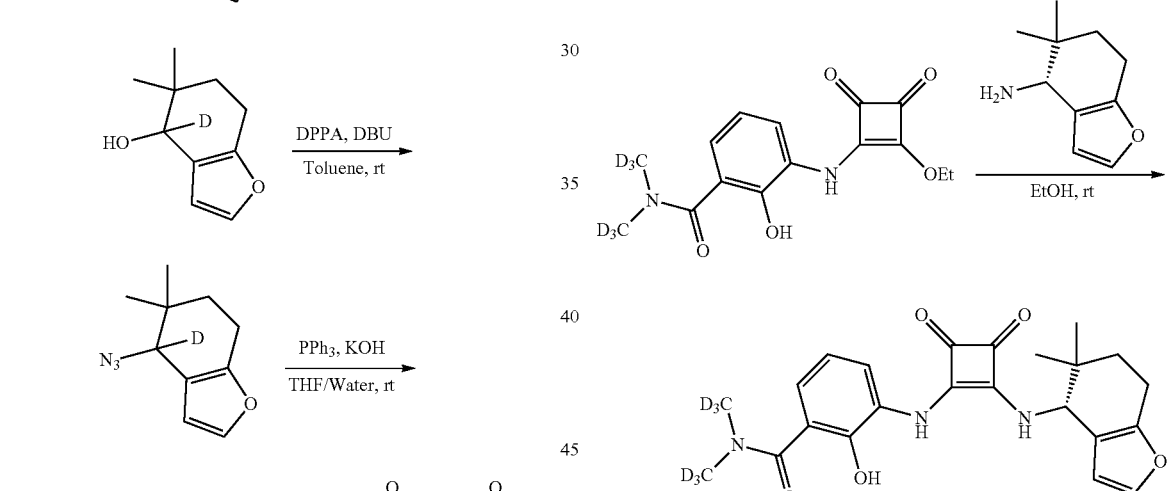
Scheme 6:
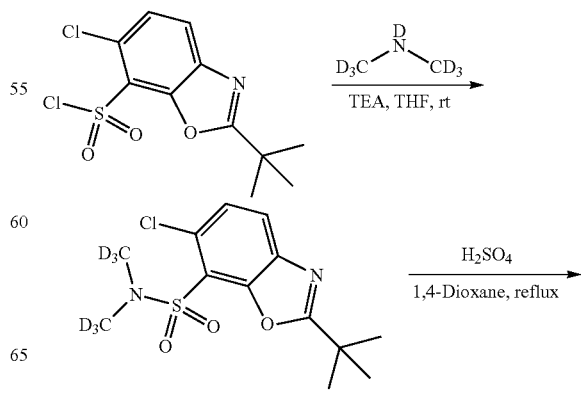

-continued
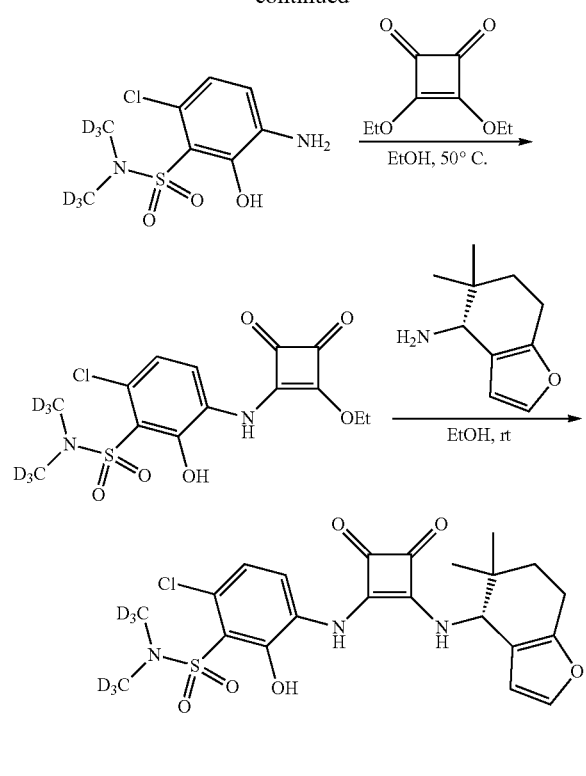
Scheme 7:
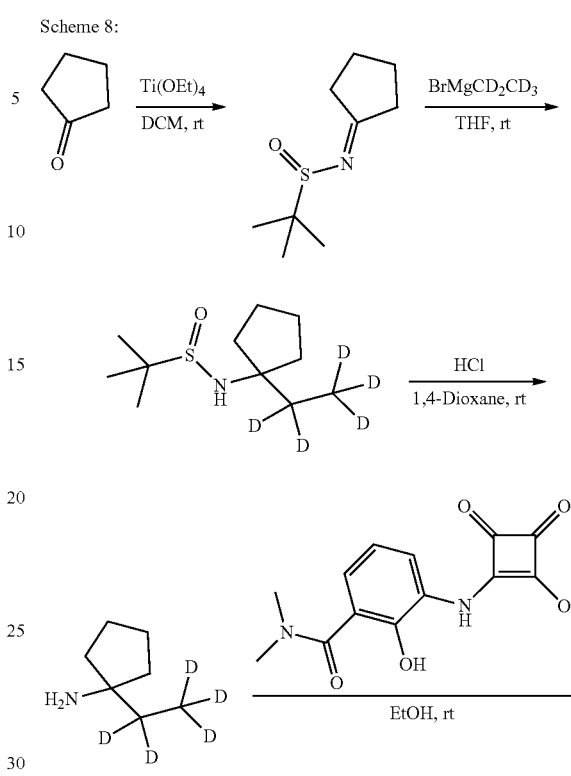
Scheme 8:
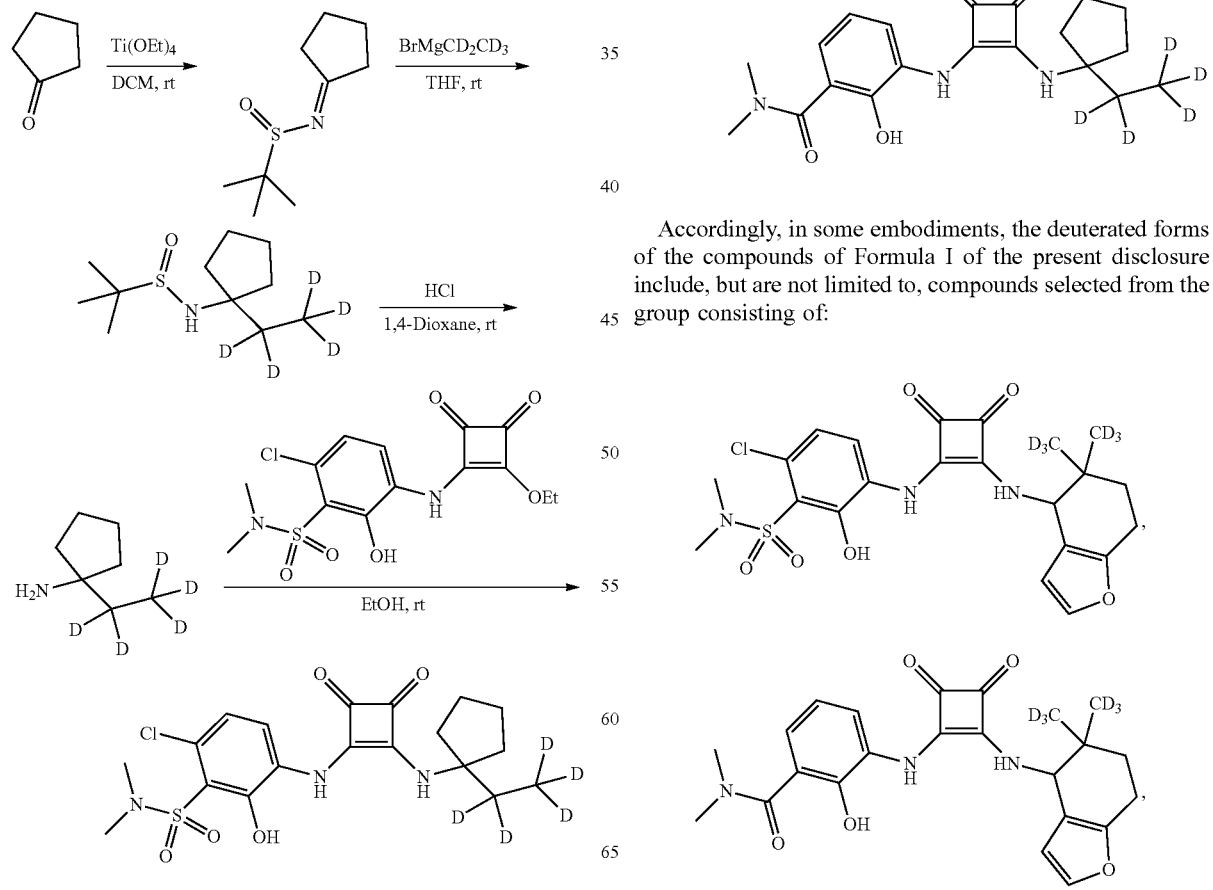
Accordingly, in some embodiments, the deuterated forms of the compounds of Formula I of the present disclosure include, but are not limited to, compounds selected from the group consisting of:
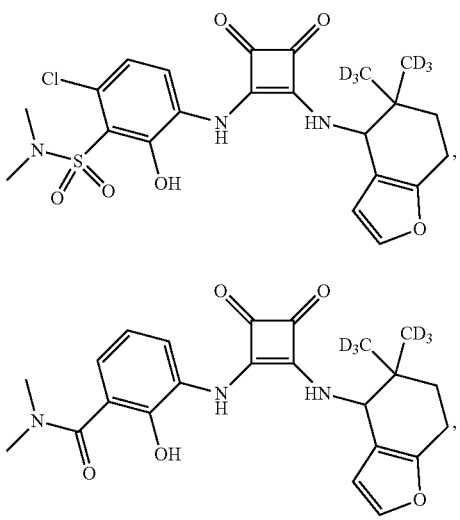

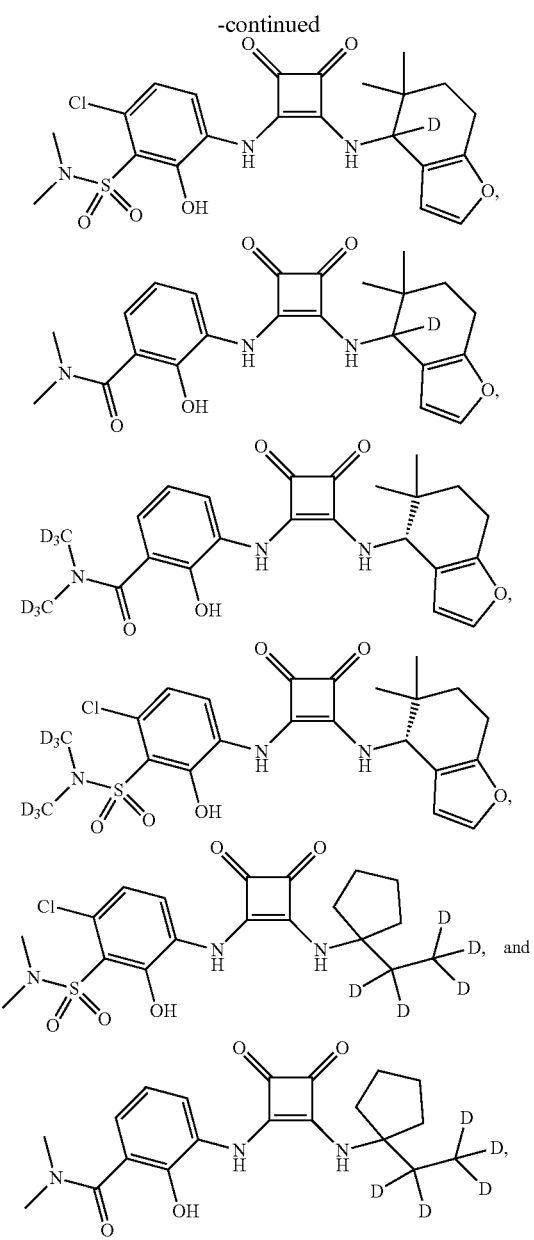

and pharmaceutically acceptable salts thereof.

III. Compositions Comprising the Compounds

In a second aspect, the present disclosure is directed to a composition comprising a compound of Formula I or a pharmaceutically acceptable salt thereof disclosed in the present specification. A composition comprising a compound of Formula I or a pharmaceutically acceptable salt thereof is generally administered to an individual as a pharmaceutical composition. As used herein, the term "pharmaceutical composition" refers to a therapeutically effective amount of an active compound (CCR6 antagonist), such as, e.g., any of the compound of Formula I or a pharmaceutically acceptable salt thereof disclosed in the present specification. A pharmaceutical composition comprising a compound of Formula I or a pharmaceutically acceptable salt thereof is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

In general, the compound of Formula I or a pharmaceutically acceptable salt thereof can be administered in a therapeutically effective amount by any of the accepted modes of administration. Therapeutically effective amounts of compounds of Formula I may range from about 0.01 to about 500 mg per kg patient body weight per day, which can be administered in single or multiple doses. For example, the dosage level will be about 0.01 to about 250 mg/kg per day, about 0.05 to about 100 mg/kg per day, about 0.1 to about 50 mg/kg per day, about 0.1 to about 250 mg/kg per day, or about 0.5 to about 100 mg/kg per day. Further for example, the dosage can be about 0.05 to about 0.5, about 0.5 to about 5 or about 5 to about 50 mg/kg per day. The compositions may be provided in the form of tablets or capsules for oral administration, containing about 1.0 to about 1000 milligrams of the compound of Formula I or a pharmaceutically acceptable salt thereof, such as about 1.0, 5.0, 10, 15, 20, 25, 50, 75, 100, 150, 200, 250, 300, 400, 500, 600, 750, 800, 900, and 1000 milligrams of the compound of Formula I or a pharmaceutically acceptable salt thereof.

A pharmaceutical composition comprising a compound of Formula I or a pharmaceutically acceptable salt thereof can optionally include a pharmaceutically acceptable carrier that facilitates processing of an active ingredient into pharmaceutically acceptable compositions. As used herein, the term "pharmaceutically acceptable carrier" is synonymous with "pharmaceutically carrier" and refers to any carrier that has substantially no long term or permanent detrimental effect when administered and encompasses terms such as "pharmaceutically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent.

Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmaceutically acceptable carrier can depend on the mode of administration. Except insofar as any pharmaceutically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine and any modifications are well within the scope of one skilled in the art and from the teaching herein.

A pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed.

Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide.

Tonicity adjustors useful in a pharmaceutical composition include, without limitation, salts such as, e.g., sodium chloride, potassium chloride, mannitol or glycerin and other pharmaceutically acceptable tonicity adjustor.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in the pharmaceutical composition disclosed herein.

Thus, in some embodiments, a composition comprises a compound of Formula I or a pharmaceutically acceptable salt thereof disclosed in the present specification. In some embodiments, a pharmaceutical composition comprises a compound of Formula I or a pharmaceutically acceptable salt thereof disclosed in the present specification and a pharmaceutically acceptable carrier. In some embodiments, a pharmaceutical composition comprises a compound of Formula I or a pharmaceutically acceptable salt thereof disclosed in the present specification and a pharmaceutical component. In some embodiments, a pharmaceutical composition comprises a compound of Formula I or a pharmaceutically acceptable salt thereof disclosed in the present specification, a pharmaceutically acceptable carrier, and a pharmaceutical component. In some embodiments, a pharmaceutical composition comprises about 0.001% to about 5% (w/v) of a compound of Formula I or a pharmaceutically acceptable salt thereof, from 0% to 10% (w/v) of a preservative, 0% to 40% (w/v) of a vehicle, 1% to 10% (w/v) of a tonicity adjustor, 0.01% to 10% (w/v) of a buffer, q.s. (w/v) of a pH adjustor, an antioxidant as needed, a surfactant as needed, and purified water as needed to make 100%.

As can be demonstrated by the assays described in Example 133, the compounds disclosed in the present specification are useful in inhibiting CCR6 receptor function. By virtue of this fact, these compounds can have therapeutic use in treating disease-states and conditions responsive to inhibition of CCR6 receptor function or that would benefit from inhibition of CCR6 receptor function.

IV. Methods for Use of the Compounds and the Compositions

In a third aspect, the present disclosure is directed to a method of treating an inflammatory or autoimmune disease in a mammal in need thereof which method comprises administering to the mammal in need thereof, a pharmaceutical composition comprising a therapeutically effective amount of a compound of Formula I (or any of the embodiments thereof described herein) or a pharmaceutically acceptable salt thereof, and a pharmaceutically acceptable carrier. In some embodiments, the anti-inflammatory disease is selected from inflammatory skin diseases and ocular inflammatory diseases. In some embodiments, the disease includes psoriasis, rheumatoid arthritis, multiple sclerosis, Sjogren's disease, GvHD, alopecia areata, uveitis, dry eye, diabetic retinopathy and allergic diseases.

In another aspect, compounds described herein can be used in the manufacture of medicaments for use in a method of treating an inflammatory or autoimmune disease in a mammal in need thereof as described above (e.g. inflammatory skin diseases and/or ocular inflammatory diseases such as psoriasis, rheumatoid arthritis, multiple sclerosis, Sjogren's disease, GvHD, alopecia areata, uveitis, dry eye, diabetic retinopathy and allergic diseases).

V. Examples

The following examples are illustrative in nature and are in no way intended to be limiting.

Example 1

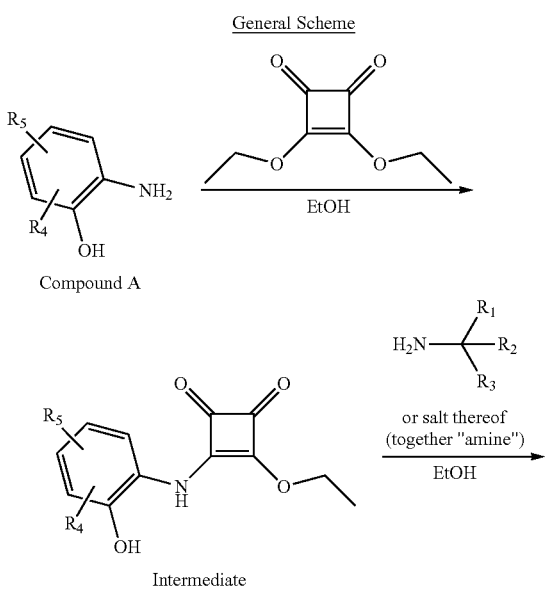

General Scheme

Compound A

Intermediate or salt thereof
(together "amine")

-continued

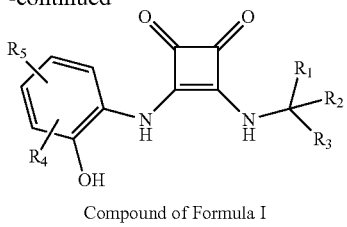

Compound of Formula I

The compound of Formula I can be prepared by following the above general scheme: a mixture of compound A in ethanol is treated with an appropriate amount of 3,4-diethoxycyclobut-3-ene-1,2-dione dropwise at an appropriate temperature that is lower than or at the room temperature. The solution is stirred at room temperature for a sufficient time. The mixture is subsequently concentrated and the resulting residue is purified by flash chromatography to afford the intermediate.

Method A: To a suspension of the intermediate in ethanol is added an appropriate amount of the amine which is in its free basic form. After stirring at room temperature overnight, the mixture is concentrated and the resulting residue is purified by flash chromatography on silica gel using a gradient solvent system of ethyl acetate/hexanes to afford a compound of Formula I.

When applying Method A to other target compounds, the order of addition is reversed in some cases in that the appropriate intermediate is added to a solution of the appropriate amine. For amine starting materials that are sterically hindered and/or less nucleophilic, the reaction medium is carried out at elevated temperatures up to, and including, 80° C. in sealed vessels. In some instances, N,N-diisopropylethylamine is added to the reaction mixture. When performing flash chromatography purification, larger column sizes are used for larger scale reactions as well as different gradients and/or mobile phases depending upon the affinity of the final target compounds towards silica gel. If further purification is required, the crude compound is 1) dissolved in ethyl acetate, washed with 1.0 N aqueous hydrochloric acid (3 times), washed with brine, dried over magnesium sulfate, filtered, and concentrated and/or 2) purified by preparative thin layer chromatography (prep-TLC).

Method B: To a suspension of the intermediate in ethanol is added an appropriate amount of N,N-diisopropylethylamine followed by an appropriate amount of the amine in a salt form. After stirring at ambient temperature overnight, the mixture is concentrated and the resulting residue is purified by flash chromatography on silica gel using a gradient solvent system of ethyl acetate/hexanes to afford a compound of Formula I.

When applying Method B to other target compounds, the order of addition is reversed in some cases in that the appropriate intermediate is added to a mixture of the appropriate amine in a salt form and N,N-diisopropylethylamine. In some instances triethylamine is used in place of N,N-diisopropylethylamine. For amine salt starting materials that are sterically hindered and/or less nucleophilic, the reaction medium is carried out at elevated temperatures up to, and including, 80° C. in sealed vessels. When performing flash chromatography purification, larger column sizes are used for larger scale reactions as well as different gradients and/or mobile phases depending upon the affinity of the final target compounds towards silica gel. If further purification is required, the crude compound is 1) dissolved in ethyl acetate, washed with 1.0 N aqueous hydrochloric acid (3 times), washed with brine, dried over magnesium sulfate, filtered, and concentrated and/or 2) purified by preparative thin layer chromatography (prep-TLC).

Example 2

Synthesis of Intermediate 1: 6-chloro-3-((2-ethoxy-3,4-dioxocyclobut-1-en-1-yl)amino)-2-hydroxy-N,N-dimethylbenzenesulfonamide

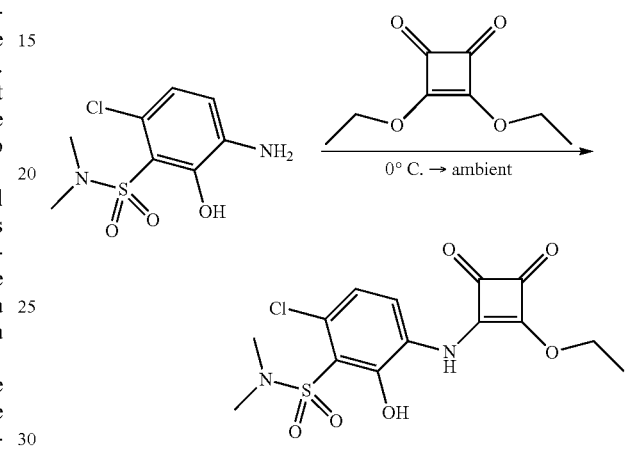

A mixture of 3-amino-6-chloro-2-hydroxy-N,N-dimethylbenzenesulfonamide (synthesized as described in US 2014/0309208, 3.02 g, 12.0 mmol) in ethanol (56 mL) was treated with 3,4-diethoxycyclobut-3-ene-1,2-dione (2.8 mL, 19 mmol) dropwise under nitrogen atmosphere at 0° C. while stirring. The reaction was allowed to warm to ambient temperature and stirring continued for 16 days. The mixture was subsequently concentrated and resulting residue purified by flash chromatography on silica gel using a Teledyne-Isco CombiFlash® Rf 200 (330 g column, 15%→50% ethyl acetate/hexanes) to afford Intermediate 1 as a yellow solid (2.10 g, 5.60 mmol, 46.7%). $^1$H NMR (600 MHz, CHLOROFORM-d): δ=10.81 (s, 1H), 7.96 (br s, 1H), 7.68 (br s, 1H), 7.07 (d, J=8.8 Hz, 1H), 4.87 (q, J=7.0 Hz, 2H), 2.94 (s, 6H), 1.52 (t, J=7.0 Hz, 3H). MS (ESI): m/z=373 [M−H]$^-$.

Example 3

Synthesis of Intermediate 2: 3-((2-ethoxy-3,4-dioxocyclobut-1-en-1-yl)amino)-2-hydroxy-N,N-dimethylbenzamide

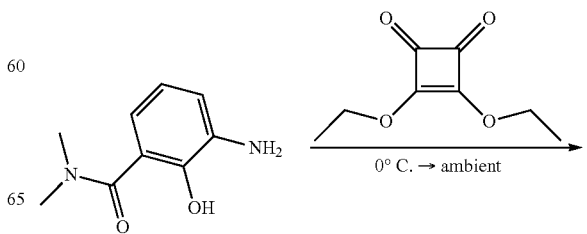

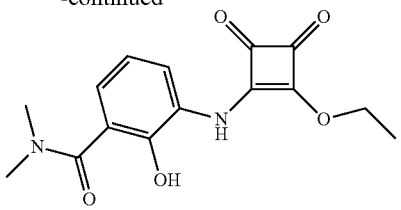

A mixture of 3-amino-2-hydroxy-N,N-dimethylbenzamide (synthesized as described in US 2014/0309208, 2.01 g, 11.2 mmol) in ethanol (52 mL) was treated with 3,4-diethoxycyclobut-3-ene-1,2-dione (2.4 mL, 16 mmol) dropwise under nitrogen atmosphere at 0° C. while stirring. The reaction was allowed to warm to ambient temperature and stirring continued for 2 days. The mixture was subsequently concentrated and resulting residue purified by flash chromatography on silica gel using a Teledyne-Isco CombiFlash® Rf 200 (220 g column, 0%→10% methanol/dichloromethane) to afford Intermediate 2 as a beige solid (2.78 g, 9.14 mmol, 81.7%). $^1$H NMR (600 MHz, METHANOL-$d_4$): δ=7.41 (br d, J=7.0 Hz, 1H), 7.11 (d, J=7.6 Hz, 1H), 6.95 (dd, J=7.6 Hz, 1H), 4.76 (q, J=7.0 Hz, 2H), 3.05 (br s, 6H), 1.43 (t, J=7.0 Hz, 3H). MS (ESI): m/z=303 [M−H]$^-$.

Example 4

Synthesis of Intermediate 3: 3-ethoxy-4-((2-hydroxy-3-(morpholine-4-carbonyl)phenyl)amino)cyclobut-3-ene-1,2-dione

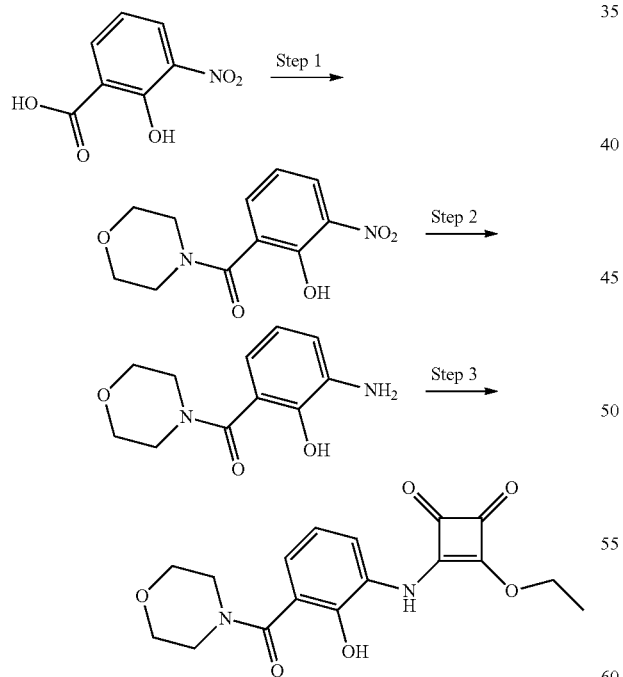

Step 1: To a suspension of 2-hydroxy-3-nitrobenzoic acid (151 mg, 0.805 mmol) in dichloromethane (6.0 mL) was added oxalyl dichloride (2.0 M in dichloromethane, 1.2 mL, 2.4 mmol), followed by N,N-dimethylformamide (4 drops). After stirring at ambient temperature for 24 hours, morpholine (0.22 mL, 2.5 mmol) was then added and stirring continued for an additional 3 days. The mixture was concentrated and residue partitioned between dichloromethane and 1.0 N aqueous sodium hydroxide. The aqueous layer was washed with dichloromethane (2 times), pH adjusted to 1 by addition of 6.0 N aqueous hydrochloric acid, and then extracted with dichloromethane (2 times). The organic layers were combined, dried over magnesium sulfate, filtered, and concentrated to afford (2-hydroxy-3-nitrophenyl)(morpholino)methanone (129 mg, 0.512 mmol, 63.7%). $^1$H NMR (600 MHz, CHLOROFORM-d): δ=10.87 (s, 1H), 8.18 (d, J=8.8 Hz, 1H), 7.63 (d, J=7.6 Hz, 1H), 7.01-7.13 (m, 1H), 3.57-4.11 (m, 6H), 3.20-3.52 (m, 2H).

Step 2: To a solution of (2-hydroxy-3-nitrophenyl)(morpholino)methanone (129 mg, 0.512 mmol) in ethanol (4.0 mL) and ethyl acetate (1.0 mL) was added 10 wt. % palladium on carbon. A hydrogen atmosphere was established by evacuating and refilling with hydrogen (3 times). The mixture was then stirred under a balloon of hydrogen at ambient temperature overnight. It was subsequently filtered through a plug of Celite®, washing with excess ethyl acetate, and filtrate concentrated to afford (3-amino-2-hydroxyphenyl)(morpholino)methanone (107 mg, 0.481 mmol, 94.0%). $^1$H NMR (600 MHz, CHLOROFORM-d): δ=9.58 (br s, 1H), 6.74 (d, J=7.6 Hz, 1H), 6.66 (dd, J=7.6 Hz, 1H), 6.61 (d, J=7.6 Hz, 1H), 3.90 (br s, 2H), 3.60-3.79 (m, 8H).

Step 3: A mixture of (3-amino-2-hydroxyphenyl)(morpholino)methanone (107 mg, 0.481 mmol) in ethanol (1.6 mL) was treated with 3,4-diethoxycyclobut-3-ene-1,2-dione (91.9 mg, 0.513 mmol) dropwise. The solution was warmed to 50° C. and stirring continued for 4 days. The mixture was subsequently concentrated and resulting residue purified by flash chromatography on silica gel using a Teledyne-Isco CombiFlash® Rf 200 (12 g column, 50%→75% ethyl acetate/hexanes) to afford Intermediate 3 as a white solid (116 mg, 0.334 mmol, 69.5%). $^1$H NMR (600 MHz, CHLOROFORM-d): δ=10.48 (s, 1H), 7.87 (br s, 1H), 7.75 (br s, 1H), 7.01 (d, J=7.6 Hz, 1H), 6.84-6.95 (m, 1H), 4.88 (q, J=7.0 Hz, 2H), 3.76-3.81 (m, 4H), 3.69-3.76 (m, 4H), 1.52 (t, J=7.0 Hz, 3H). MS (ESI): m/z=345 [M−H]$^-$.

Example 5

Synthesis of Intermediate 4: 3-((4-chloro-2-hydroxy-3-((4-methylpiperazin-1-yl)sulfonyl)phenyl)amino)-4-ethoxycyclobut-3-ene-1,2-dione

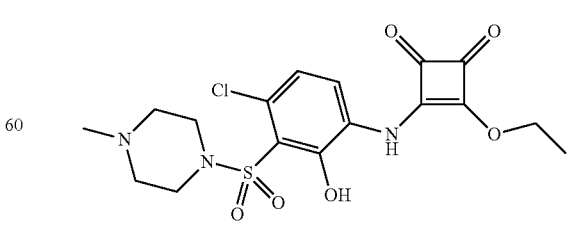

Intermediate 4 was prepared according to procedures described in US 2014/0309208.

Example 6

Synthesis of Intermediate 5: 6-chloro-3-((2-ethoxy-3,4-dioxocyclobut-1-en-1-yl)amino)-2-hydroxy-N,N-dimethylbenzamide

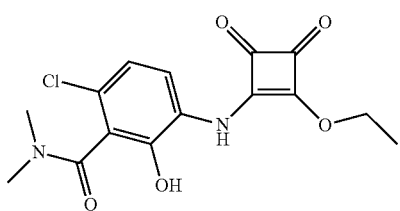 [SMILES: CCOc1c(Nc2ccc(Cl)c(C(=O)N(C)C)c2O)c(=O)c1=O]

Intermediate 5 was prepared according to procedures described in US 2014/0309208.

Example 7

Synthesis of Intermediate 6: 3-((2-ethoxy-3,4-dioxocyclobut-1-en-1-yl)amino)-N,N-diethyl-2-hydroxybenzamide

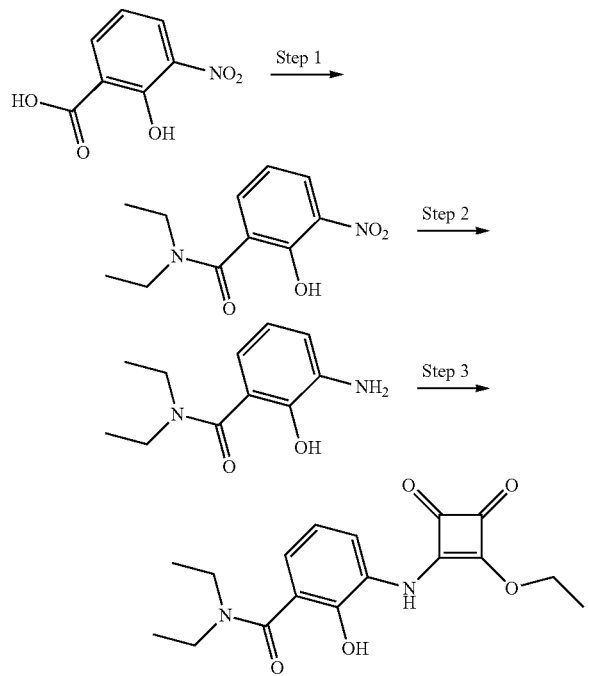

Step 1: To a suspension of 2-hydroxy-3-nitrobenzoic acid (1.00 g, 5.50 mmol) in dichloromethane (140 mL) was added diethylamine (0.62 mL, 6.0 mmol), N-[(dimethylamino)-1H-1,2,3-triazolo-[4,5-b]pyridin-1-ylmethylene]-N-methyl methanaminium hexafluorophosphate N-oxide (2.20 g, 6.60 mmol) and N,N-diisopropylethylamine (1.9 mL, 11 mmol). The resulting mixture was stirred at room temperature for 16 hours. The mixture was then washed with water, aqueous hydrochloric acid (10%), and brine. The organic phase was dried over sodium sulfate, filtered, and concentrated. Purification by flash chromatography on silica gel using a Teledyne-Isco CombiFlash® Rf 200 (40 g column, 50%→75% ethyl acetate/hexanes) afforded 2-hydroxy-N,N-dimethyl-3-nitrobenzamide as a yellow solid (800. mg, 3.36 mmol, 61.1%). $^1$H NMR (600 MHz, CHLOROFORM-d): δ=10.78 (br s, 1H), 8.15 (br d, J=8.8 Hz, 1H), 7.56 (br d, J=7.6 Hz, 1H), 7.05 (br t, J=7.9 Hz, 1H), 3.46-3.64 (m, 2H), 3.16-3.35 (m, 2H), 1.09-1.28 (m, 6H).

Step 2: To a solution of N,N-diethyl-2-hydroxy-3-nitrobenzamide (800. mg, 3.36 mmol) in ethanol (20 mL) was added 10 wt. % palladium on carbon. A hydrogen atmosphere was established by evacuating and refilling with hydrogen (3 times). The mixture was then stirred under a balloon of hydrogen at ambient temperature overnight. It was subsequently filtered through a plug of Celite®, washing with excess ethyl acetate, and filtrate concentrated. Purification by flash chromatography on silica gel using a Teledyne-Isco CombiFlash® Rf 200 (40 g column, 50%→75% ethyl acetate/hexanes) afforded 3-amino-N,N-diethyl-2-hydroxybenzamide (569 mg, 2.73 mmol, 81.3%). $^1$H NMR (600 MHz, CHLOROFORM-d): δ=9.82 (br s, 1H), 6.75 (br d, J=7.0 Hz, 1H), 6.63-6.72 (m, 2H), 3.87 (br s, 4H), 3.53 (br d, J=7.0 Hz, 6H).

Step 3: A mixture of 3-amino-N,N-diethyl-2-hydroxybenzamide (183 mg, 0.879 mmol) in ethanol (10 mL) was treated with 3,4-diethoxycyclobut-3-ene-1,2-dione (224 mg, 1.32 mmol) dropwise. The solution was stirred at ambient temperature for 5.5 days. The mixture was subsequently concentrated and resulting residue purified by flash chromatography on silica gel using a Teledyne-Isco CombiFlash® Rf 200 (12 g column, 50%→75% ethyl acetate/hexanes) to afford Intermediate 6 as a white solid (218 mg, 0.656 mmol, 74.6%). $^1$H NMR (600 MHz, CHLOROFORM-d): δ=10.86 (br s, 1H), 7.80 (br s, 1H), 7.05 (dd, J=8.2, 1.2 Hz, 1H), 6.88 (t, J=8.2 Hz, 1H), 4.88 (q, J=7.0 Hz, 2H), 3.54 (q, J=7.2 Hz, 4H), 1.52 (t, J=7.0 Hz, 3H), 1.29 (t, J=7.0 Hz, 6H).

Example 8

Synthesis of Intermediate 7: 3-((2-ethoxy-3,4-dioxocyclobut-1-en-1-yl)amino)-2-hydroxy-N,N-dimethylbenzenesulfonamide

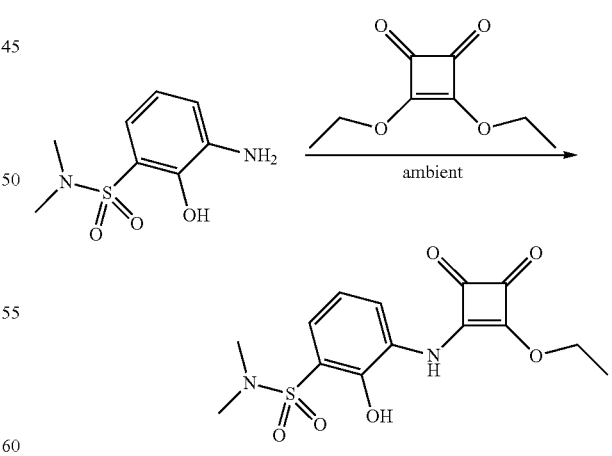

To a mixture of 3-amino-2-hydroxy-N,N-dimethylbenzenesulfonamide (548 mg, 2.53 mmol; synthesized as described in US 2014/0309208) in ethanol (10 mL) was added 3,4-diethoxycyclobut-3-ene-1,2-dione (475 mg, 2.79 mmol) dropwise. After stirring at ambient temperature for 4 days, the mixture was subsequently concentrated and resulting residue purified by flash chromatography on silica gel using a Teledyne-Isco CombiFlash® Rf 200 (40 g column, 50%→75% ethyl acetate/hexanes) to afford Intermediate 7 as a white solid (400 mg, 1.18 mmol, 46.6%). $^1$H NMR (600 MHz, CHLOROFORM-d): δ=9.44 (br s, 1H), 8.04 (br s, 1H), 7.72 (br s, 1H), 7.26-7.35 (m, 1H), 6.96-7.13 (m, 1H), 4.89 (q, J=7.0 Hz, 2H), 2.79 (s, 6H), 1.54 (t, J=7.0 Hz, 3H). MS (ESI): m/z=339 [M–H]$^-$.

Example 9

Synthesis of Compound 1: (R)-6-chloro-3-((3,4-dioxo-2-((1-phenylpropyl)amino) cyclobut-1-en-1-yl)amino)-2-hydroxy-N,N-dimethylbenzenesulfonamide

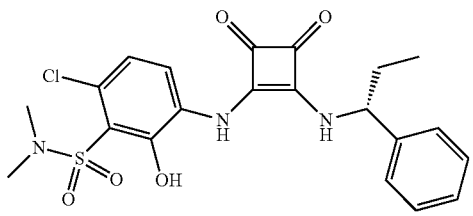 [SMILES: CC[C@@H](Nc1c(Nc2ccc(Cl)c(S(=O)(=O)N(C)C)c2O)c(=O)c1=O)c1ccccc1]

To a suspension of Intermediate 1 (11.0 mg, 0.0293 mmol) in ethanol (0.32 mL) was added (R)-1-phenylpropan-1-amine (6.9 mg, 0.051 mmol). After stirring at ambient temperature overnight, the mixture was concentrated and resulting residue purified by flash chromatography on silica gel using a Teledyne-Isco CombiFlash® Rf 200 (4 g column, 0%→50% ethyl acetate/hexanes) to afford Compound 1 (10.9 mg, 0.0235 mmol, 80.2%). $^1$H NMR (600 MHz, CHLOROFORM-d): δ=10.54 (s, 1H), 8.27 (br s, 1H), 7.91 (d, J=8.8 Hz, 1H), 7.55 (br s, 1H), 7.27-7.41 (m, 5H), 6.91 (d, J=8.8 Hz, 1H), 5.20 (br s, 1H), 2.86 (s, 6H), 1.86-2.06 (m, 2H), 0.96 (br t, J=7.0 Hz, 3H). MS (ESI): m/z=462 [M–H]$^-$.

Example 10

Synthesis of Compound 2: 6-chloro-2-hydroxy-N,N-dimethyl-3-((2-((2-methyl-1-phenylpropyl)amino)-3,4-dioxocyclobut-1-en-1-yl)amino)benzenesulfonamide

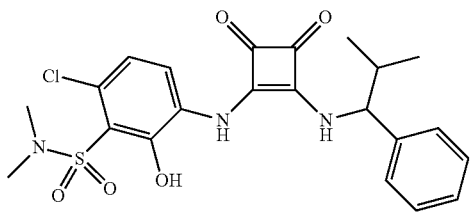 [SMILES: CC(C)C(Nc1c(Nc2ccc(Cl)c(S(=O)(=O)N(C)C)c2O)c(=O)c1=O)c1ccccc1]

To a suspension of Intermediate 1 (12.1 mg, 0.0323 mmol) in ethanol (0.32 mL) was added N,N-diisopropylethylamine (6.6 mg, 0.051 mmol) followed by 2-methyl-1-phenylpropan-1-amine hydrochloride (9.0 mg, 0.048 mmol). After stirring at ambient temperature overnight, the mixture was concentrated and resulting residue purified by flash chromatography on silica gel using a Teledyne-Isco CombiFlash® Rf 200 (4 g column, 0%→75% ethyl acetate/hexanes) to afford Compound 2 (10.5 mg, 0.0220 mmol, 68.0%). $^1$H NMR (600 MHz, CHLOROFORM-d): δ=8.38 (br s, 1H), 7.92 (br d, J=8.8 Hz, 1H), 7.64 (br s, 1H), 7.20-7.43 (m, 5H), 6.92 (d, J=8.8 Hz, 1H), 5.06 (br s, 1H), 2.87 (s, 6H), 2.11-2.23 (m, 1H), 1.07 (d, J=6.5 Hz, 3H), 0.82-0.91 (m, 3H). MS (ESI): m/z=476 [M–H]$^-$.

Example 11

Synthesis of Compound 3: 6-chloro-3-((3,4-dioxo-2-((3-phenylpentan-3-yl)amino) cyclobut-1-en-1-yl)amino)-2-hydroxy-N,N-dimethylbenzenesulfonamide

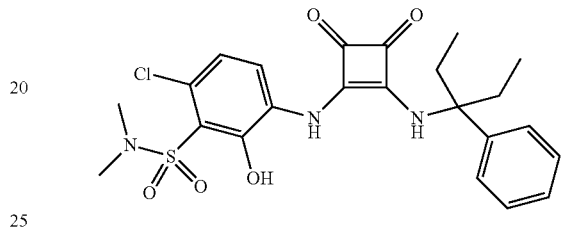

According to Method B and procedures similar to those for synthesizing Compound 2, Intermediate 1 (10.7 mg, 0.0285 mmol) and 3-phenylpentan-3-amine hydrochloride (10.0 mg, 0.0476 mmol) were converted into the title compound (2.5 mg, 0.0051 mmol, 18%). $^1$H NMR (600 MHz, CHLOROFORM-d): δ=10.23 (br s, 1H), 7.83 (br d, J=8.2 Hz, 1H), 7.41-7.49 (m, 4H), 7.31-7.40 (m, 1H), 6.95 (br d, J=8.2 Hz, 1H), 6.16 (br s, 2H), 2.90 (s, 6H), 2.10-2.23 (m, 2H), 1.92 (br s, 2H), 0.87 (br t, J=7.0 Hz, 6H). MS (ESI): m/z=490 [M–H]$^-$.

Example 12

Synthesis of Compound 4: (R)-6-chloro-3-((3,4-dioxo-2-((1,2,3,4-tetrahydronaphthalen-1-yl)amino) cyclobut-1-en-1-yl)amino)-2-hydroxy-N,N-dimethylbenzenesulfonamide

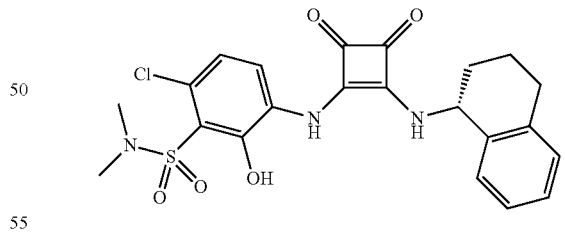

According to Method A and procedures similar to those for synthesizing Compound 1, Intermediate 1 (11.5 mg, 0.0307 mmol) and (R)-1,2,3,4-tetrahydronaphthalen-1-amine (8.6 mg, 0.057 mmol) were converted into the title compound (12.8 mg, 0.0269 mmol, 87.6%). $^1$H NMR (600 MHz, CHLOROFORM-d): δ=10.52 (s, 1H), 7.94 (br s, 1H), 7.82 (d, J=8.8 Hz, 1H), 7.27-7.31 (m, 1H), 7.13-7.22 (m, 2H), 7.02-7.13 (m, 1H), 6.94 (br s, 1H), 6.88 (d, J=8.8 Hz, 1H), 5.48 (br s, 1H), 2.44-3.03 (m, 8H), 2.14 (br s, 1H), 1.96-2.06 (m, 1H), 1.81-1.96 (m, 2H). MS (ESI): m/z=474 [M–H]$^-$.

Example 13

Synthesis of Compound 5: 6-chloro-3-((2-((2,2-dimethyl-1-phenylpropyl)amino)-3,4-dioxocyclobut-1-en-1-yl)amino)-2-hydroxy-N,N-dimethylbenzenesulfonamide

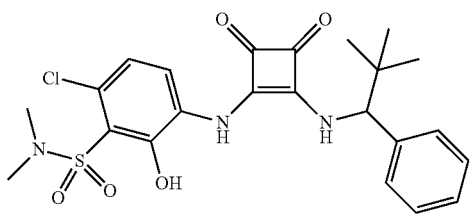

According to Method A and procedures similar to those for synthesizing Compound 1, Intermediate 1 (7.5 mg, 0.020 mmol) and 2,2-dimethyl-1-phenylpropan-1-amine (7.6 mg, 0.045 mmol) were converted into the title compound (2.4 mg, 0.0049 mmol, 24%). $^1$H NMR (600 MHz, CHLOROFORM-d): δ=10.50 (br s, 1H), 8.18 (br s, 1H), 7.90 (br d, J=8.8 Hz, 1H), 7.26-7.56 (m, 5H), 6.96 (d, J=8.8 Hz, 1H), 6.45 (br s, 1H), 5.24 (br s, 1H), 2.89 (s, 6H), 1.01 (s, 9H). MS (ESI): m/z=490 [M−H]$^-$.

Example 14

Synthesis of Compound 6: 6-chloro-3-((2-((2,2-dimethyl-1,2,3,4-tetrahydronaphthalen-1-yl)amino)-3,4-dioxocyclobut-1-en-1-yl)amino)-2-hydroxy-N,N-dimethylbenzenesulfonamide

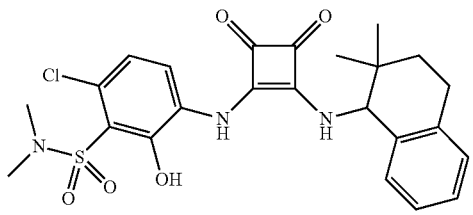 [SMILES: CN(C)S(=O)(=O)c1c(Cl)ccc(Nc2c(NC3c4ccccc4CCC3(C)C)c(=O)c2=O)c1O]

According to Method A and procedures similar to those for synthesizing Compound 1, Intermediate 1 (6.9 mg, 0.018 mmol) and 2,2-dimethyl-1,2,3,4-tetrahydronaphthalen-1-amine (5.7 mg, 0.031 mmol) were converted into the title compound (8.4 mg, 0.017 mmol, 93%). $^1$H NMR (600 MHz, CHLOROFORM-d): δ=10.53 (br s, 1H), 8.00 (br s, 1H), 7.81 (br d, J=8.2 Hz, 1H), 7.22-7.25 (m, 1H), 7.12-7.21 (m, 2H), 6.99-7.12 (m, 1H), 6.86 (br d, J=8.2 Hz, 1H), 6.72 (br d, J=9.4 Hz, 1H), 5.17 (br d, J=9.4 Hz, 1H), 2.53-2.98 (m, 8H), 1.70-1.81 (m, 1H), 1.65-1.69 (m, 1H), 0.93-1.08 (m, 6H). MS (ESI): m/z=502 [M−H]$^-$.

Example 15

Synthesis of Compound 7: (S)-6-chloro-2-hydroxy-3-((2-((2-methoxy-1-phenylethyl)amino)-3,4-dioxocyclobut-1-en-1-yl)amino)-N,N-dimethylbenzenesulfonamide

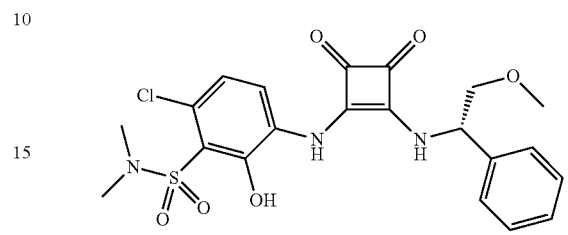

According to Method A and procedures similar to those for synthesizing Compound 1, Intermediate 1 (8.1 mg, 0.022 mmol) and (S)-2-methoxy-1-phenylethan-1-amine (9.7 mg, 0.064 mmol) were converted into the title compound (8.3 mg, 0.017 mmol, 79%). $^1$H NMR (600 MHz, METHANOL-d$_4$): δ=8.14 (br s, 1H), 7.34-7.46 (m, 4H), 7.20-7.34 (m, 1H), 7.08 (br d, J=8.8 Hz, 1H), 5.53 (br s, 1H), 3.69-3.80 (m, 2H), 3.41 (s, 3H), 2.92 (s, 6H). MS (ESI): m/z=478 [M−H]$^-$.

Example 16

Synthesis of Compound 8: (R)-6-chloro-3-((2-((2,2-dimethyl-1-phenylpropyl)amino)-3,4-dioxocyclobut-1-en-1-yl)amino)-2-hydroxy-N,N-dimethylbenzenesulfonamide

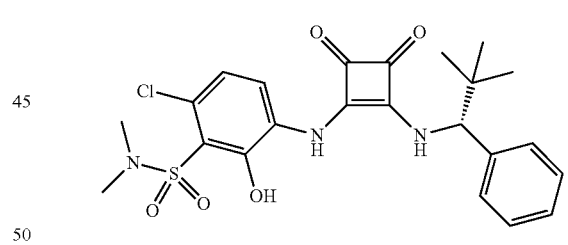

According to Method A and procedures similar to those for synthesizing Compound 1, Intermediate 1 (60.5 mg, 0.161 mmol) and 2,2-dimethyl-1-phenylpropan-1-amine (32.2 mg, 0.191 mmol) were converted into Compound 5 (75.6 mg, 0.154 mmol). Chiral separation via supercritical fluid chromatography (AD-H column, 30% isopropanol/carbon dioxide, 100 bar) afforded the title compound (31 mg, 0.063 mmol). $^1$H NMR (600 MHz, CHLOROFORM-d): δ=10.59 (s, 1H), 8.25 (br s, 1H), 7.89 (br d, J=8.8 Hz, 1H), 7.26-7.46 (m, 5H), 6.96 (d, J=8.8 Hz, 1H), 6.31 (br s, 1H), 5.21 (br s, 1H), 2.88 (s, 6H), 1.00 (s, 9H). MS (ESI): m/z=490 [M−H]$^-$.

Example 17

Synthesis of Compound 9: (S)-6-chloro-3-((2-((2,2-dimethyl-1-phenylpropyl)amino)-3,4-dioxocyclobut-1-en-1-yl)amino)-2-hydroxy-N,N-dimethylbenzenesulfonamide

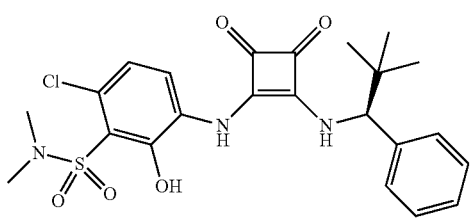 [SMILES: CN(C)S(=O)(=O)c1c(Cl)ccc(Nc2c(N[C@H](c3ccccc3)C(C)(C)C)c(=O)c2=O)c1O]

According to Method A and procedures similar to those for synthesizing Compound 1, Intermediate 1 (60.5 mg, 0.161 mmol) and 2,2-dimethyl-1-phenylpropan-1-amine (32.2 mg, 0.191 mmol) were converted into Compound 5 (75.6 mg, 0.154 mmol). Chiral separation via supercritical fluid chromatography (AD-H column, 30% isopropanol/carbon dioxide, 100 bar) afforded the title compound (31 mg, 0.063 mmol, 39%). $^1$H NMR (600 MHz, CHLOROFORM-d): δ=10.60 (s, 1H), 8.05 (br s, 1H), 7.86 (d, J=8.8 Hz, 1H), 7.27-7.43 (m, 5H), 6.97 (d, J=8.8 Hz, 1H), 6.24 (br s, 1H), 5.17 (br s, 1H), 2.89 (s, 6H), 1.01 (s, 9H). MS (ESI): m/z=490 [M−H]$^-$.

Example 18

Synthesis of Compound 10: 6-chloro-3-((2-((3,3-dimethyl-1-phenylbutyl)amino)-3,4-dioxocyclobut-1-en-1-yl)amino)-2-hydroxy-N,N-dimethylbenzenesulfonamide

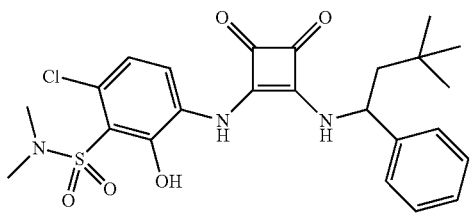 [SMILES: CN(C)S(=O)(=O)c1c(Cl)ccc(Nc2c(NC(CC(C)(C)C)c3ccccc3)c(=O)c2=O)c1O]

According to Method A and procedures similar to those for synthesizing Compound 1, Intermediate 1 (9.4 mg, 0.025 mmol) and 3,3-dimethyl-1-phenylbutan-1-amine (6.5 mg, 0.035 mmol) were converted into the title compound (12.4 mg, 0.0245 mmol, 98%). $^1$H NMR (600 MHz, DMSO-d$_6$): δ=10.54 (s, 1H), 9.39 (s, 1H), 8.75 (d, J=8.8 Hz, 1H), 7.97 (d, J=8.8 Hz, 1H), 7.38 (dd, J=7.0 Hz, 2H), 7.33 (d, J=7.0 Hz, 2H), 7.27 (dd, J=7.0 Hz, 1H), 7.17 (br s, 1H), 5.30-5.42 (m, 1H), 2.85 (s, 6H), 1.86 (dd, J=14.1, 8.8 Hz, 1H), 1.72-1.81 (m, 1H), 0.93 (s, 9H). MS (ESI): m/z=504 [M−H]$^-$.

Example 19

Synthesis of Compound 11: 6-chloro-3-((2-((3,3-dimethylbutan-2-yl)amino)-3,4-dioxocyclobut-1-en-1-yl)amino)-2-hydroxy-N,N-dimethylbenzenesulfonamide

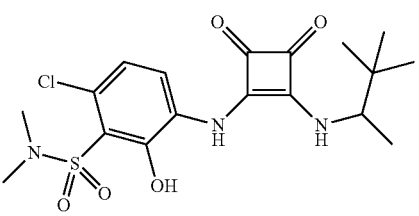

According to Method A and procedures similar to those for synthesizing Compound 1, Intermediate 1 (9.4 mg, 0.025 mmol) and 3,3-dimethylbutan-2-amine (3.2 mg, 0.031 mmol) were converted into the title compound (10.8 mg, 0.0251 mmol, 100%). $^1$H NMR (600 MHz, METHANOL-d$_4$): δ=8.17 (d, J=8.8 Hz, 1H), 7.09 (d, J=8.8 Hz, 1H), 4.16 (q, J=6.5 Hz, 1H), 2.92 (s, 6H), 1.26 (d, J=6.5 Hz, 3H), 0.99 (s, 9H). MS (ESI): m/z=428 [M−H]$^-$.

Example 20

Synthesis of Compound 12: 6-chloro-3-((3,4-dioxo-2-((6,7,8,9-tetrahydro-5H-benzo[7]annulen-5-yl)amino)cyclobut-1-en-1-yl)amino)-2-hydroxy-N,N-dimethylbenzenesulfonamide

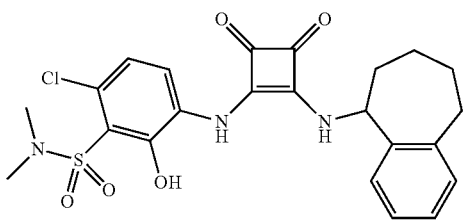 [SMILES: CN(C)S(=O)(=O)c1c(Cl)ccc(Nc2c(NC3CCCCc4ccccc43)c(=O)c2=O)c1O]

According to Method A and procedures similar to those for synthesizing Compound 1, Intermediate 1 (8.4 mg, 0.022 mmol) and 6,7,8,9-tetrahydro-5H-benzo[7]annulen-5-amine (6.8 mg, 0.040 mmol) were converted into the title compound (6.5 mg, 0.013 mmol, 60%). $^1$H NMR (600 MHz, METHANOL-d$_4$): δ=8.16 (br d, J=8.2 Hz, 1H), 7.23-7.33 (m, 1H), 7.14-7.22 (m, 3H), 7.09 (d, J=8.2 Hz, 1H), 5.51-5.64 (m, 1H), 2.75-3.07 (m, 8H), 1.89-2.11 (m, 4H), 1.70-1.84 (m, 1H), 1.57-1.70 (m, 1H). MS (ESI): m/z=488 [M−H]$^-$.

Example 21

Synthesis of Compound 13: 3-((2-((2,2-dimethyl-1-phenylpropyl)amino)-3,4-dioxocyclobut-1-en-1-yl)amino)-2-hydroxy-N,N-dimethylbenzamide

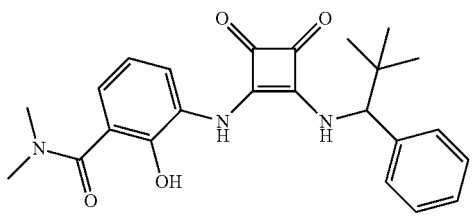 [SMILES: CN(C)C(=O)c1cccc(Nc2c(NC(c3ccccc3)C(C)(C)C)c(=O)c2=O)c1O]

According to Method A and procedures similar to those for synthesizing Compound 1, Intermediate 2 (36.3 mg, 0.119 mmol) and 2,2-dimethyl-1-phenylpropan-1-amine (21.7 mg, 0.129 mmol) were converted into the title compound (41.5 mg, 0.0985 mmol, 82.7%). $^1$H NMR (600 MHz, METHANOL-$d_4$): δ=7.95 (d, J=7.6 Hz, 1H), 7.34-7.41 (m, 2H), 7.24-7.34 (m, 3H), 6.99 (d, J=7.6 Hz, 1H), 6.92 (dd, J=7.6 Hz, 1H), 5.20 (s, 1H), 3.08 (s, 6H), 1.01 (s, 9H). MS (ESI): m/z=420 [M−H]$^−$.

Example 22

Synthesis of Compound 14: 6-chloro-3-((3,4-dioxo-2-((2,2,2-trifluoro-1-phenylethyl)amino)cyclobut-1-en-1-yl)amino)-2-hydroxy-N,N-dimethylbenzenesulfonamide

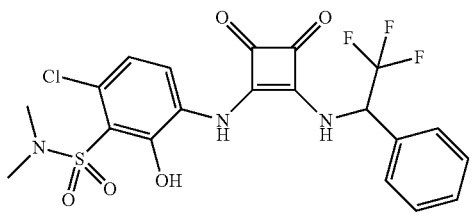 [SMILES: CN(C)S(=O)(=O)c1c(Cl)ccc(Nc2c(NC(c3ccccc3)C(F)(F)F)c(=O)c2=O)c1O]

According to Method B and procedures similar to those for synthesizing Compound 2, Intermediate 1 (12.2 mg, 0.0326 mmol) and 2,2,2-trifluoro-1-phenylethan-1-amine hydrochloride (13.3 mg, 0.0597 mmol) were converted into the title compound (5.2 mg, 0.010 mmol, 32%). $^1$H NMR (600 MHz, CHLOROFORM-d): δ=10.61 (s, 1H), 8.18 (br s, 1H), 7.84 (d, J=8.8 Hz, 1H), 7.51 (br d, J=8.2 Hz, 1H), 7.45-7.49 (m, 2H), 7.36-7.45 (m, 3H), 6.96 (d, J=8.8 Hz, 1H), 5.97-6.09 (m, 1H), 2.86 (s, 6H). MS (ESI): m/z=502 [M−H]$^−$.

Example 23

Synthesis of Compound 15: (S)-6-chloro-2-hydroxy-3-((2-((2-hydroxy-2-methyl-1-phenylpropyl)amino)-3,4-dioxocyclobut-1-en-1-yl)amino)-N,N-dimethylbenzenesulfonamide

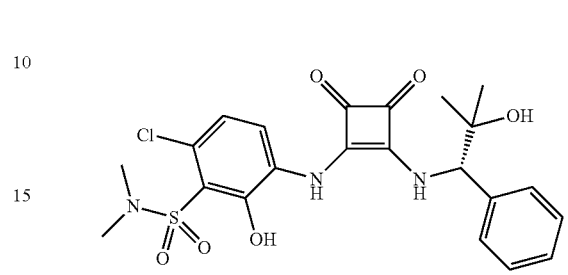

According to Method B and procedures similar to those for synthesizing Compound 2, Intermediate 1 (19.2 mg, 0.0512 mmol) and (S)-1-amino-2-methyl-1-phenylpropan-2-ol hydrochloride (12.3 mg, 0.0579 mmol) were converted into the title compound (22.1 mg, 0.0447 mmol, 87.4%). $^1$H NMR (600 MHz, CHLOROFORM-d): δ=10.62 (s, 1H), 8.42 (br s, 1H), 7.67-8.08 (m, 2H), 7.27-7.53 (m, 5H), 6.99 (d, J=8.8 Hz, 1H), 5.27 (br s, 1H), 2.90 (br s, 6H), 2.52 (br s, 1H), 1.43 (br s, 3H), 1.12 (br s, 3H). MS (ESI): m/z=492 [M−H]$^−$.

Example 24

Synthesis of Compound 16: (R)-6-chloro-3-((2-(chroman-4-ylamino)-3,4-dioxocyclobut-1-en-1-yl)amino)-2-hydroxy-N,N-dimethylbenzenesulfonamide

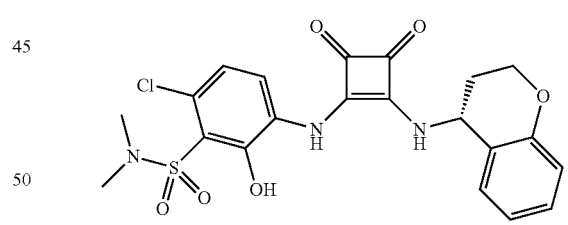

According to Method B and procedures similar to those for synthesizing Compound 2, Intermediate 1 (19.0 mg, 0.0507 mmol) and (R)-chroman-4-amine hydrochloride (13.2 mg, 0.0711 mmol) were converted into the title compound (17.1 mg, 0.0358 mmol, 70.6%). $^1$H NMR (600 MHz, CHLOROFORM-d): δ=10.52 (s, 1H), 7.98 (br s, 1H), 7.80 (d, J=8.2 Hz, 1H), 7.24 (d, J=7.6 Hz, 1H), 7.05-7.21 (m, 2H), 6.85-6.94 (m, 2H), 6.80 (d, J=8.2 Hz, 1H), 5.43 (br s, 1H), 4.27-4.35 (m, 1H), 4.18-4.26 (m, 1H), 2.75 (s, 6H), 2.29-2.40 (m, 1H), 2.11-2.21 (m, 1H). MS (ESI): m/z=476 [M−H]$^−$.

Example 25

Synthesis of Compound 17: 6-chloro-3-((3,4-dioxo-2-((4,5,6,7-tetrahydrobenzofuran-4-yl)amino)cyclobut-1-en-1-yl)amino)-2-hydroxy-N,N-dimethylbenzenesulfonamide

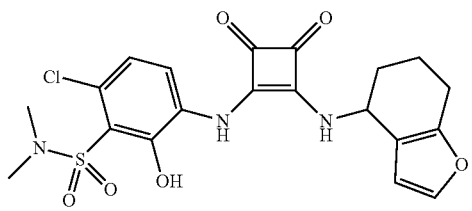 [SMILES: CN(C)S(=O)(=O)c1c(Cl)ccc(Nc2c(NC3CCCc4occc43)c(=O)c2=O)c1O]

According to Method A and procedures similar to those for synthesizing Compound 1, Intermediate 1 (21.7 mg, 0.0579 mmol) and 4,5,6,7-tetrahydrobenzofuran-4-amine (11.9 mg, 0.0824 mmol) were converted into the title compound (24.1 mg, 0.0517 mmol, 89.3%). $^1$H NMR (600 MHz, CHLOROFORM-d): δ=10.63 (s, 1H), 7.92 (br s, 1H), 7.62 (br s, 1H), 7.29 (s, 1H), 6.98 (d, J=8.2 Hz, 1H), 6.33 (d, J=1.8 Hz, 1H), 6.29 (br d, J=5.9 Hz, 2H), 5.27 (br s, 1H), 2.88 (s, 3H), 2.52-2.70 (m, 2H), 2.16 (br s, 1H), 1.99 (br s, 1H), 1.89-1.96 (m, 1H), 1.81-1.89 (m, 1H). MS (ESI): m/z=464 [M−H]$^−$.

Example 26

Synthesis of Compound 18: 6-chloro-2-hydroxy-N,N-dimethyl-3-((2-((1-methyl-1,2,3,4-tetrahydroquinolin-4-yl)amino)-3,4-dioxocyclobut-1-en-1-yl)amino)benzenesulfonamide

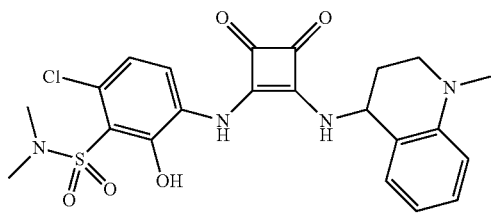

According to Method A and procedures similar to those for synthesizing Compound 1, Intermediate 1 (20.9 mg, 0.0558 mmol) and 1-methyl-1,2,3,4-tetrahydroquinolin-4-amine (15.2 mg, 0.0890 mmol) were converted into the title compound (24.0 mg, 0.0489 mmol, 87.6%). $^1$H NMR (600 MHz, CHLOROFORM-d): δ=10.59 (s, 1H), 7.83 (d, J=8.8 Hz, 1H), 7.56 (br s, 1H), 7.11-7.22 (m, 2H), 6.94 (d, J=8.8 Hz, 1H), 6.68 (dd, J=7.6 Hz, 1H), 6.63 (d, J=8.8 Hz, 1H), 6.25 (br s, 1H), 5.38 (br s, 1H), 3.22-3.35 (m, 2H), 2.93 (s, 3H), 2.80 (s, 6H), 2.23-2.34 (m, 1H), 2.13-2.21 (m, 1H). MS (ESI): m/z=489 [M−H]$^−$.

Example 27

Synthesis of Compound 19: 6-chloro-2-hydroxy-3-((2-((1-(2-methoxyphenyl)-2,2-dimethylpropyl)amino)-3,4-dioxocyclobut-1-en-1-yl)amino)-N,N-dimethylbenzenesulfonamide

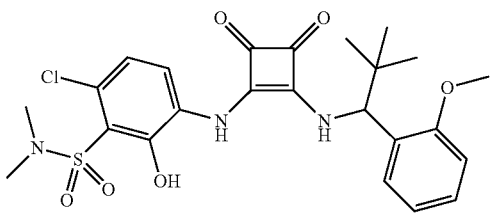

According to Method B and procedures similar to those for synthesizing Compound 2, Intermediate 1 (20.0 mg, 0.0534 mmol) and 1-(2-methoxyphenyl)-2,2-dimethylpropan-1-amine hydrochloride (14.9 mg, 0.0616 mmol) were converted into the title compound (25.2 mg, 0.0483 mmol, 90.4%). $^1$H NMR (600 MHz, CHLOROFORM-d): δ=10.75 (s, 1H), 7.66 (br s, 1H), 7.29 (br s, 1H), 7.17 (br d, J=7.6 Hz, 1H), 7.03 (br s, 1H), 6.97 (br s, 1H), 6.92 (br d, J=8.2 Hz, 1H), 6.16 (br s, 1H), 5.34 (br s, 1H), 5.10 (br s, 1H), 3.80 (br s, 3H), 2.94 (s, 6H), 1.01 (br s, 9H). MS (ESI): m/z=520 [M−H]$^−$.

Example 28

Synthesis of Compound 20: 6-chloro-3-((2-((2,2-dimethyl-1-(o-tolyl)propyl)amino)-3,4-dioxocyclobut-1-en-1-yl)amino)-2-hydroxy-N,N-dimethylbenzenesulfonamide

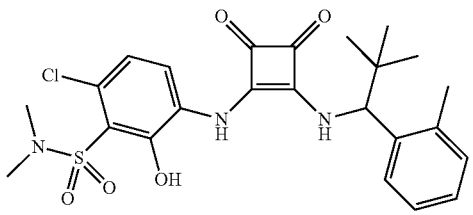 [SMILES: Cc1ccccc1C(Nc1c(Nc2ccc(Cl)c(S(=O)(=O)N(C)C)c2O)c(=O)c1=O)C(C)(C)C]

According to Method A and procedures similar to those for synthesizing Compound 1, Intermediate 1 (19.3 mg, 0.0515 mmol) and 2,2-dimethyl-1-(o-tolyl)propan-1-amine (12.0 mg, 0.0643 mmol) were converted into the title compound (23.1 mg, 0.0457 mmol, 88.6%). $^1$H NMR (600 MHz, CHLOROFORM-d): δ=10.56 (br s, 1H), 8.28 (br s, 1H), 7.80 (br s, 1H), 7.55 (br s, 1H), 7.25 (br s, 1H), 7.16 (br s, 2H), 6.93 (d, J=8.8 Hz, 1H), 5.66 (br s, 1H), 2.85 (s, 6H), 2.49 (s, 3H), 1.03 (s, 9H). MS (ESI): m/z=504 [M−H]$^−$.

Example 29

Synthesis of Compound 21: (R)-3-((3,4-dioxo-2-((1,2,3,4-tetrahydronaphthalen-1-yl)amino)cyclobut-1-en-1-yl)amino)-2-hydroxy-N,N-dimethylbenzamide

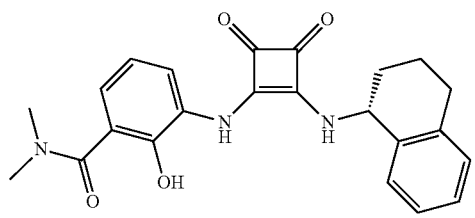 [SMILES: CN(C)C(=O)c1cccc(Nc2c(N[C@@H]3CCCc4ccccc43)c(=O)c2=O)c1O]

According to Method A and procedures similar to those for synthesizing Compound 1, Intermediate 2 (21.3 mg, 0.0700 mmol) and (R)-1,2,3,4-tetrahydronaphthalen-1-amine (14.4 mg, 0.0949 mmol) were converted into the title compound (26.0 mg, 0.0641 mmol, 91.6%). $^1$H NMR (600 MHz, METHANOL-$d_4$): δ=7.96 (br d, J=7.6 Hz, 1H), 7.27-7.37 (m, 1H), 7.17-7.23 (m, 2H), 7.12-7.17 (m, 1H), 6.96-7.01 (m, 1H), 6.93 (dd, J=8.2 Hz, 1H), 5.42 (br s, 2H), 3.05 (s, 6H), 2.84-2.93 (m, 1H), 2.75-2.84 (m, 1H), 2.10-2.23 (m, 1H), 1.94-2.09 (m, 2H), 1.81-1.94 (m, 1H). MS (ESI): m/z=404 [M−H]$^−$.

Example 30

Synthesis of Compound 22: 3-((2-((2,2-dimethyl-1,2,3,4-tetrahydronaphthalen-1-yl)amino)-3,4-dioxocyclobut-1-en-1-yl)amino)-2-hydroxy-N,N-dimethylbenzamide

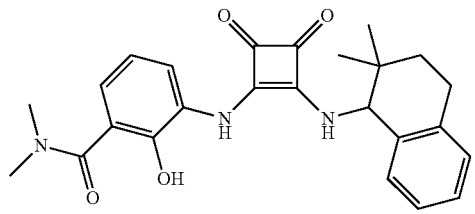 [SMILES: CN(C)C(=O)c1cccc(Nc2c(NC3c4ccccc4CCC3(C)C)c(=O)c2=O)c1O]

According to Method A and procedures similar to those for synthesizing Compound 1, Intermediate 2 (52.1 mg, 0.171 mmol) and 2,2-dimethyl-1,2,3,4-tetrahydronaphthalen-1-amine (44.7 mg, 0.242 mmol) were converted into the title compound (60.7 mg, 0.140 mmol, 81.9%). $^1$H NMR (600 MHz, METHANOL-$d_4$): δ=8.00 (dd, J=8.2, 1.2 Hz, 1H), 7.25-7.30 (m, 1H), 7.14-7.24 (m, 2H), 6.98 (dd, J=7.6, 1.0 Hz, 1H), 6.94 (dd, J=8.2 Hz, 1H), 5.14 (s, 1H), 3.06 (s, 6H), 2.80-2.96 (m, 2H), 1.78-1.89 (m, 1H), 1.66-1.75 (m, 1H), 1.06 (s, 3H), 1.06 (s, 3H). MS (ESI): m/z=432 [M−H]$^−$.

Example 31

Synthesis of Compound 23: 6-chloro-3-((2-((1-(2,4-difluorophenyl)-2,2-dimethylpropyl)amino)-3,4-dioxocyclobut-1-en-1-yl)amino)-2-hydroxy-N,N-dimethylbenzenesulfonamide

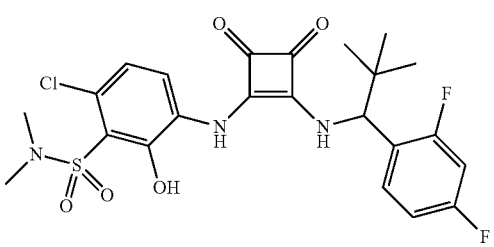 [SMILES: CN(C)S(=O)(=O)c1c(Cl)ccc(Nc2c(NC(c3ccc(F)cc3F)C(C)(C)C)c(=O)c2=O)c1O]

According to Method A and procedures similar to those for synthesizing Compound 1, Intermediate 1 (19.6 mg, 0.0523 mmol) and 1-(2,4-difluorophenyl)-2,2-dimethylpropan-1-amine (14.2 mg, 0.0677 mmol) were converted into the title compound (24.0 mg, 0.0455 mmol, 86.9%). $^1$H NMR (600 MHz, CHLOROFORM-d): δ=10.55 (s, 1H), 8.69 (br s, 1H), 8.11 (br s, 1H), 7.97 (d, J=8.8 Hz, 1H), 7.28-7.41 (m, 1H), 6.98 (d, J=8.8 Hz, 1H), 6.80-6.93 (m, 1H), 6.75 (br s, 1H), 5.52 (br s, 1H), 2.85 (s, 6H), 0.98 (s, 9H). MS (ESI): m/z=526 [M−H]$^−$.

Example 32

Synthesis of Compound 24: 6-chloro-2-hydroxy-3-((2-((1-(3-methoxyphenyl)-2,2-dimethylpropyl)amino)-3,4-dioxocyclobut-1-en-1-yl)amino)-N,N-dimethylbenzenesulfonamide

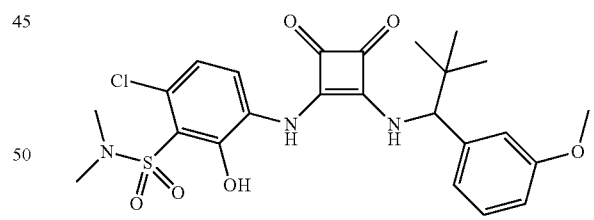

According to Method A and procedures similar to those for synthesizing Compound 1, Intermediate 1 (21.1 mg, 0.0563 mmol) and 1-(3-methoxyphenyl)-2,2-dimethylpropan-1-amine (15.8 mg, 0.0744 mmol) were converted into the title compound (25.3 mg, 0.0485 mmol, 86.1%). $^1$H NMR (600 MHz, CHLOROFORM-d): δ=10.52 (s, 1H), 8.61 (br s, 1H), 8.13 (br s, 1H), 7.91 (br s, 1H), 7.19 (br s, 1H), 6.95 (d, J=8.8 Hz, 1H), 6.87 (d, J=7.6 Hz, 1H), 6.82 (s, 1H), 6.77 (br s, 1H), 5.20 (br s, 1H), 3.75 (br s, 3H), 2.84 (br s, 6H), 0.99 (s, 9H). MS (ESI): m/z=520 [M−H]$^−$.

Example 33

Synthesis of Compound 25: 6-chloro-3-((2-((2,2-dimethyl-1-(m-tolyl)propyl)amino)-3,4-dioxocyclobut-1-en-1-yl)amino)-2-hydroxy-N,N-dimethylbenzenesulfonamide

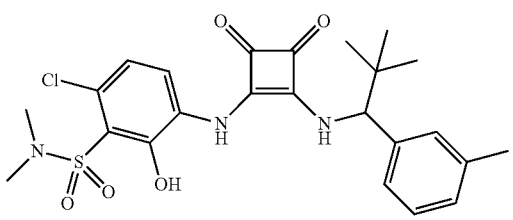

According to Method A and procedures similar to those for synthesizing Compound 1, Intermediate 1 (20.2 mg, 0.0539 mmol) and 2,2-dimethyl-1-(m-tolyl)propan-1-amine (15.7 mg, 0.0841 mmol) were converted into the title compound (24.1 mg, 0.0476 mmol, 88.4%). $^1$H NMR (600 MHz, CHLOROFORM-d): δ=10.54 (s, 1H), 8.61 (br s, 1H), 8.08 (br s, 1H), 7.93 (br s, 1H), 7.18 (br s, 1H), 6.97-7.12 (m, 2H), 6.93 (d, J=8.8 Hz, 1H), 6.29 (br s, 1H), 5.20 (br s, 1H), 2.84 (s, 6H), 2.30 (s, 3H), 0.98 (s, 9H). MS (ESI): m/z=504 [M−H]$^-$.

Example 34

Synthesis of Compound 26: 6-chloro-3-((3,4-dioxo-2-((2,3,3-trimethylbutan-2-yl)amino)cyclobut-1-en-1-yl)amino)-2-hydroxy-N,N-dimethylbenzenesulfonamide

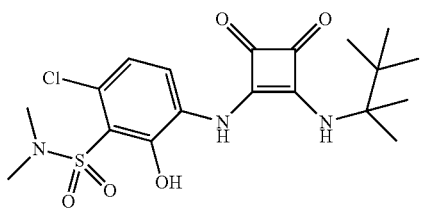 [SMILES: CN(C)S(=O)(=O)c1c(Cl)ccc(Nc2c(NC(C)(C)C(C)(C)C)c(=O)c2=O)c1O]

According to Method A and procedures similar to those for synthesizing Compound 1, Intermediate 1 (19.9 mg, 0.0531 mmol) and 2,3,3-trimethylbutan-2-amine (17.5 mg, 0.144 mmol) were converted into the title compound (7.8 mg, 0.018 mmol, 33%). $^1$H NMR (600 MHz, CHLOROFORM-d): δ=10.63 (s, 1H), 8.22 (br s, 1H), 7.90 (d, J=8.2 Hz, 1H), 6.97 (d, J=8.2 Hz, 1H), 6.84 (br s, 1H), 2.89 (s, 6H), 1.50 (s, 6H), 1.00 (s, 9H). MS (ESI): m/z=442 [M−H]$^-$.

Example 35

Synthesis of Compound 27: (R)-6-chloro-3-((2-((3,3-dimethylbutan-2-yl)amino)-3,4-dioxocyclobut-1-en-1-yl)amino)-2-hydroxy-N,N-dimethylbenzenesulfonamide

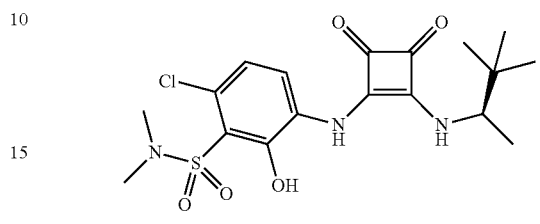

According to Method A and procedures similar to those for synthesizing Compound 1, Intermediate 1 (20.5 mg, 0.0547 mmol) and (R)-3,3-dimethylbutan-2-amine (8.8 mg, 0.086 mmol) were converted into the title compound (14.3 mg, 0.0333 mmol, 60.8%). $^1$H NMR (600 MHz, CHLOROFORM-d): δ=10.58 (s, 1H), 8.45 (br s, 1H), 7.98 (br d, J=7.6 Hz, 1H), 7.30 (br s, 1H), 6.96 (br d, J=8.2 Hz, 1H), 4.21 (br s, 1H), 2.88 (s, 6H), 1.23 (br d, J=6.5 Hz, 3H), 0.95 (s, 9H). MS (ESI): m/z=428 [M−H]$^-$.

Example 36

Synthesis of Compound 28: 3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzamide

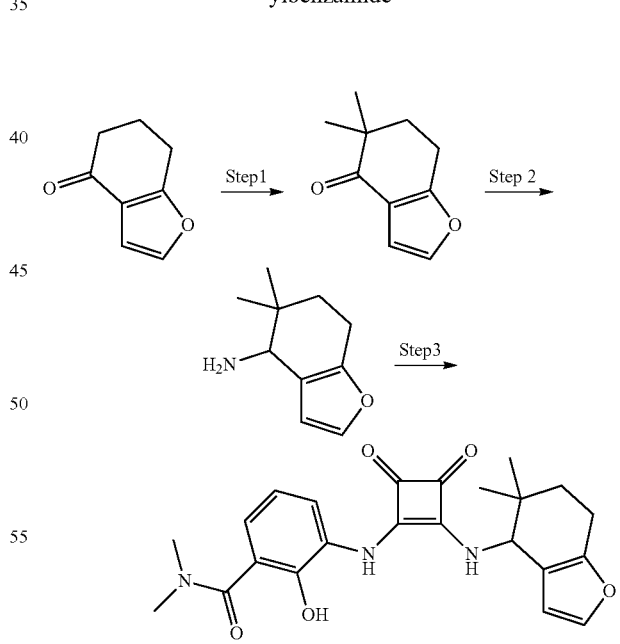

Step 1

5,5-dimethyl-6,7-dihydrobenzofuran-4(5H)-one

Step 1: To a suspension of sodium hydride (60 wt. % dispersion in mineral oil, 1.16 g, 29.0 mmol) in N,N-dimethylformamide (20.0 mL) was added a solution of 6,7-dihydrobenzofuran-4(5H)-one (1.01 g, 7.27 mmol) in N,N-dimethylformamide (3.0 mL) under nitrogen atmosphere. After stirring at ambient temperature for 40 minutes, iodomethane (2.0 M in 2-methoxy-2-methylpropane, 14.5 mL, 29 mmol) was added. After stirring at ambient temperature overnight, the mixture was quenched with water and extracted with ethyl acetate. The organic layer was then washed with water (2 times), followed by brine, dried over magnesium sulfate, filtered, and concentrated. The resulting residue was purified by flash chromatography on silica gel using a Teledyne-Isco CombiFlash® Rf 200 (80 g column, 0%→10% ethyl acetate/hexanes) to afford 5,5-dimethyl-6,7-dihydrobenzofuran-4(5H)-one (1.03 g, 6.27 mmol, 86.3%). $^1$H NMR (600 MHz, CHLOROFORM-d): δ=7.32 (s, 1H), 6.67 (s, 1H), 2.90 (t, J=6.2 Hz, 2H), 2.01 (t, J=6.2 Hz, 2H), 1.19 (s, 6H).

Step 2

5,5-dimethyl-4,5,6,7-tetrahydrobenzofuran-4-amine

Step 2: After purging a solution of 5,5-dimethyl-6,7-dihydrobenzofuran-4(5H)-one (1.03 g, 6.25 mmol) in ethanol (20.0 mL) with nitrogen for 10 minutes, ammonium acetate was added. After stirring at ambient temperature for an additional 10 minutes, sodium cyanotrihydroborate (2.43 g, 36.7 mmol) was then added and stirring continued for 10 minutes. The mixture was subsequently stirred at 65° C. for 24 hours, followed by 75° C. for 24 hours. The suspension was allowed to cool to ambient temperature and dissolved in 1.0 N aqueous hydrochloric acid, which caused significant bubble formation. Once bubble formation ceased, the aqueous solution was washed with ethyl acetate (2 times) and pH adjusted to 12 by addition of 4.0 N aqueous sodium hydroxide. This aqueous solution was then extracted with ethyl acetate (2 times), organic layers combined, dried over magnesium sulfate, filtered, and concentrated to afford 5,5-dimethyl-4,5,6,7-tetrahydrobenzofuran-4-amine (751 mg, 4.54 mmol, 72.7%). $^1$H NMR (600 MHz, CHLOROFORM-d): δ=7.25 (s, 1H), 6.36 (s, 1H), 3.42 (br s, 1H), 2.55-2.63 (m, 1H), 2.46-2.55 (m, 1H), 1.66-1.77 (m, 1H), 1.51-1.62 (m, 1H), 0.98 (s, 3H), 0.87 (s, 3H).

Step 3

3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzamide Step 3: According to Method A and procedures similar to those for synthesizing Compound 1, Intermediate 2 (343 mg, 1.13 mmol) and 5,5-dimethyl-4,5,6,7-tetrahydrobenzofuran-4-amine (223 mg, 1.35 mmol) were converted into the title compound (384 mg, 0.906 mmol, 80.2%). $^1$H NMR (600 MHz, METHANOL-d$_4$): δ=7.98 (d, J=7.6 Hz, 1H), 7.37 (s, 1H), 6.98 (d, J=7.6 Hz, 1H), 6.93 (dd, J=7.6 Hz, 1H), 6.36 (s, 1H), 4.99 (s, 1H), 3.06 (s, 6H), 2.53-2.73 (m, 2H), 1.77-1.90 (m, 1H), 1.63-1.74 (m, 1H), 1.06 (s, 3H), 1.02 (s, 3H). MS (ESI): m/z=422 [M−H]$^-$.

Example 37

Synthesis of Compound 29: (R)-3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzamide

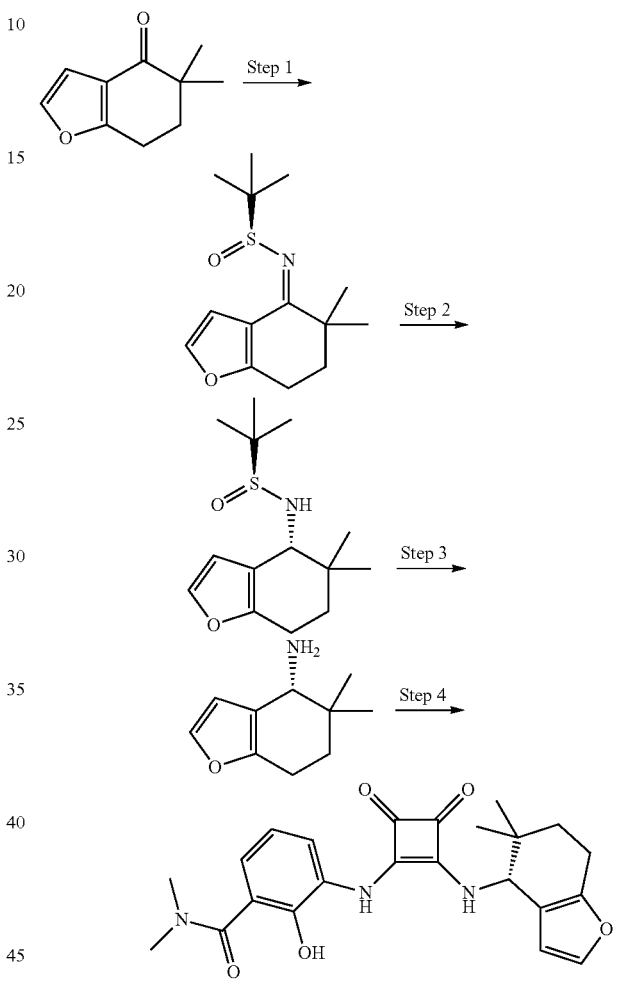

Step 1

(S,Z)—N-(5,5-dimethyl-6,7-dihydrobenzofuran-4(5H)-ylidene)-2-methylpropane-2-sulfinamide Step 1: After stirring a mixture of 5,5-dimethyl-6,7-dihydrobenzofuran-4(5H)-one (synthesized as described for Compound 28, 4.0 g, 24 mmol) and titanium(IV) ethanolate (41.0 mL, 195 mmol) under nitrogen atmosphere at 110° C. for 20 minutes, (S)-2-methyl-2-propanesulfinamide (11.8 g, 97.4 mmol) was added and stirring continued at 110° C. overnight. After cooling to ambient temperature, the mixture was slowly poured into saturated aqueous sodium chloride (200 mL) with vigorous stirring. After 30 minutes the resulting suspension was filtered through a plug of Celite®, rinsing with ethyl acetate. The phases of the combined filtrate and rinse were split and the aqueous layer was extracted with ethyl acetate (2 times). The organic layers were combined, dried over sodium sulfate, filtered, and concentrated. The resulting residue was purified by flash chromatography on silica gel using a Biotage® Isolera (50 g column, 0%→35% ethyl acetate/hexanes) to afford (S,Z)—N-(5,5-dimethyl-6,7-dihydrobenzofuran-4(5H)-ylidene)-2-methylpropane-2-sulfinamide (3.6 g, 13 mmol, 56%). MS (ESI): m/z=268 [M+H]⁺.

Step 2

(S)—N—((R)-5,5-dimethyl-4,5,6,7-tetrahydrobenzofuran-4-yl)-2-methylpropane-2-sulfinamide Step 2: To a solution of (S,Z)—N-(5,5-dimethyl-6,7-dihydrobenzofuran-4(5H)-ylidene)-2-methylpropane-2-sulfinamide (5.3 g, 20. mmol) in tetrahydrofuran (50 mL) was added titanium(IV) ethanolate (8.3 mL, 40. mmol) under nitrogen atmosphere at −50° C. After stirring for 20 minutes, sodium tetrahydroborate (3.0 g, 79 mmol) was added and stirring continued for an additional 30 minutes at −50° C. The mixture was then allowed to warm to ambient temperature while stirring overnight. After cooling to −15° C., methanol (10 mL) was slowly added and stirring continued until gas evolution stopped. The mixture was poured into saturated aqueous sodium chloride (250 mL) with vigorous stirring. After 30 minutes the resulting suspension was filtered through a plug of Celite®, rinsing with ethyl acetate. The phases of the combined filtrate and rinse were split and the aqueous layer was extracted with ethyl acetate (2 times). The organic layers were combined, dried over sodium sulfate, filtered, and concentrated. The resulting residue was purified by flash chromatography on silica gel using a Biotage® Isolera (50 g column, 20%→85% 2-methoxy-2-methylpropane/hexanes) to afford (S)—N—((R)-5,5-dimethyl-4,5,6,7-tetrahydrobenzofuran-4-yl)-2-methylpropane-2-sulfinamide (3.8 g, 14 mmol, 71%). MS (ESI): m/z=270 [M+H]⁺.

Step 3

(R)-5,5-dimethyl-4,5,6,7-tetrahydrobenzofuran-4-amine

Step 3: To a mixture of (S)—N—((R)-5,5-dimethyl-4,5,6,7-tetrahydrobenzofuran-4-yl)-2-methylpropane-2-sulfinamide (3.7 g, 14 mmol) in methanol (20 mL) was added 4.0 M hydrochloric acid in 1,4-dioxane (7.0 mL, 28 mmol) under nitrogen atmosphere. After stirring for 1 hour, the mixture was concentrated and the residue was suspended in ethoxyethane (100 mL). After stirring vigorously for 45 minutes, the resulting slurry was collected on a filter, rinsed with diethyl ether, and dried under vacuum. The solid was suspended in dichloromethane (100 mL) followed by addition of aqueous ammonia-ammonium chloride solution, (1 M in each; 10 mL). The mixture was stirred for 2 hours and settled. The organic layer was separated, washed with water, dried over sodium sulfate, filtered, and concentrated to afford (R)-5,5-dimethyl-4,5,6,7-tetrahydrobenzofuran-4-amine (1.4 g, 8.5 mmol, 61%).

Step 4

(R)-3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzamide Step 4: According to Method A and procedures similar to those for synthesizing Compound 1, Intermediate 2 (397 mg, 1.30 mmol) and (R)-5,5-dimethyl-4,5,6,7-tetrahydrobenzofuran-4-amine (233 mg, 1.41 mmol) were converted into the title compound (500. mg, 1.18 mmol, 90.7%). ¹H NMR (METHANOL-d₄): δ=7.99 (br d, J=7.6 Hz, 1H), 7.37 (br s, 1H), 6.96-7.00 (m, 1H), 6.90-6.96 (m, 1H), 6.36 (br s, 1H), 4.99 (s, 1H), 3.06 (s, 6H), 2.52-2.73 (m, 2H), 1.77-1.89 (m, 1H), 1.65-1.76 (m, 1H), 1.06 (s, 3H), 1.02 (s, 3H). MS (ESI): m/z=422 [M−H]⁻.

Example 38

Synthesis of Compound 30: (S)-3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzamide

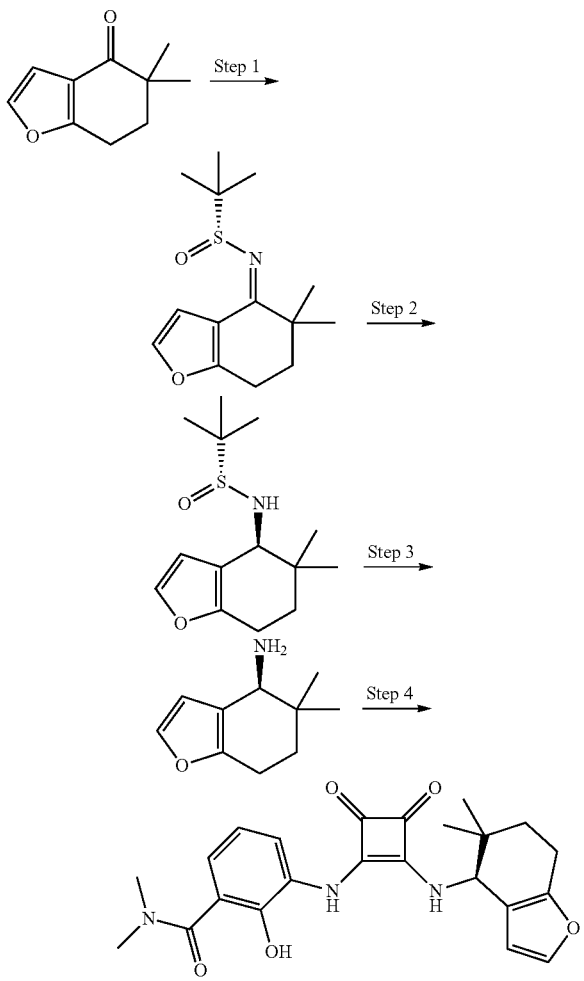

Step 1

(R,Z)—N-(5,5-dimethyl-6,7-dihydrobenzofuran-4(5H)-ylidene)-2-methylpropane-2-sulfinamide Step 1: After stirring a mixture of 5,5-dimethyl-6,7-dihydrobenzofuran-4(5H)-one (synthesized as described for Compound 28, 3.5 g, 21 mmol) and titanium(IV) ethanolate (35.7 mL, 171 mmol) under nitrogen atmosphere at 110° C. for 20 minutes, (R)-2-methyl-2-propanesulfinamide (10.3 g, 85.0 mmol) was added and stirring continued at 110° C. overnight. After cooling to ambient temperature, the mixture was slowly poured into saturated aqueous sodium chloride (200 mL) with vigorous stirring. After 30 minutes the resulting suspension was filtered through a plug of Celite®, rinsing with ethyl acetate. The phases of the combined filtrate and rinse were split and the aqueous layer was extracted with ethyl acetate (2 times). The organic layers were combined, dried over sodium sulfate, filtered, and concentrated. The resulting residue was purified by flash chromatography on silica gel using a Biotage® Isolera (50 g column, 0%→35% ethyl acetate/hexanes) to afford (R,Z)—N-(5,5-dimethyl-6,7-dihydrobenzofuran-4(5H)-ylidene)-2-methylpropane-2-sulfinamide (3.4 g, 13 mmol, 60.%). MS (ESI): m/z=268 [M+H]$^+$.

Step 2

(R)—N—((S)-5,5-dimethyl-4,5,6,7-tetrahydrobenzo-furan-4-yl)-2-methylpropane-2-sulfinamide Step 2: To a solution of (R,Z)—N-(5,5-dimethyl-6,7-dihydrobenzofuran-4(5H)-ylidene)-2-methylpropane-2-sulfinamide (3.3 g, 12 mmol) in tetrahydrofuran (50 mL) was added titanium(IV) ethanolate (5.1 mL, 24 mmol) under nitrogen atmosphere at −50° C. After stirring for 20 minutes, sodium tetrahydroborate (1.9 g, 50. mmol) was added and stirring continued for an additional 30 minutes at −50° C. The mixture was then allowed to warm to ambient temperature while stirring overnight. After cooling to −15° C., methanol (10 mL) was slowly added and stirring continued until gas evolution stopped. The mixture was poured into saturated aqueous sodium chloride (250 mL) with vigorous stirring. After 30 minutes the resulting suspension was filtered through a plug of Celite®, rinsing with ethyl acetate. The phases of the combined filtrate and rinse were split and the aqueous layer was extracted with ethyl acetate (2 times). The organic layers were combined, dried over sodium sulfate, filtered, and concentrated. The resulting residue was purified by flash chromatography on silica gel using a Biotage® Isolera (50 g column, 20%→85% 2-methoxy-2-methylpropane/hexanes) to afford (R)—N—((S)-5,5-dimethyl-4,5,6,7-tetrahydrobenzofuran-4-yl)-2-methylpropane-2-sulfinamide (2.6 g, 9.7 mmol, 78%). MS (ESI): m/z=270 [M+H]$^+$.

Step 3

(S)-5,5-dimethyl-4,5,6,7-tetrahydrobenzofuran-4-amine

Step 3: To a mixture of (R)—N—((S)-5,5-dimethyl-4,5,6,7-tetrahydrobenzofuran-4-yl)-2-methylpropane-2-sulfinamide (2.3 g, 8.5 mmol) in methanol (20 mL) was added 4.0 M hydrochloric acid in 1,4-dioxane (4.2 mL, 17 mmol) under nitrogen atmosphere. After stirring for 1 hour, the mixture was concentrated and the residue was suspended in ethoxyethane (100 mL). After stirring vigorously for 45 minutes, the resulting slurry was collected on a filter, rinsed with diethyl ether, and dried under vacuum. The solid was suspended in dichloromethane (100 mL) followed by addition of aqueous ammonia-ammonium chloride solution, (1 M in each; 10 mL). The mixture was stirred for 2 hours and settled. The organic layer was separated, washed with water, dried over sodium sulfate, filtered, and concentrated to afford (S)-5,5-dimethyl-4,5,6,7-tetrahydrobenzofuran-4-amine (1.2 g, 7.3 mmol, 85%).

Step 4

(S)-3-((2-((5,5-dimethyl-4,5,6,7-tetrahydrobenzo-furan-4-yl)amino)-3,4-dioxocyclobut-1-en-1-yl)amino)-2-hydroxy-N,N-dimethylbenzamide Step 4: According to Method A and procedures similar to those for synthesizing Compound 1, Intermediate 2 (163 mg, 0.536 mmol) and (S)-5,5-dimethyl-4,5,6,7-tetrahydrobenzofuran-4-amine (97.9 mg, 0.593 mmol) were converted into the title compound (215 mg, 0.507 mmol, 94.5%). $^1$H NMR (METHANOL-d$_4$): δ=7.99 (br d, J=7.6 Hz, 1H), 7.37 (br s, 1H), 6.96-7.00 (m, 1H), 6.90-6.96 (m, 1H), 6.36 (br s, 1H), 4.99 (s, 1H), 3.06 (s, 6H), 2.54-2.72 (m, 2H), 1.79-1.88 (m, 1H), 1.67-1.75 (m, 1H), 1.06 (s, 3H), 1.02 (s, 3H). MS (ESI): m/z=422 [M−H]$^-$.

Example 39

Synthesis of Compound 31: 6-chloro-3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzenesulfonamide

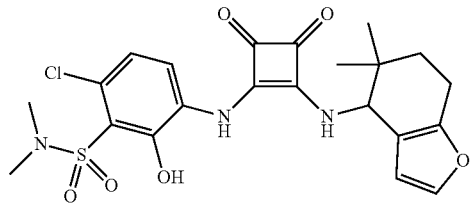

According to Method A and procedures similar to those for synthesizing Compound 1, Intermediate 1 (421 mg, 1.11 mmol) and 5,5-dimethyl-4,5,6,7-tetrahydrobenzofuran-4-amine (synthesized as described for Compound 28, 222 mg, 1.34 mmol) were converted into the title compound (458 mg, 0.926 mmol, 83.5%). $^1$H NMR (600 MHz, CHLOROFORM-d): δ=10.59 (br s, 1H), 8.11 (br s, 1H), 7.86 (br s, 1H), 7.27 (s, 1H), 6.93 (br d, J=8.2 Hz, 1H), 6.78 (br s, 1H), 6.28 (s, 1H), 5.02 (br s, 1H), 2.84 (br s, 6H), 2.59 (br s, 2H), 1.73-1.83 (m, 1H), 1.58-1.67 (m, 1H), 1.05 (br s, 3H), 1.02 (s, 3H). MS (ESI): m/z=492 [M−H]$^-$ Example 40

Synthesis of Compound 32: (R)-6-chloro-3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzenesulfonamide

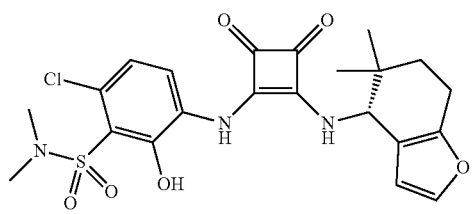 [SMILES: CN(C)S(=O)(=O)c1c(Cl)ccc(Nc2c(NC3c4ccoc4CCC3(C)C)c(=O)c2=O)c1O]

According to Method A and procedures similar to those for synthesizing Compound 1, Intermediate 1 (421 mg, 1.11 mmol) and 5,5-dimethyl-4,5,6,7-tetrahydrobenzofuran-4-amine (synthesized as described for Compound 28, 222 mg, 1.34 mmol) were converted into Compound 31 (458 mg, 0.926 mmol). Chiral separation via supercritical fluid chromatography (AS-H column, 20% methanol/carbon dioxide, 100 bar) afforded the title compound (211 mg, 0.427 mmol, 38.5%). $^1$H NMR (600 MHz, DMSO-d$_6$): δ=10.52 (s, 1H), 9.41 (s, 1H), 8.50 (d, J=9.4 Hz, 1H), 8.04 (d, J=8.8 Hz, 1H), 7.53 (s, 1H), 7.18 (br s, 1H), 6.44 (s, 1H), 4.82 (d, J=9.4 Hz, 1H), 2.84 (s, 6H), 2.60-2.69 (m, 1H), 2.52-2.60 (m, 1H), 1.67-1.77 (m, 1H), 1.58-1.64 (m, 1H), 0.95 (s, 3H), 0.91 (s, 3H). MS (ESI): m/z=492 [M−H]$^-$.

Example 41

Synthesis of Compound 33: (S)-6-chloro-3-((2-((5,5-dimethyl-4,5,6,7-tetrahydrobenzofuran-4-yl)amino)-3,4-dioxocyclobut-1-en-1-yl)amino)-2-hydroxy-N,N-dimethylbenzenesulfonamide

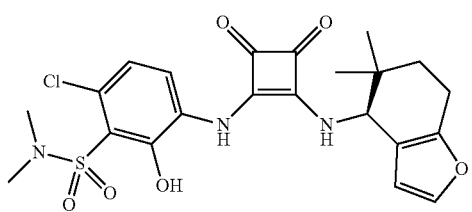 [SMILES: CN(C)S(=O)(=O)c1c(Cl)ccc(Nc2c(N[C@@H]3c4ccoc4CCC3(C)C)c(=O)c2=O)c1O]

According to Method A and procedures similar to those for synthesizing Compound 1, Intermediate 1 (421 mg, 1.11 mmol) and 5,5-dimethyl-4,5,6,7-tetrahydrobenzofuran-4-amine (synthesized as described for Compound 28, 222 mg, 1.34 mmol) were converted into Compound 31 (458 mg, 0.926 mmol). Chiral separation via supercritical fluid chromatography (AS-H column, 20% methanol/carbon dioxide, 100 bar) afforded the title compound (210 mg, 0.425 mmol, 38.3%). $^1$H NMR (600 MHz, DMSO-d$_6$): δ=10.52 (s, 1H), 9.41 (s, 1H), 8.50 (d, J=9.4 Hz, 1H), 8.04 (d, J=8.8 Hz, 1H), 7.53 (s, 1H), 7.17 (br s, 1H), 6.44 (s, 1H), 4.82 (d, J=9.4 Hz, 1H), 2.84 (s, 6H), 2.60-2.68 (m, 1H), 2.52-2.60 (m, 1H), 1.68-1.78 (m, 1H), 1.56-1.67 (m, 1H), 0.95 (s, 3H), 0.91 (s, 3H). MS (ESI): m/z=492 [M−H]$^-$.

Example 42

Synthesis of Compound 34: 6-chloro-3-((3,4-dioxo-2-((4,5,6,7-tetrahydrobenzo[b]thiophen-4-yl)amino)cyclobut-1-en-1-yl)amino)-2-hydroxy-N,N-dimethylbenzenesulfonamide

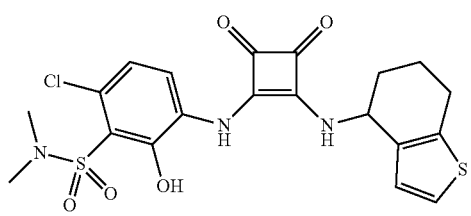 [SMILES: CN(C)S(=O)(=O)c1c(Cl)ccc(Nc2c(NC3CCCc4sccc43)c(=O)c2=O)c1O]

According to Method A and procedures similar to those for synthesizing Compound 1, Intermediate 1 (20.7 mg, 0.0552 mmol) and 4,5,6,7-tetrahydrobenzo[b]thiophen-4-amine (11.9 mg, 0.0777 mmol) were converted into the title compound (23.0 mg, 0.0477 mmol, 86.4%). $^1$H NMR (600 MHz, CHLOROFORM-d): δ=10.55 (s, 1H), 8.04 (br s, 1H), 7.87 (d, J=8.8 Hz, 1H), 7.07 (br s, 1H), 6.99 (br s, 1H), 6.92 (br d, J=8.8 Hz, 1H), 6.75-6.90 (m, 1H), 5.38 (br s, 1H), 2.82 (br s, 8H), 2.15 (br s, 1H), 1.79-2.04 (m, 3H). MS (ESI): m/z=480 [M−H]$^-$.

Example 43

Synthesis of Compound 35: methyl 3-((2-((4-chloro-3-(N,N-dimethylsulfamoyl)-2-hydroxyphenyl)amino)-3,4-dioxocyclobut-1-en-1-yl)amino)-2,2-dimethyl-3-phenylpropanoate

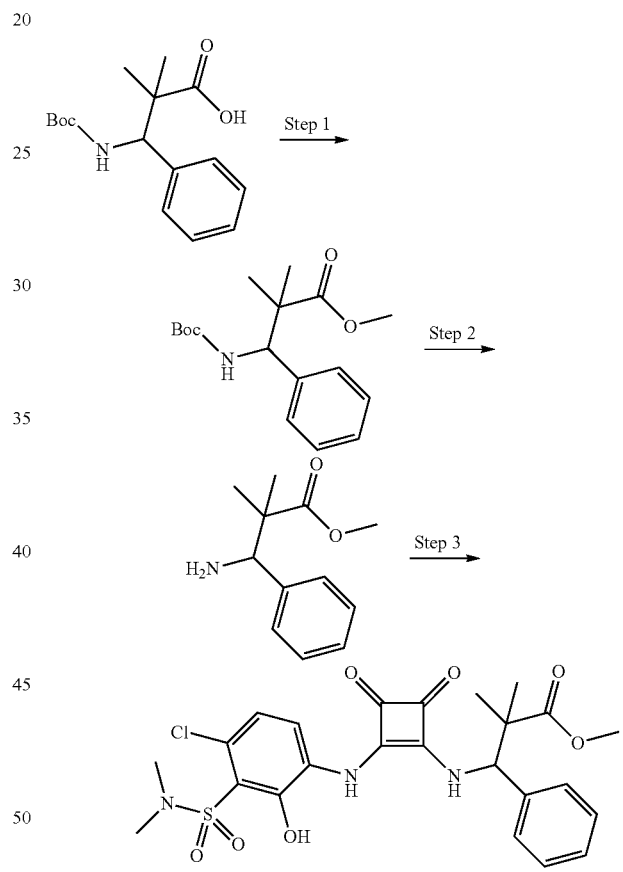

Step 1 methyl 3-((tert-butoxycarbonyl)amino)-2,2-dimethyl-3-phenylpropanoate

Step 1: To a solution of 3-((tert-butoxycarbonyl)amino)-2,2-dimethyl-3-phenylpropanoic acid (178 mg, 0.578 mmol) in N,N-dimethylformamide (2.0 mL) was added potassium carbonate (90.0 mg, 0.651 mmol) followed by iodomethane (2.0 M in 2-methoxy-2-methylpropane, 0.32 mL, 0.64 mmol). After stirring at ambient temperature overnight, the mixture was diluted in ethyl acetate, washed with water (2 times), 0.1 N aqueous hydrochloric acid (2 times), brine, dried over magnesium sulfate, filtered, and concentrated to afford methyl 3-((tert-butoxycarbonyl)amino)-2,2-dimethyl-3-phenylpropanoate (185 mg, 0.602 mmol, 104%). $^1$H NMR (600 MHz, CHLOROFORM-d): δ=7.20-7.32 (m, 3H), 7.17 (br d, J=7.0 Hz, 2H), 5.95 (d, J=8.2 Hz, 1H), 4.70 (d, J=9.4 Hz, 1H), 3.64 (s, 3H), 1.39 (s, 9H), 1.29 (s, 3H), 1.10 (s, 3H).

Step 2 methyl 3-amino-2,2-dimethyl-3-phenylpropanoate

Step 2: To a solution of methyl 3-((tert-butoxycarbonyl)amino)-2,2-dimethyl-3-phenylpropanoate (183 mg, 0.595 mmol) in dichloromethane (8.8 mL) was added 2,2,2-trifluoroacetic acid (1.0 mL, 13 mmol) at 0° C. After stirring at 0° C. for 1 hour, the solution was diluted in dichloromethane, washed with 1.0 N aqueous sodium hydroxide (3 times), brine, dried over magnesium sulfate, filtered, and concentrated to afford a crude mixture of starting material and desired intermediate (151 mg). This crude mixture (130. mg) was subjected to the reaction conditions a second time, except stirred at ambient temperature instead of 0° C., to afford methyl 3-amino-2,2-dimethyl-3-phenylpropanoate (89.3 mg, 0.431 mmol). $^1$H NMR (600 MHz, CHLOROFORM-d): δ=7.22-7.32 (m, 5H), 4.23 (s, 1H), 3.69 (s, 3H), 1.39 (br s, 2H), 1.14 (s, 3H), 1.08 (s, 3H).

Step 3

Methyl 3-((2-((4-chloro-3-(N,N-dimethyl sulfamoyl)-2-hydroxyphenyl)amino)-3,4-dioxocyclobut-1-en-1-yl)amino)-2,2-dimethyl-3-phenylpropanoate Step 3: According to Method A and procedures similar to those for synthesizing Compound 1, Intermediate 1 (19.1 mg, 0.0510 mmol) and methyl 3-amino-2,2-dimethyl-3-phenylpropanoate (20.8 mg, 0.100 mmol) in methanol solvent (0.53 mL) were converted into the title compound (24.3 mg, 0.0453 mmol, 88.9%). $^1$H NMR (600 MHz, CHLOROFORM-d): δ=10.66 (s, 1H), 8.17 (br s, 1H), 7.80 (br s, 2H), 7.25-7.38 (m, 5H), 7.01 (br d, J=8.8 Hz, 1H), 5.46 (br s, 1H), 3.67 (s, 3H), 2.90 (s, 6H), 1.38 (s, 3H), 1.15 (s, 3H). MS (ESI): m/z=534 [M−H]$^−$.

Example 44

Synthesis of Compound 36: 6-chloro-3-((2-((1-(furan-2-yl)-2,2-dimethylpropyl)amino)-3,4-dioxocyclobut-1-en-1-yl)amino)-2-hydroxy-N,N-dimethylbenzenesulfonamide

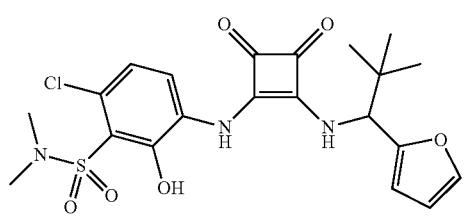 [SMILES: CN(C)S(=O)(=O)c1c(Cl)ccc(Nc2c(NC(c3ccco3)C(C)(C)C)c(=O)c2=O)c1O]

According to Method A and procedures similar to those for synthesizing Compound 1, Intermediate 1 (20.4 mg, 0.0544 mmol) and 1-(furan-2-yl)-2,2-dimethylpropan-1-amine (20.4 mg, 0.126 mmol) were converted into the title compound (24.6 mg, 0.0510 mmol, 93.8%). $^1$H NMR (600 MHz, CHLOROFORM-d): δ=10.60 (s, 1H), 8.29 (br s, 1H), 7.86 (d, J=8.8 Hz, 1H), 7.32 (br s, 2H), 6.94 (d, J=8.8 Hz, 1H), 6.31 (br s, 1H), 6.26 (br s, 1H), 5.26 (br s, 1H), 2.88 (s, 6H), 1.02 (s, 9H). MS (ESI): m/z=480 [M−H]$^−$.

Example 45

Synthesis of Compound 37: 6-chloro-3-((2-((2,2-dimethyl-1-(5-methylfuran-2-yl)propyl)amino)-3,4-dioxocyclobut-1-en-1-yl)amino)-2-hydroxy-N,N-dimethylbenzenesulfonamide

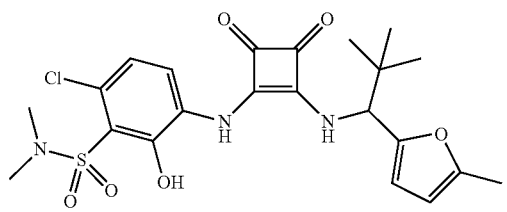

According to Method A and procedures similar to those for synthesizing Compound 1, Intermediate 1 (22.1 mg, 0.0590 mmol) and 2,2-dimethyl-1-(5-methylfuran-2-yl)propan-1-amine (12.9 mg, 0.0733 mmol) were converted into the title compound (26.3 mg, 0.0530 mmol, 89.9%). $^1$H NMR (600 MHz, CHLOROFORM-d): δ=10.72 (s, 1H), 7.85 (br d, J=6.5 Hz, 1H), 7.65 (br s, 1H), 6.99 (d, J=8.8 Hz, 1H), 6.38 (br s, 1H), 6.15 (br s, 1H), 5.91 (br s, 1H), 5.14 (br s, 1H), 2.92 (s, 6H), 2.26 (s, 3H), 1.04 (s, 9H). MS (ESI): m/z=494 [M−H]$^−$.

Example 46

Synthesis of Compound 38: 3-((3,4-dioxo-2-((2,3,3-trimethylbutan-2-yl)amino)cyclobut-1-en-1-yl)amino)-2-hydroxy-N,N-dimethylbenzamide

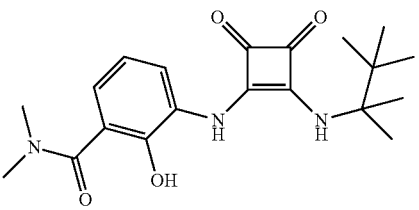 [SMILES: CN(C)C(=O)c1cccc(Nc2c(NC(C)(C)C(C)(C)C)c(=O)c2=O)c1O]

According to Method A and procedures similar to those for synthesizing Compound 1, Intermediate 2 (19.9 mg, 0.0654 mmol) and 2,3,3-trimethylbutan-2-amine (22.2 mg, 0.183 mmol) were converted into the title compound (10.4 mg, 0.0279 mmol, 42.6%). $^1$H NMR (600 MHz, METHANOL-d$_4$): δ=7.81 (d, J=7.6 Hz, 1H), 7.00 (d, J=7.6 Hz, 1H), 6.93 (dd, J=7.6 Hz, 1H), 3.07 (s, 6H), 1.52 (s, 6H), 1.04 (s, 9H). MS (ESI): m/z=372 [M−H]$^−$.

Example 47

Synthesis of Compound 39: (S)-6-chloro-3-((2-((3,3-dimethylbutan-2-yl)amino)-3,4-dioxocyclobut-1-en-1-yl)amino)-2-hydroxy-N,N-dimethylbenzenesulfonamide

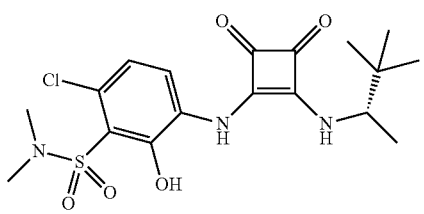 [SMILES: C[C@H](Nc1c(Nc2ccc(Cl)c(S(=O)(=O)N(C)C)c2O)c(=O)c1=O)C(C)(C)C]

According to Method A and procedures similar to those for synthesizing Compound 1, Intermediate 1 (24.8 mg, 0.0662 mmol) and (S)-3,3-dimethylbutan-2-amine (12.6 mg, 0.125 mmol) were converted into the title compound (25.1 mg, 0.0584 mmol, 88.2%). $^1$H NMR (600 MHz, CHLOROFORM-d): δ=10.55 (s, 1H), 8.64 (br s, 1H), 8.00 (d, J=8.8 Hz, 1H), 7.58 (br s, 1H), 6.95 (d, J=8.8 Hz, 1H), 4.19 (br s, 1H), 2.87 (s, 6H), 1.22 (br d, J=6.5 Hz, 3H), 0.93 (s, 9H). MS (ESI): m/z=428 [M−H]$^-$.

Example 48

Synthesis of Compound 40: 6-chloro-2-hydroxy-N,N-dimethyl-3-((2-(neopentylamino)-3,4-dioxocyclobut-1-en-1-yl)amino)benzenesulfonamide

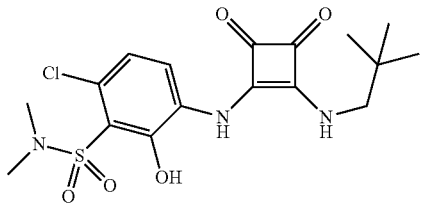 [SMILES: CN(C)S(=O)(=O)c1c(Cl)ccc(Nc2c(NCC(C)(C)C)c(=O)c2=O)c1O]

According to Method A and procedures similar to those for synthesizing Compound 1, Intermediate 1 (22.8 mg, 0.0608 mmol) and 2,2-dimethylpropan-1-amine (13.1 mg, 0.147 mmol) were converted into the title compound (8.7 mg, 0.021 mmol, 34%). $^1$H NMR (600 MHz, METHANOL-d$_4$): δ=8.16 (d, J=8.8 Hz, 1H), 7.09 (d, J=8.8 Hz, 1H), 3.52 (s, 2H), 2.92 (s, 6H), 0.99 (s, 9H). MS (ESI): m/z=414 [M−H]$^-$.

Example 49

Synthesis of Compound 41: 3-((2-((1-(bicyclo[2.2.2]octan-1-yl)ethyl)amino)-3,4-dioxocyclobut-1-en-1-yl)amino)-6-chloro-2-hydroxy-N,N-dimethylbenzenesulfonamide

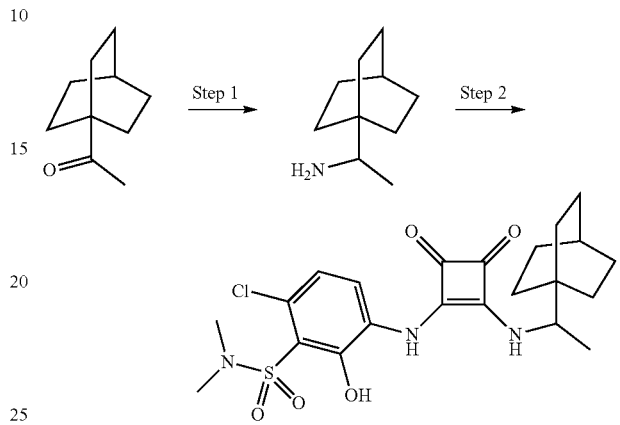

Step 1

1-(bicyclo[2.2.2]octan-1-yl)ethan-1-amine

Step 1: After purging a solution of 1-(bicyclo[2.2.2]octan-1-yl)ethan-1-one (65.2 mg, 0.407 mmol) in propan-2-ol (1.3 mL) with nitrogen for 10 minutes, sodium cyanotrihydroborate (161 mg, 2.43 mmol) was added followed by ammonium acetate (350 mg, 4.54 mmol). After stirring at 70° C. overnight, the suspension was allowed to cool to ambient temperature and partitioned between ethyl acetate and 1.0 N aqueous sodium hydroxide. The organic layer was collected and washed with 1.0 N aqueous sodium hydroxide, dried over magnesium sulfate, filtered, and concentrated to afford 1-(bicyclo[2.2.2]octan-1-yl)ethan-1-amine (26.3 mg, 0.171 mmol, 42.2%). $^1$H NMR (600 MHz, CHLOROFORM-d): δ=2.65 (br q, J=6.5 Hz, 1H), 1.48-1.66 (m, 6H), 1.27-1.47 (m, 6H), 1.24 (br s, 1H), 1.04 (br d, J=6.5 Hz, 3H).

Step 2

3-((2-((1-(2-((1-(bicyclo[2.2.2]octan-1-yl)ethyl)amino)-3,4-dioxocyclobut-1-en-1-yl)amino)-6-chloro-2-hydroxy-N,N-dimethylbenzenesulfonamide Step 2: According to Method A and procedures similar to those for synthesizing Compound 1, Intermediate 1 (35.2 mg, 0.0939 mmol) and 1-(bicyclo[2.2.2]octan-1-yl)ethan-1-amine (26.3 mg, 0.172 mmol) were converted into the title compound (32.9 mg, 0.0683 mmol, 72.7%). $^1$H NMR (600 MHz, METHANOL-d$_4$): δ=8.17 (d, J=8.8 Hz, 1H), 7.09 (d, J=8.8 Hz, 1H), 4.00 (br q, J=6.5 Hz, 1H), 2.92 (s, 6H), 1.56-1.68 (m, 6H), 1.38-1.52 (m, 6H), 1.28 (br s, 1H), 1.17 (br d, J=6.5 Hz, 3H). MS (ESI): m/z=480 [M−H]$^-$.

Example 50

Synthesis of Compound 42: 6-chloro-2-hydroxy-3-((2-((3-hydroxy-2,2-dimethyl-1-phenylpropyl)amino)-3,4-dioxocyclobut-1-en-1-yl)amino)-N,N-dimethylbenzenesulfonamide

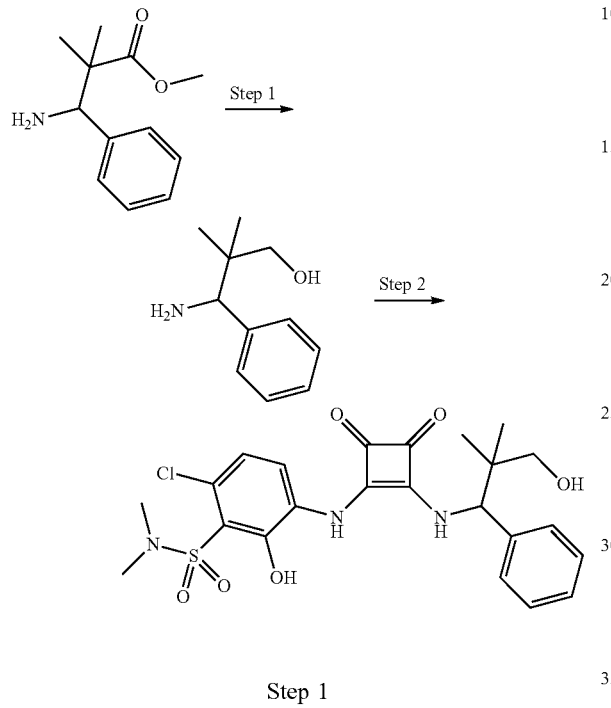

Step 1

3-amino-2,2-dimethyl-3-phenylpropan-1-ol

Step 1: To a solution of methyl 3-amino-2,2-dimethyl-3-phenylpropanoate (synthesized as described for Compound 35, 86.4 mg, 0.417 mmol) in tetrahydrofuran (2.0 mL) was added lithium tetrahydroaluminate (1.0 M in tetrahydrofuran, 0.84 mL, 0.84 mmol) under nitrogen atmosphere at 0° C. The solution was allowed to warm to ambient temperature as stirring continued for 1 hour. The reaction was then quenched with water and mixture partitioned between dichloromethane and saturated aqueous potassium sodium tartrate tetrahydrate with pH adjusted to 12 by addition of 1.0 N aqueous sodium hydroxide. The aqueous layer was subjected to extraction a second time with dichloromethane. The organic layers were combined, dried over magnesium sulfate, filtered, and concentrated to afford 3-amino-2,2-dimethyl-3-phenylpropan-1-ol (68.3 mg, 0.381 mmol, 91.4%). $^1$H NMR (600 MHz, CHLOROFORM-d): δ=7.26-7.36 (m, 5H), 3.91 (s, 1H), 3.58 (d, J=11.2 Hz, 1H), 3.38 (d, J=11.2 Hz, 1H), 1.02 (s, 3H), 0.74 (s, 3H).

Step 2

6-chloro-2-hydroxy-3-((2-((3-hydroxy-2,2-dimethyl-1-phenylpropyl)amino)-3,4-dioxocyclobut-1-en-1-yl)amino)-N,N-dimethylbenzenesulfonamide Step 2: According to Method A and procedures similar to those for synthesizing Compound 1, Intermediate 1 (35.5 mg, 0.0947 mmol) and 3-amino-2,2-dimethyl-3-phenylpropan-1-ol (32.6 mg, 0.182 mmol) were converted into the title compound (16.9 mg, 0.0333 mmol, 35.1%). $^1$H NMR (600 MHz, METHANOL-d$_4$): δ=8.08 (d, J=8.8 Hz, 1H), 7.32-7.42 (m, 4H), 7.25-7.32 (m, 1H), 7.07 (d, J=8.8 Hz, 1H), 5.43 (s, 1H), 3.40 (d, J=10.6 Hz, 1H), 3.24 (d, J=10.6 Hz, 1H), 2.91 (s, 6H), 0.97 (s, 3H), 0.96 (s, 3H). MS (ESI): m/z=507 [M−H]$^-$.

Example 51

Synthesis of Compound 43: 6-chloro-3-((2-((2,2-dimethyl-1-phenylbutyl)amino)-3,4-dioxocyclobut-1-en-1-yl)amino)-2-hydroxy-N,N-dimethylbenzenesulfonamide

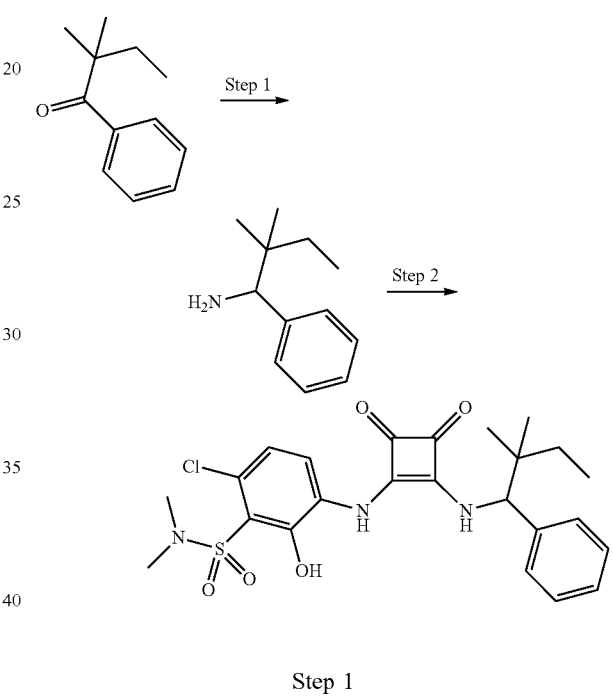

Step 1

2,2-dimethyl-1-phenylbutan-1-amine

Step 1: After purging a solution of 2,2-dimethyl-1-phenylbutan-1-one (107 mg, 0.587 mmol) in propan-2-ol (2.0 mL) with nitrogen for 10 minutes, sodium cyanotrihydroborate (266 mg, 4.02 mmol) was added followed by ammonium acetate (573 mg, 7.43 mmol). After stirring at 70° C. overnight, the suspension was allowed to cool to ambient temperature and partitioned between ethyl acetate and 1.0 N aqueous sodium hydroxide. The organic layer was collected and washed with 1.0 N aqueous sodium hydroxide, dried over magnesium sulfate, filtered, and concentrated to afford a crude mixture that was carried through to the next step without further purification. Crude yield=107 mg.

Step 2

6-chloro-3-((2-((2,2-dimethyl-1-phenylbutyl)amino)-3,4-dioxocyclobut-1-en-1-yl)amino)-2-hydroxy-N,N-dimethylbenzenesulfonamide Step 2: According to Method A and procedures similar to those for synthesizing Compound 1, Intermediate 1 (15.6 mg, 0.0416 mmol) and 2,2-dimethyl-1-phenylbutan-1-amine (crude mixture, 61.1 mg) were converted into the title compound (17.1 mg, 0.0338 mmol, 81.2%). $^1$H NMR (600 MHz, METHANOL-$d_4$): δ=8.14 (d, J=8.8 Hz, 1H), 7.19-7.42 (m, 5H), 7.05 (d, J=8.8 Hz, 1H), 5.26 (s, 1H), 2.91 (s, 6H), 1.31-1.46 (m, 2H), 0.99 (s, 3H), 0.92 (t, J=7.6 Hz, 3H), 0.89 (s, 3H). MS (ESI): m/z=504 [M−H]$^-$.

Example 52

Synthesis of Compound 44: 6-chloro-3-((3,4-dioxo-2-((2,2,4,4-tetramethylpentan-3-yl)amino)cyclobut-1-en-1-yl)amino)-2-hydroxy-N,N-dimethylbenzenesulfonamide

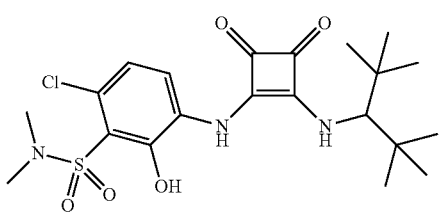 [SMILES: CN(C)S(=O)(=O)c1c(Cl)ccc(Nc2c(NC(C(C)(C)C)C(C)(C)C)c(=O)c2=O)c1O]

According to Method B and procedures similar to those for synthesizing Compound 2, Intermediate 1 (24.0 mg, 0.0640 mmol) and 2,2,4,4-tetramethylpentan-3-amine hydrochloride (23.3 mg, 0.130 mmol) were converted into the title compound (6.8 mg, 0.014 mmol, 23%). $^1$H NMR (600 MHz, METHANOL-$d_4$): δ=8.20 (br d, J=8.8 Hz, 1H), 7.07 (br d, J=8.8 Hz, 1H), 3.95 (s, 1H), 2.92 (s, 6H), 1.10 (s, 18H). MS (ESI): m/z=470 [M−H]$^-$.

Example 53

Synthesis of Compound 45: 6-chloro-3-((2-((2,2-dimethylpentan-3-yl)amino)-3,4-dioxocyclobut-1-en-1-yl)amino)-2-hydroxy-N,N-dimethylbenzenesulfonamide

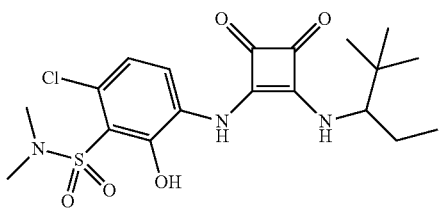 [SMILES: CCC(Nc1c(Nc2ccc(Cl)c(S(=O)(=O)N(C)C)c2O)c(=O)c1=O)C(C)(C)C]

According to Method A and procedures similar to those for synthesizing Compound 1, Intermediate 1 (21.6 mg, 0.0576 mmol) and 2,2-dimethylpentan-3-amine (10.7 mg, 0.0882 mmol) were converted into the title compound (22.2 mg, 0.0500 mmol, 86.8%). $^1$H NMR (600 MHz, CHLOROFORM-d/METHANOL-$d_4$): δ=8.18 (d, J=8.8 Hz, 1H), 6.99 (d, J=8.8 Hz, 1H), 3.81-3.93 (m, 1H), 2.88 (s, 6H), 1.72-1.83 (m, 1H), 1.23-1.33 (m, 1H), 0.87-0.96 (m, 12H). MS (ESI): m/z=442 [M−H]$^-$.

Example 54

Synthesis of Compound 46: 6-chloro-3-((2-((5,5-dimethyl-5,6,7,8-tetrahydro-4H-cyclohepta[b]furan-4-yl)amino)-3,4-dioxocyclobut-1-en-1-yl)amino)-2-hydroxy-N,N-dimethylbenzenesulfonamide

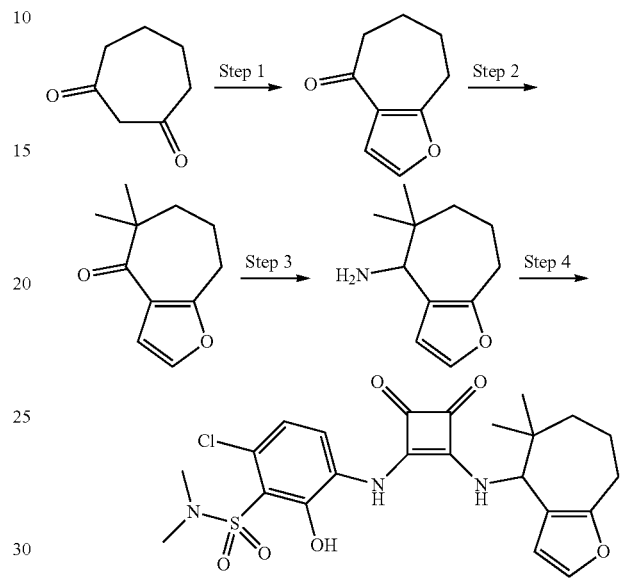

Step 1

5,6,7,8-tetrahydro-4H-cyclohepta[b]furan-4-one

Step 1: To a solution of sodium bicarbonate (156 mg, 1.85 mmol) in water (1.2 mL) was added 2-chloroacetaldehyde (50 wt. % in water, 0.25 mL, 2.0 mmol) at 0° C., followed by a mixture of cycloheptane-1,3-dione (202 mg, 1.52 mmol) in water (0.75 mL). The mixture was allowed to warm to ambient temperature while stirring overnight. Ethyl acetate (2.0 mL) was then added and the pH of the aqueous layer was adjusted to 1 by dropwise addition of 6.0 N aqueous hydrochloric acid. Stirring continued for an additional 3 hours and the mixture was subsequently partitioned between ethyl acetate and water. The aqueous layer was subjected to extraction a second time with ethyl acetate. The organic layers were combined, dried over magnesium sulfate, filtered, and concentrated. The resulting residue was purified by flash chromatography on silica gel using a Teledyne-Isco CombiFlash® Rf 200 (12 g column, 0%→25% ethyl acetate/hexanes) to afford 5,6,7,8-tetrahydro-4H-cyclohepta[b]furan-4-one (152 mg, 1.01 mmol, 66.5%). $^1$H NMR (CHLOROFORM-d): δ=7.22 (br s, 1H), 6.71 (br s, 1H), 2.93-3.15 (m, 2H), 2.66-2.84 (m, 2H), 1.97-2.07 (m, 2H), 1.86-1.95 (m, 2H).

Step 2

5,5-dimethyl-5,6,7,8-tetrahydro-4H-cyclohepta[b]furan-4-one

Step 2: To a suspension of sodium hydride (60 wt. % dispersion in mineral oil, 131 mg, 3.28 mmol) in N,N-dimethylformamide (3.4 mL) was added a solution of 5,6, 7,8-tetrahydro-4H-cyclohepta[b]furan-4-one (145 mg, 0.962 mmol) in N,N-dimethylformamide (1.4 mL) under nitrogen atmosphere. After stirring at ambient temperature for 30 minutes, iodomethane (2.0 M in 2-methoxy-2-methylpropane, 1.7 mL, 3.4 mmol) was added. After stirring at ambient temperature overnight, the mixture was quenched with 0.1 N aqueous hydrochloric acid and extracted with ethyl acetate. The organic layer was then washed with 0.1 N aqueous hydrochloric acid (2 times), followed by brine, dried over magnesium sulfate, filtered, and concentrated. The resulting residue was purified by flash chromatography on silica gel using a Teledyne-Isco CombiFlash® Rf 200 (24 g column, 0%→10% ethyl acetate/hexanes) to afford 5,5-dimethyl-5,6,7,8-tetrahydro-4H-cyclohepta[b]furan-4-one (78.9 mg, 0.443 mmol, 46.0%). $^1$H NMR (600 MHz, CHLOROFORM-d): δ=7.22 (br s, 1H), 6.68 (br s, 1H), 2.87-2.98 (m, 2H), 1.90-2.02 (m, 2H), 1.76-1.87 (m, 2H), 1.21 (s, 6H).

Step 3

5,5-dimethyl-5,6,7,8-tetrahydro-4H-cyclohepta[b]furan-4-amine

Step 3: After purging a solution of 5,5-dimethyl-5,6,7,8-tetrahydro-4H-cyclohepta[b]furan-4-one (78.4 mg, 0.440 mmol) in propan-2-ol (1.5 mL) with nitrogen for 10 minutes, sodium cyanotrihydroborate (194 mg, 2.94 mmol) was added followed by ammonium acetate (415 mg, 5.39 mmol). After stirring at 70° C. overnight, the suspension was allowed to cool to ambient temperature and partitioned between ethyl acetate and 1.0 N aqueous sodium hydroxide. The organic layer was collected and washed with 1.0 N aqueous sodium hydroxide, dried over magnesium sulfate, filtered, and concentrated to afford a crude mixture that was carried through to the next step without further purification. Crude yield=78.9 mg.

Step 4

6-chloro-3-((2-((5,5-dimethyl-5,6,7,8-tetrahydro-4H-cyclohepta[b]furan-4-yl)amino)-3,4-dioxocyclobut-1-en-1-yl)amino)-2-hydroxy-N,N-dimethylbenzenesulfonamide Step 4: According to Method A and procedures similar to those for synthesizing Compound 1, Intermediate 1 (14.8 mg, 0.0395 mmol) and 5,5-dimethyl-5,6,7,8-tetrahydro-4H-cyclohepta[b]furan-4-amine (crude mixture, 39.8 mg) were converted into the title compound (17.3 mg, 0.0341 mmol, 86.2%). $^1$H NMR (600 MHz, CHLOROFORM-d/METHANOL-d$_4$): δ=7.93 (d, J=8.8 Hz, 1H), 7.12 (s, 1H), 6.90 (d, J=8.8 Hz, 1H), 6.28 (s, 1H), 5.04 (br s, 1H), 2.83 (s, 6H), 2.60-2.79 (m, 2H), 1.81-1.92 (m, 1H), 1.64-1.79 (m, 2H), 1.53-1.63 (m, 1H), 1.02 (s, 3H), 1.00 (s, 3H). MS (ESI): m/z=506 [M−H]$^-$.

Example 54

Synthesis of Compound 47: 3-((2-((5,5-dimethyl-5,6,7,8-tetrahydro-4H-cyclohepta[b]furan-4-yl)amino)-3,4-dioxocyclobut-1-en-1-yl)amino)-2-hydroxy-N,N-dimethylbenzamide

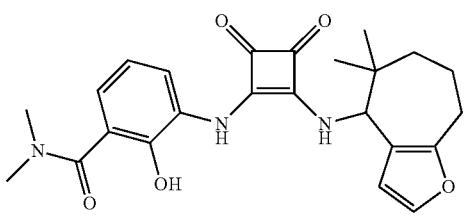 [SMILES: CN(C)C(=O)c1cccc(Nc2c(NC3c4ccoc4CCCC3(C)C)c(=O)c2=O)c1O]

According to Method A and procedures similar to those for synthesizing Compound 1, Intermediate 2 (14.4 mg, 0.0473 mmol) and 5,5-dimethyl-5,6,7,8-tetrahydro-4H-cyclohepta[b]furan-4-amine (crude mixture, synthesized as described for Compound 46, 41.5 mg) were converted into the title compound (14.1 mg, 0.0322 mmol, 68.1%). $^1$H NMR (600 MHz, CHLOROFORM-d/METHANOL-d$_4$): δ=8.01 (br d, J=7.6 Hz, 1H), 7.11 (s, 1H), 6.84-6.95 (m, 1H), 6.70-6.84 (m, 1H), 6.27 (s, 1H), 4.99 (br s, 1H), 3.10 (s, 6H), 2.76-2.86 (m, 1H), 2.64-2.76 (m, 1H), 1.80-1.90 (m, 1H), 1.64-1.80 (m, 2H), 1.52-1.62 (m, 1H), 1.01 (s, 3H), 0.98 (s, 3H). MS (ESI): m/z=436 [M−H]$^-$.

Example 56

Synthesis of Compound 48: 3-((5,5-dimethyl-4,5,6,7-tetrahydrobenzofuran-4-yl)amino)-4-((2-hydroxy-3-(morpholine-4-carbonyl)phenyl)amino)cyclobut-3-ene-1,2-dione

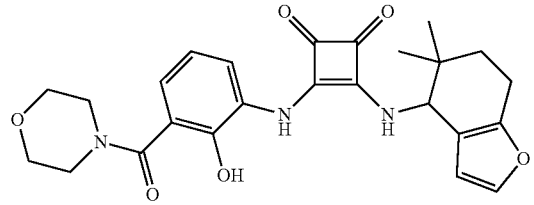 [SMILES: CC1(C)CCc2occc2C1Nc1c(Nc2cccc(C(=O)N3CCOCC3)c2O)c(=O)c1=O]

According to Method A and procedures similar to those for synthesizing Compound 1, Intermediate 3 (20.8 mg, 0.0601 mmol) and 5,5-dimethyl-4,5,6,7-tetrahydrobenzofuran-4-amine (synthesized as described for Compound 28, 18.7 mg, 0.113 mmol) were converted into the title compound (19.2 mg, 0.0412 mmol, 68.6%). $^1$H NMR (600 MHz, METHANOL-d$_4$): δ=7.96 (br d, J=7.0 Hz, 1H), 7.37 (s, 1H), 6.85-7.04 (m, 2H), 6.36 (s, 1H), 4.99 (br s, 1H), 3.68 (br s, 4H), 3.60 (br s, 4H), 2.51-2.75 (m, 2H), 1.77-1.92 (m, 1H), 1.65-1.77 (m, 1H), 1.06 (s, 3H), 1.02 (s, 3H). MS (ESI): m/z=464 [M−H]$^-$.

Example 57

Synthesis of Compound 49:3-((4-chloro-2-hydroxy-3-((4-methylpiperazin-1-yl)sulfonyl)phenyl)amino)-4-((5,5-dimethyl-4,5,6,7-tetrahydrobenzofuran-4-yl)amino)cyclobut-3-ene-1,2-dione

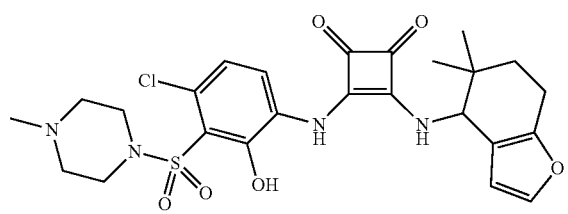 [SMILES: CN1CCN(S(=O)(=O)c2c(Cl)ccc(Nc3c(NC4c5ccoc5CCC4(C)C)c(=O)c3=O)c2O)CC1]

According to Method A and procedures similar to those for synthesizing Compound 1, Intermediate 4 (24.7 mg, 0.0558 mmol) and 5,5-dimethyl-4,5,6,7-tetrahydrobenzofuran-4-amine (synthesized as described for Compound 28, 19.5 mg, 0.118 mmol) were converted into the title compound (4.8 mg, 0.0087 mmol, 16%). $^1$H NMR (600 MHz, METHANOL-$d_4$): δ=8.20 (d, J=8.8 Hz, 1H), 7.37 (s, 1H), 7.09 (d, J=8.8 Hz, 1H), 6.35 (s, 1H), 4.98 (br s, 1H), 3.37 (br s, 4H), 2.57-2.71 (m, 2H), 2.50 (br s, 4H), 2.30 (s, 3H), 1.77-1.87 (m, 1H), 1.66-1.75 (m, 1H), 1.06 (s, 3H), 1.02 (s, 3H). MS (ESI): m/z=547 [M−H]$^-$.

Example 58

Synthesis of Compound 50: 6-chloro-3-((2-((3,3-dimethylpentan-2-yl)amino)-3,4-dioxocyclobut-1-en-1-yl)amino)-2-hydroxy-N,N-dimethylbenzenesulfonamide

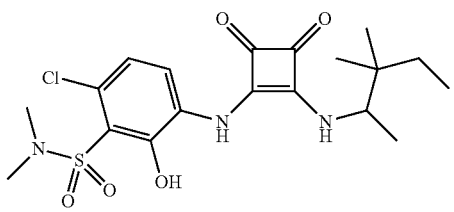 [SMILES: CCC(C)(C)C(C)Nc1c(Nc2ccc(Cl)c(S(=O)(=O)N(C)C)c2O)c(=O)c1=O]

According to Method B and procedures similar to those for synthesizing Compound 2, Intermediate 1 (23.4 mg, 0.0619 mmol) and 3,3-dimethylpentan-2-amine hydrochloride (16.9 mg, 0.106 mmol) were converted into the title compound (27.5 mg, 0.0620 mmol, 100.%). $^1$H NMR (METHANOL-$d_4$): δ=8.17 (d, J=8.8 Hz, 1H), 7.09 (d, J=8.8 Hz, 1H), 4.25 (q, J=7.0 Hz, 1H), 2.92 (s, 6H), 1.38 (q, J=7.6 Hz, 2H), 1.24 (d, J=7.0 Hz, 3H), 0.93 (s, 3H), 0.92 (s, 3H), 0.89 (t, J=7.6 Hz, 3H). MS (ESI): m/z=442 [M−H]$^-$.

Example 59

Synthesis of Compound 51: 6-chloro-3-((2-((6,6-dimethyl-4,5,6,7-tetrahydrobenzofuran-7-yl)amino)-3,4-dioxocyclobut-1-en-1-yl)amino)-2-hydroxy-N,N-dimethylbenzenesulfonamide

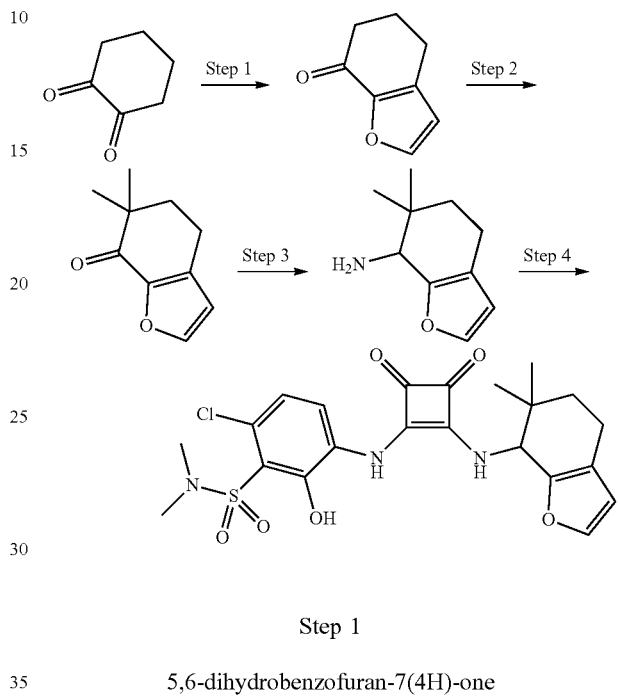

Step 1

5,6-dihydrobenzofuran-7(4H)-one

Step 1: To a solution of sodium bicarbonate (350. mg, 4.16 mmol) in water (2.7 mL) was added 2-chloroacetaldehyde (50 wt. % in water, 0.46 mL, 3.6 mmol) at 0° C., followed by a mixture of cyclohexane-1,2-dione (416 mg, 3.63 mmol) in water (3.0 mL). The mixture was allowed to warm to ambient temperature while stirring overnight. Ethyl acetate (3.4 mL) was then added and the pH of the aqueous layer was adjusted to 1 by dropwise addition of 6.0 N aqueous hydrochloric acid. Stirring continued for an additional 3 hours and the mixture was subsequently partitioned between ethyl acetate and water. The aqueous layer was subjected to extraction a second time with ethyl acetate. The organic layers were combined, dried over magnesium sulfate, filtered, and concentrated. The resulting residue was purified by flash chromatography on silica gel using a Teledyne-Isco CombiFlash® Rf 200 (40 g column, 10%→35% ethyl acetate/hexanes) to afford 5,6-dihydrobenzofuran-7(4H)-one (108 mg, 0.796 mmol, 21.9%). $^1$H NMR (CHLOROFORM-d): δ=7.55 (br s, 1H), 6.40 (br s, 1H), 2.76 (br t, J=5.9 Hz, 2H), 2.56 (br t, J=6.2 Hz, 2H), 2.11-2.20 (m, 2H).

Step 2

6,6-dimethyl-5,6-dihydrobenzofuran-7(4H)-one

Step 2: To a suspension of sodium hydride (60 wt. % dispersion in mineral oil, 111 mg, 2.78 mmol) in N,N-dimethylformamide (1.9 mL) was added a solution of 5,6-dihydrobenzofuran-7(4H)-one (108 mg, 0.796 mmol) in N,N-dimethylformamide (0.70 mL) under nitrogen atmosphere. After stirring at ambient temperature for 30 minutes, iodomethane (2.0 M in 2-methoxy-2-methylpropane, 1.4 mL, 2.8 mmol) was added. After stirring at ambient temperature overnight, the mixture was quenched with 0.1 N aqueous hydrochloric acid and extracted with ethyl acetate. The organic layer was then washed with 0.1 N aqueous hydrochloric acid (2 times), followed by brine, dried over magnesium sulfate, filtered, and concentrated. The resulting residue was purified by flash chromatography on silica gel using a Teledyne-Isco CombiFlash® Rf 200 (12 g column, 0%→25% ethyl acetate/hexanes) to afford 6,6-dimethyl-5,6-dihydrobenzofuran-7(4H)-one (83.6 mg, 0.509 mmol, 64.0%). $^1$H NMR (CHLOROFORM-d): δ=7.55 (s, 1H), 6.36 (s, 1H), 2.75 (t, J=6.2 Hz, 2H), 1.98 (t, J=6.2 Hz, 2H), 1.20 (s, 6H).

Step 3

6,6-dimethyl-4,5,6,7-tetrahydrobenzofuran-7-amine

Step 3: After purging a solution of 6,6-dimethyl-5,6-dihydrobenzofuran-7(4H)-one (83.6 mg, 0.509 mmol) in ethanol (1.7 mL) with nitrogen for 10 minutes, ammonium acetate (523 mg, 6.79 mmol) was added. After stirring for 10 minutes, sodium cyanotrihydroborate (203 mg, 3.07 mmol) was then added. After stirring for 10 additional minutes, the mixture was warmed to 70° C. and stirring continued overnight. The suspension was allowed to cool to ambient temperature and dissolved in 1.0 N aqueous hydrochloric acid, which caused significant bubble formation. Once bubble formation ceased, the aqueous solution was washed with ethyl acetate (2 times) and pH adjusted to 12 by addition of 4.0 N aqueous sodium hydroxide. This aqueous solution was then extracted with ethyl acetate (2 times), organic layers combined, washed with 1.0 N aqueous sodium hydroxide, dried over magnesium sulfate, filtered, and concentrated to afford a crude mixture that was carried through to the next step without further purification. Crude yield=55.7 mg.

Step 4

6-chloro-3-((2-((6,6-dimethyl-4,5,6,7-tetrahydrobenzofuran-7-yl)amino)-3,4-dioxocyclobut-1-en-1-yl)amino)-2-hydroxy-N,N-dimethylbenzenesulfonamide Step 4: According to Method A and procedures similar to those for synthesizing Compound 1, Intermediate 1 (20.3 mg, 0.0537 mmol) and 6,6-dimethyl-4,5,6,7-tetrahydrobenzofuran-7-amine (crude mixture, 18.7 mg) were converted into the title compound (23.8 mg, 0.0482 mmol, 89.7%). $^1$H NMR (CHLOROFORM-d): δ=10.62 (br s, 1H), 7.82 (br s, 1H), 7.71 (br s, 1H), 7.32 (br s, 1H), 6.96 (br d, J=8.2 Hz, 1H), 5.96-6.40 (m, 2H), 5.13 (br s, 1H), 2.84 (s, 6H), 2.34-2.57 (m, 2H), 1.59-1.70 (m, 2H), 1.06 (br s, 6H). MS (ESI): m/z=492 [M−H]$^-$.

Example 60

Synthesis of Compound 52: 3-((2-((6,6-dimethyl-4,5,6,7-tetrahydrobenzofuran-7-yl)amino)-3,4-dioxocyclobut-1-en-1-yl)amino)-2-hydroxy-N,N-dimethylbenzamide

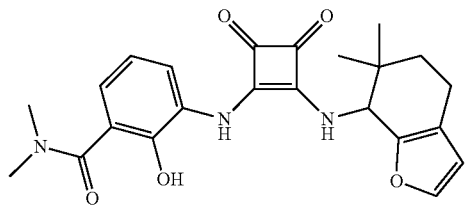 [SMILES: CN(C)C(=O)c1cccc(Nc2c(NC3c4occc4CCC3(C)C)c(=O)c2=O)c1O]

According to Method A and procedures similar to those for synthesizing Compound 1, Intermediate 2 (17.2 mg, 0.0565 mmol) and 6,6-dimethyl-4,5,6,7-tetrahydrobenzofuran-7-amine (synthesized as described for Compound 51, crude mixture, 19.0 mg) were converted into the title compound (20.2 mg, 0.0477 mmol, 84.4%). $^1$H NMR (METHANOL-d$_4$): δ=7.97 (br d, J=7.6 Hz, 1H), 7.42 (s, 1H), 6.96-7.01 (m, 1H), 6.90-6.95 (m, 1H), 6.28 (s, 1H), 5.05 (s, 1H), 3.06 (s, 6H), 2.51-2.58 (m, 1H), 2.43-2.51 (m, 1H), 1.68-1.79 (m, 1H), 1.57-1.64 (m, 1H), 1.07 (s, 6H). MS (ESI): m/z=422 [M−H]$^-$.

Example 61

Synthesis of Compound 53: 6-chloro-3-((2-((3-(furan-3-yl)-6,6-dimethylcyclohex-2-en-1-yl)amino)-3,4-dioxocyclobut-1-en-1-yl)amino)-2-hydroxy-N,N-dimethylbenzenesulfonamide

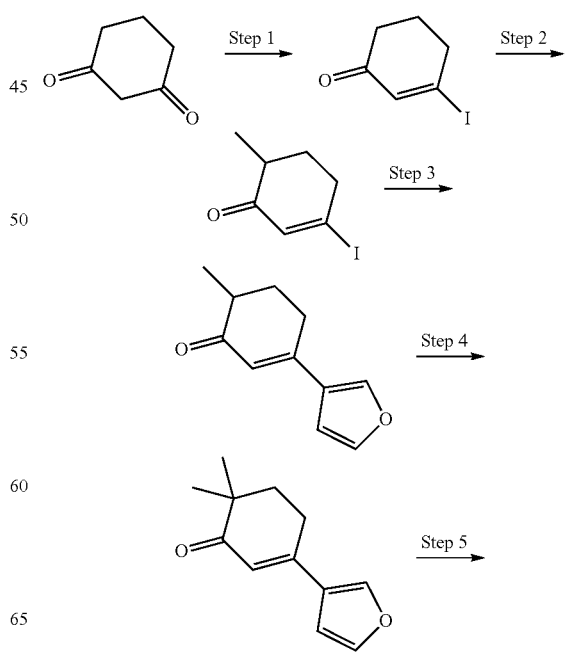

129

-continued

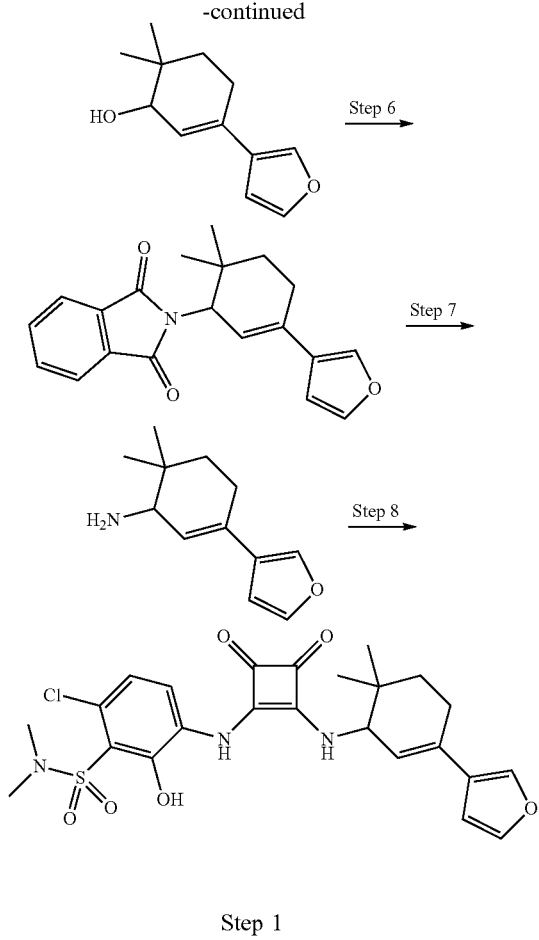

Step 1

3-iodocyclohex-2-en-1-one

Step 1: To a mixture of triphenylphosphane (2.63 g, 10.0 mmol) in acetonitrile (40 mL) was added diiodine (2.52 g, 9.95 mmol) under nitrogen atmosphere. After stirring at ambient temperature for 2 hours, a mixture of cyclohexane-1,3-dione (1.06 g, 9.45 mmol) in acetonitrile (5.0 mL) was added by cannula followed by triethylamine (1.5 mL, 10. mmol). After stirring for an additional 3 days, the mixture was concentrated and the resulting residue was purified by flash chromatography on silica gel using a Teledyne-Isco CombiFlash® Rf 200 (120 g column, 0%→100% ethyl acetate/hexanes) to afford 3-iodocyclohex-2-en-1-one (1.45 g, 6.53 mmol, 69.1%). $^1$H NMR (600 MHz, CHLOROFORM-d): δ=6.70 (s, 1H), 2.83 (t, J=5.7 Hz, 2H), 2.34 (t, J=6.5 Hz, 2H), 1.89-2.00 (m, 2H).

Step 2

3-iodo-6-methylcyclohex-2-en-1-one

Step 2: To a solution of lithium diisopropylamide (2.0 M in tetrahydrofuran, 4.0 mL, 8.0 mmol) in tetrahydrofuran (26 mL) was added a solution of 3-iodocyclohex-2-en-1-one (1.45 g, 6.53 mmol) in tetrahydrofuran (4.0 mL) by cannula over the course of 15 minutes at −78° C. under nitrogen atmosphere. After stirring at −78° C. for 2.5 hours, iodomethane (0.82 mL, 13 mmol) was then added. The mixture was allowed to warm to ambient temperature while stirring overnight. After quenching with saturated aqueous ammonium chloride, the mixture was extracted with ethyl acetate (3 times), organic layers were combined, dried over sodium sulfate, filtered, and concentrated. The resulting residue was purified by flash chromatography on silica gel using a Teledyne-Isco CombiFlash® Rf 200 (220 g column, 0%→100% ethyl acetate/hexanes) to afford 3-iodo-6-methylcyclohex-2-en-1-one (319 mg, 1.35 mmol, 20.7%). $^1$H NMR (600 MHz, CHLOROFORM-d): δ=6.74 (s, 1H), 2.92-2.98 (m, 2H), 2.34-2.43 (m, 1H), 1.95-2.04 (m, 1H), 1.77-1.87 (m, 1H), 1.13 (d, J=7.0 Hz, 3H).

Step 3

3-(furan-3-yl)-6-methylcyclohex-2-en-1-one

Step 3: To a mixture of furan-3-ylboronic acid (178 mg, 1.59 mmol), potassium carbonate (399 mg, 2.89 mmol), and bis(triphenylphosphine)palladium(II) chloride (40.4 mg, 0.0576 mmol) in N,N-dimethylformamide (20 mL) in a seal tube was added a solution of 3-iodo-6-methylcyclohex-2-en-1-one (319 mg, 1.35 mmol) in N,N-dimethylformamide (7.0 mL) by cannula under nitrogen atmosphere followed by distilled water (1.4 mL). The reaction vessel was sealed and stirred at 100° C. for 4 hours. After cooling to ambient temperature, the mixture was partitioned between water and ethyl acetate. The organic layer was collected and washed with water (3 times), followed by brine, dried over sodium sulfate, filtered, and concentrated. The resulting residue was purified by flash chromatography on silica gel using a Teledyne-Isco CombiFlash® Rf 200 (40 g column, 0%→100% ethyl acetate/hexanes) to afford 3-(furan-3-yl)-6-methylcyclohex-2-en-1-one (213 mg, 1.21 mmol, 89.5%). $^1$H NMR (600 MHz, CHLOROFORM-d): δ=7.71 (s, 1H), 7.46 (s, 1H), 6.61 (s, 1H), 6.23 (s, 1H), 2.65-2.69 (m, 2H), 2.40-2.46 (m, 1H), 2.15-2.21 (m, 1H), 1.78-1.88 (m, 1H), 1.19 (d, J=7.0 Hz, 3H).

Step 4

3-(furan-3-yl)-6,6-dimethylcyclohex-2-en-1-one

Step 4: To a suspension of sodium hydride (60 wt. % dispersion in mineral oil, 100. mg, 2.5 mmol) in N,N-dimethylformamide (1.6 mL) was added a solution of 3-(furan-3-yl)-6-methylcyclohex-2-en-1-one (213 mg, 1.21 mmol) in N,N-dimethylformamide (1.0 mL) by cannula under nitrogen atmosphere. After stirring at ambient temperature for 45 minutes, iodomethane (0.15 mL, 2.4 mmol) was then added. After stirring at ambient temperature overnight, the reaction was quenched with water and subjected to extraction with ethyl acetate. The organic layer was collected and washed with distilled water (3 times), followed by brine, dried over sodium sulfate, filtered, and concentrated. The resulting residue was purified by flash chromatography on silica gel using a Teledyne-Isco CombiFlash® Rf 200 (40 g column, 0%→40% ethyl acetate/hexanes) to afford 3-(furan-3-yl)-6,6-dimethylcyclohex-2-en-1-one (55.0 mg, 0.289 mmol, 23.9%). $^1$H NMR (600 MHz, CHLOROFORM-d): δ=7.68 (s, 1H), 7.42-7.43 (m, 1H), 6.57-6.58 (m, 1H), 6.13 (s, 1H), 2.63 (t, J=6.2 Hz, 2H), 1.90 (t, J=6.2 Hz, 2H), 1.13 (s, 6H).

Step 5

3-(furan-3-yl)-6,6-dimethylcyclohex-2-en-1-ol

Step 5: To a mixture of 3-(furan-3-yl)-6,6-dimethylcyclohex-2-en-1-one (64.5 mg, 0.339 mmol) and cerium(III)

chloride (120. mg, 0.487 mmol) in methanol (2.0 mL) was added sodium tetrahydroborate (45.0 mg, 1.19 mmol) at 0° C. After stirring at 0° C. for 1.5 hours, the mixture was quenched with saturated aqueous ammonium chloride solution and extracted with ethyl acetate (3 times). The organic layers were combined, dried over sodium sulfate, filtered, and concentrated. The resulting residue was purified by flash chromatography on silica gel using a Teledyne-Isco CombiFlash® Rf 200 (4 g column, 0%→40% ethyl acetate/hexanes) to afford 3-(furan-3-yl)-6,6-dimethylcyclohex-2-en-1l-ol (46.3 mg, 0.241 mmol, 71.0%). $^1$H NMR (600 MHz, CHLOROFORM-d): δ=7.41 (br s, 1H), 7.36 (br s, 1H), 6.54 (br s, 1H), 5.90 (br s, 1H), 3.91 (br s, 1H), 2.17-2.41 (m, 2H), 1.41-1.70 (m, 3H), 1.00 (br s, 3H), 0.94 (br s, 3H).

Step 6

2-(3-(furan-3-yl)-6,6-dimethylcyclohex-2-en-1-yl)isoindoline-1,3-dione

Step 6: To a mixture of triphenylphosphane (95.0 mg, 0.362 mmol) and isoindoline-1,3-dione (50.5 mg, 0.343 mmol) in tetrahydrofuran (1.4 mL) was added a solution of 3-(furan-3-yl)-6,6-dimethylcyclohex-2-en-1-ol (46.3 mg, 0.241 mmol) in tetrahydrofuran (0.90 mL) followed by diethyl azodicarboxylate (40 wt. % in toluene, 0.17 mL, 0.37 mmol). After stirring at ambient temperature overnight, the mixture was concentrated and the resulting residue was purified by flash chromatography on silica gel using a Teledyne-Isco CombiFlash® Rf 200 (12 g column, 0%→40% ethyl acetate/hexanes) to afford 2-(3-(furan-3-yl)-6,6-dimethylcyclohex-2-en-1-yl)isoindoline-1,3-dione (15.8 mg, 0.0492 mmol, 20.4%). $^1$H NMR (600 MHz, CHLOROFORM-d): δ=7.87 (br s, 2H), 7.71-7.73 (m, 2H), 7.46 (br s, 1H), 7.35 (s, 1H), 6.50 (br s, 1H), 5.79 (br s, 1H), 4.72-4.79 (m, 1H), 2.51-2.54 (m, 1H), 2.35-2.38 (m, 1H), 1.85-1.92 (m, 1H), 1.65-1.71 (m, 1H), 1.06 (br s, 3H), 0.97 (br s, 3H).

Step 7

3-(furan-3-yl)-6,6-dimethylcyclohex-2-en-1-amine

Step 7: A mixture of 2-(3-(furan-3-yl)-6,6-dimethylcyclohex-2-en-1-yl)isoindoline-1,3-dione (15.8 mg, 0.0492 mmol) and hydrazine hydrate (50-60 wt. %, 0.01 mL, 0.2 mmol) in ethanol (1 mL) was refluxed for 3 hours. After cooling to ambient temperature, the reaction was quenched with saturated aqueous ammonium chloride and subjected to extraction with dichloromethane (3 times). The organic layers were combined, washed with brine, dried over sodium sulfate, filtered, and concentrated to afford a crude mixture that was carried through to the next step without further purification.

Step 8

6-chloro-3-((2-((3-(furan-3-yl)-6,6-dimethylcyclohex-2-en-1-yl)amino)-3,4-dioxocyclobut-1-en-1-yl)amino)-2-hydroxy-N,N-dimethylbenzenesulfonamide Step 8: According to Method A and procedures similar to those for synthesizing Compound 1, Intermediate 1 (17.0 mg, 0.0454 mmol) and 3-(furan-3-yl)-6,6-dimethylcyclohex-2-en-1-amine (crude mixture from step 7) were converted into the title compound (5.2 mg, 0.010 mmol, 22%). $^1$H NMR (600 MHz, CHLOROFORM-d): δ=10.60 (br s, 1H), 8.10 (br s, 1H), 7.94 (br s, 1H), 7.40 (br s, 1H), 7.35 (br s, 1H), 6.94 (br d, J=7.6 Hz, 1H), 6.74 (br s, 1H), 6.51 (br s, 1H), 5.83 (br s, 1H), 4.73 (br s, 1H), 2.85 (br s, 6H), 2.30 (br s, 2H), 1.61 (br s, 2H), 1.03 (br s, 3H), 0.96 (br s, 3H). MS (ESI): m/z=518 [M−H]$^-$.

Example 62

Synthesis of Compound 54: 6-chloro-3-((3,4-dioxo-2-(spiro[4.5]decan-1-ylamino)cyclobutan-1-yl)amino)-2-hydroxy-N,N-dimethylbenzenesulfonamide

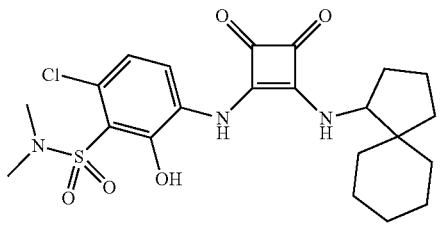 [SMILES: CN(C)S(=O)(=O)c1c(Cl)ccc(Nc2c(NC3CCCC34CCCCC4)c(=O)c2=O)c1O]

According to Method B and procedures similar to those for synthesizing Compound 2, Intermediate 1 (18.6 mg, 0.0496 mmol) and spiro[4.5]decan-1-amine hydrochloride (19.0 mg, 0.100 mmol) were converted into the title compound (22.7 mg, 0.0471 mmol, 95.0%). $^1$H NMR (600 MHz, CHLOROFORM-d): δ=10.56 (br s, 1H), 8.87 (br s, 1H), 8.09 (d, J=8.8 Hz, 1H), 7.86 (br s, 1H), 6.98 (d, J=8.8 Hz, 1H), 4.28 (br s, 1H), 2.88 (s, 6H), 1.99-2.14 (m, 1H), 1.62-1.73 (m, 3H), 1.50-1.62 (m, 4H), 1.40-1.48 (m, 1H), 1.21-1.39 (m, 6H), 1.08-1.19 (m, 1H). MS (ESI): m/z=480 [M−H]$^-$.

Example 63

Synthesis of Compound 55: 3-((3,4-dioxo-2-(spiro[4.5]decan-6-ylamino)cyclobutan-1-yl)amino)-2-hydroxy-N,N-dimethylbenzamide

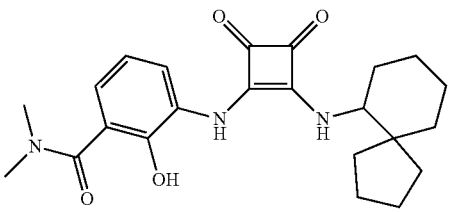 [SMILES: CN(C)C(=O)c1cccc(Nc2c(NC3CCCCC34CCCC4)c(=O)c2=O)c1O]

According to Method A and procedures similar to those for synthesizing Compound 1, Intermediate 2 (20.8 mg, 0.0684 mmol) and spiro[4.5]decan-6-amine (15.0 mg, 0.0979 mmol) were converted into the title compound (26.4 mg, 0.0642 mmol, 93.8%). $^1$H NMR (600 MHz, METHANOL-d$_4$): δ=7.97 (d, J=7.6 Hz, 1H), 6.99 (d, J=7.6 Hz, 1H), 6.93 (dd, J=7.6 Hz, 1H), 4.14 (br dd, J=3.2, 8.5 Hz, 1H), 3.09 (s, 6H), 1.81-1.89 (m, 1H), 1.52-1.72 (m, 10H), 1.43-1.52 (m, 4H), 1.35-1.42 (m, 1H). MS (ESI): m/z=410 [M−H]$^-$.

Example 64

Synthesis of Compound 56: 6-chloro-3-((2-(cyclopentylamino)-3,4-dioxocyclobut-1-en-1-yl)amino)-2-hydroxy-N,N-dimethylbenzenesulfonamide

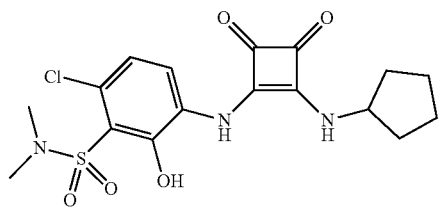 [SMILES: CN(C)S(=O)(=O)c1c(Cl)ccc(Nc2c(NC3CCCC3)c(=O)c2=O)c1O]

According to Method A and procedures similar to those for synthesizing Compound 1, Intermediate 1 (17.7 mg, 0.0472 mmol) and cyclopentanamine (20. L, 0.20 mmol) were converted into the title compound (17.7 mg, 0.0428 mmol, 90.6%). $^1$H NMR (600 MHz, CHLOROFORM-d): δ=8.18 (d, J=8.8 Hz, 1H), 7.05 (d, J=8.8 Hz, 1H), 4.48-4.70 (m, 1H), 2.92 (s, 6H), 2.00-2.19 (m, 2H), 1.50-1.86 (m, 6H). MS (ESI): m/z=412 [M–H]$^-$.

Example 65

Synthesis of Compound 57: 6-chloro-3-((2-((1-cyclohexyl-3,3-dimethylbutan-2-yl)amino)-3,4-dioxocyclobut-1-en-1-yl)amino)-2-hydroxy-N,N-dimethylbenzenesulfonamide

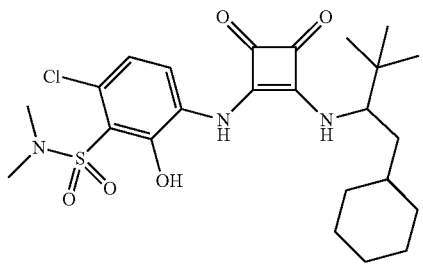 [SMILES: CN(C)S(=O)(=O)c1c(Cl)ccc(Nc2c(NC(CC3CCCCC3)C(C)(C)C)c(=O)c2=O)c1O]

According to Method A and procedures similar to those for synthesizing Compound 1, Intermediate 1 (16.6 mg, 0.0443 mmol) and 1-cyclohexyl-3,3-dimethylbutan-2-amine (12.1 mg, 0.0660 mmol) were converted into the title compound (16.5 mg, 0.0322 mmol, 72.7%). $^1$H NMR (CHLOROFORM-d/METHANOL-d$_4$): δ=8.17 (d, J=8.8 Hz, 1H), 6.96 (d, J=8.8 Hz, 1H), 3.87-4.08 (m, 1H), 2.85 (s, 6H), 1.78-1.90 (m, 1H), 1.45-1.67 (m, 4H), 1.33-1.44 (m, 1H), 0.99-1.22 (m, 5H), 0.89-0.98 (m, 1H), 0.85 (s, 9H), 0.64-0.76 (m, 1H). MS (ESI): m/z=510 [M–H]$^-$.

Example 66

Synthesis of Compound 58: 6-chloro-3-((3,4-dioxo-2-(spiro[4.5]decan-6-ylamino)cyclobutan-1-yl)amino)-2-hydroxy-N,N-dimethylbenzenesulfonamide

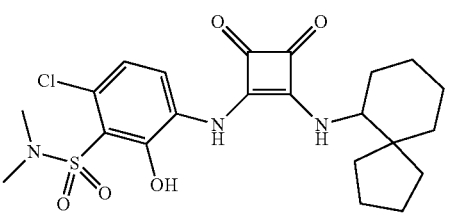 [SMILES: CN(C)S(=O)(=O)c1c(Cl)ccc(Nc2c(NC3CCCCC34CCCC4)c(=O)c2=O)c1O]

According to Method A and procedures similar to those for synthesizing Compound 1, Intermediate 1 (16.9 mg, 0.0451 mmol) and spiro[4.5]decan-6-amine (11.8 mg, 0.0770 mmol) were converted into the title compound (19.3 mg, 0.0400 mmol, 88.8%). $^1$H NMR (600 MHz, METHANOL-d$_4$): d=8.17 (d, J=8.8 Hz, 1H), 7.09 (d, J=8.8 Hz, 1H), 4.11-4.21 (m, 1H), 2.93 (s, 6H), 1.78-1.93 (m, 1H), 1.30-1.74 (m, 15H). MS (ESI): m/z=480 [M–H]$^-$.

Example 67

Synthesis of Compound 59: 6-chloro-3-((2-(((1-ethylcyclobutyl)methyl)amino)-3,4-dioxocyclobut-1-en-1-yl)amino)-2-hydroxy-N,N-dimethylbenzenesulfonamide

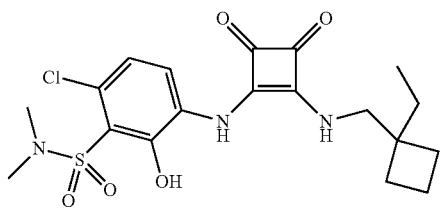 [SMILES: CCC1(CNc2c(Nc3ccc(Cl)c(S(=O)(=O)N(C)C)c3O)c(=O)c2=O)CCC1]

According to Method A and procedures similar to those for synthesizing Compound 1, Intermediate 1 (17.0 mg, 0.0454 mmol) and (1-ethylcyclobutyl)methanamine (11.5 mg, 0.102 mmol) were converted into the title compound (18.5 mg, 0.0419 mmol, 92.2%). $^1$H NMR (600 MHz, METHANOL-d$_4$): δ=8.19 (d, J=8.8 Hz, 1H), 7.09 (d, J=8.8 Hz, 1H), 3.80 (s, 2H), 2.95 (s, 6H), 1.74-2.02 (m, 6H), 1.59 (q, J=7.6 Hz, 2H), 0.91 (t, J=7.6 Hz, 3H). MS (ESI): m/z=440 [M–H]$^-$.

Example 68

Synthesis of Compound 60: 6-chloro-3-((2-(cycloheptylamino)-3,4-dioxocyclobut-1-en-1-yl)amino)-2-hydroxy-N,N-dimethylbenzenesulfonamide

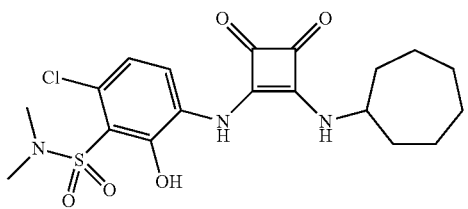 [SMILES: CN(C)S(=O)(=O)c1c(Cl)ccc(Nc2c(NC3CCCCCC3)c(=O)c2=O)c1O]

According to Method A and procedures similar to those for synthesizing Compound 1, Intermediate 1 (17.4 mg, 0.0464 mmol) and cycloheptanamine (12 μL, 0.094 mmol) were converted into the title compound (20.0 mg, 0.0453 mmol, 97.5%). $^1$H NMR (600 MHz, CHLOROFORM-d): δ=10.57 (br s, 1H), 8.65 (br s, 1H), 8.09 (br d, J=8.2 Hz, 1H), 7.93 (br s, 1H), 6.96 (d, J=8.8 Hz, 1H), 4.19-4.46 (m, 1H), 2.90 (s, 6H), 1.98-2.14 (m, 2H), 1.41-1.76 (m, 10H). MS (ESI): m/z=440 [M−H]$^-$.

Example 69

Synthesis of Compound 61: 6-chloro-3-((2-(cyclohexylamino)-3,4-dioxocyclobut-1-en-1-yl)amino)-2-hydroxy-N,N-dimethylbenzenesulfonamide

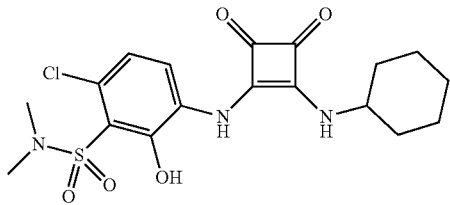 [SMILES: CN(C)S(=O)(=O)c1c(Cl)ccc(Nc2c(NC3CCCCC3)c(=O)c2=O)c1O]

According to Method A and procedures similar to those for synthesizing Compound 1, Intermediate 1 (16.4 mg, 0.0438 mmol) and cyclohexanamine (12 μL, 0.10 mmol) were converted into the title compound (17.3 mg, 0.0404 mmol, 92.3%). $^1$H NMR (600 MHz, METHANOL-d$_4$): δ=8.16 (d, J=8.8 Hz, 1H), 7.10 (d, J=8.8 Hz, 1H), 3.98-4.05 (m, 1H), 2.93 (s, 6H), 2.00-2.07 (m, 2H), 1.77-1.84 (m, 2H), 1.32-1.48 (m, 4H), 1.16-1.32 (m, 2H). MS (ESI): m/z=426 [M−H]$^-$.

Example 70

Synthesis of Compound 62: 6-chloro-3-((2-((cyclobutyl(cyclohexyl)methyl)amino)-3,4-dioxocyclobut-1-en-1-yl)amino)-2-hydroxy-N,N-dimethylbenzenesulfonamide

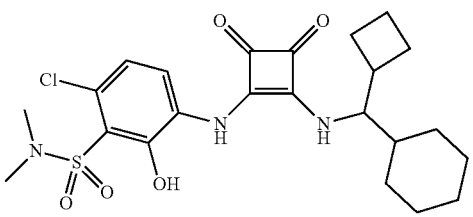 [SMILES: CN(C)S(=O)(=O)c1c(Cl)ccc(Nc2c(NC(C3CCCCC3)C3CCC3)c(=O)c2=O)c1O]

According to Method A and procedures similar to those for synthesizing Compound 1, Intermediate 1 (17.4 mg, 0.0464 mmol) and cyclobutyl(cyclohexyl)methanamine (13.9 mg, 0.0831 mmol) were converted into the title compound (22.1 mg, 0.0446 mmol, 96.0%). $^1$H NMR (600 MHz, CHLOROFORM-d): δ=10.58 (s, 1H), 8.75 (br s, 1H), 8.05 (br d, J=8.8 Hz, 1H), 7.47 (br s, 1H), 6.97 (d, J=8.8 Hz, 1H), 3.95-4.16 (m, 1H), 2.89 (s, 6H), 2.51-2.62 (m, 1H), 1.58-2.09 (m, 11H), 1.41-1.51 (m, 1H), 0.93-1.29 (m, 5H). MS (ESI): m/z=494 [M−H]$^-$.

Example 71

Synthesis of Compound 63: 6-chloro-3-((2-((cyclohexyl(cyclopentyl)methyl)amino)-3,4-dioxocyclobut-1-en-1-yl)amino)-2-hydroxy-N,N-dimethylbenzenesulfonamide

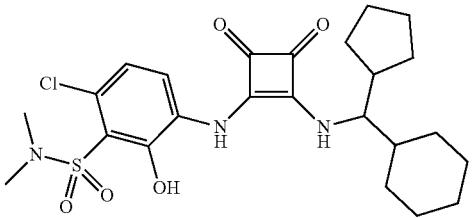 [SMILES: CN(C)S(=O)(=O)c1c(Cl)ccc(Nc2c(NC(C3CCCCC3)C3CCCC3)c(=O)c2=O)c1O]

According to Method A and procedures similar to those for synthesizing Compound 1, Intermediate 1 (16.7 mg, 0.0446 mmol) and cyclohexyl(cyclopentyl)methanamine (11.9 mg, 0.0656 mmol) were converted into the title compound (20.5 mg, 0.0402 mmol, 90.1%). $^1$H NMR (600 MHz, CHLOROFORM-d): δ=10.61 (s, 1H), 8.65 (br s, 1H), 8.03 (br d, J=8.8 Hz, 1H), 7.37 (br s, 1H), 6.96 (d, J=8.8 Hz, 1H), 3.97-4.05 (m, 1H), 2.88 (s, 6H), 2.01-2.14 (m, 1H), 1.42-1.98 (m, 11H), 0.90-1.35 (m, 7H). MS (ESI): m/z=508 [M−H]$^-$.

Example 72

Synthesis of Compound 64: 6-chloro-3-((2-((2,2-dimethylcyclohexyl)amino)-3,4-dioxocyclobut-1-en-1-yl)amino)-2-hydroxy-N,N-dimethylbenzenesulfonamide

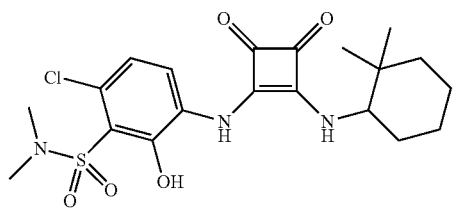 [SMILES: CN(C)S(=O)(=O)c1c(Cl)ccc(Nc2c(NC3CCCCC3(C)C)c(=O)c2=O)c1O]

According to Method A and procedures similar to those for synthesizing Compound 1, Intermediate 1 (17.0 mg, 0.0454 mmol) and 2,2-dimethylcyclohexan-1-amine (11.7 mg, 0.0920 mmol) were converted into the title compound (20.9 mg, 0.0458 mmol, 101%). $^1$H NMR (600 MHz, CHLOROFORM-d): δ=10.55 (br s, 1H), 8.89 (br s, 1H), 8.04 (br d, J=8.2 Hz, 1H), 7.82 (br s, 1H), 6.96 (d, J=8.8 Hz, 1H), 3.94-4.11 (m, 1H), 2.87 (s, 6H), 1.98-2.24 (m, 1H), 1.65-1.86 (m, 2H), 1.40-1.59 (m, 2H), 1.19-1.39 (m, 3H), 0.99 (s, 3H), 0.89 (s, 3H). MS (ESI): m/z=454 [M−H]$^-$.

Example 73

Synthesis of Compound 65: 6-chloro-3-((2-((1-cyclohexylprop-2-yn-1-yl)amino)-3,4-dioxocyclobut-1-en-1-yl)amino)-2-hydroxy-N,N-dimethylbenzenesulfonamide

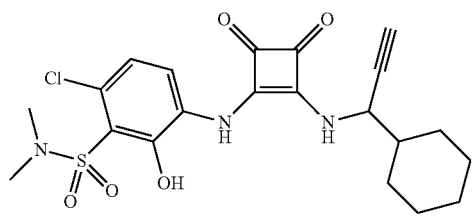 [SMILES: C#CC(Nc1c(Nc2ccc(Cl)c(S(=O)(=O)N(C)C)c2O)c(=O)c1=O)C1CCCCC1]

According to Method A and procedures similar to those for synthesizing Compound 1, Intermediate 1 (16.7 mg, 0.0446 mmol) and 1-cyclohexylprop-2-yn-1-amine (13.1 mg, 0.0955 mmol) were converted into the title compound (22.1 mg, 0.0474 mmol, 106%). $^1$H NMR (CHLOROFORM-d/METHANOL-d$_4$): δ=7.98 (br d, J=8.8 Hz, 1H), 6.99 (br d, J=8.8 Hz, 1H), 4.90 (br s, 1H), 2.90 (s, 6H), 2.47 (br s, 1H), 1.56-2.02 (m, 6H), 0.94-1.35 (m, 5H). MS (ESI): m/z=464 [M−H]$^-$.

Example 74

Synthesis of Compound 66: 6-chloro-3-((3,4-dioxo-2-((1,7,7-trimethylbicyclo[2.2.1]heptan-2-yl)amino)cyclobut-1-en-1-yl)amino)-2-hydroxy-N,N-dimethylbenzenesulfonamide

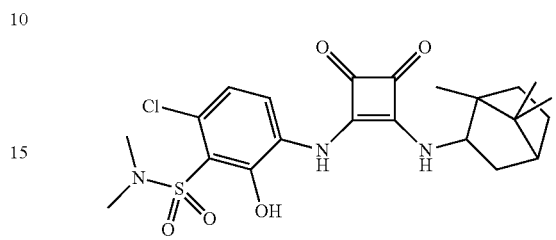

According to Method B and procedures similar to those for synthesizing Compound 2, Intermediate 1 (16.5 mg, 0.0440 mmol) and 1,7,7-trimethylbicyclo[2.2.1]heptan-2-amine hydrochloride (19.0 mg, 0.100 mmol) were converted into the title compound as a mixture of diastereomers (20.1 mg, 0.0417 mmol, 94.8%). MS (ESI): m/z=480 [M−H]$^-$.

Example 75

Synthesis of Compound 67: 6-chloro-3-((2-((1-ethylcyclopentyl)amino)-3,4-dioxocyclobut-1-en-1-yl)amino)-2-hydroxy-N-(2-hydroxyethyl)-N-methyl-benzenesulfonamide

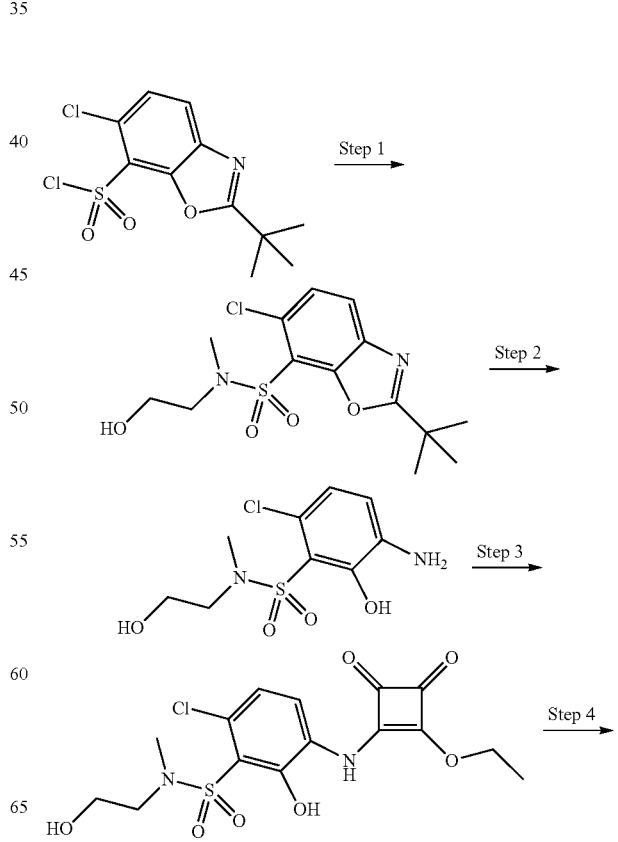

-continued

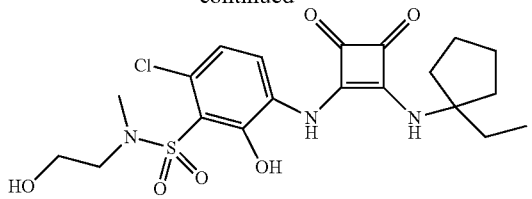

Step 1

2-(tert-butyl)-6-chloro-N-(2-hydroxyethyl)-N-methylbenzo[d]oxazole-7-sulfonamide Step 1: Following a procedure analogous to compound 70 step 1, 2-(tert-butyl)-6-chlorobenzo[d]oxazole-7-sulfonyl chloride (308 mg, 0.999 mmol) was converted into 2-(tert-butyl)-6-chloro-N-(2-hydroxyethyl)-N-methylbenzo[d]oxazole-7-sulfonamide (334 mg, 0.963 mmol, 96.4%). $^1$H NMR (600 MHz, CHLOROFORM-d): δ=7.66-7.79 (m, J=8.2 Hz, 1H), 7.40-7.48 (m, J=8.2 Hz, 1H), 3.82 (t, J=5.0 Hz, 2H), 3.47 (t, J=5.3 Hz, 2H), 3.06 (s, 3H), 1.49 (s, 9H).

Step 2

3-amino-6-chloro-2-hydroxy-N-(2-hydroxyethyl)-N-methylbenzenesulfonamide

Step 2: Following a procedure analogous to compound 70 step 2, 2-(tert-butyl)-6-chloro-N-(2-hydroxyethyl)-N-methylbenzo[d]oxazole-7-sulfonamide (334 mg, 0.963 mmol) was converted into 3-amino-6-chloro-2-hydroxy-N-(2-hydroxyethyl)-N-methylbenzenesulfonamide (148 mg, 0.527 mmol, 54.7%). $^1$H NMR (600 MHz, CHLOROFORM-d): δ=10.32 (s, 1H), 6.79-6.89 (m, J=8.8 Hz, 1H), 6.71-6.77 (m, J=8.8 Hz, 1H), 4.00 (br s, 2H), 3.73-3.86 (m, 2H), 3.44 (t, J=5.3 Hz, 2H), 2.97 (s, 3H).

Step 3

6-chloro-3-((2-ethoxy-3,4-dioxocyclobut-1-en-1-yl)amino)-2-hydroxy-N-(2-hydroxyethyl)-N-methylbenzenesulfonamide Step 3: Following a procedure analogous to compound 70 step 3, 3-amino-6-chloro-2-hydroxy-N-(2-hydroxyethyl)-N-methylbenzenesulfonamide (148 mg, 0.527 mmol) was converted into 6-chloro-3-((2-ethoxy-3,4-dioxocyclobut-1-en-1-yl)amino)-2-hydroxy-N-(2-hydroxyethyl)-N-methylbenzenesulfonamide (62 mg, 0.15 mmol, 29%). $^1$H NMR (600 MHz, CHLOROFORM-d): δ=10.69-10.87 (m, 1H), 7.95 (br d, J=7.0 Hz, 1H), 7.73 (br s, 1H), 7.07 (d, J=8.8 Hz, 1H), 4.87 (q, J=7.4 Hz, 2H), 3.82 (t, J=5.3 Hz, 2H), 3.47 (t, J=5.3 Hz, 2H), 3.00 (s, 3H), 1.52 (t, J=7.3 Hz, 3H).

Step 4

6-chloro-3-((2-((1-ethylcyclopentyl)amino)-3,4-dioxocyclobut-1-en-1-yl)amino)-2-hydroxy-N-(2-hydroxyethyl)-N-methylbenzenesulfonamide Step 4: According to Method B and procedures similar to those for synthesizing Compound 2, 6-chloro-3-((2-ethoxy-3,4-dioxocyclobut-1-en-1-yl)amino)-2-hydroxy-N-(2-hydroxyethyl)-N-methylbenzenesulfonamide (28 mg, 0.069 mmol) and 1-ethylcyclopentan-1-amine hydrochloride (16 mg, 0.11 mmol) were converted into the title compound (15 mg, 0.032 mmol, 46%). $^1$H NMR (600 MHz, METHANOL-d$_4$): δ=8.14 (d, J=8.8 Hz, 1H), 7.09 (d, J=8.8 Hz, 1H), 3.69 (t, J=5.9 Hz, 2H), 3.41 (t, J=5.9 Hz, 2H), 2.96 (s, 3H), 2.04 (br s, 2H), 1.92 (br d, J=7.0 Hz, 2H), 1.71-1.83 (m, 6H), 0.92 (t, J=7.3 Hz, 3H). MS (ESI): m/z=470 [M–H]$^-$.

Example 76

Synthesis of Compound 68: 6-chloro-3-((3,4-dioxo-2-((2-phenylbutan-2-yl)amino)cyclobut-1-en-1-yl)amino)-2-hydroxy-N,N-dimethylbenzenesulfonamide

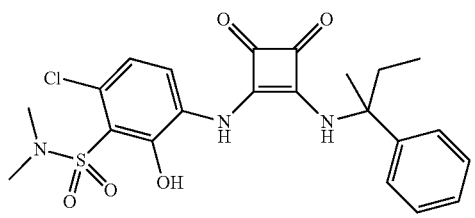 [SMILES: CCC(C)(Nc1c(Nc2ccc(Cl)c(S(=O)(=O)N(C)C)c2O)c(=O)c1=O)c1ccccc1]

According to Method A and procedures similar to those for synthesizing Compound 1, Intermediate 1 (400. mg, 1.06 mmol) and 2-phenylbutan-2-amine (240. mg, 1.61 mmol) were converted into the title compound (250. mg, 0.523 mmol, 49.3%). $^1$H NMR (600 MHz, DMSO-d$_6$): δ=10.56 (br s, 1H), 9.66 (br s, 1H), 8.79 (br s, 1H), 7.89 (br d, J=8.8 Hz, 1H), 7.30-7.38 (m, 4H), 7.21-7.27 (m, 1H), 7.19 (br d, J=8.3 Hz, 1H), 2.86 (s, 6H), 2.06-2.24 (m, 1H), 1.93-2.06 (m, 1H), 1.75 (s, 3H), 0.76 (br t, J=6.7 Hz, 3H). MS (ESI): m/z=476 [M–H]$^-$.

Example 76a

Synthesis of Compound 68a: (R)-6-chloro-3-((3,4-dioxo-2-((2-phenylbutan-2-yl)amino)cyclobut-1-en-1-yl)amino)-2-hydroxy-N,N-dimethylbenzenesulfonamide

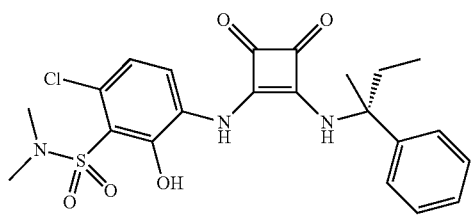 [SMILES: CC[C@@](C)(Nc1c(Nc2ccc(Cl)c(S(=O)(=O)N(C)C)c2O)c(=O)c1=O)c1ccccc1]

The racemic mixture (Compound 68) was subjected to supercritical fluid chromatography separation using AD-H (2×25 cm) column with 30% ethanol/carbon dioxide at 100 bar to afford the title compound. $^1$H NMR (600 MHz, DMSO-d$_6$): δ=10.56 (br s, 1H), 9.66 (br s, 1H), 8.79 (br s, 1H), 7.89 (br d, J=8.8 Hz, 1H), 7.30-7.38 (m, 4H), 7.21-7.27 (m, 1H), 7.19 (br d, J=8.3 Hz, 1H), 2.86 (s, 6H), 2.06-2.24 (m, 1H), 1.93-2.06 (m, 1H), 1.75 (s, 3H), 0.76 (br t, J=6.7 Hz, 3H). MS (ESI): m/z=476 [M–H]$^-$.

Example 77

Synthesis of Compound 69: 6-chloro-3-((2-((2-cyclopentylpropan-2-yl)amino)-3,4-dioxocyclobut-1-en-1-yl)amino)-2-hydroxy-N,N-dimethylbenzenesulfonamide

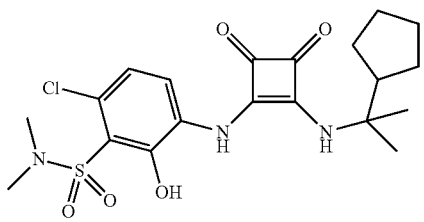 [SMILES: CN(C)S(=O)(=O)c1c(Cl)ccc(Nc2c(NC(C)(C)C3CCCC3)c(=O)c2=O)c1O]

According to Method A and procedures similar to those for synthesizing Compound 1, Intermediate 1 (40. mg, 0.11 mmol) and 2-cyclopentylpropan-2-amine (26 mg, 0.16 mmol) were converted into the title compound (7 mg, 0.02 mmol, 10%). $^1$H NMR (600 MHz, CHLOROFORM-d): δ=10.63 (br d, J=1.2 Hz, 1H), 8.10 (br s, 1H), 7.96 (br d, J=8.2 Hz, 1H), 6.98 (br d, J=8.2 Hz, 1H), 6.91 (br s, 1H), 2.89 (s, 6H), 2.38-2.42 (m, 1H), 1.62-1.72 (m, 4H), 1.51-1.62 (m, 4H), 1.44 (s, 6H). MS (ESI): m/z=454 [M−H]$^-$.

Example 78

Synthesis of Compound 70: 6-chloro-3-((2-((1-ethylcyclopentyl)amino)-3,4-dioxocyclobut-1-en-1-yl)amino)-2-hydroxy-N-methyl-N-(pyridin-2-ylmethyl)benzenesulfonamide

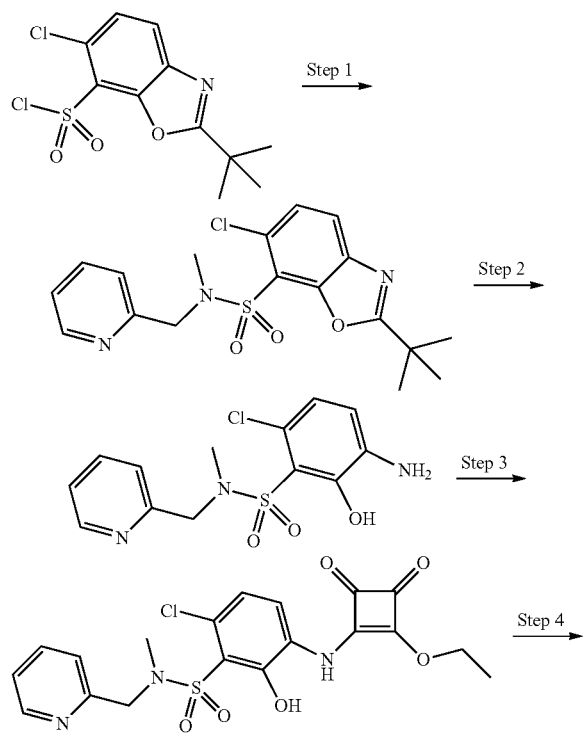

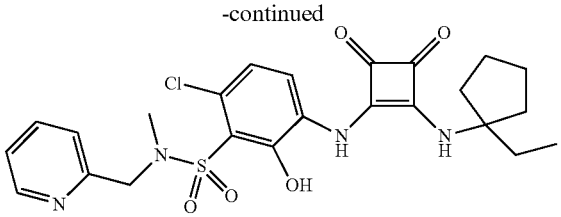

Step 1

2-(tert-butyl)-6-chloro-N-methyl-N-(pyridin-2-ylmethyl)benzo[d]oxazole-7-sulfonamide Step 1: To a solution of 2-(tert-butyl)-6-chlorobenzo[d]oxazole-7-sulfonyl chloride (308 mg, 0.999 mmol) in tetrahydrofuran (4.5 mL) at ambient temperature was added triethylamine (121 mg, 1.20 mmol) followed by N-methyl-1-(pyridin-2-yl)methanamine (134 mg, 1.10 mmol). The mixture was stirred at ambient temperature for 2 hours and treated with water. The reaction medium was extracted with ethyl acetate. The organic layers were combined, dried over sodium sulfate, filtered, and concentrated to yield 2-(tert-butyl)-6-chloro-N-methyl-N-(pyridin-2-ylmethyl)benzo[d]oxazole-7-sulfonamide (394 mg, 1.00 mmol, 100. %) as a white solid. $^1$H NMR (600 MHz, CHLOROFORM-d): δ=8.48 (br d, J=4.7 Hz, 1H), 7.75 (d, J=8.7 Hz, 1H), 7.71 (t, J=7.7 Hz, 1H), 7.55 (d, J=7.6 Hz, 1H), 7.47 (d, J=8.8 Hz, 1H), 7.20 (br t, J=5.9 Hz, 1H), 4.66 (s, 2H), 2.95 (s, 3H), 1.51 (s, 9H).

Step 2

3-amino-6-chloro-2-hydroxy-N-methyl-N-(pyridin-2-ylmethyl)benzenesulfonamide

Step 2: Sulfuric acid (0.85 mL, 50% in water) was added dropwise to a solution of 2-(tert-butyl)-6-chloro-N-methyl-N-(pyridin-2-ylmethyl)benzo[d]oxazole-7-sulfonamide (394 mg, 1.00 mmol) in 1,4-dioxane (1.5 mL). The reaction mixture was refluxed for 6.5 hours and 1,4-dioxane was removed. Aqueous sodium hydroxide (1 N) was added to reach pH 8. The mixture was extracted with dichloromethane. The organic layers were combined, dried over sodium sulfate, filtered, and concentrated. The resulting residue was purified by flash chromatography on silica gel using a Teledyne-Isco CombiFlash® Rf 200 (40 g column, 60% ethyl acetate/hexanes) to afford 3-amino-6-chloro-2-hydroxy-N-methyl-N-(pyridin-2-ylmethyl)benzenesulfonamide (252 mg, 0.773 mmol, 77.0%). $^1$H NMR (600 MHz, CHLOROFORM-d): δ=10.37 (s, 1H), 8.54 (br d, J=4.7 Hz, 1H), 7.72 (t, J=7.6 Hz, 1H), 7.47 (d, J=7.6 Hz, 1H), 7.21-7.23 (m, 1H), 6.85 (d, J=8.2 Hz, 1H), 6.75 (d, J=8.2 Hz, 1H), 4.62 (s, 2H), 4.01 (br s, 2H), 2.85 (s, 3H).

143

Step 3

6-chloro-3-((2-ethoxy-3,4-dioxocyclobut-1-en-1-yl)amino)-2-hydroxy-N-methyl-N-(pyridin-2-ylmethyl)benzenesulfonamide Step 3: Following a procedure analogous to intermediate 6 step 3, 3-amino-6-chloro-2-hydroxy-N-methyl-N-(pyridin-2-ylmethyl)benzenesulfonamide (252 mg, 0.773 mmol) was converted into 6-chloro-3-((2-ethoxy-3,4-dioxocyclobut-1-en-1-yl)amino)-2-hydroxy-N-methyl-N-(pyridin-2-ylmethyl)benzenesulfonamide (165 mg, 0.365 mmol, 47.3%). $^1$H NMR (600 MHz, CHLOROFORM-d): δ=8.53 (br d, J=4.7 Hz, 1H), 7.72 (br t, J=7.6 Hz, 2H), 7.42 (d, J=7.6 Hz, 1H), 7.16-7.31 (m, 1H), 7.08 (d, J=8.8 Hz, 1H), 4.87 (q, J=7.0 Hz, 2H), 4.63 (s, 2H), 2.89 (s, 3H), 1.48-1.54 (m, 3H).

Step 4

6-chloro-3-((2-((1-ethylcyclopentyl)amino)-3,4-dioxocyclobut-1-en-1-yl)amino)-2-hydroxy-N-methyl-N-(pyridin-2-ylmethyl)benzenesulfonamide Step 4: According to Method B and procedures similar to those for synthesizing Compound 2, 6-chloro-3-((2-ethoxy-3,4-dioxocyclobut-1-en-1-yl)amino)-2-hydroxy-N-methyl-N-(pyridin-2-ylmethyl)benzenesulfonamide (40. mg, 0.088 mmol) and 1-ethylcyclopentan-1-amine hydrochloride (20. mg, 0.13 mmol) were converted into the title compound (9.6 mg, mmol, 0.018 mmol, 21%). $^1$H NMR (600 MHz, CHLOROFORM-d): δ=8.52 (br s, 1H), 8.11 (br s, 1H), 7.70 (br t, J=7.6 Hz, 1H), 7.37 (br d, J=8.2 Hz, 1H), 7.17-7.24 (m, 1H), 7.01 (br d, J=8.8 Hz, 1H), 4.57 (br s, 2H), 2.85 (s, 3H), 1.95 (br s, 2H), 1.88 (br d, J=6.5 Hz, 2H), 1.65-1.83 (m, 6H), 0.90 (br t, J=6.7 Hz, 3H). MS (ESI): m/z=517 [M−H]$^-$.

Example 79

Synthesis of Compound 71: 6-chloro-3-((2-((3-ethylpentan-3-yl)amino)-3,4-dioxocyclobut-1-en-1-yl)amino)-2-hydroxy-N,N-dimethylbenzenesulfonamide

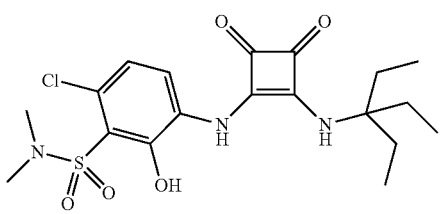 [SMILES: CCC(CC)(CC)Nc1c(Nc2ccc(Cl)c(S(=O)(=O)N(C)C)c2O)c(=O)c1=O]

According to Method A and procedures similar to those for synthesizing Compound 1, Intermediate 1 (40. mg, 0.11 mmol) and 3-ethylpentan-3-amine (18 mg, 0.16 mmol) were converted into the title compound (15 mg, 0.034 mmol, 32%). $^1$H NMR (600 MHz, CHLOROFORM-d): δ=10.62 (br s, 1H), 8.26 (br s, 1H), 8.01 (d, J=8.2 Hz, 1H), 6.98 (d, J=8.8 Hz, 1H), 6.66-6.84 (m, 1H), 2.89 (s, 6H), 1.78 (q, J=7.0 Hz, 6H), 0.83 (t, J=7.3 Hz, 9H). MS (ESI): m/z=442 [M−H]$^-$.

144

Example 80

Synthesis of Compound 72: 6-chloro-3-((3,4-dioxo-2-((2-phenylbutan-2-yl)amino)cyclobut-1-en-1-yl)amino)-2-hydroxy-N,N-dimethylbenzamide

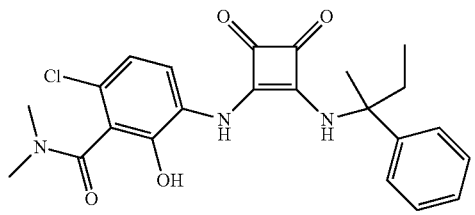 [SMILES: CCC(C)(Nc1c(Nc2ccc(Cl)c(C(=O)N(C)C)c2O)c(=O)c1=O)c1ccccc1]

According to Method A and procedures similar to those for synthesizing Compound 1, Intermediate 5 (27 mg, 0.080 mmol) and 2-phenylbutan-2-amine (18 mg, 0.12 mmol) were converted into the title compound (17 mg, 0.038 mmol, 48%). $^1$H NMR (600 MHz, METHANOL-d$_4$): δ=7.81 (br s, 1H), 7.41 (br d, J=7.0 Hz, 2H), 7.34 (br t, J=7.0 Hz, 2H), 7.11-7.29 (m, 1H), 6.96 (br d, J=8.8 Hz, 1H), 3.12 (s, 3H), 2.93 (s, 3H), 2.21 (br s, 1H), 2.09 (br dd, J=13.8, 6.7 Hz, 1H), 1.85 (s, 3H), 0.85 (br t, J=7.3 Hz, 3H). MS (ESI): m/z=440 [M−H]$^-$.

Example 81

Synthesis of Compound 73: (R)-6-chloro-3-((2-((cyclohexyl(phenyl)methyl)amino)-3,4-dioxocyclobut-1-en-1-yl)amino)-2-hydroxy-N,N-dimethylbenzenesulfonamide

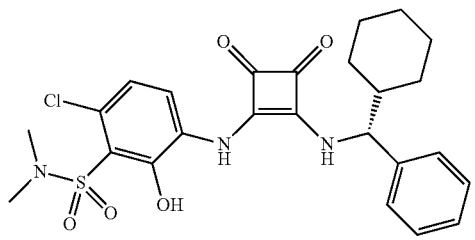 [SMILES: CN(C)S(=O)(=O)c1c(Cl)ccc(Nc2c(N[C@@H](c3ccccc3)C3CCCCC3)c(=O)c2=O)c1O]

According to Method A and procedures similar to those for synthesizing Compound 1, Intermediate 1 (30. mg, 0.080 mmol) and (R)-cyclohexyl(phenyl)methanamine (27 mg, 0.14 mmol) were converted into the title compound (33 mg, 0.064 mmol, 80.%). $^1$H NMR (600 MHz, ACETONE-d$_6$): δ=10.67 (br s, 1H), 8.48 (br s, 1H), 8.19 (br d, J=8.2 Hz, 1H), 7.96 (br d, J=8.2 Hz, 1H), 7.37 (br s, 4H), 7.29 (br s, 1H), 7.12 (br d, J=8.8 Hz, 1H), 5.15 (br t, J=8.5 Hz, 1H), 2.94 (s, 6H), 1.93-2.01 (m, 1H), 1.83-1.92 (m, 1H), 1.77 (br d, J=12.3 Hz, 1H), 1.64 (br d, J=12.9 Hz, 2H), 1.42 (br d, J=12.3 Hz, 1H), 1.11-1.29 (m, 4H), 0.93-1.07 (m, 1H). MS (ESI): m/z=516 [M−H]$^-$.

Example 82

Synthesis of Compound 74: (R)-6-chloro-3-((2-((cyclopentyl(phenyl)methyl)amino)-3,4-dioxocyclobut-1-en-1-yl)amino)-2-hydroxy-N,N-dimethylbenzenesulfonamide

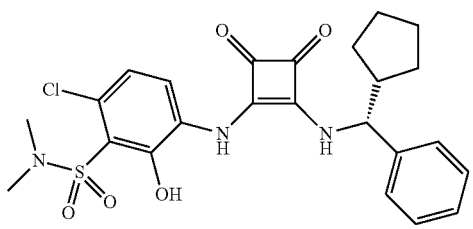 [SMILES: CN(C)S(=O)(=O)c1c(Cl)ccc(Nc2c(N[C@@H](c3ccccc3)C3CCCC3)c(=O)c2=O)c1O]

According to Method A and procedures similar to those for synthesizing Compound 1, Intermediate 1 (31 mg, 0.083 mmol) and (R)-cyclopentyl(phenyl)methanamine (26 mg, 0.15 mmol) were converted into the title compound (34 mg, 0.067 mmol, 81%). $^1$H NMR (600 MHz, ACETONE-$d_6$): δ=10.68 (br s, 1H), 8.46 (br s, 1H), 8.17 (br d, J=7.6 Hz, 1H), 8.04 (br d, J=9.4 Hz, 1H), 7.32-7.45 (m, 4H), 7.22-7.32 (m, 1H), 7.10 (br d, J=8.2 Hz, 1H), 5.16 (br t, J=8.2 Hz, 1H), 2.93 (s, 6H), 2.45-2.57 (m, 1H), 1.89-1.95 (m, 1H), 1.44-1.71 (m, 6H), 1.16-1.22 (m, 1H). MS (ESI): m/z=502 [M−H]$^-$.

Example 83

Synthesis of Compound 75: 3-((2-((2,2-dimethyl-1-phenylpropyl)amino)-3,4-dioxocyclobut-1-en-1-yl)amino)-N,N-diethyl-2-hydroxybenzamide

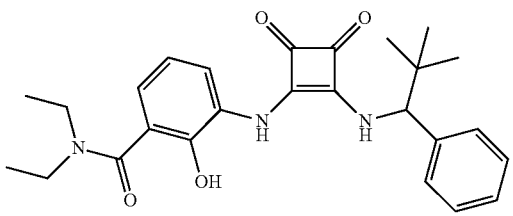 [SMILES: CCN(CC)C(=O)c1cccc(Nc2c(NC(c3ccccc3)C(C)(C)C)c(=O)c2=O)c1O]

According to Method A and procedures similar to those for synthesizing Compound 1, Intermediate 6 (34 mg, 0.10 mmol) and 2,2-dimethyl-1-phenylpropan-1-amine (25 mg, 0.15 mmol) were converted into the title compound (40. mg, 0.089 mmol, 89%). $^1$H NMR (600 MHz, ACETONE-$d_6$): δ=8.44 (br s, 1H), 8.05 (br d, J=7.0 Hz, 2H), 7.32-7.39 (m, 4H), 7.18-7.32 (m, 1H), 7.06 (d, J=7.6 Hz, 1H), 6.86 (t, J=7.9 Hz, 1H), 5.33 (br d, J=10.0 Hz, 1H), 3.55 (q, J=7.0 Hz, 4H), 1.25 (t, J=7.0 Hz, 6H), 1.00 (s, 9H). MS (ESI): m/z=448 [M−H]$^-$.

Example 84

Synthesis of Compound 76: 6-chloro-2-hydroxy-3-((2-((2-isopropylphenyl)amino)-3,4-dioxocyclobut-1-en-1-yl)amino)-N,N-dimethylbenzenesulfonamide

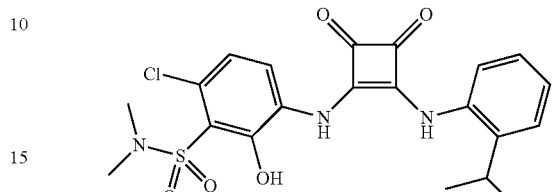

According to Method A and procedures similar to those for synthesizing Compound 1, Intermediate 1 (30. mg, 0.080 mmol) and 2-isopropylaniline (16 mg, 0.12 mmol) were converted into the title compound (6 mg, 0.01 mmol, 16%). $^1$H NMR (600 MHz, ACETONE-$d_6$): δ=10.54-10.71 (m, 1H), 9.27 (br s, 1H), 8.19 (d, J=8.2 Hz, 1H), 7.42 (br d, J=7.6 Hz, 1H), 7.24-7.39 (m, 3H), 7.15 (d, J=8.8 Hz, 1H), 3.38 (dt, J=13.8, 6.6 Hz, 1H), 2.94 (s, 6H), 1.24 (d, J=6.5 Hz, 6H). MS (ESI): m/z=462 [M−H]$^-$.

Example 85

Synthesis of Compound 77: 6-chloro-3-((3,4-dioxo-2-((2-phenylpropan-2-yl)amino)cyclobut-1-en-1-yl)amino)-2-hydroxy-N,N-dimethylbenzenesulfonamide

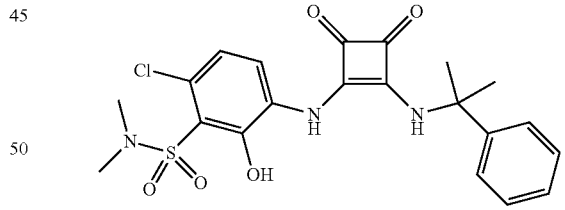

According to Method A and procedures similar to those for synthesizing Compound 1, Intermediate 1 (44 mg, 0.12 mmol) and 2-phenylpropan-2-amine (24 mg, 0.18 mmol) were converted into the title compound (25 mg, 0.054 mmol, 45%). $^1$H NMR (600 MHz, CHLOROFORM-d): δ=10.25 (br s, 1H), 7.82 (br d, J=8.2 Hz, 1H), 7.40-7.52 (m, 4H), 7.30-7.39 (m, 1H), 6.94 (br d, J=7.6 Hz, 1H), 2.88 (s, 6H), 1.78 (s, 6H). MS (ESI): m/z=462 [M−H]$^-$.

Example 86

Synthesis of Compound 78: (R)-6-chloro-2-hydroxy-N,N-dimethyl-3-((2-((1-(5-methylthiophen-2-yl)propyl)amino)-3,4-dioxocyclobut-1-en-1-yl)amino)benzenesulfonamide

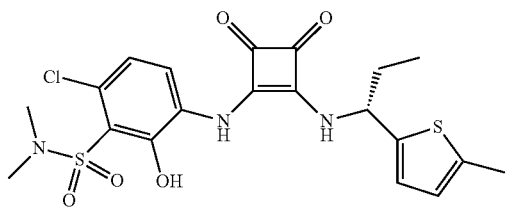

According to Method A and procedures similar to those for synthesizing Compound 1, Intermediate 1 (30. mg, 0.080 mmol) and (R)-1-(5-methylthiophen-2-yl)propan-1-amine (23 mg, 0.15 mmol) were converted into the title compound (23 mg, 0.048 mmol, 59%). $^1$H NMR (600 MHz, CHLOROFORM-d): δ=10.56-10.70 (m, 1H), 7.91 (br d, J=8.2 Hz, 1H), 6.98 (br d, J=9.4 Hz, 1H), 6.86 (br s, 1H), 6.61 (br s, 1H), 6.31-6.48 (m, 1H), 5.30 (br s, 1H), 2.90 (s, 6H), 2.44 (s, 3H), 1.99-2.01 (m, 2H), 1.03 (br t, J=7.0 Hz, 3H). MS (ESI): m/z=482 [M−H]$^-$.

Example 87

Synthesis of Compound 79: (R)-6-chloro-3-((2-((cyclobutyl(phenyl)methyl)amino)-3,4-dioxocyclobut-1-en-1-yl)amino)-2-hydroxy-N,N-dimethylbenzenesulfonamide

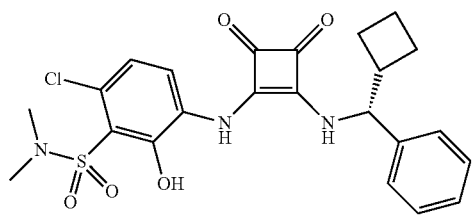 [SMILES: CN(C)S(=O)(=O)c1c(Cl)ccc(Nc2c(N[C@@H](c3ccccc3)C3CCC3)c(=O)c2=O)c1O]

According to Method B and procedures similar to those for synthesizing Compound 2, Intermediate 1 (29 mg, 0.077 mmol) and (R)-cyclobutyl(phenyl)methanamine hydrochloride (23 mg, 0.12 mmol) were converted into the title compound (24 mg, 0.049 mmol, 64%). $^1$H NMR (600 MHz, METHANOL-d$_4$): δ=8.14 (br d, J=8.8 Hz, 1H), 7.31-7.39 (m, 4H), 7.20-7.31 (m, 1H), 7.07 (d, J=8.8 Hz, 1H), 5.22 (br d, J=9.4 Hz, 1H), 2.91 (s, 6H), 2.84-2.90 (m, 1H), 2.11-2.25 (m, 1H), 1.97-2.09 (m, 1H), 1.85-1.97 (m, 3H), 1.66-1.84 (m, 1H). MS (ESI): m/z=488 [M−H]$^-$.

Example 88

Synthesis of Compound 80: (R)-6-chloro-3-((2-((cyclopropyl(phenyl)methyl)amino)-3,4-dioxocyclobut-1-en-1-yl)amino)-2-hydroxy-N,N-dimethyl-benzenesulfonamide

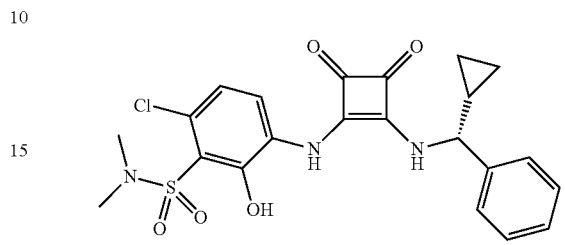

According to Method B and procedures similar to those for synthesizing Compound 2, Intermediate 1 (50. mg, 0.13 mmol) and (R)-cyclobutyl(phenyl)methanamine hydrochloride (37 mg, 0.19 mmol) were converted into the title compound (60. mg, 0.13 mmol, 95%). $^1$H NMR (600 MHz, CHLOROFORM-d): δ=10.43-10.60 (m, 1H), 7.88 (br d, J=8.8 Hz, 1H), 7.34-7.44 (m, 4H), 7.31 (br s, 1H), 6.93 (d, J=8.8 Hz, 1H), 4.61 (br, 1H), 2.86 (s, 6H), 1.30-1.48 (m, 1H), 0.59-0.75 (m, 2H), 0.53 (br s, 1H), 0.44 (br s, 1H). MS (ESI): m/z=474 [M−H]$^-$.

Compounds 81-83 were prepared by following the following general scheme:

General Scheme for Compounds 81-83

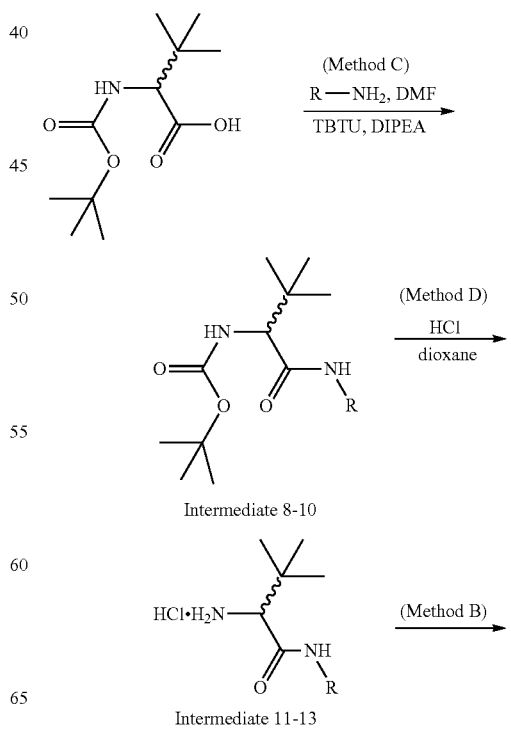

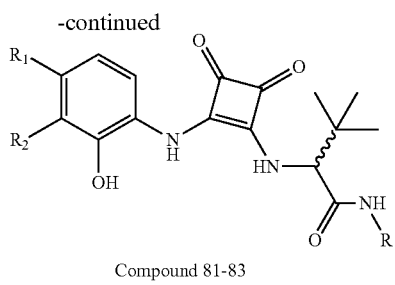

Compound 81-83

Example 89

Synthesis of Intermediate 8: tert-butyl (R)-(1-(cyclopropylamino)-3,3-dimethyl-1-oxobutan-2-yl)carbamate

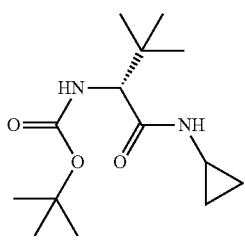 [SMILES: CC(C)(C)OC(=O)N[C@@H](C(=O)NC1CC1)C(C)(C)C]

Method C: To a solution of (R)—N-Boc-2-amino-3,3-dimethylbutyric acid (100. mg, 0.432 mmol) in N,N-dimethylformamide (1.0 mL) was added cyclopropylamine (25 mg, 0.44 mmol), O-(Benzotriazol-1-yl)-N,N,N',N'-tetramethyluronium tetrafluoroborate (TBTU) (139 mg, 0.432 mmol), and N,N-diisopropylethylamine (0.15 mL, 0.86 mmol). After stirring at ambient temperature for 12 hours, the mixture was diluted with ethyl acetate, washed with 1.0 N aqueous hydrochloric acid, water, then brine. The organic layer was dried over sodium sulfate, filtered, and concentrated. The resulting residue purified by flash chromatography on silica gel using a Teledyne-Isco CombiFlash® Rf 200 (4 g column, 10%-80% ethyl acetate/hexanes) to afford tert-butyl (R)-(1-(cyclopropylamino)-3,3-dimethyl-1-oxobutan-2-yl)carbamate as a white solid (91 mg, 0.34 mmol, 78%). $^1$H NMR (600 MHz, CHLOROFORM-d): δ=5.75 (br s, 1H), 5.15-5.31 (br s, 1H), 3.68 (br d, J=8.8 Hz, 1H), 2.70 (br s, 1H), 1.42 (s, 9H), 0.96 (s, 9H), 0.70-0.87 (m, 2H), 0.49 (m, 2H).

Example 90

Synthesis of Intermediate 9: tert-butyl (R)-(3,3-dimethyl-1-(methylamino)-1-oxobutan-2-yl)carbamate

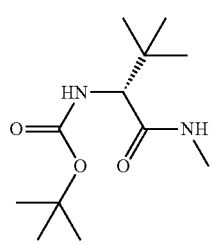 [SMILES: CNC(=O)[C@H](NC(=O)OC(C)(C)C)C(C)(C)C]

In accordance with Method C, (R)—N-Boc-2-amino-3,3-dimethylbutyric acid (50. mg, 0.22 mmol) and methylamine hydrochloride (15 mg, 0.22 mmol) were converted into Intermediate 9 (52 mg, 0.21 mmol, 99%). $^1$H NMR (600 MHz, CHLOROFORM-d): δ=5.71-5.77 (s, 1H), 5.25-5.34 (m, 1H), 3.72-3.81 (m, 1H), 2.77-2.83 (m, 3H), 1.42 (s, 9H), 0.97 (s, 9H).

Example 91

Synthesis of Intermediate 10: tert-butyl-(3,3-dimethyl-1-(methylamino)-1-oxobutan-2-yl)carbamate

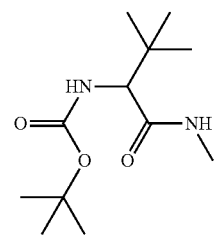 [SMILES: CNC(=O)C(NC(=O)OC(C)(C)C)C(C)(C)C]

In accordance with Method C, N-Boc-2-amino-3,3-dimethylbutyric acid (100. mg, 0.432 mmol) and methylamine hydrochloride (30. mg, 0.43 mmol) were converted into Intermediate 10 (88 mg, 0.36 mmol, 84%).

Example 92

Synthesis of Intermediate 11: (R)-2-amino-N-cyclopropyl-3,3-dimethylbutanamide hydrochloride

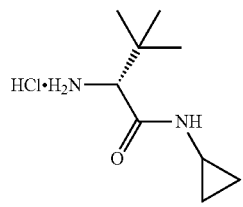

Method D: To a solution of tert-butyl (R)-(1-(cyclopropylamino)-3,3-dimethyl-1-oxobutan-2-yl)carbamate (Intermediate 8, 91 mg, 0.34 mmol) in 1,4-dioxane (1.5 mL) was added 4 M hydrochloric acid in 1,4-dioxane (0.67 mL, 2.7 mmol). After stirring at ambient temperature for 8 hours, the mixture was concentrated to afford (R)-2-amino-N-cyclopropyl-3,3-dimethylbutanamide hydrochloride (Intermediate 11) as a white solid (69 mg, 0.34 mmol, 100.%). $^1$H NMR (600 MHz, METHANOL-d$_4$): δ=3.62-3.68 (m, 1H), 2.69-2.76 (m, 1H), 1.06 (s, 9H), 0.75-0.81 (m, 2H), 0.49-0.60 (m, 2H).

Example 93

Synthesis of Intermediate 12: (R)-2-amino-N,3,3-trimethylbutanamide hydrochloride

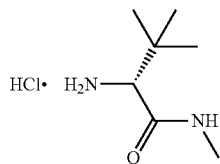

In accordance with Method D, tert-butyl (R)-(3,3-dimethyl-1-(methylamino)-1-oxobutan-2-yl)carbamate (Intermediate 9, 76 mg, 0.31 mmol) was converted into Intermediate 12 (56 mg, 0.31 mmol, 100.%). $^1$H NMR (600 MHz, CHLOROFORM-d): δ=8.02-8.13 (br s, 1H), 3.63-3.65 (m, 1H), 2.75 (s, 3H), 0.98-1.10 (s, 9H).

Example 94

Synthesis of Intermediate 13: 2-amino-N,3,3-trimethylbutanamide hydrochloride

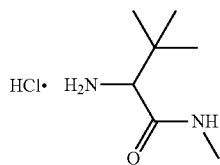

In accordance with Method D, tert-butyl-(3,3-dimethyl-1-(methylamino)-1-oxobutan-2-yl)carbamate (Intermediate 10, 85 mg, 0.35 mmol) was converted into Intermediate 13 (63 mg, 0.35 mmol, 100.%). $^1$H NMR (600 MHz, CHLOROFORM-d): δ=8.03-8.12 (br s, 1H), 3.58-3.62 (m, 1H), 2.72 (s, 3H), 0.95-1.00 (s, 9H).

Example 95

Synthesis of Compound 81: (R)-2-((2-((4-chloro-3-(N,N-dimethylsulfamoyl)-2-hydroxyphenyl)amino)-3,4-dioxocyclobut-1-en-1-yl)amino)-N-cyclopropyl-3,3-dimethylbutanamide

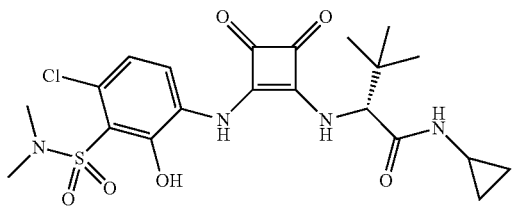 [SMILES: CN(C)S(=O)(=O)c1c(Cl)ccc(Nc2c(N[C@@H](C(=O)NC3CC3)C(C)(C)C)c(=O)c2=O)c1O]

According to Method B and procedures similar to those for synthesizing Compound 2, Intermediate 1 (33 mg, 0.088 mmol) and (R)-2-amino-N-cyclopropyl-3,3-dimethylbutanamide hydrochloride (Intermediate 11, 18 mg, 0.088 mmol) were converted into the title compound (33 mg, 0.066 mmol, 75%). $^1$H NMR (600 MHz, CHLOROFORM-d): δ=10.68 (s, 1H), 8.80 (s, 1H), 7.94-8.07 (m, 1H), 7.70 (br s, 1H), 7.04 (br d, J=8.8 Hz, 1H), 4.76 (br d, J=7.6 Hz, 1H), 2.92 (s, 6H), 2.60-2.72 (m, 1H), 1.08 (s, 9H), 0.64-0.76 (m, 2H), 0.49-0.64 (m, 2H). MS (ESI): m/z=497 [M−H]$^-$.

Example 96

Synthesis of Compound 82: (R)-2-((2-((4-chloro-3-(N,N-dimethylsulfamoyl)-2-hydroxyphenyl)amino)-3,4-dioxocyclobut-1-en-1-yl)amino)-N,3,3-trimethylbutanamide

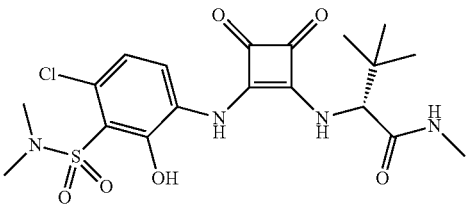

According to Method B and procedures similar to those for synthesizing Compound 2, Intermediate 1 (33 mg, 0.088 mmol) and (R)-2-amino-N,3,3-trimethylbutanamide hydrochloride (Intermediate 12, 16 mg, 0.088 mmol) were converted into the title compound (32 mg, 0.068 mmol, 76%). $^1$H NMR (CHLOROFORM-d): δ=10.62 (br s, 1H), 8.84 (br s, 1H), 7.88-8.09 (m, 2H), 7.76 (br s, 1H), 7.02 (d, J=8.8 Hz, 1H), 4.96 (br d, J=10.0 Hz, 1H), 2.89 (s, 6H), 2.77 (d, J=4.7 Hz, 3H), 1.11 (s, 9H). MS (ESI): m/z=471 [M−H]$^-$.

Example 97

Synthesis of Compound 83: 2-((2-((4-chloro-3-(N,N-dimethylsulfamoyl)-2-hydroxyphenyl)amino)-3,4-dioxocyclobut-1-en-1-yl)amino)-N,3,3-trimethylbutanamide

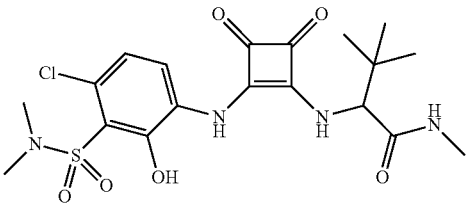

According to Method B and procedures similar to those for synthesizing Compound 2, Intermediate 1 (33 mg, 0.088 mmol) and 2-amino-N,3,3-trimethylbutanamide hydrochloride (Intermediate 13, 16 mg, 0.088 mmol) were converted into the title compound (30 mg, 0.064 mmol, 72%). $^1$H NMR (CHLOROFORM-d/METHANOL-d$_4$): δ=8.05 (d, J=8.8 Hz, 1H), 7.61 (br d, J=4.1 Hz, 1H), 6.99 (d, J=8.8 Hz, 1H), 4.43 (s, 1H), 2.87 (s, 6H), 2.69-2.74 (m, 3H), 0.97 (s, 9H). MS (ESI): m/z=471 [M−H]$^-$.

Example 98

Synthesis of Compound 84: 6-chloro-3-((2-((cyclopentyl(phenyl)methyl)amino)-3,4-dioxocyclobut-1-en-1-yl)amino)-2-hydroxy-N,N-dimethylbenzenesulfonamide

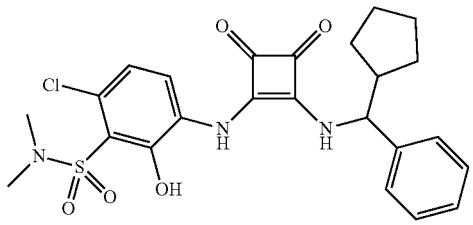 [SMILES: CN(C)S(=O)(=O)c1c(Cl)ccc(Nc2c(NC(c3ccccc3)C3CCCC3)c(=O)c2=O)c1O]

According to Method A and procedures similar to those for synthesizing Compound 1, Intermediate 1 (40. mg, 0.11 mmol) and cyclopentyl(phenyl)methanamine (18 mg, 0.10 mmol) were converted into the title compound (10. mg, 0.020 mmol, 19%). $^1$H NMR (METHANOL-$d_4$): δ=8.13 (d, J=8.8 Hz, 1H), 7.30-7.41 (m, 4H), 7.25-7.30 (m, 1H), 7.05 (d, J=8.8 Hz, 1H), 5.03 (d, J=10.0 Hz, 1H), 2.90 (s, 6H), 2.41-2.52 (m, 1H), 1.86-1.96 (m, 1H), 1.70-1.79 (m, 1H), 1.40-1.70 (m, 5H), 1.12-1.22 (m, 1H). MS (ESI): m/z=502 [M−H]$^-$.

Example 99

Synthesis of Compound 85: 6-chloro-2-hydroxy-3-((2-((1-(2-methoxyethyl)cyclopentyl)amino)-3,4-dioxocyclobut-1-en-1-yl)amino)-N,N-dimethylbenzenesulfonamide

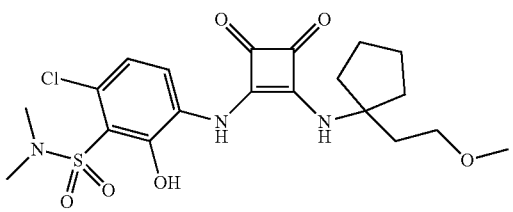

According to Method A and procedures similar to those for synthesizing Compound 1, Intermediate 1 (30 mg, 0.080 mmol) and 1-(2-methoxyethyl)cyclopentan-1-amine (17 mg, 0.12 mmol) were converted into the title compound (18 mg, 0.038 mmol, 48%). $^1$H NMR (600 MHz, CHLOROFORM-d): δ=10.70 (br s, 1H), 8.06 (br d, J=8.8 Hz, 1H), 7.84 (br s, 1H), 7.02 (br d, J=8.8 Hz, 2H), 3.55 (br s, 2H), 3.29 (s, 3H), 2.91 (s, 6H), 2.08 (br s, 2H), 1.84 (br s, 4H), 1.68 (br s, 4H). MS (ESI): m/z=470 [M−H]$^-$.

Example 100

Synthesis of Compound 86: 3-((2-((1-allylcyclopentyl)amino)-3,4-dioxocyclobut-1-en-1-yl)amino)-6-chloro-2-hydroxy-N,N-dimethylbenzenesulfonamide

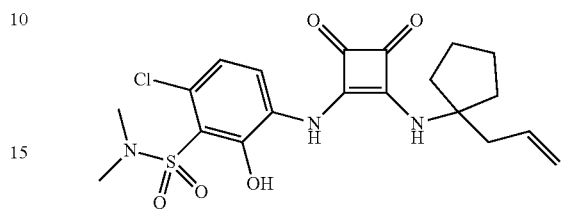

According to Method A and procedures similar to those for synthesizing Compound 1, Intermediate 1 (30. mg, 0.080 mmol) and 1-allylcyclopentan-1-amine (17 mg, 0.13 mmol) were converted into the title compound (19 mg, 0.042 mmol, 52%). $^1$H NMR (600 MHz, CHLOROFORM-d): δ=10.69 (br s, 1H), 7.99 (br d, J=7.0 Hz, 1H), 7.78-7.93 (m, 1H), 7.01 (d, J=8.8 Hz, 1H), 6.45 (br s, 1H), 5.80 (td, J=17.0, 7.0 Hz, 1H), 5.01-5.17 (m, 2H), 2.91 (s, 6H), 2.63 (br d, J=7.0 Hz, 2H), 1.85-2.01 (m, 4H), 1.69-1.83 (m, 4H). MS (ESI): m/z=452 [M−H]$^-$.

Example 101

Synthesis of Compound 87: 6-chloro-2-hydroxy-N,N-dimethyl-3-((2-((1-methylcycloheptyl)amino)-3,4-dioxocyclobut-1-en-1-yl)amino)benzenesulfonamide

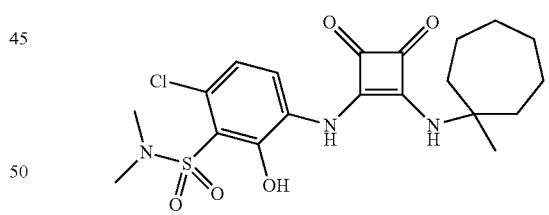

According to Method B and procedures similar to those for synthesizing Compound 2, Intermediate 1 (15 mg, 0.040 mmol) and 1-methylcycloheptan-1-amine hydrochloride (10. mg, 0.061 mmol) were converted into the title compound (5 mg, 0.01 mmol, 30%). $^1$H NMR (600 MHz, CHLOROFORM-d): δ=10.64 (br s, 1H), 7.95-8.10 (m, 2H), 6.99 (d, J=8.2 Hz, 1H), 6.84 (br s, 1H), 2.90 (s, 6H), 1.95-2.07 (m, 2H), 1.88-1.91 (m, 2H), 1.61 (s, 3H), 1.53-1.59 (m, 4H), 1.44-1.52 (m, 4H). MS (ESI): m/z=455 [M−H]$^-$.

Example 102

Synthesis of Compound 88: 6-chloro-3-((3,4-dioxo-2-((1,4,4-trimethylcyclohexyl)amino) cyclobut-1-en-1-yl)amino)-2-hydroxy-N,N-dimethylbenzenesulfonamide

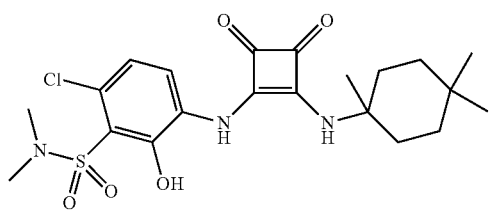

According to Method A and procedures similar to those for synthesizing Compound 1, Intermediate 1 (30. mg, 0.080 mmol) and 1,4,4-trimethylcyclohexan-1-amine (23 mg, 0.16 mmol) were converted into the title compound (18 mg, 0.038 mmol, 48%). $^1$H NMR (600 MHz, CHLOROFORM-d): δ=10.70 (br s, 1H), 7.96 (br d, J=8.8 Hz, 1H), 7.74 (br s, 1H), 7.01 (d, J=8.8 Hz, 1H), 6.25 (br s, 1H), 2.92 (s, 6H), 1.85-2.00 (m, 2H), 1.67-1.85 (m, 2H), 1.58 (s, 3H), 1.48 (s, 3H), 1.28-1.41 (m, 4H), 0.94 (d, J=14.1 Hz, 3H). MS (ESI): m/z=468 [M–H]$^-$.

Example 103

Synthesis of Compound 89: 6-chloro-3-((2-((1-ethylcyclohexyl)amino)-3,4-dioxocyclobut-1-en-1-yl)amino)-2-hydroxy-N,N-dimethylbenzenesulfonamide

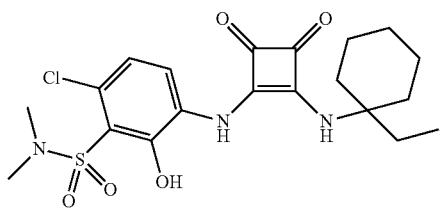 [SMILES: CCC1(Nc2c(Nc3ccc(Cl)c(S(=O)(=O)N(C)C)c3O)c(=O)c2=O)CCCCC1]

According to Method A and procedures similar to those for synthesizing Compound 1, Intermediate 1 (18 mg, 0.048 mmol) and 1-ethylcyclohexan-1-amine (12 mg, 0.072 mmol) were converted into the title compound (9 mg, 0.02 mmol, 40%). $^1$H NMR (600 MHz, CHLOROFORM-d): δ=10.58 (br s, 1H), 8.56 (br s, 1H), 7.99 (br d, J=8.8 Hz, 1H), 7.25 (br s, 1H), 6.97 (br d, J=8.8 Hz, 1H), 2.88 (s, 6H), 1.97-2.01 (m, 2H), 1.81-1.85 (m, 2H), 1.43-1.60 (m, 6H), 1.28-1.38 (m, 2H), 0.84 (br t, J=7.0 Hz, 3H). MS (ESI): m/z=454 [M–H]$^-$.

Example 104

Synthesis of Compound 90: 3-((4-chloro-2-hydroxy-3-((4-methylpiperazin-1-yl)sulfonyl)phenyl)amino)-4-((1-ethylcyclopentyl)amino)cyclobut-3-ene-1,2-dione

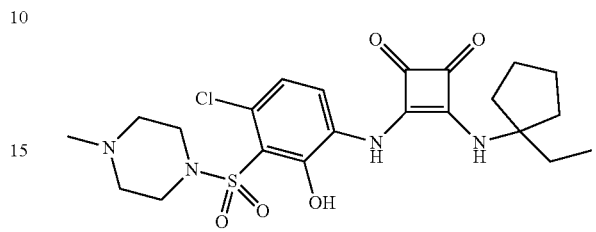

According to Method B and procedures similar to those for synthesizing Compound 2, Intermediate 4 (36 mg, 0.084 mmol) and 1-ethylcyclopentan-1-amine hydrochloride (25 mg, 0.17 mmol) were converted into the title compound (21 mg, 0.042 mmol, 50.%). $^1$H NMR (600 MHz, METHANOL-d$_4$): δ=8.14 (d, J=8.2 Hz, 1H), 7.09 (d, J=8.8 Hz, 1H), 3.35-3.40 (m, 4H), 2.47-2.53 (m, 4H), 2.31 (s, 3H), 2.02-2.07 (m, 2H), 1.88-1.96 (m, 2H), 1.72-1.82 (m, 6H), 0.88-0.95 (m, 3H). MS (ESI): m/z=495 [M–H]$^-$.

Example 105

Synthesis of Compound 91: 6-chloro-2-hydroxy-3-((2-((1-(methoxymethyl)cyclohexyl)amino)-3,4-dioxocyclobut-1-en-1-yl)amino)-N,N-dimethylbenzenesulfonamide

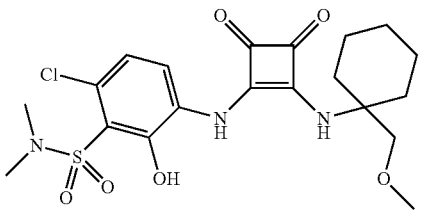 [SMILES: COCC1(Nc2c(Nc3ccc(Cl)c(S(=O)(=O)N(C)C)c3O)c(=O)c2=O)CCCCC1]

According to Method A and procedures similar to those for synthesizing Compound 1, Intermediate 1 (35 mg, 0.093 mmol) and 1-(methoxymethyl)cyclohexan-1-amine (27 mg, 0.19 mmol) were converted into the title compound (24 mg, 0.051 mmol, 55%). $^1$H NMR (600 MHz, CHLOROFORM-d): δ=10.72 (s, 1H), 9.04 (br s, 1H), 7.92 (d, J=8.8 Hz, 1H), 7.04 (d, J=8.8 Hz, 1H), 5.69 (br s, 1H), 3.40-3.50 (m, 5H), 2.94 (s, 6H), 2.04 (s, 2H), 1.86-1.90 (m, 2H), 1.54-1.65 (m, 4H), 1.42-1.54 (m, 2H). MS (ESI): m/z=470 [M–H]$^-$.

Example 106

Synthesis of Compound 92: 6-chloro-3-((2-((1-ethylcyclopentyl)amino)-3,4-dioxocyclobut-1-en-1-yl)amino)-2-hydroxy-N,N-dimethylbenzamide

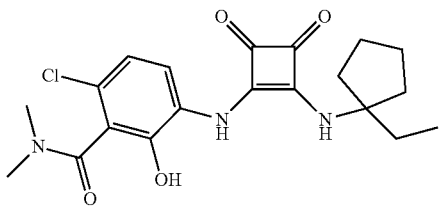 [SMILES: CCC1(Nc2c(Nc3ccc(Cl)c(C(=O)N(C)C)c3O)c(=O)c2=O)CCCC1]

According to Method B and procedures similar to those for synthesizing Compound 2, Intermediate 5 (26 mg, 0.077 mmol) and 1-ethylcyclopentan-1-amine hydrochloride (23 mg, 0.15 mmol) were converted into the title compound (21 mg, 0.052 mmol, 67%). $^1$H NMR (600 MHz, ACETONE-$d_6$): δ=8.44 (br s, 1H), 7.88-8.01 (m, 1H), 7.42 (br s, 1H), 6.97 (br d, J=8.8 Hz, 1H), 3.03 (br s, 3H), 2.92 (br s, 3H), 2.73-2.86 (m, 2H), 1.92 (q, J=7.2 Hz, 2H), 1.66-1.81 (m, 6H), 0.90 (t, J=7.3 Hz, 3H). MS (ESI): m/z=404 [M−H]$^-$.

Example 107

Synthesis of Compound 93: 6-chloro-3-((3,4-dioxo-2-((1-(thiophen-2-yl)cyclohexyl)amino)cyclobut-1-en-1-yl)amino)-2-hydroxy-N,N-dimethylbenzenesulfonamide

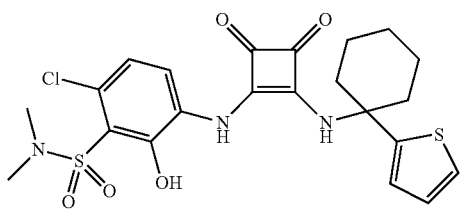 [SMILES: CN(C)S(=O)(=O)c1c(Cl)ccc(Nc2c(NC3(c4cccs4)CCCCC3)c(=O)c2=O)c1O]

According to Method A and procedures similar to those for synthesizing Compound 1, Intermediate 1 (30. mg, 0.080 mmol) and 1-(thiophen-2-yl)cyclohexan-1-amine (29 mg, 0.16 mmol) were converted into the title compound (26 mg, 0.051 mmol, 64%). $^1$H NMR (600 MHz, CHLOROFORM-d): δ=10.41 (s, 1H), 7.89 (d, J=8.8 Hz, 1H), 7.27-7.44 (m, 1H), 7.07-7.24 (m, 1H), 6.88-7.05 (m, 2H), 6.77 (br s, 1H), 6.19 (br s, 1H), 2.90 (s, 6H), 2.12-2.21 (m, 2H), 2.01-2.12 (m, 2H), 1.76-1.80 (m, 3H), 1.52-1.66 (m, 2H), 1.35-1.39 (m, 1H). MS (ESI): m/z=508 [M−H]$^-$.

Example 108

Synthesis of Compound 94: 6-chloro-2-hydroxy-N,N-dimethyl-3-((2-((1-methylcyclohexyl)amino)-3,4-dioxocyclobut-1-en-1-yl)amino)benzamide

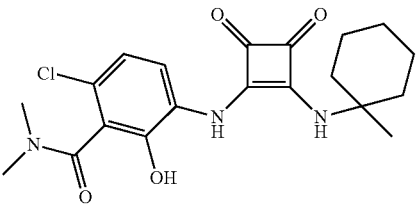 [SMILES: CN(C)C(=O)c1c(Cl)ccc(Nc2c(NC3(C)CCCCC3)c(=O)c2=O)c1O]

According to Method B and procedures similar to those for synthesizing Compound 2, Intermediate 5 (25 mg, 0.074 mmol) and 1-methylcyclohexan-1-amine hydrochloride (17 mg, 0.11 mmol) were converted into the title compound (15 mg, 0.037 mmol, 50.%). $^1$H NMR (600 MHz, ACETONE-$d_6$): δ=8.88 (br s, 1H), 7.72 (br s, 1H), 7.41 (br s, 1H), 6.90 (br s, 1H), 3.08 (br s, 3H), 2.92 (br s, 3H), 1.58-1.64 (m, 4H), 1.42-1.57 (m, 6H), 1.44 (br s, 3H). MS (ESI): m/z=404 [M−H]$^-$.

Example 109

Synthesis of Compound 95: 6-chloro-3-((2-((1-ethylcyclopentyl)amino)-3,4-dioxocyclobut-1-en-1-yl)amino)-2-hydroxy-N,N-dimethylbenzenesulfonamide

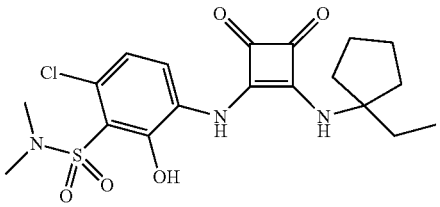 [SMILES: CCC1(Nc2c(Nc3ccc(Cl)c(S(=O)(=O)N(C)C)c3O)c(=O)c2=O)CCCC1]

According to Method B and procedures similar to those for synthesizing Compound 2, Intermediate 1 (11 mg, 0.029 mmol) and 1-ethylcyclopentan-1-amine hydrochloride (9 mg, 0.06 mmol) were converted into the title compound (8 mg, 0.02 mmol, 60%). $^1$H NMR (600 MHz, CHLOROFORM-d): δ=10.67 (br s, 1H), 8.07 (br s, 2H), 7.00 (d, J=8.2 Hz, 1H), 6.88 (br s, 1H), 2.90 (s, 6H), 1.93-2.00 (m, 2H), 1.87-1.91 (m, 2H), 1.69-1.84 (m, 6H), 0.92 (t, J=7.3 Hz, 3H). MS (ESI): m/z=440 [M−H]$^-$.

Example 110

Synthesis of Compound 96: 6-chloro-2-hydroxy-3-((2-((1-(methoxymethyl)cyclopentyl)amino)-3,4-dioxocyclobut-1-en-1-yl)amino)-N,N-dimethylbenzenesulfonamide

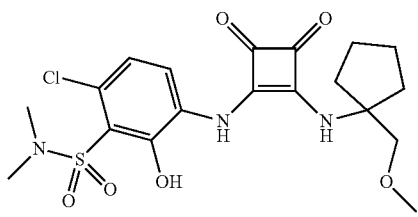

According to Method A and procedures similar to those for synthesizing Compound 1, Intermediate 1 (28 mg, 0.075 mmol) and 1-(methoxymethyl)cyclopentan-1-amine (20 mg, 0.15 mmol) were converted into the title compound (18 mg, 0.039 mmol, 52%). $^1$H NMR (600 MHz, CHLOROFORM-d): δ=10.71 (br s, 1H), 9.08 (br s, 1H), 7.96 (br d, J=8.8 Hz, 1H), 7.04 (br d, J=8.8 Hz, 1H), 5.96 (br s, 1H), 3.46 (s, 3H), 2.94 (s, 6H), 1.77-1.91 (m, 6H), 1.73 (br s, 2H), 1.61 (br s, 2H). MS (ESI): m/z=456 [M–H]$^-$.

Example 111

Synthesis of Compound 97: 3-((4-chloro-2-hydroxy-3-((4-methylpiperazin-1-yl)sulfonyl)phenyl)amino)-4-((1-methylcyclohexyl)amino)cyclobut-3-ene-1,2-dione

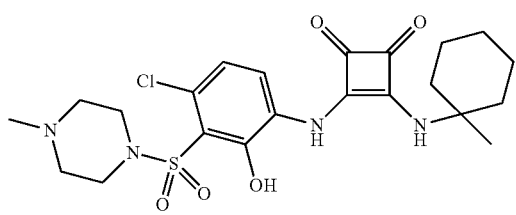 [SMILES: CN1CCN(S(=O)(=O)c2c(Cl)ccc(Nc3c(NC4(C)CCCCC4)c(=O)c3=O)c2O)CC1]

According to Method A and procedures similar to those for synthesizing Compound 1, Intermediate 4 (20. mg, 0.047 mmol) and 1-methylcyclohexan-1-amine (12 mg, 0.11 mmol) were converted into the title compound (10. mg, 0.020 mmol, 43%). $^1$H NMR (600 MHz, METHANOL-d$_4$): δ=8.10 (d, J=8.8 Hz, 1H), 7.09 (d, J=8.8 Hz, 1H), 3.31-3.44 (m, 4H), 2.45-2.57 (m, 4H), 2.31 (s, 3H), 2.03-2.09 (m, 2H), 1.60-1.77 (m, 2H), 1.58 (br s, 6H), 1.45 (s, 3H). MS (ESI): m/z=495 [M–H]$^-$.

Example 112

Synthesis of Compound 98: 3-((2-([1,1'-bi(cyclopropan)]-1-ylamino)-3,4-dioxocyclobut-1-en-1-yl)amino)-6-chloro-2-hydroxy-N,N-dimethylbenzenesulfonamide

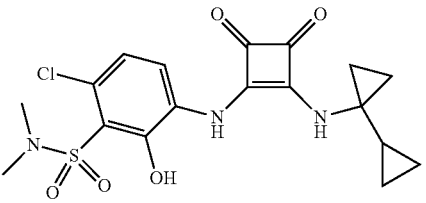 [SMILES: CN(C)S(=O)(=O)c1c(Cl)ccc(Nc2c(NC3(C4CC4)CC3)c(=O)c2=O)c1O]

According to Method B and procedures similar to those for synthesizing Compound 2, Intermediate 1 (25 mg, 0.067 mmol) and [1,1'-bi(cyclopropan)]-1-amine hydrochloride (14 mg, 0.10 mmol) were converted into the title compound (16 mg, 0.038 mmol, 56%). $^1$H NMR (600 MHz, CHLOROFORM-d): δ=10.82 (br s, 1H), 8.36 (br s, 1H), 8.08-8.27 (m, 1H), 7.08 (d, J=8.8 Hz, 1H), 6.58-6.77 (m, 1H), 2.95 (s, 6H), 1.16-1.31 (m, 2H), 1.01 (br s, 2H), 0.82-0.96 (m, 2H), 0.55-0.61 (m, 2H), 0.27-0.36 (m, 1H). MS (ESI): m/z=424 [M–H]$^-$.

Example 113

Synthesis of Compound 99: 6-chloro-3-((3,4-dioxo-2-((1-propylcyclopropyl) amino)cyclobut-1-en-1-yl)amino)-2-hydroxy-N,N-dimethylbenzenesulfonamide

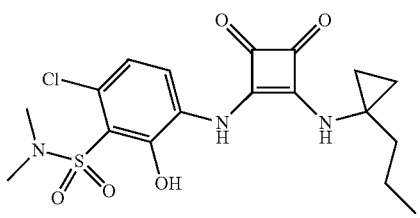 [SMILES: CCCC1(Nc2c(Nc3ccc(Cl)c(S(=O)(=O)N(C)C)c3O)c(=O)c2=O)CC1]

According to Method B and procedures similar to those for synthesizing Compound 2, Intermediate 1 (25 mg, 0.067 mmol) and 1-propylcyclopropan-1-amine hydrochloride (14 mg, 0.10 mmol) were converted into the title compound (20. mg, 0.047 mmol, 70.%). $^1$H NMR (600 MHz, CHLOROFORM-d): δ=10.83 (br s, 1H), 8.38 (br s, 1H), 8.14 (br s, 1H), 7.08 (d, J=8.2 Hz, 1H), 6.57 (br s, 1H), 2.95 (s, 6H), 1.57-1.65 (m, 4H), 1.39-1.57 (m, 2H), 1.04 (br s, 2H), 0.95 (t, J=7.3 Hz, 3H). MS (ESI): m/z=426 [M–H]$^-$.

Example 114

Synthesis of Compound 100: 6-chloro-2-hydroxy-N,N-dimethyl-3-((2-((1-methylcyclobutyl)amino)-3,4-dioxocyclobut-1-en-1-yl)amino)benzenesulfonamide

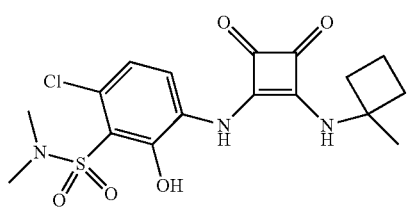 [SMILES: CN(C)S(=O)(=O)c1c(Cl)ccc(Nc2c(NC3(C)CCC3)c(=O)c2=O)c1O]

According to Method B and procedures similar to those for synthesizing Compound 2, Intermediate 1 (25 mg, 0.067 mmol) and 1-methylcyclobutan-1-amine hydrochloride (13 mg, 0.11 mmol) were converted into the title compound (16 mg, 0.039 mmol, 58%). $^1$H NMR (600 MHz, CHLOROFORM-d): δ=10.76 (br s, 1H), 8.09-8.23 (m, 1H), 7.62 (br s, 1H), 7.04 (br d, J=8.8 Hz, 1H), 6.45 (br s, 1H), 2.93 (s, 6H), 2.35-2.41 (m, 2H), 2.14-2.29 (m, 2H), 1.97-2.09 (m, 1H), 1.81-1.97 (m, 1H), 1.57 (s, 3H). MS (ESI): m/z=412 [M−H]$^-$.

Example 115

Synthesis of Compound 101: 3-((2-((1-(tert-butyl)cyclopropyl)amino)-3,4-dioxocyclobut-1-en-1-yl)amino)-6-chloro-2-hydroxy-N,N-dimethylbenzenesulfonamide

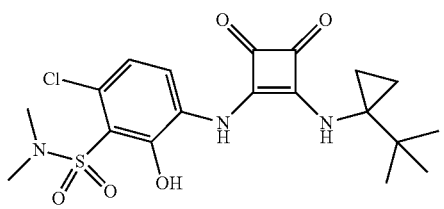 [SMILES: CN(C)S(=O)(=O)c1c(Cl)ccc(Nc2c(NC3(C(C)(C)C)CC3)c(=O)c2=O)c1O]

According to Method B and procedures similar to those for synthesizing Compound 2, Intermediate 1 (10. mg, 0.027 mmol) and 1-(tert-butyl)cyclopropan-1-amine hydrochloride (6 mg, 0.04 mmol) were converted into the title compound (3 mg, 0.007 mmol, 30%). $^1$H NMR (600 MHz, CHLOROFORM-d): δ=10.87 (br s, 1H), 8.28-8.44 (m, 1H), 7.96 (br s, 1H), 7.07 (br d, J=8.8 Hz, 1H), 6.33 (br s, 1H), 2.96 (s, 6H), (br s, 2H), 1.01 (br s, 9H), 0.91 (br s, 2H). MS (ESI): m/z=440 [M−H]$^-$.

Example 116

Synthesis of Compound 102: 6-chloro-3-((3,4-dioxo-2-((1-(thiophen-2-yl)cyclopentyl) amino)cyclobut-1-en-1-yl)amino)-2-hydroxy-N,N-dimethylbenzenesulfonamide

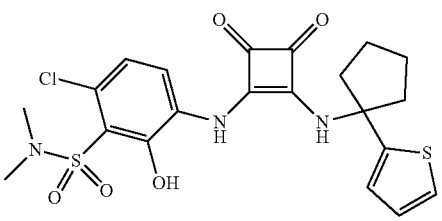 [SMILES: CN(C)S(=O)(=O)c1c(Cl)ccc(Nc2c(NC3(c4cccs4)CCCC3)c(=O)c2=O)c1O]

According to Method B and procedures similar to those for synthesizing Compound 2, Intermediate 1 (15 mg, 0.040 mmol) and 1-(thiophen-2-yl)cyclopentan-1-amine hydrochloride (13 mg, 0.064 mmol) were converted into the title compound (6 mg, 0.01 mmol, 30%). $^1$H NMR (600 MHz, CHLOROFORM-d): δ=10.43 (br s, 1H), 7.95 (br d, J=8.8 Hz, 1H), 7.31 (br d, J=4.1 Hz, 1H), 7.09 (br s, 1H), 6.91-7.04 (m, 3H), 6.45 (br s, 1H), 2.90 (s, 6H), 2.29 (br s, 2H), 2.14-2.26 (m, 2H), 1.83-2.00 (m, 4H). MS (ESI): m/z=494 [M−H]$^-$.

Example 117

Synthesis of Compound 103: 6-chloro-3-((3,4-dioxo-2-((1-(p-tolyl)cyclobutyl)amino) cyclobut-1-en-1-yl)amino)-2-hydroxy-N,N-dimethylbenzenesulfonamide

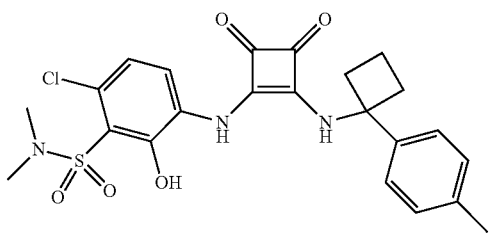

According to Method B and procedures similar to those for synthesizing Compound 2, Intermediate 1 (26 mg, 0.069 mmol) and 1-(p-tolyl)cyclobutan-1-amine hydrochloride (20. mg, 0.10 mmol) were converted into the title compound (25 mg, 0.051 mmol, 74%). $^1$H NMR (600 MHz, CHLOROFORM-d): δ=10.44 (br s, 1H), 7.93-8.03 (m, 1H), 7.38-7.45 (m, 2H), 7.16-7.23 (m, 2H), 7.04-7.12 (m, 1H), 6.90-6.98 (m, 2H), 2.89 (s, 6H), 2.64-2.80 (m, 2H), 2.48-2.64 (m, 2H), 2.32 (s, 3H), 2.25-2.20 (m, 2H). MS (ESI): m/z=488 [M−H]$^-$.

Example 118

Synthesis of Compound 104: 6-chloro-3-((2-((1-(3-fluorophenyl)cyclobutyl)amino)-3,4-dioxocyclobut-1-en-1-yl)amino)-2-hydroxy-N,N-dimethylbenzenesulfonamide

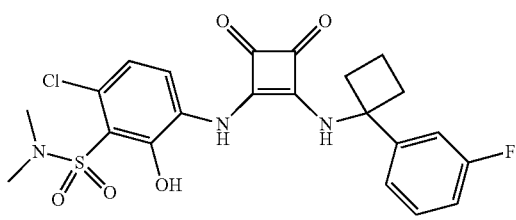 [SMILES: CN(C)S(=O)(=O)c1c(Cl)ccc(Nc2c(NC3(c4cccc(F)c4)CCC3)c(=O)c2=O)c1O]

According to Method B and procedures similar to those for synthesizing Compound 2, Intermediate 1 (15 mg, 0.040 mmol) and 1-(3-fluorophenyl)cyclobutan-1-amine hydrochloride (12 mg, 0.060 mmol) were converted into the title compound (13 mg, 0.026 mmol, 66%). $^1$H NMR (600 MHz, CHLOROFORM-d): δ=10.53 (br s, 1H), 7.97-8.08 (m, 1H), 7.34-7.53 (m, 2H), 7.48 (br s, 1H), 7.29-7.34 (m, 1H), 7.19-7.24 (m, 1H), 6.99 (br s, 1H), 6.79-6.97 (m, 1H), 2.88 (s, 6H), 2.68-2.79 (m, 2H), 2.65 (br s, 2H), 2.18-2.35 (m, 2H). MS (ESI): m/z=492 [M−H]$^-$.

Example 119

Synthesis of Compound 105: 6-chloro-3-((2-((1-(2,6-difluorophenyl)cyclopentyl)amino)-3,4-dioxocyclobut-1-en-1-yl)amino)-2-hydroxy-N,N-dimethylbenzenesulfonamide

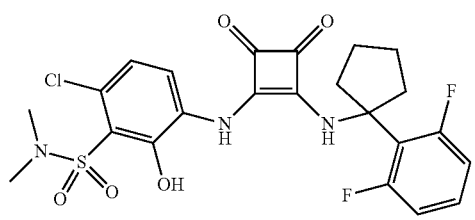 [SMILES: CN(C)S(=O)(=O)c1c(Cl)ccc(Nc2c(NC3(c4c(F)cccc4F)CCCC3)c(=O)c2=O)c1O]

According to Method B and procedures similar to those for synthesizing Compound 2, Intermediate 1 (15 mg, 0.040 mmol) and 1-(2,6-difluorophenyl)cyclobutan-1-amine hydrochloride (14 mg, 0.064 mmol) were converted into the title compound (5 mg, 0.01 mmol, 20%). $^1$H NMR (600 MHz, CHLOROFORM-d): δ=8.06 (br d, J=7.6 Hz, 1H), 7.14 (br d, J=7.0 Hz, 1H), 6.98 (br d, J=8.2 Hz, 1H), 6.77-6.83 (m, 2H), 2.89 (m, 6H), 2.66-2.69 (m, 2H), 2.24-2.29 (m, 2H), 1.78-1.85 (m, 4H). MS (ESI): m/z=524 [M−H]$^-$.

Example 120

Synthesis of Compound 106: 6-chloro-3-((2-((1-ethynylcyclohexyl)amino)-3,4-dioxocyclobut-1-en-1-yl)amino)-2-hydroxy-N,N-dimethylbenzenesulfonamide

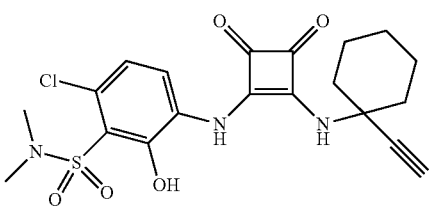 [SMILES: C#CC1(Nc2c(Nc3ccc(Cl)c(S(=O)(=O)N(C)C)c3O)c(=O)c2=O)CCCCC1]

According to Method A and procedures similar to those for synthesizing Compound 1, Intermediate 1 (18 mg, 0.048 mmol) and 1-ethynylcyclohexan-1-amine (9 mg, 0.07 mmol) were converted into the title compound (7 mg, 0.02 mmol, 30%). $^1$H NMR (600 MHz, CHLOROFORM-d): δ=10.75 (s, 1H), 8.69 (br s, 1H), 8.04 (d, J=8.8 Hz, 1H), 7.06 (d, J=8.8 Hz, 1H), 6.35 (br s, 1H), 2.94 (s, 6H), 2.83 (s, 1H), 2.16 (br s, 2H), 1.64-1.78 (m, 6H), 1.27-1.34 (m, 2H). MS (ESI): m/z=450 [M−H]$^-$.

Example 121

Synthesis of Compound 107: 6-chloro-3-((3,4-dioxo-2-((1-phenylcyclohexyl)amino) cyclobut-1-en-1-yl)amino)-2-hydroxy-N,N-dimethylbenzenesulfonamide

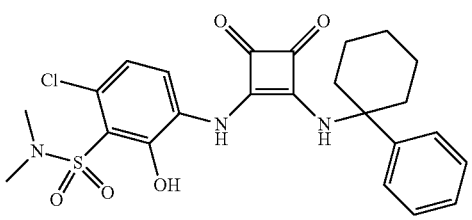 [SMILES: CN(C)S(=O)(=O)c1c(Cl)ccc(Nc2c(NC3(c4ccccc4)CCCCC3)c(=O)c2=O)c1O]

According to Method B and procedures similar to those for synthesizing Compound 2, Intermediate 1 (17 mg, 0.045 mmol) and 1-phenylcyclohexan-1-amine hydrochloride (14 mg, 0.066 mmol) were converted into the title compound (7 mg, 0.01 mmol, 30%). $^1$H NMR (600 MHz, CHLOROFORM-d): δ=10.27 (br s, 1H), 7.83 (br d, J=8.8 Hz, 1H), 7.49 (d, J=7.2 Hz, 2H), 7.40-7.46 (m, 2H), 7.29-7.37 (m, 1H), 6.93 (d, J=8.8 Hz, 1H), 6.27-6.45 (m, 1H), 2.88 (s, 6H), 1.97-2.10 (m, 2H), 1.73-1.84 (m, 4H), 1.55-1.73 (m, 2H), 1.30-1.47 (m, 2H). MS (ESI): m/z=502 [M−H]$^-$.

Example 122

Synthesis of Compound 108: 3-((2-((1-benzylcyclobutyl)amino)-3,4-dioxocyclobut-1-en-1-yl)amino)-6-chloro-2-hydroxy-N,N-dimethylbenzenesulfonamide

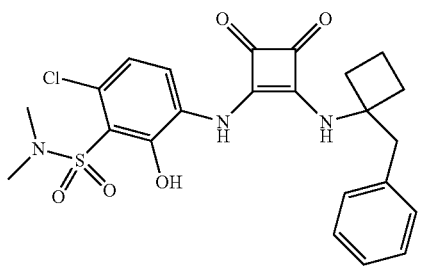 [SMILES: CN(C)S(=O)(=O)c1c(Cl)ccc(Nc2c(NC3(Cc4ccccc4)CCC3)c(=O)c2=O)c1O]

According to Method B and procedures similar to those for synthesizing Compound 2, Intermediate 1 (14 mg, 0.037 mmol) and 1-benzylcyclobutan-1-amine hydrochloride (11 mg, 0.056 mmol) were converted into the title compound (10. mg, 0.020 mmol, 55%). $^1$H NMR (600 MHz, CHLOROFORM-d): δ=10.67 (br s, 1H), 7.80-7.96 (m, 1H), 7.20-7.29 (m, 2H), 7.09-7.20 (m, 3H), 6.94 (br d, J=8.8 Hz, 1H), 6.66 (br s, 1H) 3.16 (br s, 2H), 2.89 (br s, 6H), 2.41 (br s, 2H), 2.25 (q, J=9.2 Hz, 2H), 1.78-1.96 (m, 1H), 1.65 (br s, 1H). MS (ESI): m/z=488 [M−H]$^-$.

Example 123

Synthesis of Compound 109: (R)-3-((3-chloro-2-hydroxyphenyl)amino)-4-((5,5-dimethyl-4,5,6,7-tetrahydrobenzofuran-4-yl)amino)cyclobut-3-ene-1,2-dione

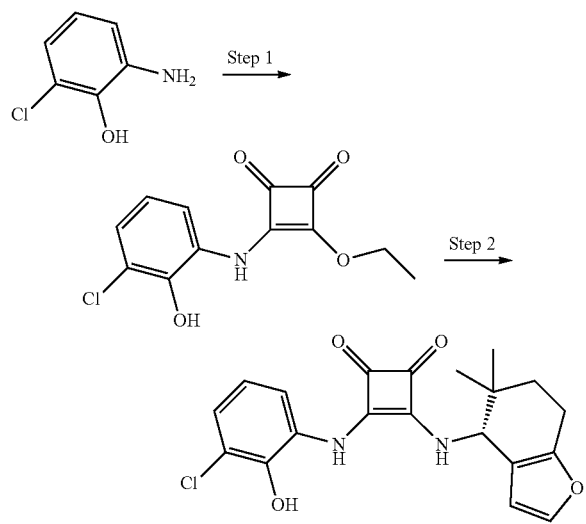

Step 1

3-((3-chloro-2-hydroxyphenyl)amino)-4-ethoxycyclobut-3-ene-1,2-dione

Step 1: To a solution of 2-amino-6-chlorophenol (20.6 mg, 0.136 mmol) in ethanol (0.45 mL) was added 3,4-diethoxycyclobut-3-ene-1,2-dione (33.7 mg, 0.188 mmol). After stirring at 40° C. for 18 hr, the mixture was concentrated and purified by flash chromatography on silica gel using a Teledyne-Isco CombiFlash® Rf 200 (4 g column, 10%→60% ethyl acetate/hexanes) to afford 3-((3-chloro-2-hydroxyphenyl)amino)-4-ethoxycyclobut-3-ene-1,2-dione (22.9 mg, 0.0856 mmol, 62.9%). $^1$H NMR (CHLOROFORM-d/METHANOL-d$_4$): δ=7.43 (br s, 1H), 7.06 (d, J=8.2 Hz, 1H), 6.82 (dd, J=8.2 Hz, 1H), 4.84 (q, J=7.0 Hz, 2H), 1.47 (t, J=7.0 Hz, 3H). MS (ESI): m/z=266 [M−H]$^-$.

Step 2

(R)-3-((3-chloro-2-hydroxyphenyl)amino)-4-((5,5-dimethyl-4,5,6,7-tetrahydrobenzofuran-4-yl)amino)cyclobut-3-ene-1,2-dione Step 2: According to Method A and procedures similar to those for synthesizing Compound 1, 3-((3-chloro-2-hydroxyphenyl)amino)-4-ethoxycyclobut-3-ene-1,2-dione (24.8 mg, 0.0927 mmol) and (R)-5,5-dimethyl-4,5,6,7-tetrahydrobenzofuran-4-amine (synthesized as described for Compound 29, 23.8 mg, 0.144 mmol) were converted into the title compound (10.5 mg, 0.0271 mmol, 29.3%). $^1$H NMR (METHANOL-d$_4$): δ=7.89 (d, J=8.2 Hz, 1H), 7.37 (s, 1H), 7.01 (d, J=8.2 Hz, 1H), 6.83 (dd, J=8.2 Hz, 1H), 6.36 (s, 1H), 4.99 (s, 1H), 2.54-2.74 (m, 2H), 1.77-1.89 (m, 1H), 1.66-1.76 (m, 1H), 1.06 (s, 3H), 1.02 (s, 3H). MS (ESI): m/z=385 [M−H]$^-$.

Example 124

Synthesis of Compound 110: 6-chloro-2-hydroxy-N,N-dimethyl-3-((2-((1-methylcyclohexyl)amino)-3,4-dioxocyclobut-1-en-1-yl)amino)benzenesulfonamide

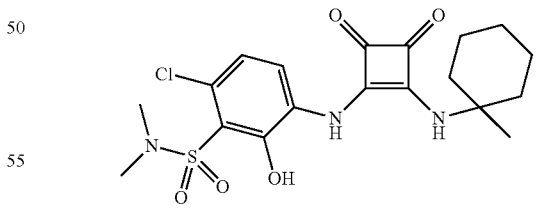

According to Method A and procedures similar to those for synthesizing Compound 1, Intermediate 1 (22 mg, 0.059 mmol) and 1-methylcyclohexan-1-amine (13 mg, 0.11 mmol) were converted into the title compound (13 mg, 0.029 mmol, 50.%). $^1$H NMR (600 MHz, CHLOROFORM-d): δ=10.57 (s, 1H), 8.46 (br s, 1H), 7.94-8.04 (m, 1H), 7.44 (br s, 1H), 6.93-7.07 (m, 1H), 2.88 (s, 6H), 1.91-1.96 (m, 2H), 1.59-1.68 (m, 2H), 1.48-1.56 (m, 4H), 1.46 (s, 3H), 1.31-1.42 (m, 2H). MS (ESI): m/z=440 [M−H]$^-$.

Example 125

Synthesis of Compound 111: 6-chloro-3-((3,4-dioxo-2-((1-phenylcyclopropyl)amino) cyclobut-1-en-1-yl)amino)-2-hydroxy-N,N-dimethylbenzenesulfonamide

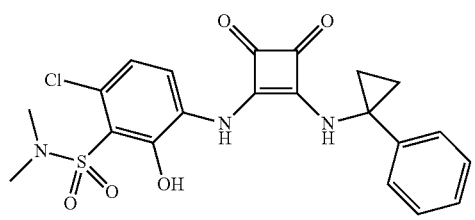 [SMILES: CN(C)S(=O)(=O)c1c(Cl)ccc(Nc2c(NC3(c4ccccc4)CC3)c(=O)c2=O)c1O]

According to Method B and procedures similar to those for synthesizing Compound 2, Intermediate 1 (26 mg, 0.069 mmol) and 1-phenylcyclopropan-1-amine hydrochloride (18 mg, 0.11 mmol) were converted into the title compound (24 mg, 0.052 mmol, 75%). $^1$H NMR (600 MHz, CHLOROFORM-d): δ=10.51 (s, 1H), 8.23 (br s, 1H), 7.75 (br s, 1H), 7.33-7.39 (m, 2H), 7.11-7.29 (m, 4H), 7.00 (d, J=8.8 Hz, 1H), 2.89 (s, 6H), 1.54-1.65 (m, 2H), 1.47-1.54 (m, 2H). MS (ESI): m/z=460 [M–H]$^-$.

Example 126

Synthesis of Compound 112: 6-chloro-3-((3,4-dioxo-2-((1-(m-tolyl)cyclobutyl)amino) cyclobut-1-en-1-yl)amino)-2-hydroxy-N,N-dimethylbenzenesulfonamide

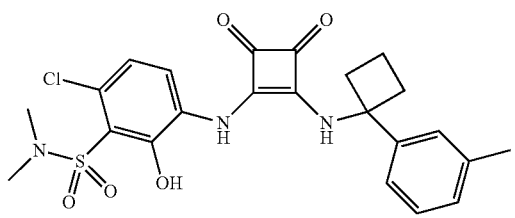

According to Method B and procedures similar to those for synthesizing Compound 2, Intermediate 1 (29 mg, 0.077 mmol) and 1-(m-tolyl)cyclobutan-1-amine hydrochloride (23 mg, 0.12 mmol) were converted into the title compound (23 mg, 0.047 mmol, 61%). $^1$H NMR (600 MHz, CHLOROFORM-d): δ=10.49 (br s, 1H), 7.99 (br d, J=8.8 Hz, 1H), 7.20-7.36 (m, 3H), 7.13 (br s, 2H), 6.95 (br d, J=8.8 Hz, 2H), 2.89 (s, 6H), 2.69-2.80 (m, 2H), 2.53-2.66 (m, 2H), 2.38 (s, 3H), 2.19-2.29 (m, 1H), 1.62-1.73 (m, 1H). MS (ESI): m/z=488 [M–H]$^-$.

Example 127

Synthesis of Compound 113: 6-chloro-3-((2-((1-(2-fluorophenyl)cyclobutyl)amino)-3,4-dioxocyclobut-1-en-1-yl)amino)-2-hydroxy-N,N-dimethylbenzenesulfonamide

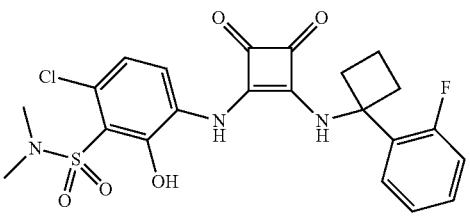 [SMILES: CN(C)S(=O)(=O)c1c(Cl)ccc(Nc2c(NC3(c4ccccc4F)CCC3)c(=O)c2=O)c1O]

According to Method B and procedures similar to those for synthesizing Compound 2, Intermediate 1 (21 mg, 0.056 mmol) and 1-(2-fluorophenyl)cyclobutan-1-amine hydrochloride (17 mg, 0.084 mmol) were converted into the title compound (14 mg, 0.028 mmol, 51%). $^1$H NMR (600 MHz, CHLOROFORM-d): δ=8.05 (d, J=8.8 Hz, 2H), 7.62-7.70 (m, 1H), 7.17-7.25 (m, 1H), 7.05-7.13 (m, 2H), 6.91-7.01 (m, 2H), 2.88 (s, 6H), 2.74-2.85 (m, 2H), 2.56-2.70 (m, 2H), 2.10-2.23 (m, 1H), 1.81-1.92 (m, 1H). MS (ESI): m/z=492 [M–H]$^-$.

Example 128

Synthesis of Compound 114: 3-((3,4-dioxo-2-((1-phenylcyclopentyl)amino)cyclobut-1-en-1-yl) amino)-2-hydroxy-N,N-dimethylbenzamide

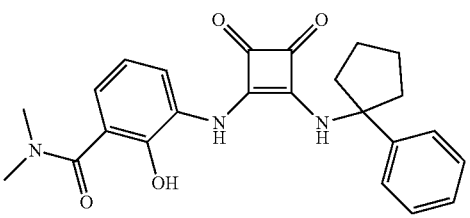 [SMILES: CN(C)C(=O)c1cccc(Nc2c(NC3(c4ccccc4)CCCC3)c(=O)c2=O)c1O]

According to Method A and procedures similar to those for synthesizing Compound 1, Intermediate 2 (50. mg, 0.16 mmol) and 1-phenylcyclopentan-1-amine (40. mg, 0.25 mmol) were converted into the title compound (41 mg, 0.097 mmol, 61%). $^1$H NMR (600 MHz, CHLOROFORM-d): δ=7.90 (d, J=7.8 Hz, 1H), 7.45-7.48 (m, 3H), 7.30-7.42 (m, 2H), 7.22 (br s, 1H), 6.94 (d, J=7.8 Hz, 1H), 6.75-6.83 (m, 1H), 6.37 (br s, 1H), 3.13 (s, 6H), 2.22-2.32 (m, 2H), 2.10-2.20 (m, 2H), 1.96-1.90 (m, 4H). MS (ESI): m/z=418 [M–H]$^-$.

Example 129

Synthesis of Compound 115: 3-((3,4-dioxo-2-((1-phenylcyclopentyl)amino)cyclobut-1-en-1-yl)amino)-2-hydroxy-N,N-dimethylbenzenesulfonamide

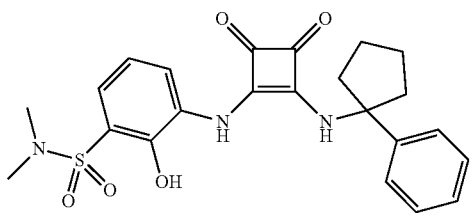 [SMILES: CN(C)S(=O)(=O)c1cccc(Nc2c(NC3(c4ccccc4)CCCC3)c(=O)c2=O)c1O]

According to Method A and procedures similar to those for synthesizing Compound 1, Intermediate 7 (33 mg, 0.097 mmol) and 1-phenylcyclopentan-1-amine (24 mg, 0.15 mmol) were converted into the title compound (11 mg, 0.024 mmol, 25%). $^1$H NMR (600 MHz, CHLOROFORM-d): δ=8.94 (br s, 1H), 8.01 (d, J=8.2 Hz, 1H), 7.48 (d, J=7.6 Hz, 2H), 7.35-7.43 (m, 2H), 7.26-7.34 (m, 1H), 7.02-7.16 (m, 1H), 6.90-6.98 (m, 1H), 6.73 (br s, 1H), 2.71 (s, 6H), 2.15-2.32 (m, 4H), 1.97-1.93 (m, 4H). MS (ESI): m/z=454 [M−H]⁻.

Example 130

Synthesis of Compound 116: 6-chloro-3-((3,4-dioxo-2-((1-phenylcyclopentyl)amino) cyclobut-1-en-1-yl)amino)-2-hydroxy-N,N-dimethylbenzenesulfonamide

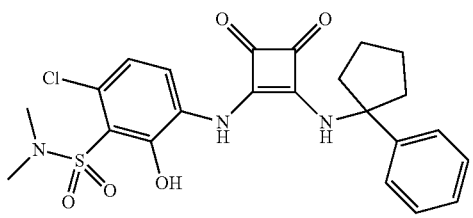 [SMILES: CN(C)S(=O)(=O)c1c(Cl)ccc(Nc2c(NC3(c4ccccc4)CCCC3)c(=O)c2=O)c1O]

According to Method A and procedures similar to those for synthesizing Compound 1, Intermediate 1 (18 mg, 0.048 mmol) and 1-phenylcyclopentan-1-amine (12 mg, 0.074 mmol) were converted into the title compound (6.1 mg, 0.012 mmol, 26%). $^1$H NMR (600 MHz, CHLOROFORM-d): δ=10.30 (br s, 1H), 7.94 (br d, J=8.2 Hz, 1H), 7.47 (br d, J=7.0 Hz, 2H), 7.37-7.45 (m, 2H), 7.28-7.36 (m, 1H), 6.95 (br d, J=8.8 Hz, 1H), 6.63 (br s, 2H), 2.89 (s, 6H), 2.24-2.40 (m, 2H), 2.21 (br s, 2H), 1.97 (br s, 4H). MS (ESI): m/z=488 [M−H]⁻.

Example 131

Synthesis of Compound 117: 3-((3,4-dioxo-2-((1-phenylcyclobutyl)amino)cyclobut-1-en-1-yl)amino)-2-hydroxy-N,N-dimethylbenzenesulfonamide

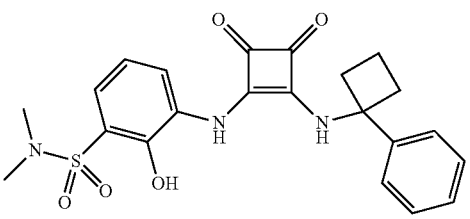 [SMILES: CN(C)S(=O)(=O)c1cccc(Nc2c(NC3(c4ccccc4)CCC3)c(=O)c2=O)c1O]

According to Method B and procedures similar to those for synthesizing Compound 2, Intermediate 7 (34 mg, 0.10 mmol) and 1-phenylcyclobutan-1-amine hydrochloride (28 mg, 0.15 mmol) were converted into the title compound (20 mg, 0.045 mmol, 45%). $^1$H NMR (600 MHz, CHLOROFORM-d): δ=9.07 (br s, 1H), 8.05 (br d, J=7.6 Hz, 1H), 7.65 (br s, 1H), 7.53 (br d, J=7.0 Hz, 2H), 7.38 (br s, 2H), 7.26 (br s, 1H), 7.09 (br d, J=7.6 Hz, 1H), 6.88-6.96 (m, 1H), 2.70 (br s, 6H), 2.16-2.28 (m, 2H), 1.95-2.06 (m, 2H), 1.73-1.84 (m, 2H). MS (ESI): m/z=440 [M−H]⁻.

Example 132

Synthesis of Compound 118: 6-chloro-3-((3,4-dioxo-2-((1-phenylcyclobutyl)amino)cyclobut-1-en-1-yl)amino)-2-hydroxy-N,N-dimethylbenzenesulfonamide

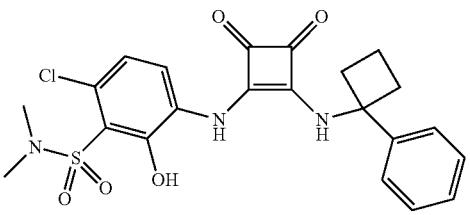 [SMILES: CN(C)S(=O)(=O)c1c(Cl)ccc(Nc2c(NC3(c4ccccc4)CCC3)c(=O)c2=O)c1O]

According to Method B and procedures similar to those for synthesizing Compound 2, Intermediate 1 (26 mg, 0.069 mmol) and 1-phenylcyclobutan-1-amine hydrochloride (19 mg, 0.10 mmol) were converted into the title compound (11 mg, 0.023 mmol, 33%). $^1$H NMR (600 MHz, CHLOROFORM-d): δ=10.43 (br s, 1H), 7.99 (d, J=8.8 Hz, 1H), 7.53 (br d, J=8.2 Hz, 2H), 7.39-7.47 (m, 2H), 7.28-7.37 (m, 1H), 7.12 (br s, 1H), 6.95 (d, J=8.8 Hz, 2H), 2.89 (s, 6H), 2.68-2.83 (m, 2H), 2.49-2.68 (m, 2H), 2.20-2.38 (m, 1H), 2.03-2.11 (m, 1H). MS (ESI): m/z=474 [M−H]⁻.

Example 133

Biological Assay

HEK-Gqi5 cells stably expressing human CCR6 were cultured in DMEM high glucose, 10% FBS, 1% PSA, 400 ug/ml geneticin and 50 ug/ml hygromycin. Appropriate positive control chemokine (MIP3α) was used as the positive control agonist for screening compound-induced calcium activity assayed on the FLIPR$^{Tetra}$. The drug plates were prepared in 384-well microplates using the EP3 and the MultiPROBE robotic liquid handling systems. Compounds disclosed herein were tested for CCR6 activity.

The results set forth below in Table 1 demonstrate that the compounds disclosed herein are CCR6 antagonists, and thus can be useful for the treatment of pathological conditions associated with CCR6 receptors.

TABLE 1

| Comp. No. | CCR6 IC$_{50}$ (nM) | CCR6 % Antagonism |
| --- | --- | --- |
| 1 | 162 | 73 |
| 2 | 183 | 93 |
| 3 | 286 | 96 |
| 4 | 136 | 87 |
| 5 | 40 | 86 |
| 6 | 26 | 72 |
| 7 | 252 | 101 |
| 8 | 6 | 90 |
| 9 | 247 | 84 |
| 10 | 140 | 63 |
| 11 | 38 | 100 |
| 12 | 163 | 85 |
| 13 | 62 | 100 |
| 14 | 293 | 88 |
| 15 | 83 | 96 |
| 16 | 485 | 97 |
| 17 | 14 | 100 |
| 18 | 180 | 97 |
| 19 | 119 | 95 |
| 20 | 58 | 86 |
| 21 | 248 | 93 |
| 22 | 106 | 98 |
| 23 | 58 | 82 |
| 24 | 30 | 85 |
| 25 | 24 | 82 |
| 26 | 30 | 100 |
| 27 | 144 | 98 |
| 28 | 17 | 94 |
| 29 | 8 | 94 |
| 30 | 264 | 95 |
| 31 | 28 | 98 |
| 32 | 12 | 101 |
| 33 | 227 | 94 |
| 34 | 120 | 91 |
| 35 | 197 | 102 |
| 36 | 26 | 96 |
| 37 | 19 | 85 |
| 38 | 474 | 94 |
| 39 | 53 | 102 |
| 40 | 272 | 101 |
| 41 | 476 | 96 |
| 42 | 248 | 102 |
| 43 | 9 | 87 |
| 44 | 37 | 95 |
| 45 | 37 | 104 |
| 46 | 37 | 95 |
| 47 | 85 | 98 |
| 48 | 25 | 95 |
| 49 | 31 | 98 |
| 50 | 51 | 100 |
| 51 | 17 | 99 |
| 52 | 18 | 95 |
| 53 | 106 | 94 |
| 54 | 113 | 95 |
| 55 | 140 | 99 |
| 56 | 455 | 101 |
| 57 | 90 | 89 |
| 58 | 75 | 93 |
| 59 | 272 | 94 |
| 60 | 74 | 98 |
| 61 | 169 | 106 |
| 62 | 290 | 85 |
| 63 | 40 | 84 |
| 64 | 25 | 100 |
| 65 | 225 | 99 |
| 66 | 270 | 87 |
| 67 | 85 | 94 |
| 68 | 194 | 94 |
| 68a | 48 | 99 |
| 69 | 233 | 97 |
| 70 | 147 | 97 |
| 71 | 134 | 100 |
| 72 | 46 | 95 |
| 73 | 98 | 88 |
| 74 | 162 | 94 |
| 75 | 394 | 101 |
| 76 | 100 | 96 |
| 77 | 336 | 98 |
| 78 | 178 | 98 |
| 79 | 106 | 86 |
| 80 | 150 | 87 |
| 81 | 173 | 96 |
| 82 | 173 | 95 |
| 83 | 180 | 89 |
| 84 | 27 | 61 |
| 85 | 28 | 98 |
| 86 | 49 | 102 |
| 87 | 160 | 101 |
| 88 | 248 | 95 |
| 89 | 60 | 101 |
| 90 | 19 | 98 |
| 91 | 373 | 100 |
| 92 | 46 | 95 |
| 93 | 88 | 96 |
| 94 | 131 | 96 |
| 95 | 30 | 101 |
| 96 | 138 | 98 |
| 97 | 35 | 99 |
| 98 | 407 | 99 |
| 99 | 194 | 96 |
| 100 | 293 | 95 |
| 101 | 74 | 98 |
| 102 | 162 | 97 |
| 103 | 90 | 93 |
| 104 | 408 | 94 |
| 105 | 121 | 95 |
| 106 | 274 | 100 |
| 107 | 118 | 92 |
| 108 | 175 | 95 |
| 109 | 6 | 99 |
| 110 | 35 | 101 |
| 111 | 154 | 98 |
| 112 | 106 | 95 |
| 113 | 67 | 91 |
| 114 | 338 | 102 |
| 115 | 201 | 101 |
| 116 | 43 | 97 |
| 117 | 190 | 100 |
| 118 | 162 | 91 |

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed:

1. A compound of Formula I or a pharmaceutically acceptable salt thereof, including an enantiomer, a diastereoisomer, a tautomer thereof:

Formula I

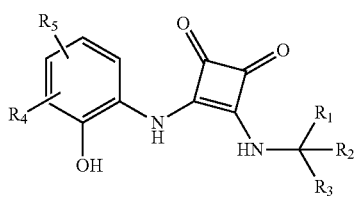

wherein

R₁ is

C₁₋₁₀ alkyl optionally substituted with at least one group selected from OR₆, —CO₂R₆, and halo;

R₂ is hydrogen;

R₃ is 6 to 12 membered aryl optionally substituted with at least one group selected from C₁₋₆ alkyl, halo, and OR₆;

R₄ is —SO₂NR₆R₇;

R₅ is halo; and

R₆ and R₇ are independently selected from hydrogen and C₁₋₆ alkyl.

2. The compound or a pharmaceutically acceptable salt thereof of claim 1, wherein R₁ is C₁₋₁₀ alkyl substituted with at least one group selected from OR₆, halo, and —CO₂R₆.

3. The compound or a pharmaceutically acceptable salt thereof of claim 1, wherein R₆ is hydrogen.

4. The compound or a pharmaceutically acceptable salt thereof of claim 1, wherein the moiety:

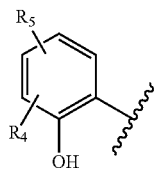

is of the form:

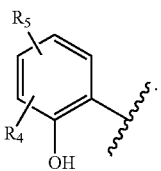

5. The compound or a pharmaceutically acceptable salt thereof of any one of claim 1, wherein the moiety:

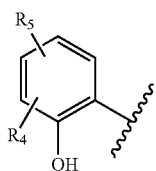

is of the form:

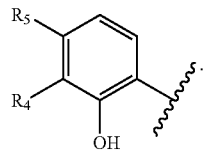

6. The compound or a pharmaceutically acceptable salt thereof of claim 1, wherein the compound is

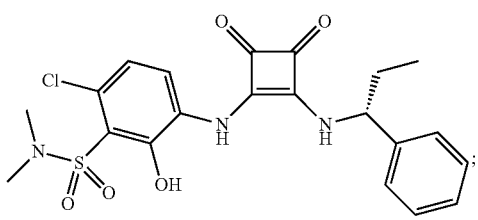

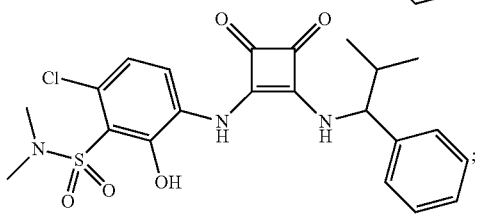

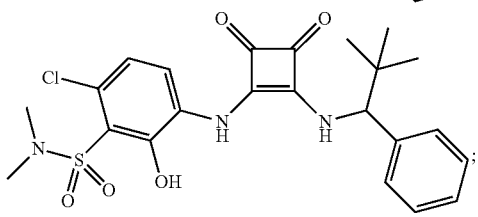

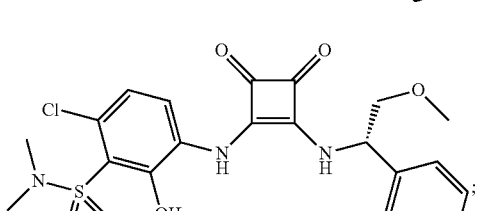

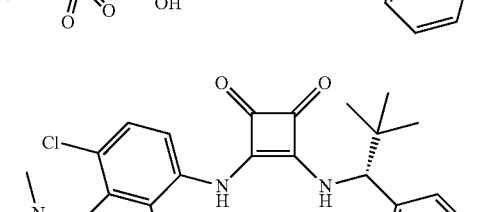

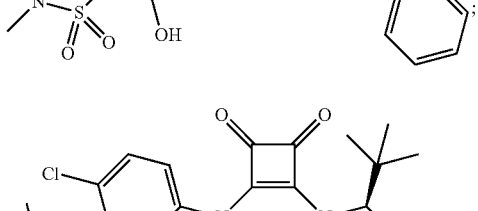

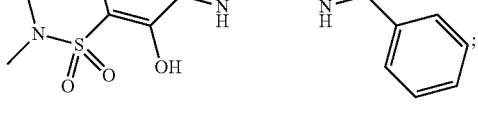

-continued
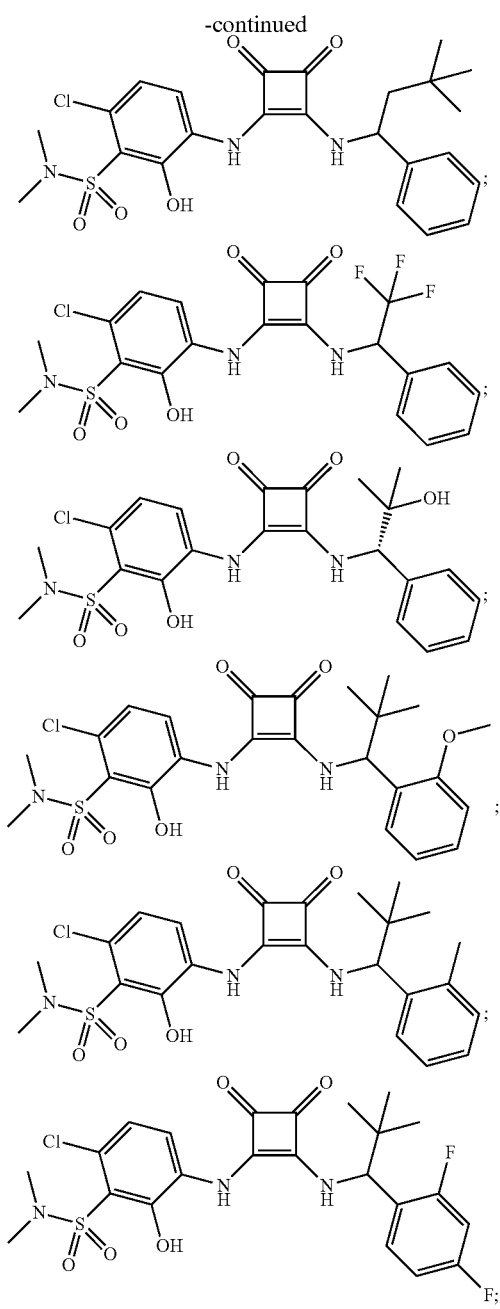
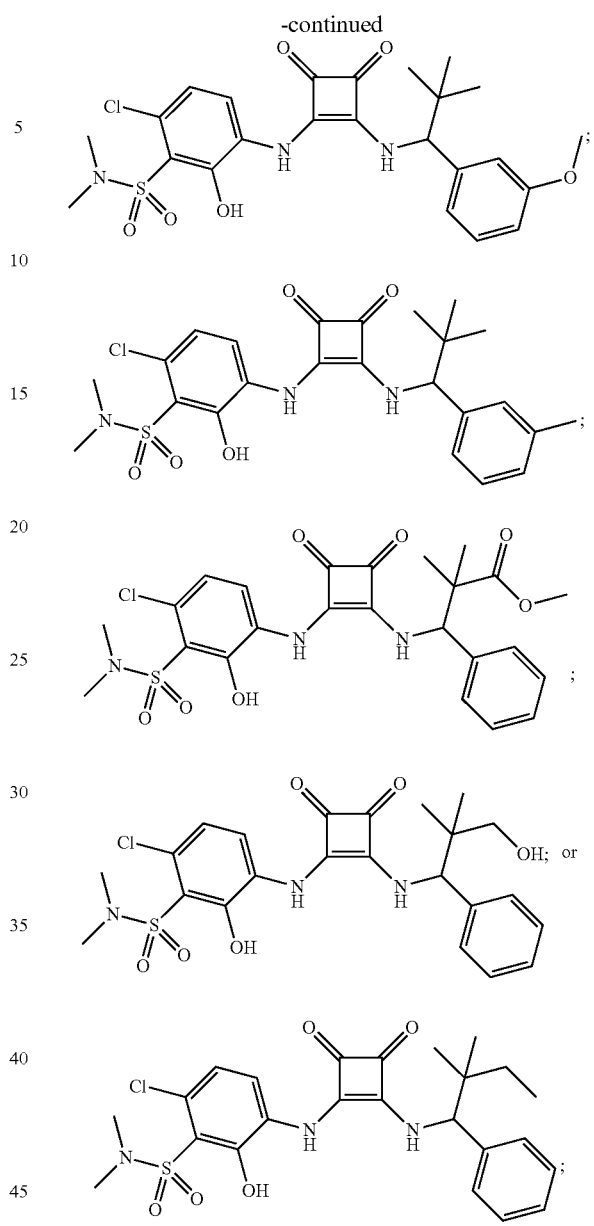
or a pharmaceutically acceptable salt thereof.
* * * * *

UNITED STATES PATENT AND TRADEMARK OFFICE
CERTIFICATE OF CORRECTION

PATENT NO. : 11,208,377 B2
APPLICATION NO. : 16/103607
DATED : December 28, 2021
INVENTOR(S) : Christopher D. Hein et al.

It is certified that error appears in the above-identified patent and that said Letters Patent is hereby corrected as shown below:

On the Title Page

On the Page 2, in Column 1, Item (56) under "Other Publications", Line 23, delete "Biology" and insert -- Biology, --.

On the Page 2, in Column 2, Item (56) under "Other Publications", Line 17, delete "Reseach," and insert -- Research, --.

On the Page 2, in Column 2, Item (56) under "Other Publications", Line 18, delete "Associted" and insert -- Associated --.

On the Page 2, in Column 2, Item (56) under "Other Publications", Line 33, delete "Imuunity," and insert -- Immunity, --.

On the Page 2, in Column 2, Item (56) under "Other Publications", Line 41, delete "N,N0-" and insert -- N,N'- --.

On the Page 2, in Column 2, Item (56) under "Other Publications", Line 42, delete "N,N0-" and insert -- N,N'- --.

On the Page 2, in Column 2, Item (56) under "Other Publications", Line 51, delete "susceptibilty" and insert -- susceptibility --.

On the Page 3, in Column 1, Item (56) under "Other Publications", Line 11, delete "Allegan," and insert -- Allergan, --.

In the Specification

In Column 2, Line 14, delete "CD4+T" and insert -- CD4+ T --.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,208,377 B2

In Column 2, Line 23, delete "11-82007;" and insert -- 11-8, 2007; --.

In Column 2, Line 32, delete "1167-117 2009;" and insert -- 1167-1177, 2009; --.

In Column 2, Line 34, delete "911-9222010;" and insert -- 911-922, 2010; --.

In Column 2, Line 35, delete "613-6192011;" and insert -- 613-619, 2011; --.

In Column 2, Line 36, delete "CCR6+Th17" and insert -- CCR6+ Th17 --.

In Column 3, Line 3, delete "29462003;" and insert -- 2946, 2003; --.

In Column 6, Line 63, delete "—NR$_6$CO$_2$RT," and insert -- —NR$_6$CO$_2$R$_7$, --.

In Column 10, Line 19, delete "—NR$_6$CO$_2$RT," and insert -- —NR$_6$CO$_2$R$_7$, --.

In Column 14, Line 26, delete "—NR$_6$CO$_2$RT," and insert -- —NR$_6$CO$_2$R$_7$, --.

In Column 26, Lines 2-9, delete " 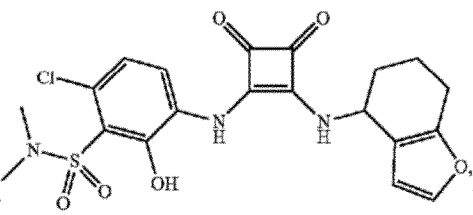 " and insert -- 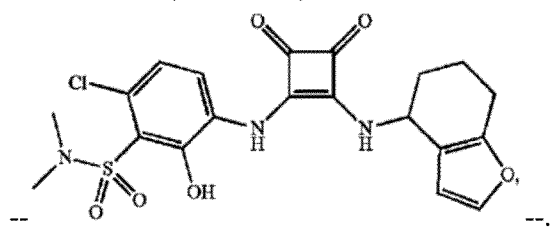 --.

In Column 42, Line 2, delete "—O-alknyl," and insert -- —O-alkynyl, --.

In Column 52, Line 16, delete "—NR$_6$CO$_2$RT," and insert -- —NR$_6$CO$_2$R$_7$, --.

In Column 65, Lines 27-34, after " 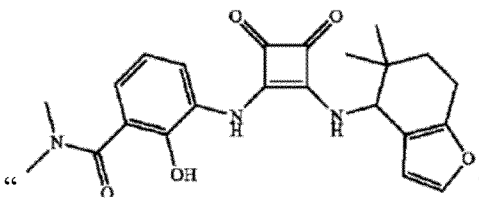 " insert -- , --.

CERTIFICATE OF CORRECTION (continued)
U.S. Pat. No. 11,208,377 B2

In Column 67, Lines 11-18, after " 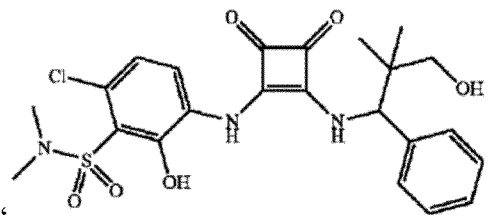 " insert -- , --.

In Column 67, Lines 59-66, after " 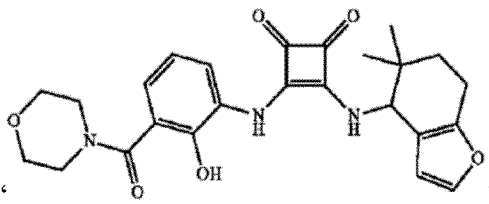 " insert -- , --.

In Column 69, Lines 27-33, after " 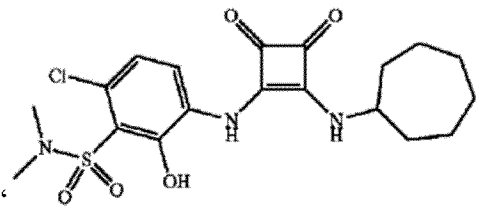 " insert -- , --.

In Column 75, Lines 53-58, after " 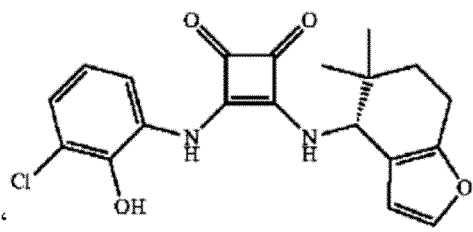 " insert -- , --.

In Column 92, Line 19, delete "6=" and insert -- δ= --.

In Column 112, Line 48, after "[M-H]⁻" insert -- . --.

In Column 115, Line 35, delete "Methyl" and insert -- methyl --.

In Column 115, Lines 35-36, delete "dimethyl sulfamoyl)" and insert -- dimethylsulfamoyl) --.

In Column 116, Line 45, delete "38:3" and insert -- 38: 3 --.

In Column 124, Line 1, delete "54" and insert -- 55 --.

In Column 124, Line 3, delete "47:3" and insert -- 47: 3 --.

In Column 125, Line 4, delete "49:3" and insert -- 49: 3 --.

In Column 131, Line 11, delete "1l-ol" and insert -- 1-ol --.

In Column 133, Line 22, delete "(20. L," and insert -- (20. μL, --.

In Column 149, Line 43, delete "10%-80%" and insert -- 10%→80% --.

In Column 151, Lines 9-15, delete " " and insert -- 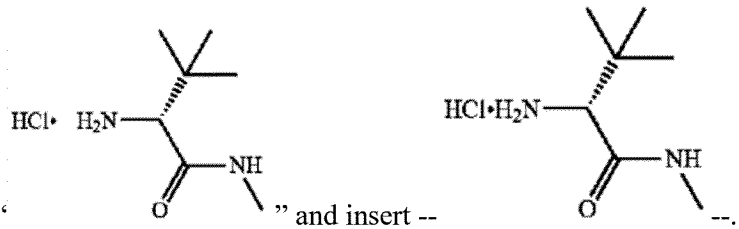 --.

In Column 151, Lines 31-36, delete " " and insert -- 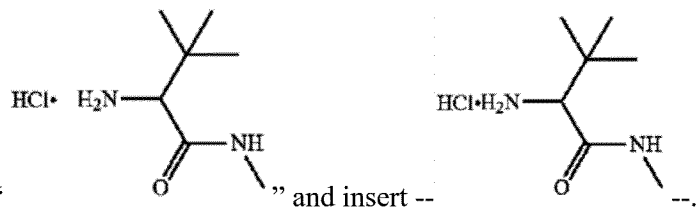 --.

In Column 157, Line 36, delete "93:6" and insert -- 93: 6 --.

In Column 171, Line 1, delete "FLIPR$^{Tetra}$." and insert -- FLIPR Tetra. --.

In the Claims

In Column 173, Lines 48-53, in Claim 4, delete " 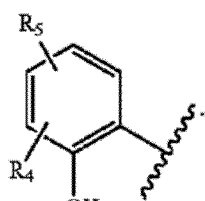 " and insert 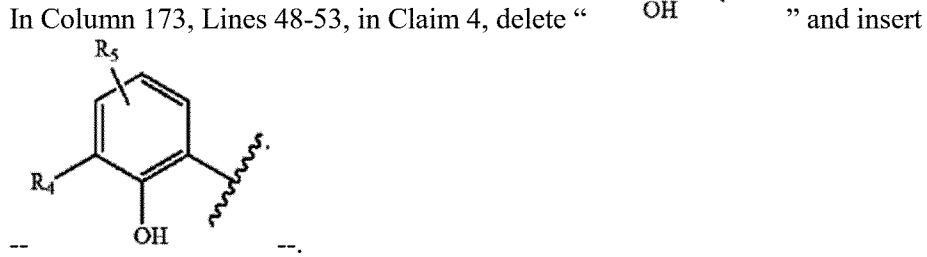.

In Column 173, Line 57, in Claim 5, before "claim" delete "any one of".